United States Patent
Soares et al.

(10) Patent No.: US 11,046,773 B2
(45) Date of Patent: Jun. 29, 2021

(54) BISPECIFIC CXCR4-CD4 POLYPEPTIDES WITH POTENT ANTI-HIV ACTIVITY

(71) Applicant: Ablynx N.V., Ghent-Zwijnaarde (BE)

(72) Inventors: Hugo Soares, Loures (PT); Dominique Schols, Herent (BE); Peter Vanlandschoot, Bellem (BE); Philippe Van Rompaey, Melle (BE); Catelijne Stortelers, Ghent (BE)

(73) Assignee: Ablynx N.V., Ghent-Zwijnaarde (BE)

( * ) Notice: Subject to any disclaimer, the term of this patent is extended or adjusted under 35 U.S.C. 154(b) by 0 days.

(21) Appl. No.: 16/295,041

(22) Filed: Mar. 7, 2019

(65) Prior Publication Data
US 2019/0292267 A1 Sep. 26, 2019

Related U.S. Application Data

(62) Division of application No. 15/562,437, filed as application No. PCT/EP2016/057215 on Apr. 1, 2016, now Pat. No. 10,273,305.

(60) Provisional application No. 62/142,127, filed on Apr. 2, 2015.

(51) Int. Cl.
| | | |
|---|---|---|
| *A61K 39/00* | (2006.01) | |
| *C07K 16/28* | (2006.01) | |
| *A61K 39/395* | (2006.01) | |
| *C07K 16/00* | (2006.01) | |
| *C07K 16/46* | (2006.01) | |
| *A61K 47/60* | (2017.01) | |
| *C07K 16/18* | (2006.01) | |

(52) U.S. Cl.
CPC .... *C07K 16/2866* (2013.01); *A61K 39/39541* (2013.01); *A61K 47/60* (2017.08); *C07K 16/18* (2013.01); *C07K 16/2812* (2013.01); *A61K 2039/507* (2013.01); *C07K 2317/31* (2013.01); *C07K 2317/565* (2013.01); *C07K 2317/567* (2013.01); *C07K 2317/569* (2013.01); *C07K 2317/76* (2013.01); *C07K 2317/92* (2013.01); *C07K 2317/94* (2013.01)

(58) Field of Classification Search
CPC .......... C07K 2317/76; C07K 2317/569; C07K 2317/92; C07K 2317/31; A61K 2039/505
See application file for complete search history.

(56) References Cited

U.S. PATENT DOCUMENTS

| 10,273,305 B2 | 4/2019 | Soares et al. |
| 2011/0318347 A1 | 12/2011 | Blanchetot et al. |

FOREIGN PATENT DOCUMENTS

| WO | WO 2007/025276 A2 | 3/2007 |
| WO | WO 2010/043650 A2 | 4/2010 |
| WO | WO2010043650 | * 4/2010 |
| WO | WO 2011/083140 A1 | 7/2011 |

OTHER PUBLICATIONS

Matthias et al. "Preferential targeting of CD4-CCR5 complexes with bifunctional inhibitors; a novel approach to block HIV-1 infection", The journal of immunology, the american association of immunologists, US, 2005, 175(11)7586-7593.*
Rozan et al. "Single-Domain Antibody-Based and Linker-Free Bispecific Antibodies Targeting FcgRIII Induce Potent Antitumor Activity without Recruiting Regulatory T Cells", 2013, Molecular Cancer Therapeutics, 12(8):1481-1491.*
Anderson et al., Bispecific short hairpin siRNA constructs targeted to CD4, CXCR4, and CCR5 confer HIV-1 resistance, Oligonucleotides, 2003, 12(5):303-312.*
PCT/EP2016/057215, Jun. 22, 2016, International Search Report and Written Opinion.
PCT/EP2016/057215, Oct. 12, 2017, International Preliminary Report on Patentability.
Anderson et al., Bispecific short hairpin siRNA constructs targeted to CD4, CXCR4, and CCR5 confer HIV-1 resistance. Oligonucleotides. 2003;13(5):303-12.
Jahnichen et al., CXCR4 nanobodies (VHH-based single variable domains) potently inhibit chemotaxis and HIV-1 replication and mobilize stem cells. Proc Natl Acad Sci USA. Nov. 23, 2010; 107(47): 20565-20570.
Mack et al., Preferential targeting of CD4-CCR5 complexes with bifunctional inhibitors: a novel approach to block HIV-1 infection. J Immunol. Dec. 1, 2005; 175(11): 7586-7593.
Rozan et al., Single-domain antibody-based and linker-free bispecific antibodies targeting Fc RIII induce potent antitumor activity without recruiting regulatory T cells. Mol Cancer Ther. Aug. 1, 2013; 12(8): 1481-1491.
Stortelers et al., Bispecific Nanobodies with Enhanced Cell Specificity—Nanobodies creating better medicines. PEGS 2015 Boston. May 8, 2015; pp. 1-26.

* cited by examiner

*Primary Examiner* — Barry A Chestnut
(74) *Attorney, Agent, or Firm* — Wolf, Greenfield & Sacks, P.C.

(57) ABSTRACT

The present invention relates to bispecific polypeptides that are directed against the cellular receptor CD4 as well as a cellular co-receptor for HIV. Said polypeptides may be used to prevent human cell entry of HIV.

16 Claims, 9 Drawing Sheets

Specification includes a Sequence Listing.

Figure 2.1
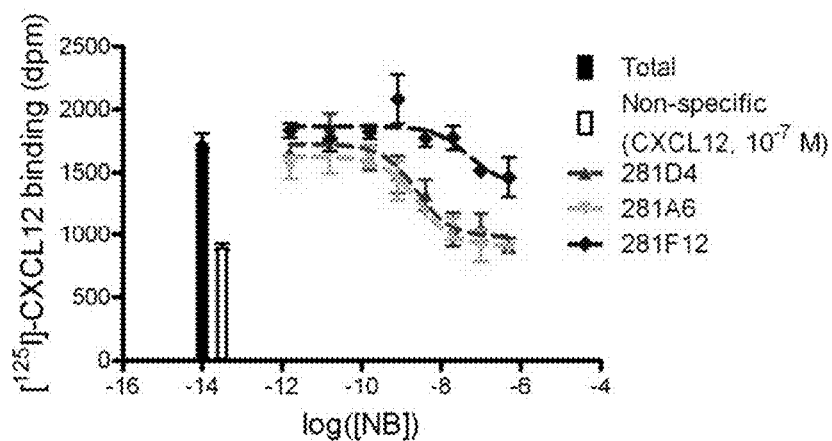
Figure 2.2
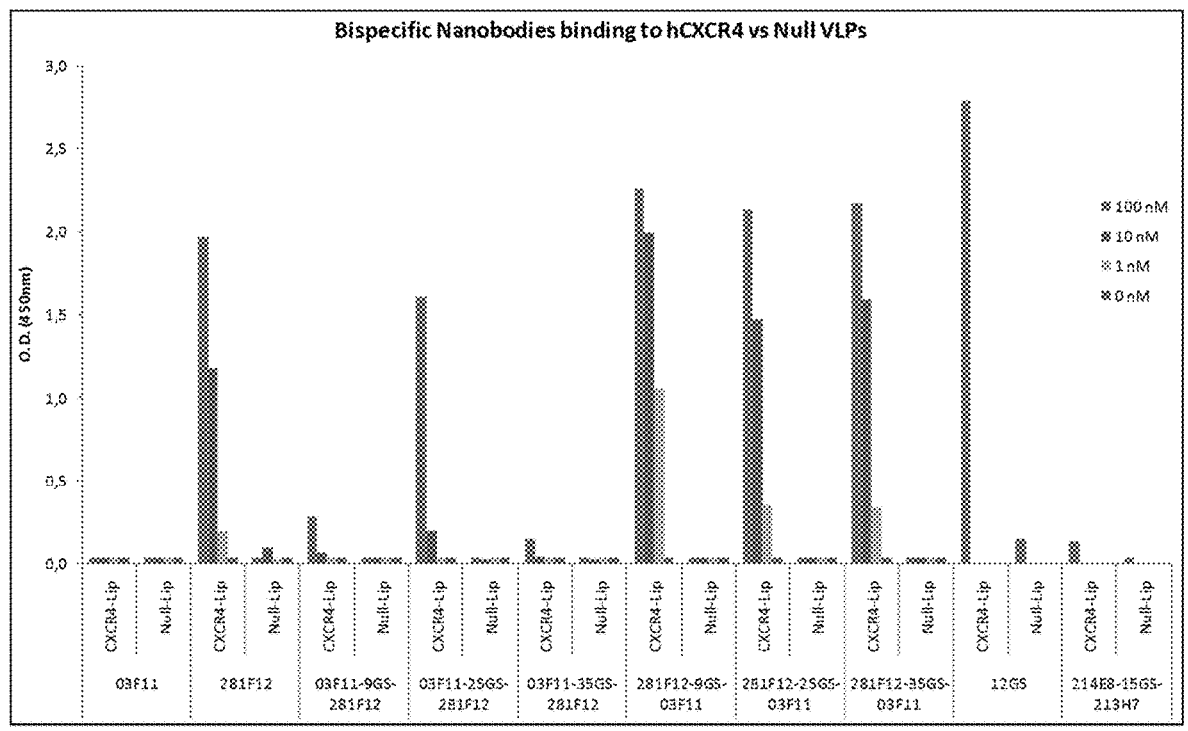

Figure 2.3
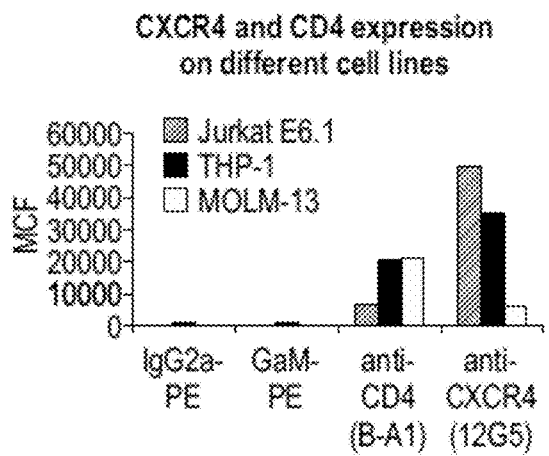
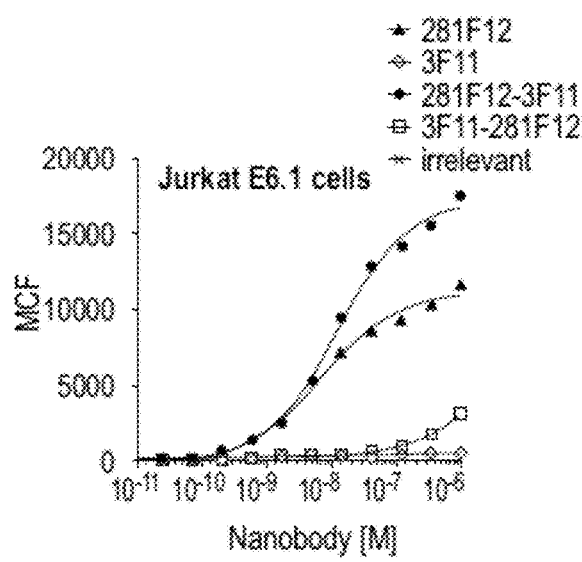
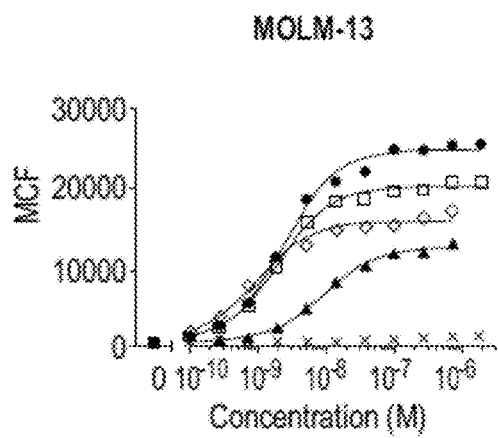
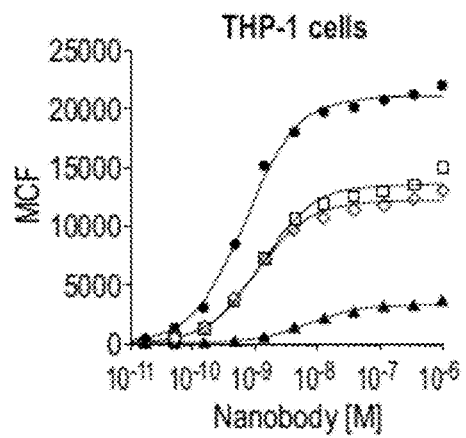
Figure 2.4
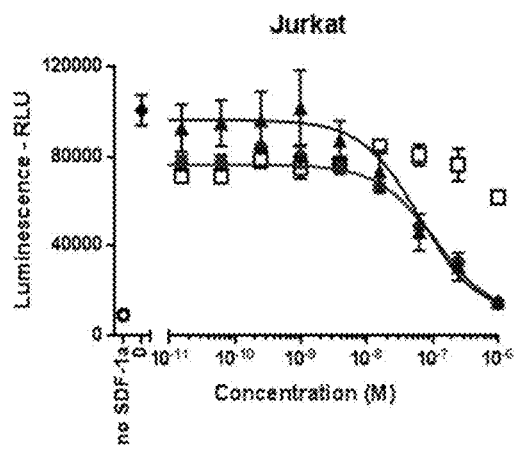
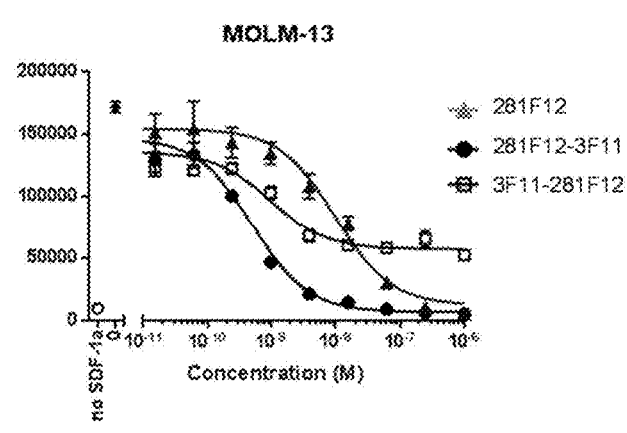

BISPECIFIC CXCR4-CD4 POLYPEPTIDES WITH POTENT ANTI-HIV ACTIVITY

RELATED APPLICATIONS

This application is a divisional of U.S. application Ser. No. 15/562,437, filed Sep. 28, 2017, which is a national stage filing under 35 U.S.C. § 371 of International Application No. PCT/EP2016/057215, filed Apr. 1, 2016, and claims the benefit under 35 U.S.C. § 119(e) of U.S. provisional application Ser. No. 62/142,127, filed Apr. 2, 2015, the entire contents of each of which is incorporated by reference herein in its entirety.

FIELD OF THE INVENTION

The present invention relates to bispecific polypeptides that are directed against the cellular receptor CD4 as well as the cellular co-receptor for HIV. Said polypeptides may be used to prevent human cell entry of HIV.

BACKGROUND

Any discussion of the prior art throughout the specification should in no way be considered as an admission that such prior art is widely known or forms part of common general knowledge in the field.

Infection with the Human Immunodeficiency Virus (HIV), if left untreated, almost always leads to death of the infected person. HIV infects the $CD4^+$ T-cells and leads to a decline in the number of $CD4^+$ T-cells in the infected person. When $CD4^+$ T-cell numbers decline below a critical level, cell-mediated immunity is effectively lost, and infections with a variety of opportunistic microbes appear, resulting in Acquired Immunodeficiency Syndrome (AIDS). Because the HIV-infected person can no longer defend against these opportunistic infections, the patient will ultimately succumb to one of these infections.

Infection by HIV is mediated by the envelope glycoprotein (Env). Env forms a heterotrimer composed of the receptor binding subunit gp120 and the HIV membrane anchored fusion protein subunit gp41 (see FIG. 1). Entry into host cells is mediated by gp120 interaction with CD4 that triggers a conformational change allowing subsequent interaction with a cellular co-receptor, principally CCR5 or CXCR4 (Dalgleish et al. (1984) Nature 312: 763-767; Klatzmann et al. (1984) Nature 312: 767-768; Moore et al. (1997) Curr Opin Immunol 9: 551-562; Clapham & McKnight (2002) J Gen Virol 83: 1809-1829). CCR5 is the predominant co-receptor used, but an altered use of CCR5 is selected for during progressive HIV infection. Association of gp120 with the co-receptor induces additional conformational changes in gp41, which in turn promote mixing of the membrane lipids, ultimately facilitating fusion of the viral and cellular membranes (Weissenhorn et al. (1997) Nature 387: 426-430; Chan et al. (1997) Cell 89: 263-273; Weissenhorn et al. (2007) FEBS Lett 581: 2150-2155). Once the virus has entered the T-cells, the virus hijacks the replication machinery of the T-cell to produce additional copies of HIV thereby furthering the infection.

Currently there is no cure available for HIV/AIDS. However, HIV infected persons can suppress replication of the virus through a variety of anti-viral treatment options. Current treatment for HIV infection consists of anti-retroviral therapy, or ART. ART consists of the administration of a cocktail of multiple anti-viral compounds. However, because HIV readily mutates the virus often becomes resistant to one or more compounds in the ART cocktail. In addition, ART is associated with a number of side effects. While anti-retroviral adherence is the second strongest predictor of progression to AIDS and death, after CD4 count, incomplete adherence to ART is common in all groups of treated individuals. The average rate of adherence to ART is approximately 70%, despite the fact that long-term viral suppression requires near-perfect adherence. The resulting virologic treatment failure diminishes the potential for long-term clinical success and increases the risk of drug resistance.

New therapies to treat HIV infection are needed therefore.

Next to the small-molecule anti-HIV compounds, neutralizing antibodies have been engineered and tested. However, antibodies are necessarily directed against the exterior of the virus. Indeed, Env is a main target for entry inhibitors (Matthews et al. (2004) Nat Rev Drug Discov 3: 215-225) and most neutralizing antibodies are directed against gp120 or gp41 (Sattentau Q (2008) Curr Opin HIV AIDS 3: 368-374). Also in this case a crucial problem in HIV vaccine research is the generation of cross-subtype neutralizing antibodies, which is due to the fact that HIV employs a number of strategies to evade the immune response. This includes highly variable gp120 regions, a carbohydrate shield (Wyatt et al. (1998) Nature 393: 705-711) and conformational masking of the receptor binding site (Kwong et al. (2002) Nature 420: 678-682).

Nanobodies directed against various HIV-1 proteins have been described (Hinz et al. 2010 PLoS ONE 5:e10482; McCoy et al. 2014 Retrovirology 11:83; Vercruysse et al. 2010 JBC 285:21768-21780; Bouchet et al., 2011 Blood 117:3559-3568). However, various Nanobodies were directed against intra-cellular HIV proteins, necessitating intracellular expression of the Nanobody. Moreover, in none of the cases, the development of resistance by HIV against the Nanobody has been addressed.

Interestingly, the options for HIV to "mutate around" therapies directed at blocking cell entry appear to be more limited. Indeed, in a study using ibalizumab, an anti-CD4 monoclonal antibody, resistance was developed but the resistant isolates remained dependent on CD4 for viral entry, suggesting that resistance did not develop through the use of alternative receptors (cf. Bruno & Jacobson 2010 J Antimicrob Chemother 65:1839-1841). Nevertheless, also in this case resistance against ibalizumab developed eventually (cf. Fessel et al., 2011 Antiviral Res 92:484-487).

PRO140 is a fully humanized IgG4 monoclonal antibody directed against the co-receptor CCR5. PRO140 blocks the HIV R5 subtype entry into T-cells by masking the required co-receptor CCR5. In short term studies, resistance against PRO140 has not been observed. However, the potential development of resistance in long term studies has not been addressed. PRO140 does not prevent the usage of the CXCR4 co-receptor. For instance, in up to 40 to 50% of individuals infected with B-HIV, progression to late stages of infection is associated with a switch in co-receptor specificity, with emergence of X4 (CXCR4) or R5X4 (CCR5/CXCR4) viral variants (Bjorndal et al. J Virol 1997, 71(10):7478-7487; Connor et al. J Exp Med 1997, 185(4): 621-628). The emergence of CXCR4-using HIV viruses is associated with rapid $CD4^+$ T-cell decline and progression from chronic to advanced stages of HIV infection.

SUMMARY OF THE INVENTION

It is an object of the present invention to overcome or ameliorate at least one of the disadvantages of the prior art, or to provide a useful alternative.

The inventors demonstrated that binding by a bispecific polypeptide directed against a co-receptor (CR) and the receptor CD4 resulted in a synergy of the two binding moieties against HIV infection (see Example 4). Surprisingly, bispecific polypeptides were more effective than the combination of the two individual moieties (see Example 8).

The combination of moieties in the bispecific polypeptide with non-overlapping effects, i.e., a first moiety is directed against CD4 and the second moiety is directed against a co-receptor, allows the application of more effective binders without increasing the overall negative toxic effects to the host beyond unacceptable limits.

The inventors further demonstrated that accomplishing resistance by HIV against the bispecific polypeptide is extremely difficult, even in a forced laboratory setting (see Example 8). On the other hand, it was surprisingly observed that even in a HIV strain made resistant against one receptor, e.g. the anti-CD4 moiety, the bispecific polypeptide was still efficacious. Hence, this property expands the use of a bispecific polypeptide to a possible efficacy against heterogeneous strains not inherently resistant to one moiety agent and another HIV strain not inherently resistant against another moiety.

Accordingly, the present invention relates to a polypeptide comprising a first and a second immunoglobulin single variable domain (ISV), wherein said first ISV binds to CD4 and polymorphic variants present on the surface of a cell; said second ISV binds to a co-receptor (CR) present on the surface of said cell, preferably wherein said CR is chosen from the group consisting of CXCR4, CCR5, CCR1, CCR2, CCR3, CCR8, CX3CR1, CXCR6, FPRL1, GPR1, GPR15, APJ, and D6 and related polymorphic variants, preferably CXCR4, preferably human CR, preferably human CXCR4; and wherein said CR is not CD4, preferably said polypeptide inhibits infection of human immunodeficiency virus (HIV) or simian immunodeficiency virus (SIV), more preferably said HIV is chosen from the group consisting of HIV-1 and HIV-2 (preferably HIV-1, preferably subtype C), and preferably said cell is a human cell, preferably a human CD4+-cell, even more preferably a human CD4+ T-cell.

Accordingly, the present invention relates to a polypeptide as described supra, wherein the average $EC_{50}$ value of HIV inhibition is of between 10 nM and 0.1 pM, such as at an average $EC_{50}$ value of 10 nM or less, even more preferably at an average $EC_{50}$ value of 9 nM or less, such as than 8, 7, 6, 5, 4, 3, 2, 1, 0.5 nM or even less, such as less than 400, 300, 200, 100, 50, 40, 30, 20, 10, 9, 8, 7, 6, 5, 4, 3, 2, 1, 0.5 pM, or even less such as less than 0.4 pM; and/or wherein the $IC_{50}$ of HIV inhibition is lower than 50 nM, lower than 10 nM, lower than 1 nM or less, such as less than 0.5 nM or even less, such as less than 400, 300, 200, 100, 50, 40, 30, 20, 10, 9, 8, 7, 6, 5, 4, 3, 2, 1, 0.5 pM, or even less such as less than 0.4 pM; and/or wherein said polypeptide inhibits HIV infection by about 10%, 20%, 30%, 40%, 50%, 60%, 80%, 90% and preferably 95% or more, such as 100% (as measured in a HIV infection assay); and/or wherein said polypeptide inhibits HIV fusion with CD4 CXCR4+ cells; and/or wherein said polypeptide has an on rate constant (Kon) to said CD4 selected from the group consisting of at least about $10^2$ $M^{-1}s^{-1}$, at least about $10^3$ $M^{-1}s^{-1}$, at least about $10^4$ $M^{-1}s^{-1}$, at least about $10^5$ $M^{-1}s^{-1}$, at least about $10^6$ $M^{-1}s^{-1}$, $10^7$ $M^{-1}s^{-1}$, at least about $10^8$ $M^{-1}s^{-1}$, at least about $10^9$ $M^{-1}s^{-1}$, and at least about $10^{10}$ $M^{-1}s^{-1}$, preferably as measured by surface plasmon resonance; and/or wherein said polypeptide has an off rate constant (Koff) to said CD4 selected from the group consisting of at most about $10^3 s^{-1}$, at most about $10^4 s^{-1}$, at most about $10^{-5} s^{-1}$, at most about $10^{-6} s^{-1}$, at most about $10^{-7} s^{-1}$, at most about $10^{-8} s^{-1}$, at most about $10^{-9} s^{-1}$, and at most about $10^{-10} s^{-1}$, preferably as measured by surface plasmon resonance; and/or wherein said polypeptide has a dissociation constant ($K_D$) to said CD4 selected from the group consisting of: at most about $10^{-7}$ M, at most about $10^{-8}$ M, at most about $10^{-9}$ M, at most about $10^{-10}$ M, at most about $10^{-11}$ M, and at most about $10^{-12}$ M, preferably as measured by surface plasmon resonance.

The present invention relates also to a polypeptide as described herein, wherein said first ISV binds to CD4 with an average KD value of between 10 nM and 0.1 pM, such as at an average KD value of 10 nM or less, even more preferably at an average KD value of 9 nM or less, such as less than 8, 7, 6, 5, 4, 3, 2, 1, 0.5 nM or even less, such as less than 400, 300, 200, 100, 50, 40, 30, 20, 10, 9, 8, 7, 6, 5, 4, 3, 2, 1, 0.5 pM, or even less such as less than 0.4 pM, preferably measured by SPR, for instance as determined by a KinExA; and/or said polypeptide inhibits multimerisation by CD4 by less than about 50%, such as 40%, 30%, or 20% or even less than 10%, such as less than 5%; and/or said polypeptide inhibits recruiting Lck by CD4 by less than about 50%, such as 40%, 30%, or 20% or even less than 10%, such as less than 5%.

The present invention relates also to a polypeptide as described herein, wherein said polypeptide has an on rate constant (Kon) to said CR selected from the group consisting of at least about $10^2$ $M^{-1}s^{-1}$, at least about $10^3$ $M^{-1}s^{-1}$, at least about $10^4$ $M^{-1}s^{-1}$, at least about $10^5$ $M^{-1}s^{-1}$, at least about $10^6$ $M^{-1}s^{-1}$, $10^7$ $M^{-1}s^{-1}$, at least about $10^8$ $M^{-1}s^{-1}$, at least about $10^9$ $M^{-1}s^{-1}$, and at least about $10^{10}$ $M^{-1}s^{-1}$, preferably as measured by surface plasmon resonance, said CR is preferably CXCR4; and/or wherein said polypeptide has an off rate constant (Koff) to said CR selected from the group consisting of at most about $10^3 s^{-1}$, at most about $10^{-4} s^{-1}$, at most about $10^{-5} s^{-1}$, at most about $10^{-6} s^{-1}$, at most about $10^{-7} s^{-1}$, at most about $10^{-8} s^{-1}$, at most about $10^{-9} s^{-1}$, and at most about $10^{-10} s^{-1}$, preferably as measured by surface plasmon resonance, said CR is preferably CXCR4; and/or said polypeptide has a dissociation constant ($K_D$) to said CR selected from the group consisting of: at most about $10^{-7}$ M, at most about $10^{-8}$ M, at most about $10^{-9}$ M, at most about $10^{-10}$ M, at most about $10^{-11}$ M, and at most about $10^{-12}$ M, preferably as measured by surface plasmon resonance, said CR is preferably CXCR4; and/or said second ISV binds to said CR with an average KD value of between 10 nM and 0.1 pM, such as at an average KD value of 10 nM or less, even more preferably at an average KD value of 9 nM or less, such as less than 8, 7, 6, 5, 4, 3, 2, 1, 0.5 nM or even less, such as less than 400, 300, 200, 100, 50, 40, 30, 20, 10, 9, 8, 7, 6, 5, 4, 3, 2, 1, 0.5 pM, or even less such as less than 0.4 pM, preferably measured by SPR, for instance as determined by a KinExA, said CR is preferably CXCR4; and/or said polypeptide inhibits binding of a natural ligand to said CR by less than about 50%, such as 40%, 30%, or 20% or even less than 10%, such as less than 5%.

The present invention relates also to a polypeptide as described herein, wherein said CR is preferably CXCR4, and preferably the natural ligand is Stromal Cell-Derived Factor-1 beta (SDF-1β) or Stromal Cell-Derived Factor-1 alpha (SDF-1α); and preferably the $IC_{50}$ of SDF-1α or SDF-1β displacement from CXCR4 in the presence of the polypeptide is 10 nM or higher, 250 nM or higher, or 1 μM or higher; and even more preferably the $IC_{50}$ of SDF-1α or SDF-1β displacement from CXCR4 in the presence of the polypeptide is greater than the $IC_{50}$ of HIV inhibition.

The present invention relates also to a polypeptide as described herein, further comprising a serum protein binding moiety, preferably binding serum albumin, a non-antibody based polypeptide or PEG. Preferably said serum protein binding moiety is an immunoglobulin single variable domain binding serum albumin More preferably, said ISV binding serum albumin essentially consists of 4 framework regions (FR1 to FR4, respectively) and 3 complementarity determining regions (CDR1 to CDR3 respectively), in which CDR1 is SEQ ID NO: 124, CDR2 is SEQ ID NO: 125 CDR3 is SEQ ID NO: 126, such as chosen from the group consisting of Alb8, Alb23, Alb129, Alb132, Alb11, Alb11 (S112K)-A, Alb82, Alb82-A, Alb82-AA, Alb82-AAA, Alb82-G, Alb82-GG, Alb82-GGG.

The present invention relates also to a polypeptide as described herein, wherein said first ISV and said second ISV and possibly said ISV binding serum albumin are directly linked to each other or are linked via a linker; preferably chosen from the group consisting of linkers of 5GS, 7GS, 9GS, 10GS, 15GS, 18GS, 20GS, 25GS, 30GS and 35GS.

The present invention relates also to a polypeptide as described herein, wherein said ISV is a Nanobody®, a $V_{HH}$, a humanized $V_{HH}$ or a camelized $V_H$.

The present invention relates also to a polypeptide as described herein, wherein said first ISV essentially consists of 4 framework regions (FR1 to FR4, respectively) and 3 complementarity determining regions (CDR1 to CDR3 respectively), in which (i) CDR1 is chosen from the group consisting of SEQ ID NOs: 82-85; and amino acid sequences that have 1, 2 or 3 amino acid difference(s) with SEQ ID NOs: 82-85; (ii) CDR2 is chosen from the group consisting of SEQ ID NOs: 88-91; and amino acid sequences that have 1, 2 or 3 amino acid difference(s) with SEQ ID NOs: 88-91; and (iii) CDR3 is chosen from the group consisting of SEQ ID NO: 96-99 and amino acid sequences that have 1, 2, 3 or 4 amino acid difference(s) with SEQ ID NOs: 96-99; preferably CDR1 is SEQ ID NO: 85, CDR2 is SEQ ID NO: 91 and CDR3 is SEQ ID NO: 99. Also, the present invention relates also to a polypeptide as described supra, wherein said first ISV is chosen from the group consisting of 01B6 (SEQ ID NO: 17), 01E2 (SEQ ID NO: 18), 01H12 (SEQ ID NO: 19) and 03F11 (SEQ ID NO: 20), preferably said first ISV is clone 03F11 (SEQ ID NO: 20).

The present invention relates also to a polypeptide as described herein, wherein said second ISV essentially consists of 4 framework regions (FR1 to FR4, respectively) and 3 complementarity determining regions (CDR1 to CDR3 respectively), in which (i) CDR1 is chosen from the group consisting of SEQ ID NOs: 34-40 and amino acid sequences that have 1, 2 or 3 amino acid difference(s) with SEQ ID NOs: 34-40; (ii) CDR2 is chosen from the group consisting of SEQ ID NOs: 48-56; and amino acid sequences that have 1, 2 or 3 amino acid difference(s) with SEQ ID NOs: 48-56; and (iii) CDR3 is chosen from the group consisting of SEQ ID NO: 67-75 and amino acid sequences that have 1, 2, 3 or 4 amino acid difference(s) with SEQ ID NOs: 67-75; preferably CDR1 is SEQ ID NO: 35, CDR2 is SEQ ID NO: 50 and CDR3 is SEQ ID NO: 69. Also, the present invention relates also to a polypeptide as described supra, wherein said second ISV is chosen from the group consisting of 238D4 (SEQ ID NO: 4), 281A5 (SEQ ID NO: 5), 281E10 (SEQ ID NO: 6), 281D4 (SEQ ID NO: 7), 281A6 (SEQ ID NO: 8), 281F12 (SEQ ID NO: 9), 283B6 (SEQ ID NO: 10), 283E2 (SEQ ID NO: 11), 283F1 (SEQ ID NO: 12), 15F5 (SEQ ID NO: 13), 15G11 (SEQ ID NO: 14), 15A1 (SEQ ID NO: 15) and 10C3 (SEQ ID NO: 16), preferably in which said second ISV is 281F12 (SEQ ID NO: 9).

Also, the present invention relates to a polypeptide as described herein, wherein said first ISV is chosen from the group consisting of 01B6 (SEQ ID NO: 17), 01E2 (SEQ ID NO: 18), 01H12 (SEQ ID NO: 19) and 03F11 (SEQ ID NO: 20), and wherein said second ISV is chosen from the group consisting of 238D4 (SEQ ID NO: 4), 281A5 (SEQ ID NO: 5), 281E10 (SEQ ID NO: 6), 281D4 (SEQ ID NO: 7), 281A6 (SEQ ID NO: 8), 281F12 (SEQ ID NO: 9), 283B6 (SEQ ID NO: 10), 283E2 (SEQ ID NO: 11), 283F1 (SEQ ID NO: 12), 15F5 (SEQ ID NO: 13), 15G11 (SEQ ID NO: 14), 15A1 (SEQ ID NO: 15) and 10C3 (SEQ ID NO: 16), preferably said polypeptide is chosen from the group consisting of 03F11-9GS-281F12 (SEQ ID NO: 101), 03F11-25GS-281F12 (SEQ ID NO: 102), 03F11-35GS-281F12 (SEQ ID NO: 103), 281F12-9GS-03F11 (SEQ ID NO: 104), 281F12-25GS-03F11 (SEQ ID NO: 105), 281F12-35GS-03F11 (SEQ ID NO: 106), 15G11(Q108L)-15GS-ALB11-15GS-03F11(Q108L) (SEQ ID NO: 107), 15F05(Q108L)-15GS-ALB11-15GS-03F11(Q108L) (SEQ ID NO: 108), and 281F12(Q108L)-15GS-ALB11-15GS-03F11(Q108L) (SEQ ID NO: 109).

In addition, the present invention relates also to a polypeptide as described supra, for use in treating a subject in need thereof (infected with HIV, HIV-1, subtype C). Also, the present invention relates also to a (pharmaceutical) composition comprising the polypeptide as described supra.

The present invention relates also to a method for delivering a prophylactic or therapeutic polypeptide to a specific location, tissue or cell type in the body, the method comprising the steps of administering to a subject a polypeptide as described supra.

The present invention relates also to a method for treating a subject in need thereof comprising administering a polypeptide as described herein, preferably wherein said subject is infected with HIV R5, HIV X4, and/or HIV X4R5.

The present invention relates also to a method for treating a subject infected with HIV, comprising administering a polypeptide as described herein, wherein said HIV infected subject does not develop resistance to said polypeptide for at least 6 months, etc., preferably, in a combination treatment with PR, RTI and/or NRTI.

The present invention relates also to a method for treating a subject infected with HIV, comprising administering a polypeptide as described herein, wherein said subject is resistant against at least one other anti-HIV agent, such as to one or more protease inhibitors (PRs), e.g. amprenavir (AMP), atazanavir (ATV), indinavir (IDV), lopinavir (LPV), nelfinavir (NFV), ritonavir (RTV) or saquinavir (SQV); and/or reverse transcriptase inhibitors (RTIs), e.g. a non-nucleoside reverse transcriptase inhibitor (NNRTI) [abacavir (ABC), delavirdine (DLV), efavirenz (EFV), nevirapine (NVP) and tenofovir (TFV)]; or a nucleoside analogue reverse transcriptase inhibitor (NRTI) [didanosine (ddl), stavudine (d4T), lamivudine (3TC) and zidovudine (ZDV)].

The present invention relates also to a method for lowering the HIV-titer in a subject, the method comprising administering to the subject a therapeutically effective amount of a polypeptide as described herein to lower the HIV-titer in the subject.

The present invention relates also to a method of treating a symptom of acquired immune deficiency syndrome in a human subject infected with HIV that is, or has become, resistant to a non-antibody CD4 and/or CR antagonist, comprising administering to the human subject a polypeptide as described herein in an amount effective to treat the symptom of acquired immune deficiency syndrome in the human subject.

The present invention relates also to a method for preventing HIV infection in a subject, the method comprising administering to the subject a therapeutically effective amount of a polypeptide as described herein to prevent infection of the subject by HIV.

The present invention relates also to a method of inhibiting HIV infection of a susceptible cell in a subject by an HIV virus that is resistant, or has become resistant, to a CD4 antagonist, which comprises subjecting the susceptible cell to an effective HIV infection inhibiting dose of a polypeptide as described herein (which inhibits HIV fusion with CD4+ CXCR4+ cells), preferably wherein the effective HIV infection inhibiting dose comprises from 0.1 mg per kg to 25 mg per kg of the subject's body weight, so as to thereby inhibit the infection of the susceptible cell by HIV1 that is resistant, or has become resistant, to the CD4 antagonist.

The present invention relates also to a polypeptide comprising a first and a second immunoglobulin single variable domain (ISV), wherein said first ISV binds to CD4 present on the surface of a cell; said second ISV binds to CXCR4 present on the surface of said cell; and wherein said first ISV essentially consists of 4 framework regions (FR1 to FR4, respectively) and 3 complementarity determining regions (CDR1 to CDR3, respectively), in which
(i) CDR1 is chosen from the group consisting of SEQ ID NOs: 85, 84, 83 and 82; and amino acid sequences that have 1, 2 or 3 amino acid difference(s) with SEQ ID NOs: 85, 84, 83 and 82;
(ii) CDR2 is chosen from the group consisting of SEQ ID NOs: 91, 90, 89 and 88; and amino acid sequences that have 1, 2 or 3 amino acid difference(s) with SEQ ID NOs: 91, 90, 89 and 88; and
(iii) CDR3 is chosen from the group consisting of SEQ ID NO: 99, 98, 97 and 96; and amino acid sequences that have 1, 2, 3 or 4 amino acid difference(s) with SEQ ID NOs: 99, 98, 97 and 96;
and, wherein said second ISV essentially consists of 4 framework regions (FR1 to FR4, respectively) and 3 complementarity determining regions (CDR1 to CDR3, respectively), in which
(i) CDR1 is chosen from the group consisting of SEQ ID NOs: 35, 34, 36-40; and amino acid sequences that have 1, 2 or 3 amino acid difference(s) with SEQ ID NOs: 35, 34, 36-40;
(ii) CDR2 is chosen from the group consisting of SEQ ID NOs: 50, 48-49 and 51-56; and amino acid sequences that have 1, 2 or 3 amino acid difference(s) with SEQ ID NOs: 50, 48-49 and 51-56; and
(iii) CDR3 is chosen from the group consisting of SEQ ID NO: 69, 67-68, 70-75 and amino acid sequences that have 1, 2, 3 or 4 amino acid difference(s) with SEQ ID NOs: 69, 67-68, 70-75.

The present invention relates also to a polypeptide as described herein, wherein said first ISV is chosen from the group consisting of 03F11 (SEQ ID NO: 20), 01B6 (SEQ ID NO: 17), 01E2 (SEQ ID NO: 18), and 01H12 (SEQ ID NO: 19), and wherein said second ISV is chosen from the group consisting of 281F12 (SEQ ID NO: 9), 238D4 (SEQ ID NO: 4), 281A5 (SEQ ID NO: 5), 281E10 (SEQ ID NO: 6), 281D4 (SEQ ID NO: 7), 281A6 (SEQ ID NO: 8), 283B6 (SEQ ID NO: 10), 283E2 (SEQ ID NO: 11), 283F1 (SEQ ID NO: 12), 15F5 (SEQ ID NO: 13), 15G11 (SEQ ID NO: 14), 15A1 (SEQ ID NO: 15) and 10C3 (SEQ ID NO: 16).

The present invention relates also to a polypeptide as described herein, wherein said polypeptide prevents infection of said HIV for at least 3 months, such as at least 6 months, or even longer such as e.g. 9 m, 11 m, 1 y, 1.5 y, 2 y or even longer.

The present invention relates also to a polypeptide as described herein, wherein said polypeptide inhibits binding of a natural ligand to said CXCR4 by less than about 50%, such as 40%, 30%, or 20% or even less than 10%, such as less than 5%, wherein the natural ligand is Stromal Cell-Derived Factor-1 beta (SDF-1β) or Stromal Cell-Derived Factor-1 alpha (SDF-1α).

The present invention relates also to a polypeptide as described herein, for use in treating and/or preventing HIV infection in a subject. Preferably, said polypeptide prevents HIV infection for at least 3 months, such as at least 6 months, or even longer such as e.g. 9 m, 11 m, 1 y, 1.5 y, 2 y or even longer. The present invention relates also to a polypeptide as described herein, wherein said polypeptide inhibits HIV infection by about 10%, 20%, 30%, 40%, 50%, 60%, 80%, 90% and preferably 95% or more, such as 100%, for instance as measured in a HIV infection assay. The present invention relates also to a polypeptide as described herein, for use in treating and/or preventing HIV infection in a subject, wherein the polypeptide inhibits HIV fusion with CD4+CXCR4+ cells. The present invention relates also to a polypeptide as described herein, for use in treating and/or preventing HIV infection in a subject, wherein said polypeptide inhibits binding of a natural ligand to said CXCR4 by less than about 50%, such as 40%, 30%, or 20% or even less than 10%, such as less than 5%, wherein the natural ligand is Stromal Cell-Derived Factor-1 beta (SDF-1β) or Stromal Cell-Derived Factor-1 alpha (SDF-1α).

BRIEF DESCRIPTION OF THE FIGURES

FIG. 2A: Phage binding to recombinant human CD4 in ELISA. FIG. 2B: Binding to cell-expressed CD4 on Jurkat and THP-1 cells, but not Ba/F3 cells by flow cytometry, using detection of the myc-tag. FIG. 2C: Blockade of CD4-gp120 interaction in competition ELISA for selected CD4 Nanobodies. In FIGS. 2B and 2C anti-hCD4 monoclonal mAb A-1 (Diaclone) was used as positive control. FIG. 2D: Binding of Nanobody 3F11 to human T cells.

FIG. 2.1: Radio-ligand displacement analysis of CXCR4 Nanobodies for binding to human CXCR4. Membrane extracts of Hek293 cells transfected with CXCR4 were incubated with serial dilutions of purified Nanobodies and 75 pM of [$^{125}$I]-CXCL12. Non-specific binding was determined in presence of 100 nM cold SDF-1. Means of 3 experiments are shown.

FIG. 2.2: Binding of the monovalent and bispecific CD4-CXCR4 Nanobodies to CXCR4 on viral lipoparticles (CXCR4-lip) versus empty control lipoparticles (null-lip) in ELISA. Bound Nanobodies were detected with mouse anti-c-myc and rabbit anti-Mouse-HRP antibodies.

FIG. 2.3: Binding affinity analysis of monovalent and bispecific CXCR4-CD4 polypeptides to cell lines that expresses both CXCR4 and CD4, Jurkat E6.1, THP-1 and MOLM-13 cells. Onset shows the relative expression levels of CD4 and CXCR4 on these cell lines, as determined with anti-CD4 mAb A-1 (Diaclone) and anti-CXCR4 mAb 12G5

(R&D systems) control antibodies. Bispecific polypeptides with the 35GS linker were used. Nanobody detection was done via anti-tag antibodies.

FIG. 2.4: Inhibition of SDF-1 mediated chemotaxis of monovalent and CXCR4-CD4 bispecific polypeptides to Jurkat E6.1 and Molm-13 cells. Bispecific polypeptides with the 35GS-linkers are shown.

Figure 3:
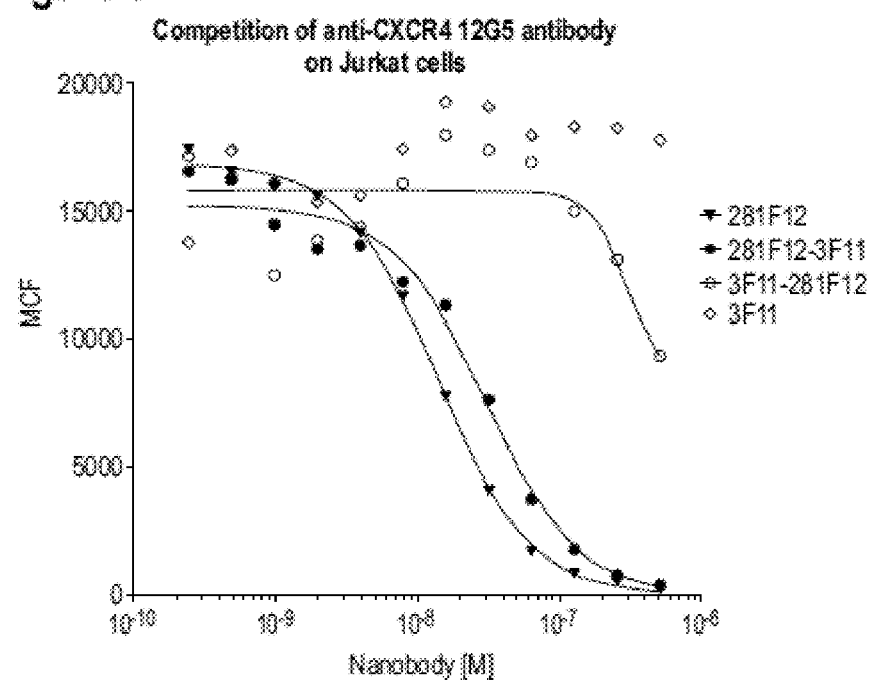
Figure 3:
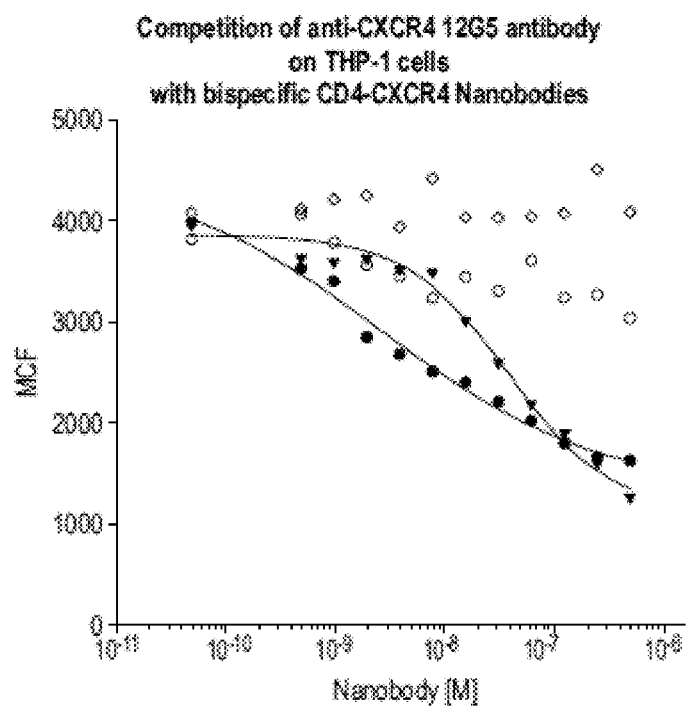

FIG. 3: Inhibition of anti-CXCR4 mAb 12G5 binding by monovalent and CXCR4-CD4 bispecific polypeptides to Jurkat E6.1 cells and THP-1 cells. Bound 12G5 antibody was detected with Goat anti-Mouse-PE (Jackson ImmunoResearch).

Figure 4:
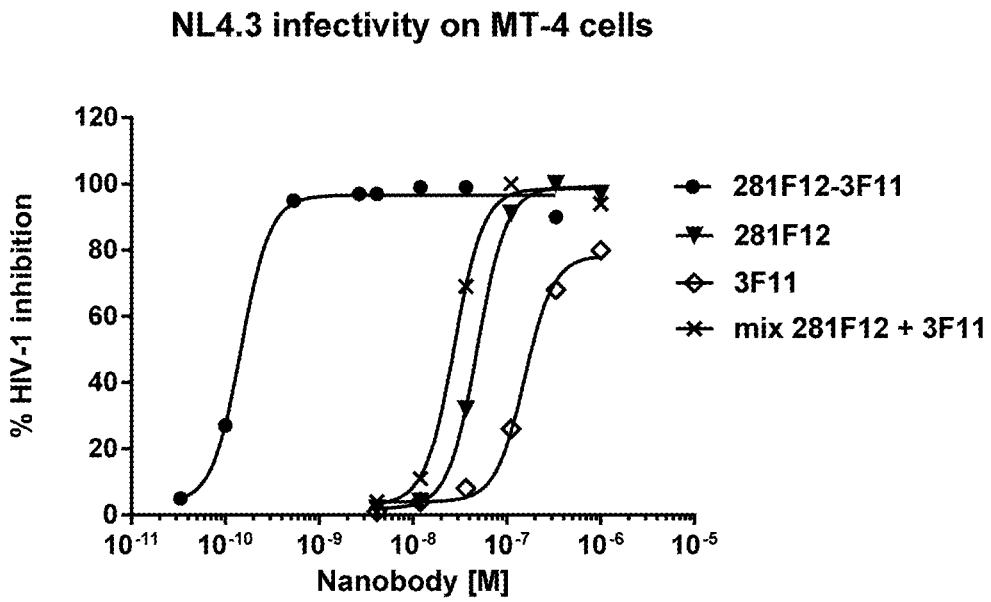

FIG. 4: Dose-dependent inhibition of HIV-1 NL4.3 infectivity in MT-4 cells by bispecific CXCR4-CD4 polypeptides in comparison with a mixture of monovalent Nanobodies. Detection was done with the MTS viability staining method.

Figure 5:
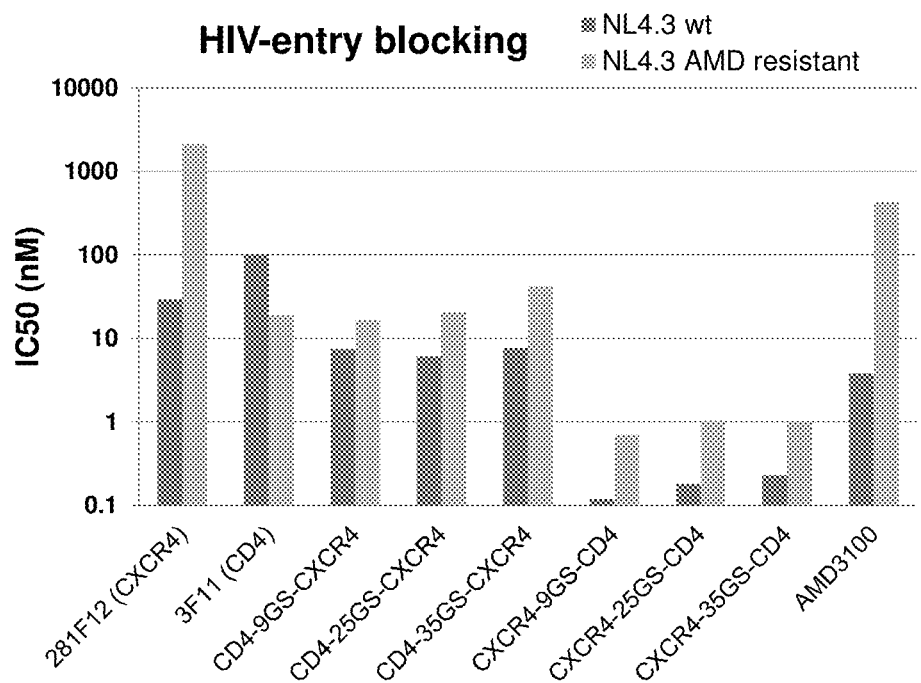

FIG. 5: Inhibition of HIV1 infectivity by CXCR4-CD4 polypeptides with different linker lengths of wild-type NL4.3 and AMD3100-resistant HIV-1 variants in MT-4 cells. AMD-3100 was used as control compound. Average $IC_{50}$ of three experiments is shown.

Figure 6:
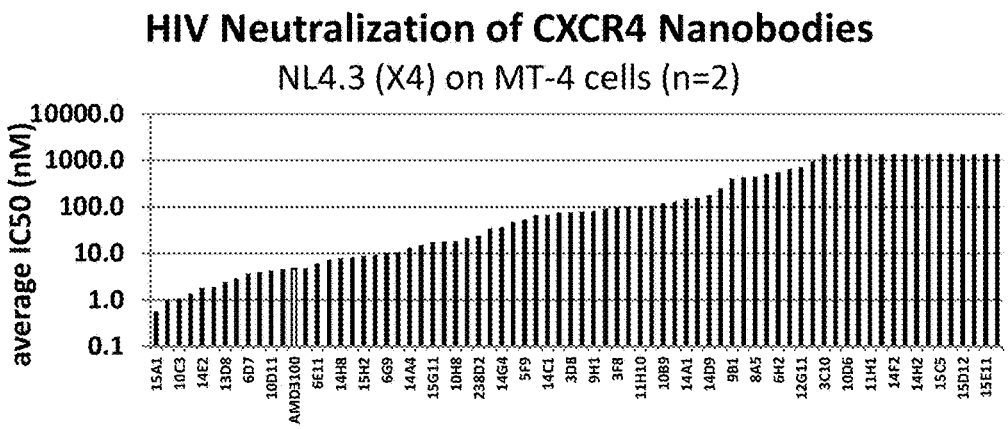

FIG. 6: Ranking of a large panel of CXCR4 Nanobodies for HIV-1 neutralization capacity, assessed on NL4.1 infection in MT-4 cells. AMD-3100 was included as control compound. Average $IC_{50}$ values of two experiments is shown.

Figure 7A:
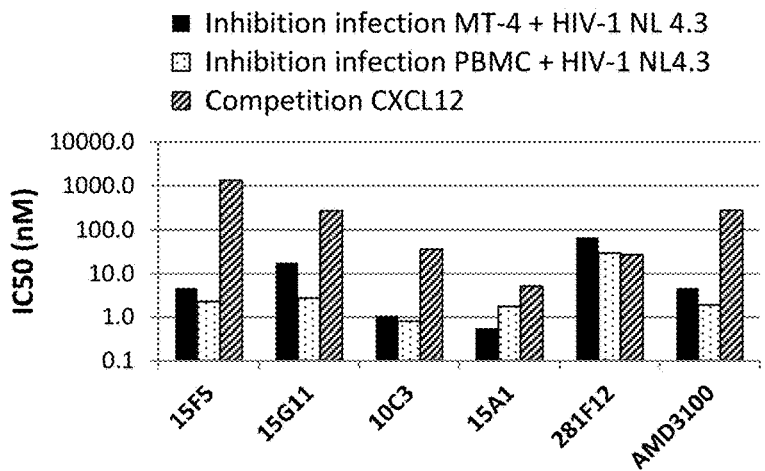
Figure 7B:
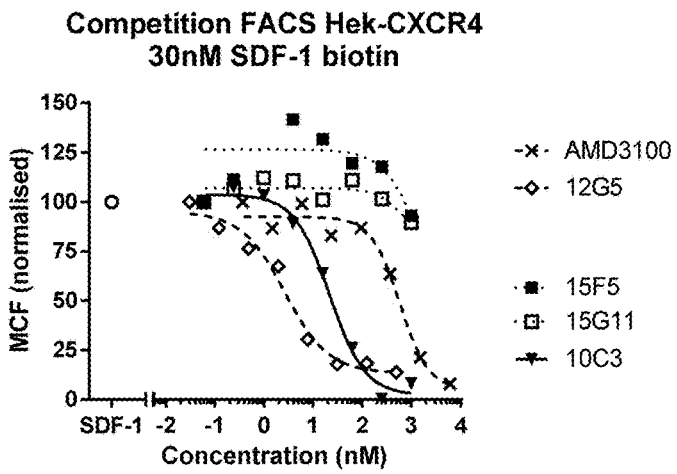

FIGS. 7A-7B: Identification of CXCR4 Nanobodies directed against the gp120 binding site on CXCR4 but not competing with the ligand. FIG. 7A: Comparison of ligand competing and HIV-1 neutralisation affinities of a selection of CXCR4 Nanobodies. CXCR4 Nanobody 281F12 and AMD-3100 are included as references. FIG. 7B: Ligand displacement analysis of selected CXCR4 Nanobodies to CXCR4 expressed on Hek-293 cells. Biotinylated-SDF-1 (30 nM, $EC_{30}$ concentration) was used for detection. AMD-3100 and anti-CXCR4 mAb 12G5 are included as reference compounds.

Figure 8:
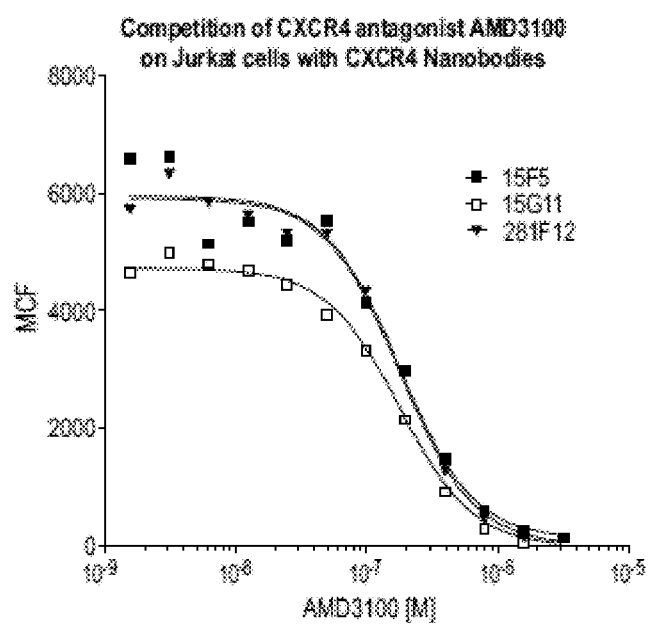
Figure 8:
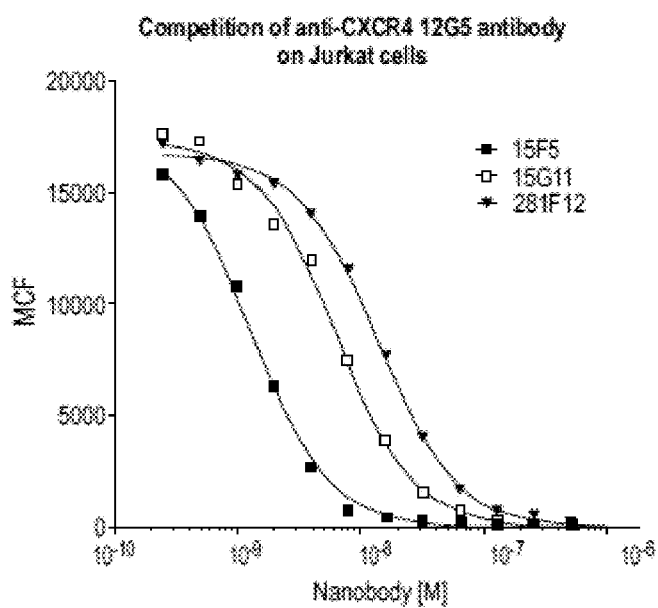

FIG. 8: Inhibition of anti-CXCR4 mAb 12G5 and AMD-3100 binding to CXCR4 by monovalent CXCR4 Nanobodies on Jurkat E6.1 cells by flow cytometry. Bound 12G5 antibody was detected with Goat anti-Mouse-PE (Jackson ImmunoResearch). In case of AMD-3100 competition, Nanobodies were used at the $EC_{30}$ concentrations and competed with increasing concentrations of AMD-3100. Bound Nanobody was detected via anti-myc detection.

Figure 9A:
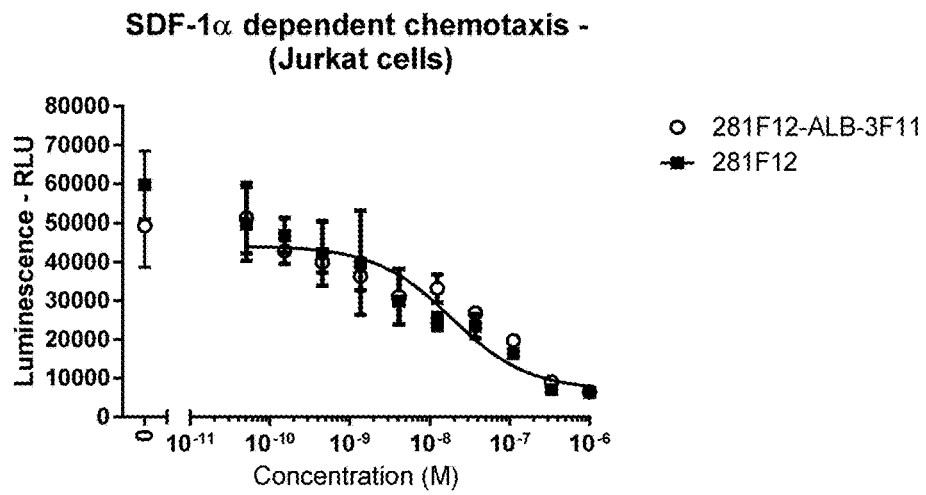
Figure 9B:
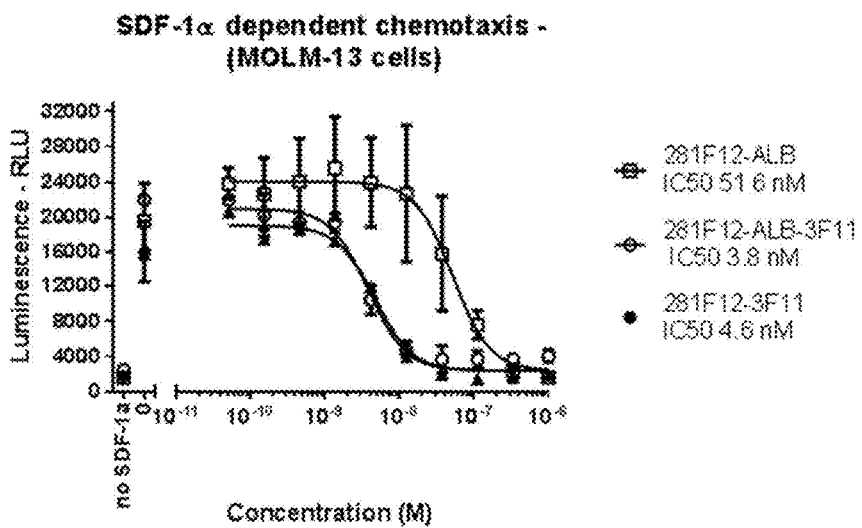

FIGS. 9A-9B: Inhibition of SDF-1 mediated chemotaxis of half-life extended CXCR4-CD4 bispecific polypeptides to Jurkat E6.1 cells (FIG. 9A) and Molm-13 cells (FIG. 9B). Chemotaxis was assessed to 750 pM SDF-1 (Jurkat) or 1 nM SDF-1 (MOLM-13) over three hours.

Figure 10:
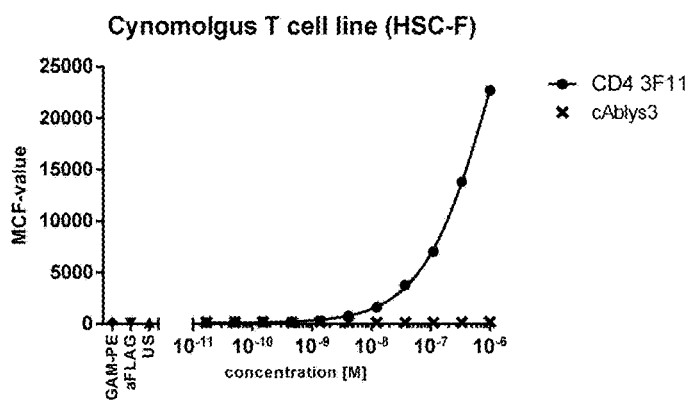

FIG. 10: Binding analysis of monovalent anti-CD4 Nanobody 3F11 to CD4+ cynomolgus HSC-F T cells by flow cytometry. Bound Nanobodies were detected with mouse anti-Flag and Goat anti-Mouse-PE (Jackson ImmunoResearch) antibodies.

DESCRIPTION OF THE INVENTION

The present invention relates to particular polypeptides, also referred to as "polypeptides of the invention" that comprise or essentially consist of (i) a first building block consisting essentially of a first immunoglobulin single variable domain, wherein said first immunoglobulin single variable domain binds a first target, preferably an HIV receptor, such as CD4, on the surface of a cell; and (ii) a second building block consisting essentially of a second immunoglobulin single variable domain, wherein said second immunoglobulin single variable domain binds a second target, preferably an HIV co-receptor (CR), on the surface of a cell, and wherein said CR is not CD4.

a) Unless indicated or defined otherwise, all terms used have their usual meaning in the art, which will be clear to the skilled person. Reference is for example made to the standard handbooks mentioned in paragraph a) on page 46 of WO 08/020079.

b) Unless indicated otherwise, the term "immunoglobulin single variable domain" or "ISV" is used as a general term to include but not limited to antigen-binding domains or fragments such as $V_{HH}$ domains or $V_H$ or $V_L$ domains, respectively. The terms antigen-binding molecules or antigen-binding protein are used interchangeably and include also the term Nanobodies. The immunoglobulin single variable domains can be light chain variable domain sequences (e.g., a $V_L$-sequence), or heavy chain variable domain sequences (e.g., a $V_H$-sequence); more specifically, they can be heavy chain variable domain sequences that are derived from a conventional four-chain antibody or heavy chain variable domain sequences that are derived from a heavy chain antibody. Accordingly, the immunoglobulin single variable domains can be domain antibodies, or immunoglobulin sequences that are suitable for use as domain antibodies, single domain antibodies, or immunoglobulin sequences that are suitable for use as single domain antibodies, "dAbs", or immunoglobulin sequences that are suitable for use as dAbs, or Nanobodies, including but not limited to $V_{HH}$ sequences, as well as humanized $V_{HH}$ sequences and camelized $V_H$ sequences. The invention includes immunoglobulin sequences of different origin, comprising mouse, rat, rabbit, donkey, human and camelid immunoglobulin sequences. The immunoglobulin single variable domain includes fully human, humanized, otherwise sequence optimized or chimeric immunoglobulin sequences. The immunoglobulin single variable domain and structure of an immunoglobulin single variable domain can be considered—without however being limited thereto—to be comprised of four framework regions or "FR's", which are referred to in the art and herein as "Framework region 1" or "FR1"; as "Framework region 2" or "FR2"; as "Framework region 3" or "FR3"; and as "Framework region 4" or "FR4", respectively; which framework regions are interrupted by three complementary determining regions or "CDR's", which are referred to in the art as "Complementarity Determining Region 1" or "CDR1"; as "Complementarity Determining Region 2" or "CDR2"; and as "Complementarity Determining Region 3" or "CDR3", respectively. It is noted that the terms Nanobody or Nanobodies are registered trademarks of Ablynx N.V. and thus may also be referred to as NANOBODY® or NANOBODIES®, respectively.

c) Unless indicated otherwise, the terms "immunoglobulin sequence", "sequence", "nucleotide sequence" and "nucleic acid" are as described in paragraph b) on page 46 of WO 08/020079.

d) Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews Presta, Adv. Drug Deliv. Rev. 2006, 58 (5-6): 640-56; Levin and Weiss, Mol. Biosyst. 2006, 2(1): 49-57; Irving et al., J.

Immunol. Methods, 2001, 248(1-2), 31-45; Schmitz et al., Placenta, 2000, 21 Suppl. A, 5106-12, Gonzales et al., Tumour Biol., 2005, 26(1), 31-43, which describe techniques for protein engineering, such as affinity maturation and other techniques for improving the specificity and other desired properties of proteins such as immunoglobulins.

e) Amino acid residues will be indicated according to the standard three-letter or one-letter amino acid code. Reference is made to Table A-2 on page 48 of the International application WO 08/020079 of Ablynx N.V. entitled "*Immunoglobulin single variable domains directed against IL-6R and polypeptides comprising the same for the treatment of diseases and disorders associated with IL-6 mediated signalling*".

f) For the purposes of comparing two or more nucleotide sequences, the percentage of "sequence identity" between a first nucleotide sequence and a second nucleotide sequence may be calculated or determined as described in paragraph e) on page 49 of WO 08/020079 (incorporated herein by reference), such as by dividing [the number of nucleotides in the first nucleotide sequence that are identical to the nucleotides at the corresponding positions in the second nucleotide sequence] by [the total number of nucleotides in the first nucleotide sequence] and multiplying by [100%], in which each deletion, insertion, substitution or addition of a nucleotide in the second nucleotide sequence—compared to the first nucleotide sequence—is considered as a difference at a single nucleotide (position); or using a suitable computer algorithm or technique, again as described in paragraph e) on pages 49 of WO 08/020079 (incorporated herein by reference).

g) For the purposes of comparing two or more immunoglobulin single variable domains or other amino acid sequences such e.g. the polypeptides of the invention etc., the percentage of "sequence identity" between a first amino acid sequence and a second amino acid sequence (also referred to herein as "amino acid identity") may be calculated or determined as described in paragraph f) on pages 49 and 50 of WO 08/020079 (incorporated herein by reference), such as by dividing [the number of amino acid residues in the first amino acid sequence that are identical to the amino acid residues at the corresponding positions in the second amino acid sequence] by [the total number of amino acid residues in the first amino acid sequence] and multiplying by [100%], in which each deletion, insertion, substitution or addition of an amino acid residue in the second amino acid sequence—compared to the first amino acid sequence—is considered as a difference at a single amino acid residue (position), i.e., as an "amino acid difference" as defined herein; or using a suitable computer algorithm or technique, again as described in paragraph f) on pages 49 and 50 of WO 08/020079 (incorporated herein by reference).

Also, in determining the degree of sequence identity between two immunoglobulin single variable domains, the skilled person may take into account so-called "conservative" amino acid substitutions, as described on page 50 of WO 08/020079.

Any amino acid substitutions applied to the polypeptides described herein may also be based on the analysis of the frequencies of amino acid variations between homologous proteins of different species developed by Schulz et al., Principles of Protein Structure, Springer-Verlag, 1978, on the analyses of structure forming potentials developed by Chou and Fasman, Biochemistry 13: 211, 1974 and Adv. Enzymol., 47: 45-149, 1978, and on the analysis of hydrophobicity patterns in proteins developed by Eisenberg et al., Proc. Natl. Acad. Sci. USA 81: 140-144, 1984; Kyte & Doolittle; J Molec. Biol. 157: 105-132, 198 1, and Goldman et al., Ann. Rev. Biophys. Chem. 15: 321-353, 1986, all incorporated herein in their entirety by reference. Information on the primary, secondary and tertiary structure of Nanobodies is given in the description herein and in the general background art cited above. Also, for this purpose, the crystal structure of a $V_{HH}$ domain from a llama is for example given by Desmyter et al., Nature Structural Biology, Vol. 3, 9, 803 (1996); Spinelli et al., Natural Structural Biology (1996); 3, 752-757; and Decanniere et al., Structure, Vol. 7, 4, 361 (1999). Further information about some of the amino acid residues that in conventional $V_H$ domains form the $V_H/V_L$ interface and potential camelizing substitutions on these positions can be found in the prior art cited above.

h) Immunoglobulin single variable domains and nucleic acid sequences are said to be "exactly the same" if they have 100% sequence identity (as defined herein) over their entire length.

i) When comparing two immunoglobulin single variable domains, the term "amino acid difference" refers to an insertion, deletion or substitution of a single amino acid residue on a position of the first sequence, compared to the second sequence; it being understood that two immunoglobulin single variable domains can contain one, two or more such amino acid differences.

j) When a nucleotide sequence or amino acid sequence is said to "comprise" another nucleotide sequence or amino acid sequence, respectively, or to "essentially consist of" another nucleotide sequence or amino acid sequence, this has the meaning given in paragraph i) on pages 51-52 of WO 08/020079.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

k) The term "in essentially isolated form" has the meaning given to it in paragraph j) on pages 52 and 53 of WO 08/020079.

l) The terms "domain" and "binding domain" have the meanings given to it in paragraph k) on page 53 of WO 08/020079.

m) The terms "antigenic determinant" and "epitope", which may also be used interchangeably herein, have the meanings given to it in paragraph l) on page 53 of WO 08/020079.

n) As further described in paragraph m) on page 53 of WO 08/020079, an amino acid sequence (such as an antibody, a polypeptide of the invention, or generally an antigen binding protein or polypeptide or a fragment thereof) that can (specifically) bind to, that has affinity for and/or that has specificity for a specific antigenic determinant, epitope, antigen or protein (or for at least one part, fragment or epitope thereof) is said to be "against" or "directed against" said antigenic determinant, epitope, antigen or protein.

o) The term "specificity" refers to the number of different types of antigens or antigenic determinants to which a particular antigen-binding molecule or antigen-binding protein (such as an ISV, such as e.g. a Nanobody, or a polypeptide of the invention) molecule can bind. The specificity of an antigen-binding protein can be determined based on affinity and/or avidity.

The affinity, represented by the equilibrium constant for the dissociation of an antigen with an antigen-binding protein ($K_D$ or KD), is a measure for the binding strength between an antigenic determinant, i.e. the target, and an antigen-binding site on the antigen-binding protein, i.e. the ISV or Nanobody: the lesser the value of the $K_D$, the stronger the binding strength between an antigenic determinant and the antigen-binding molecule (alternatively, the affinity can also be expressed as the affinity constant ($K_A$), which is $1/K_D$). As will be clear to the skilled person (for example on the basis of the further disclosure herein), affinity can be determined in a manner known per se, depending on the specific antigen of interest.

Avidity is the affinity of the polypeptide, i.e. the ligand is able to bind via two (or more) pharmacophores (ISV) in which the multiple interactions synergize to enhance the "apparent" affinity. Avidity is the measure of the strength of binding between the polypeptide of the invention and the pertinent antigens. The polypeptide of the invention is able to bind via its two (or more) building blocks, such as ISVs or Nanobodies, to the at least two targets, in which the multiple interactions, e.g. the first building block, ISV or Nanobody binding to the first target and the second building block, ISV, or Nanobody binding to the second target, synergize to enhance the "apparent" affinity. Avidity is related to both the affinity between an antigenic determinant and its antigen binding site on the antigen-binding molecule and the number of pertinent binding sites present on the antigen-binding molecules. For example, and without limitation, polypeptides that contain two or more building blocks, such as ISVs or Nanobodies directed against different targets on a cell and in particular against human CXCR4 and human CD4 may (and usually will) bind with higher avidity than each of the individual monomers or individual building blocks, such as, for instance, the monovalent ISVs or Nanobodies, comprised in the polypeptides of the invention.

In the present invention, monovalent antigen-binding proteins (such as the building blocks, ISVs, amino acid sequences, Nanobodies and/or polypeptides of the invention) are said to bind to their antigen with a high affinity when the dissociation constant ($K_D$) is $10^{0.9}$ to $10^{-12}$ moles/liter or less, and preferably $10^{-10}$ to $10^{-12}$ moles/liter or less and more preferably $10^{-11}$ to $10^{-12}$ moles/liter (i.e. with an association constant ($K_A$) of $10^9$ to $10^{12}$ liter/moles or more, and preferably $10^{10}$ to $10^{12}$ liter/moles or more and more preferably $10^{11}$ to $10^{12}$ liter/moles).

In the present invention, monovalent antigen-binding proteins (such as the building blocks, ISVs, amino acid sequences, Nanobodies and/or polypeptides of the invention) are said to bind to their antigen with a low affinity when the dissociation constant ($K_D$) is $10^{-6}$ to $10^{-9}$ moles/liter or more, and preferably $10^{-6}$ to $10^{-8}$ moles/liter or more and more preferably $10^{-6}$ to $10^{-7}$ moles/liter (i.e. with an association constant ($K_A$) of $10^6$ to $10^9$ liter/moles or more, and preferably $10^6$ to $10^8$ liter/moles or more and more preferably $10^6$ to $10^7$ liter/moles).

A medium affinity can be defined as values ranging in between high-low, e.g. $10^{-10}$ to $10^{-8}$ moles/liter.

Any $K_D$ value greater than $10^{-4}$ mol/liter (or any $K_A$ value lower than $10^4$ liter/mol) is generally considered to indicate non-specific binding.

The polypeptides of the invention comprise a first and a second building block, e.g. a first and a second ISV, or a first and a second Nanobody. Preferably the affinity of each building block, e.g. ISV or Nanobody, is determined individually. In other words, the affinity is determined for the monovalent building block, ISV or Nanobody, independent of avidity effects due to the other building block, ISV or Nanobody, which might or might not be present. The affinity for a monovalent building block, ISV or Nanobody can be determined on the monovalent building block, ISV or Nanobody per se, i.e. when said monovalent building block, ISV or Nanobody is not comprised in the polypeptide of the invention. In the alternative or in addition, the affinity for a monovalent building block, ISV or Nanobody can be determined on one target while the other target is absent.

The binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as the other techniques mentioned herein.

The dissociation constant may be the actual or apparent dissociation constant, as will be clear to the skilled person. Methods for determining the dissociation constant will be clear to the skilled person, and for example include the techniques mentioned herein. In this respect, it will also be clear that it may not be possible to measure dissociation constants of more than $10^{-4}$ moles/liter or $10^{-3}$ moles/liter (e.g., of $10^{-2}$ moles/liter). Optionally, as will also be clear to the skilled person, the (actual or apparent) dissociation constant may be calculated on the basis of the (actual or apparent) association constant ($K_A$), by means of the relationship [$K_D=1/K_A$].

The affinity denotes the strength or stability of a molecular interaction. The affinity is commonly given as by the $K_D$, or dissociation constant, which has units of mol/liter (or M). The affinity can also be expressed as an association constant, $K_A$, which equals $1/K_D$ and has units of (mol/liter)$^{-1}$ (or M-1). In the present specification, the stability of the interaction between two molecules (such as an amino acid sequence, ISV, such as e.g. a Nanobody, or polypeptide of the invention and its intended target) will mainly be expressed in terms of the $K_D$ value of their interaction; it being clear to the skilled person that in view of the relation $K_A=1/K_D$, specifying the strength of molecular interaction by its $K_D$ value can also be used to calculate the corresponding $K_A$ value. The $K_D$-value characterizes the strength of a molecular interaction also in a thermodynamic sense as it is related to the free energy (DG) of binding by the well-known relation DG=RT·ln($K_D$) (equivalently DG=−RT·ln($K_A$)), where R equals the gas constant, T equals the absolute temperature and ln denotes the natural logarithm.

The $K_D$ for biological interactions which are considered meaningful (e.g. specific) are typically in the range of $10^{-10}$M (0.1 nM) to $10^{-5}$M (10000 nM). The stronger an interaction is, the lower is its $K_D$.

The $K_D$ can also be expressed as the ratio of the dissociation rate constant of a complex, denoted as $k_{off}$, to the rate of its association, denoted $k_{on}$ (so that $K_D=k_{off}/k_{on}$ and $K_A=k_{on}/k_{off}$). The off-rate $k_{off}$ has units s$^{-1}$ (where s is the SI unit notation of second). The on-rate $k_{on}$ has units M$^{-1}$s$^{-1}$. The on-rate may vary between $10^2$ M$^{-1}$s$^{-1}$ to about $10^7$ M$^{-1}$s$^{-1}$, approaching the diffusion-limited association rate constant for bimolecular interactions. The off-rate is related to the half-life of a given molecular interaction by the relation $t_{1/2}=\ln(2)/k_{off}$. The off-rate may vary between $10^{-6}$s$^{-1}$ (near irreversible complex with a $t_{1/2}$ of multiple days) to 1s$^{-1}$ ($t_{1/2}=0.69$s).

The affinity of a molecular interaction between two molecules can be measured via different techniques known per se, such as the well-known surface plasmon resonance (SPR) biosensor technique (see for example Ober et al., Intern. Immunology, 13, 1551-1559, 2001). The term "surface plasmon resonance", as used herein, refers to an optical phenomenon that allows for the analysis of real-time biospecific interactions by detection of alterations in protein concentrations within a biosensor matrix, where one molecule is immobilized on the biosensor chip and the other molecule is passed over the immobilized molecule under flow conditions yielding $k_{on}$, $k_{off}$ measurements and hence $K_D$ (or $K_A$) values. This can for example be performed using the well-known BIACORE® system (BIAcore International AB, a GE Healthcare company, Uppsala, Sweden and Piscataway, N.J.). For further descriptions, see Jonsson, U., et al. (1993) Ann. Biol. Clin. 51:19-26; Jonsson, U., et al. (1991) Biotechniques 11:620-627; Johnsson, B., et al. (1995) J Mol. Recognit. 8: 125-131; and Johnnson, B., et al. (1991) Anal. Biochem. 198:268-277.

It will also be clear to the skilled person that the measured $K_D$ may correspond to the apparent $K_D$ if the measuring process somehow influences the intrinsic binding affinity of the implied molecules for example by artefacts related to the coating on the biosensor of one molecule. Also, an apparent $K_D$ may be measured if one molecule contains more than one recognition site for the other molecule. In such situation the measured affinity may be affected by the avidity of the interaction by the two molecules.

Another approach that may be used to assess affinity is the 2-step ELISA (Enzyme-Linked Immunosorbent Assay) procedure of Friguet et al. (J. Immunol. Methods, 77, 305-19, 1985). This method establishes a solution phase binding equilibrium measurement and avoids possible artefacts relating to adsorption of one of the molecules on a support such as plastic.

However, the accurate measurement of $K_D$ may be quite labour-intensive and as consequence, often apparent $K_D$ values are determined to assess the binding strength of two molecules. It should be noted that as long all measurements are made in a consistent way (e.g. keeping the assay conditions unchanged) apparent $K_D$ measurements can be used as an approximation of the true $K_D$ and hence in the present document $K_D$ and apparent $K_D$ should be treated with equal importance or relevance.

Finally, it should be noted that in many situations the experienced scientist may judge it to be convenient to determine the binding affinity relative to some reference molecule. For example, to assess the binding strength between molecules A and B, one may e.g. use a reference molecule C that is known to bind to B and that is suitably labelled with a fluorophore or chromophore group or other chemical moiety, such as biotin for easy detection in an ELISA or FACS (Fluorescent activated cell sorting) or other format (the fluorophore for fluorescence detection, the chromophore for light absorption detection, the biotin for streptavidin-mediated ELISA detection). Typically, the reference molecule C is kept at a fixed concentration and the concentration of A is varied for a given concentration or amount of B. As a result an $IC_{50}$ value is obtained corresponding to the concentration of A at which the signal measured for C in absence of A is halved. Provided $K_{D\ ref}$, the $K_D$ of the reference molecule, is known, as well as the total concentration $c_{ref}$ of the reference molecule, the apparent $K_D$ for the interaction A-B can be obtained from following formula: $K_D = IC_{50}/(1+c_{ref}/K_{D\ ref})$. Note that if $c_{ref} \ll K_{D\ ref}$, $K_D = IC_{50}$. Provided the measurement of the $IC_{50}$ is performed in a consistent way (e.g. keeping $c_{ref}$ fixed) for the binders that are compared, the strength or stability of a molecular interaction can be assessed by the $IC_{50}$ and this measurement is judged as equivalent to $K_D$ or to apparent $K_D$ throughout this text.

p) The half-life of an amino acid sequence, compound or polypeptide of the invention can generally be defined as described in paragraph o) on page 57 of WO 08/020079 and as mentioned therein refers to the time taken for the serum concentration of the amino acid sequence, compound or polypeptide to be reduced by 50%, in vivo, for example due to degradation of the sequence or compound and/or clearance or sequestration of the sequence or compound by natural mechanisms. The in vivo half-life of an amino acid sequence, compound or polypeptide of the invention can be determined in any manner known per se, such as by pharmacokinetic analysis. Suitable techniques will be clear to the person skilled in the art, and may for example generally be as described in paragraph o) on page 57 of WO 08/020079. As also mentioned in paragraph o) on page 57 of WO 08/020079, the half-life can be expressed using parameters such as the t1/2-alpha, t1/2-beta and the area under the curve (AUC). Reference is for example made to the Experimental Part below, as well as to the standard handbooks, such as Kenneth, A et al: Chemical Stability of Pharmaceuticals: A Handbook for Pharmacists and Peters et al, Pharmacokinete analysis: A Practical Approach (1996). Reference is also made to "Pharmacokinetics", M Gibaldi & D Perron, published by Marcel Dekker, 2nd Rev. edition (1982). The terms "increase in half-life" or "increased half-life" as also as defined in paragraph o) on page 57 of WO 08/020079 and in particular refer to an increase in the t1/2-beta, either with or without an increase in the t1/2-alpha and/or the AUC or both.

q) In respect of a target or antigen, the term "interaction site" on the target or antigen means a site, epitope, antigenic determinant, part, domain or stretch of amino acid residues on the target or antigen that is a site for binding to a ligand, receptor or other binding partner, a catalytic site, a cleavage site, a site for allosteric interaction, a site involved in multimerisation (such as homomerization or heterodimerization) of the target or antigen; or any other site, epitope, antigenic determinant, part, domain or stretch of amino acid residues on the target or antigen that is involved in a biological action or mechanism of the target or antigen. More generally, an "interaction site" can be any site, epitope, antigenic determinant, part, domain or stretch of amino acid residues on the target or antigen to which an amino acid sequence or polypeptide of the invention can bind such that the target or antigen (and/or any pathway, interaction, signalling, biological mechanism or biological effect in which the target or antigen is involved) is modulated (as defined herein).

r) An immunoglobulin single variable domain or polypeptide is said to be "specific for" a first target or antigen compared to a second target or antigen when it binds to the first antigen with an affinity/avidity (as described above, and suitably expressed as a $K_D$ value, $K_A$ value, $K_{off}$ rate and/or $K_{on}$ rate) that is at least 10 times, such as at least 100 times, and preferably at least 1000 times, and up to 10000 times or more better than the affinity with which said amino acid sequence or polypeptide binds to the second target or polypeptide. For example, the first antigen may bind to the target or antigen with a $K_D$ value that is at least 10 times less, such as at least 100 times less, and preferably at least 1000 times less, such as 10000 times less or even less than that, than the $K_D$ with which said amino acid sequence or polypeptide binds to the second target or polypeptide. Preferably, when an immunoglobulin single variable domain or polypeptide is "specific for" a first target or antigen compared to a second target or antigen, it is directed against (as defined herein) said first target or antigen, but not directed against said second target or antigen.

s) The terms "cross-block", "cross-blocked" and "cross-blocking" are used interchangeably herein to mean the ability of an immunoglobulin single variable domain or polypeptide to interfere with the binding of the natural ligand to its receptor(s). The extent to which an immunoglobulin single variable domain or polypeptide of the invention is able to interfere with the binding of another compound such as the natural ligand to its target, e.g., CXCR4, and therefore whether it can be said to cross-block according to the invention, can be determined using competition binding assays. One particularly suitable quantitative cross-blocking assay uses a FACS- or an ELISA-based approach or ALPHASCREEN® to measure competition between the labelled (e.g., His tagged or biotinylated) immunoglobulin single variable domain or polypeptide according to the invention and the other binding agent in terms of their binding to the target. The experimental part generally describes suitable FACS-, ELISA- or ALPHASCREEN®-displacement-based assays for determining whether a binding molecule cross-blocks or is capable of cross-blocking an immunoglobulin single variable domain or polypeptide according to the invention. It will be appreciated that the assay can be used with any of the immunoglobulin single variable domains or other binding agents described herein. Thus, in general, a cross-blocking amino acid sequence or other binding agent according to the invention is for example one which will bind to the target in the above cross-blocking assay such that, during the assay and in the presence of a second amino acid sequence or other binding agent of the invention, the recorded displacement of the immunoglobulin single variable domain or polypeptide according to the invention is between 60% and 100% (e.g., in ELISA/ALPHASCREEN® based competition assay) or between 80% to 100% (e.g., in FACS based competition assay) of the maximum theoretical displacement (e.g. displacement by cold (e.g., unlabeled) immunoglobulin single variable domain or polypeptide that needs to be cross-blocked) by the to be tested potentially cross-blocking agent that is present in an amount of 0.01 mM or less (cross-blocking agent may be another conventional monoclonal antibody such as IgG, classic monovalent antibody fragments (Fab, scFv)) and engineered variants (e.g., diabodies, triabodies, minibodies, VHHs, dAbs, VHs, VLs).

t) An amino acid sequence such as e.g. an immunoglobulin single variable domain or polypeptide according to the invention is said to be a "VHH1 type immunoglobulin single variable domain" or "VHH type 1 sequence", if said VHH1 type immunoglobulin single variable domain or VHH type 1 sequence has 85% identity (using the VHH1 consensus sequence as the query sequence and use the blast algorithm with standard setting, i.e., blosom62 scoring matrix) to the VHH1 consensus sequence (QVQLVESGGGLVQPGGSLRLS-CAASGFTLDYYAIGWFRQAPGKEREGVSCISSS-DGSTYYADSVKGRFTISRD-NAKNTVYLQMNSLKPEDTAVYYCAA), and mandatorily has a cysteine in position 50, i.e., C50 (using Kabat numbering).

u) An amino acid sequence such as e.g., an immunoglobulin single variable domain or polypeptide according to the invention is said to be "cross-reactive" for two different antigens or antigenic determinants (such as serum albumin from two different species of mammal, such as human serum albumin and cynomolgus monkey serum albumin) if it is specific for (as defined herein) both these different antigens or antigenic determinants.

v) As further described in paragraph q) on pages 58 and 59 of WO 08/020079 (incorporated herein by reference), the amino acid residues of an immunoglobulin single variable domain are numbered according to the general numbering for $V_H$ domains given by Kabat et al. ("Sequence of proteins of immunological interest", US Public Health Services, NIH Bethesda, Md., Publication No. 91), as applied to $V_{HH}$ domains from Camelids in the article of Riechmann and Muyldermans, J. Immunol. Methods 2000 Jun. 23; 240 (1-2): 185-195 (see for example FIG. 2 of this publication), and accordingly FR1 of an immunoglobulin single variable domain comprises the amino acid residues at positions 1-30, CDR1 of an immunoglobulin single variable domain comprises the amino acid residues at positions 31-35, FR2 of an immunoglobulin single variable domain comprises the amino acids at positions 36-49, CDR2 of an immunoglobulin single variable domain comprises the amino acid residues at positions 50-65, FR3 of an immunoglobulin single variable domain comprises the amino acid residues at positions 66-94, CDR3 of an immunoglobulin single variable domain comprises the amino acid residues at positions 95-102, and FR4 of an immunoglobulin single variable domain comprises the amino acid residues at positions 103-113.

w) The Figures, Sequence Listing and the Experimental Part/Examples are only given to further illustrate the invention and should not be interpreted or construed as limiting the scope of the invention and/or of the appended claims in any way, unless explicitly indicated otherwise herein.

x) The half maximal inhibitory concentration ($IC_{50}$) is a measure of the effectiveness of a compound in inhibiting a biological or biochemical function, e.g. a pharmacological effect. This quantitative measure indicates how much of the ISV or Nanobody (inhibitor) is needed to inhibit a given biological process (or component of a process, i.e. an enzyme, cell, cell receptor, chemotaxis, HIV entry, HIV replication, HIV reverse transcriptase activity, etc.) by half. In other words, it is the half maximal (50%) inhibitory concentration (IC) of a substance (50% IC, or $IC_{50}$). The $IC_{50}$ of a drug can be determined by constructing a dose-response curve and examining the effect of different concentrations of antagonist such as the ISV or Nanobody of the invention on reversing agonist activity. $IC_{50}$ values can be calculated for a given antagonist such as the ISV or Nanobody of the invention by determining the concentration needed to inhibit half of the maximum biological response of the agonist.

The term half maximal effective concentration ($EC_{50}$) refers to the concentration of a compound which induces a response halfway between the baseline and maximum after a specified exposure time. In the present context it is used as a measure of a polypeptide's, ISV's or Nanobody's potency. The $EC_{50}$ of a graded dose response curve represents the concentration of a compound where 50% of its maximal effect is observed. Concentration is preferably expressed in molar units.

In biological systems, small changes in ligand concentration typically result in rapid changes in response, following a sigmoidal function. The inflection point at which the increase in response with increasing ligand concentration begins to slow is the $EC_{50}$. This can be determined mathematically by derivation of the best-fit line. Relying on a graph for estimation is convenient in most cases. In case the $EC_{50}$ is provided in the experimental section, the experiments were designed to reflect the KD as accurate as possible. In other words, the $EC_{50}$ values may then be considered as KD values. The term "average KD" relates to the average KD value obtained in at least 1, but preferably more than 1, such as at least 2 experiments. The term "average" refers to the mathematical term "average" (sums of data divided by the number of items in the data).

It is also related to $IC_{50}$ which is a measure of a compound's inhibition (50% inhibition). For competition binding assays and functional antagonist assays $IC_{50}$ is the most common summary measure of the dose-response curve. For agonist/stimulator assays the most common summary measure is the $EC_{50}$.

The synergistic inhibition of HIV infection by different classes of small molecule inhibitors is known. In general these inhibitors are directed against virus derived components, but less to the cellular host components involved in HIV infection, such as the human receptor (CD4) and co-receptor(s). The present inventors demonstrated that binding by a bispecific polypeptide directed against a co-receptor (CR) and the receptor CD4 resulted in a synergy of the two binding moieties in inhibiting HIV infection (see Example 4). Surprisingly, the bispecific polypeptides were exceptionally more effective than a combination of the two individual moieties (see Example 8).

The present invention relates to particular polypeptides, also referred to as "polypeptides of the invention", "bispecific polypeptides", "bispecific constructs" or "bispecific Nanobody constructs" that comprise or essentially consist of (i) a first building block consisting essentially of a first immunoglobulin single variable domain, wherein said first immunoglobulin single variable domain binds a first target, an HIV receptor, such as CD4, on the surface of a cell; and (ii) a second building block consisting essentially of a second immunoglobulin single variable domain, wherein said second immunoglobulin single variable domain binds a second target, preferably an HIV co-receptor, on the surface of a cell, and wherein said CR is not CD4.

"Synergy" between two or more agents refers to the combined effect of the agents which is greater than their additive effects. Illustratively, agents may be peptides, proteins, such as antibodies, small molecules, organic compounds, and drug forms thereof. Synergistic, additive or antagonistic effects between agents may be quantified by analysis of the dose-response curves using the Combination Index (CI) method. A CI value greater than 1 indicates antagonism; a CI value equal to 1 indicates an additive effect; and a CI value less than 1 indicates a synergistic effect. In one embodiment, the CI value of a synergistic interaction is less than 0.9. In another embodiment, the CI value is less than 0.8. In a preferred embodiment, the CI value is less than 0.7 (cf. Example 4 and Chou and Talalay, 1984, which is incorporated herein by reference). The term antagonist is well known in the art. In essence, the term antagonist relates to a substance that acts against and blocks an action. For instance, antagonists have affinity but no efficacy for their cognate receptors, and binding will disrupt the interaction and inhibit the function of an agonist or inverse agonist at receptors.

"HIV" refers to the human immunodeficiency virus. HIV shall include, without limitation, HIV-1 and HIV-2. HIV-1 includes but is not limited to extracellular virus particles and the forms of HIV-1 associated with HIV-1 infected cells. The human immunodeficiency virus (HIV) may be either of the two known types of HIV (HIV-1 or HIV-2). The HIV-1 virus may represent any of the known major subtypes (classes A, B, C, D, E, F, G, H, or J), outlying subtype (Group 0), or an as yet to be determined subtype of HIV-1. HIV-1 JRFL is a strain that was originally isolated at autopsy from the brain tissue of an AIDS patient. The virus has been cloned and the DNA sequences of its envelope glycoproteins are known (GenBank Accession No. U63632). In terms of sensitivity to inhibitors of viral entry, HIV-1 JFRL is known to be highly representative of primary HIV-1 isolates. "JRCSF" refers to a HIV-1 isolate of subtype B. JRCSF is a strain originally isolated from cerebral spinal fluid and brain tissue of an AIDS patient (Science 236, 819-822, 1987). The virus has been cloned and its genome DNA sequence is known (GenBank Accession No. M38429). Unlike HIV isolate JRFL, JRCSF does not productively infect macrophages. The CXCR4-using (X4) HIV-1 clone NL4.3 was obtained from the National Institutes of Health NIAID AIDS Reagent program (Bethesda, Md.). The CCR5-using (R5) HIV-1 strain BaL was obtained from the Medical Research Council AIDS reagent project (Herts, UK). The dual-tropic (R5/X4) HIV-1 HE strain was initially isolated from a patient at the University Hospital in Leuven.

The polypeptides of the invention are designed to inhibit HIV infection.

The term "HIV infection" refers to the entry of HIV into a susceptible cell. Infection of cells by human immunodeficiency virus type 1 (HIV-1) is mediated by the viral envelope (Env) glycoproteins gp120 and gp41, which are expressed as a non-covalent, oligomeric complex on the surface of virus and virally infected cells. Entry of the virus into target cells proceeds through a cascade of events at the cell surface that include (1) high-affinity interaction between the HIV surface glycoprotein gp120 to the cell surface receptor CD4, (2) Env binding to fusion co-receptors, and (3) conformational changes in the viral transmembrane glycoprotein gp41, which mediates fusion of the viral and cellular membranes.

In essence, inhibiting HIV infection relates to inhibiting at least one function in the HIV life cycle, preferably more than one function. These functions include, for instance, binding of HIV to the receptor CD4, binding of HIV to the co-receptor, entry of HIV into a target cell, replication of HIV, HIV reverse transcriptase activity, HIV-induced cell death, and/or HIV-induced cell-cell syncytia formation. Preferably, the transmission of HIV is inhibited. Inhibition of HIV infection can be measured by various methods, both in vitro and in vivo. Preferably, inhibiting HIV infection results in reducing the viral load or the maintenance of a reduced viral load and preferably by ameliorating the medical condition of the HIV infected subject. The term "viral load" refers to the amount of HIV particles in a sample of blood, generally indicated as the number of copies per ml blood. For instance, a viral load of more than 100,000 copies/ml would be considered high, while a viral load of less than 10,000 copies/ml would be considered low. Preferably, the viral load is reduced to undetectable levels (<50 copies per ml).

Inhibition, as used herein, includes both complete and partial inhibition. Thus, the disclosure embraces polypeptides comprising two or more immunoglobulin single variable domains that inhibit binding of HIV to CD4 and/or a co-receptor, such as e.g. CXCR4, by more than 1%, more than 2%, more than 5%, more than 10%, more than 20%, more than 30%, more than 40%, more than 50%, more than 60%, more than 70%, more than 80%, more than 90%, or up to 100% inhibition.

The present invention thus relates to a polypeptide as described herein, wherein said polypeptide inhibits HIV infection by about 10%, 20%, 30%, 40%, 50%, 60%, 80%, 90% and preferably 95% or more, such as 100% (as measured in a HIV infection assay).

It should be appreciated that inhibition can also be expressed in $IC_{50}$ (Inhibitory Concentration), defined as the inhibitory concentration at which 50% of HIV is inhibited from binding to a receptor or co-receptor, such as e.g. CXCR4. In some embodiments, the $IC_{50}$ of inhibition of HIV binding to CD4 or a co-receptor such as e.g. CXCR4 by a polypeptide comprising two or more immunoglobulin single variable domains is lower than 500 µM, lower than 100 µM, lower than 50 µM, lower than 10 µM, lower than 50 µM, lower than 1 µM, lower than 500 nM, lower than 100 nM, lower than 90 nM, lower than 80 nM, lower than 70 nM, lower than 60 nM, lower than 50 nM, lower than 40 nM, lower than 30 nM, lower than 20 nM, lower than 10 nM, lower than 9 nM, lower than 8 nM, lower than 7 nM, lower than 6 nM, lower than 5 nM, lower than 4 nM, lower than 3 nM, lower than 2 nM, lower than 1 nM, lower than 100 pM, lower than 50 pM, lower than 10 pM, lower than 5 pM, 4, 3, 2, 1, 0.5 pM, or even less such as less than 0.4 pM.

In some embodiments, the $IC_{50}$ of inhibition of HIV binding to CD4 and/or a co-receptor such as e.g. CXCR4 by the polypeptide of the invention is lower than 50 nM. In some embodiments, the $IC_{50}$ of inhibition of HIV binding to CD4 and/or a co-receptor such as e.g. CXCR4 by the polypeptide of the invention is lower than 1 nM. In some embodiments, the $IC_{50}$ of inhibition of HIV binding to CD4 and/or a co-receptor such as e.g. CXCR4 by the polypeptide of the invention is lower than 10 pM.

Similarly, inhibition can also be expressed by $EC_{50}$ (cf. supra). Accordingly, the present invention relates to a polypeptide as described herein, wherein the average $EC_{50}$ value of HIV inhibition is of between 10 nM and 0.1 pM, such as at an average $EC_{50}$ value of 10 nM or less, even more preferably at an average $EC_{50}$ value of 9 nM or less, such as less than 8, 7, 6, 5, 4, 3, 2, 1, 0.5 nM or even less, such as less than 400, 300, 200, 100, 50, 40, 30, 20, 10, 9, 8, 7, 6, 5, 4, 3, 2, 1, 0.5 pM, or even less such as less than 0.4 pM.

In one aspect, the disclosure provides polypeptides comprising two or more immunoglobulin single variable domains that inhibit binding of HIV to CD4 and/or a co-receptor such as e.g. CXCR4.

Accordingly, the present invention relates to polypeptides as described herein, wherein said polypeptides inhibit HIV fusion with CD4$^+$CXCR4$^+$ cells.

The efficacy of an anti-HIV compound in inhibiting HIV infection can be measured by various methods, ubiquitously known to the person skilled in the art. For instance, cell-based anti-viral assays can be performed with either transformed T-cell lines (SupT1, H9, Molt4), primary blood-derived mononuclear cells (PBMCs) or macrophages. Experimental readout of HIV replication can be performed by ELISA of p24 viral antigen, monitoring reverse transcriptase, tat-expression, monitoring reporter virus or by intracellular or surface staining of viral antigens (e.g. Gag protein or Env, respectively). Single-cycle infectivity assays using a variety of stable reporter cell lines expressing HIV receptor and co-receptors can be used to evaluate infectivity of HIV or HIV-based pseudotypes using single cycle or quasi-single cycle assays. The efficacy of an anti-HIV compound in inhibiting HIV infection can also be measured by in vitro models for HIV including assays evaluating the ability to reactivate viral replication from latently infected cells and produce HIV virus; assays in synchronized infections, evaluation of viral entry inhibition, determination of HIV reverse transcriptase activity, integrase assays; characterization of resistant variants including determination of genotypic and phenotypic variations; evaluation of HIV protease activity, entry assays, integration assays, antibody neutralization assays, co-receptor determination, HIV-induced down-modulation of CD4 and class I MHC, anti-HIV activity in chronically infected cells (with established HIV replication), evaluation of CPE effect in infected cells (syncytia formation, apoptosis, direct killing). All these methods are established methods and well known to the person skilled in the art.

In some embodiments, the (inhibition of) binding of HIV to CD4 or a CR such as e.g. CXCR4 is determined by biochemical assays. In some embodiments, the (inhibition of) binding of HIV to CD4 or a CR such as e.g. CXCR4 is determined by functional assays. In some embodiments, the assays are competition assays, e.g., with a natural ligand, and/or may include comparisons to a standard.

In some embodiments, biochemical assays include a step of contacting a polypeptide encompassing the complete or partial CD4 or CR sequence, such as e.g. a CXCR4 sequence, or cells expressing such sequences, with HIV or one of more HIV proteins, or protein fragments of HIV, that can bind to CD4 or a CR such as e.g. CXCR4. Binding can subsequently be determined through a variety of methods including ELISA, e.g., by using antibodies that detect the presence of one or both binding partners, surface plasmon resonance, or fluorescence based techniques such as FRET.

Functional assays include assays based on the suppression or increase of one or more biological functions of CD4 and/or a CR, such as e.g. CXCR4, and/or HIV, and are generally performed on live cells (e.g., cells expressing CD4 and/or CXCR4, cf. experimental section). For instance, CXCR4 activation, e.g., by natural ligand binding, triggers cell signaling pathways that are suppressed when CXCR4 is bound by HIV. Thus, monitoring the downstream events of such pathways e.g., the level of cAMP, provides a functional assay that allows for the determination of binding of CXCR4 by HIV and/or the displacement of natural ligand (See Example section). Alternatively, binding of a cell expressing CD4 and/or a CR, such as e.g. CXCR4, by HIV may result in a change in cellular function (e.g., phagocytosis) and inhibition of HIV binding can be monitored by quantifying the cellular function induced by HIV-binding.

During HIV transmission, CD4$^+$ T-cells can not only become infected by cell-free virions but, importantly, also by close cell-cell contacts with donor HIV-infected T-cells. As set out in Example 9, this can be measured based on the appearance of giant cells or syncytia in the cell co-cultures. Accordingly, the present invention relates to polypeptides as described herein, wherein said polypeptides inhibit HIV-induced cell-cell syncytia formation.

The polypeptides of the present invention provide a more specific inhibition of HIV infection than prior art antibodies. Preferably, the bispecific polypeptides of the invention comprise at least two binding moieties, such as for instance two building blocks, ISVs or Nanobodies, wherein at least the first binding moiety (functional ISV) is specific for CD4.

The terms polypeptide of the invention, bispecific polypeptide, bispecific construct, bispecific Nanobody construct, bispecific and bispecific antibody are used interchangeably herein.

Accordingly, the present invention relates to a polypeptide comprising a first and a second immunoglobulin single variable domain (ISV), wherein said first ISV binds to CD4 present on the surface of a cell;
said second ISV binds to a co-receptor (CR) present on the surface of said cell; and wherein said CR is not CD4.

In one aspect, the disclosure provides polypeptides that include one or more immunoglobulin single variable domains that inhibit binding of HIV to CXCR4.

In some embodiments, the polypeptides comprise at least two or more immunoglobulin single variable domains disclosed herein. In some embodiments, the polypeptides essentially consist of two or more immunoglobulin single variable domains disclosed herein. A polypeptide that "essentially consists of" two or more immunoglobulin single variable domains, is a polypeptide that in addition to the two or more immunoglobulin single variable domains disclosed herein does not have additional immunoglobulin single variable domains. For instance, a polypeptide that essentially consists of two immunoglobulin single variable domains does not include any additional immunoglobulin single variable domains. However, it should be appreciated that a polypeptide that essentially consists of two or more immunoglobulin single variable domains may include additional functionalities, such as a label, a toxin, one or more linkers, a binding sequence, etc. These additional functionalities include both amino acid based and non-amino acid based groups. In some embodiments, the polypeptides consist of one or more immunoglobulin single variable domains disclosed herein. It should be appreciated that the terms "polypeptide construct" and "polypeptide" can be used interchangeably herein (unless the context clearly dictates otherwise).

In some embodiments, the polypeptides include multivalent or multispecific constructs comprising immunoglobulin single variable domains disclosed herein. In some embodiments, the polypeptides comprise one or more antibody based-scaffolds and/or non-antibody based scaffolds disclosed herein. In some embodiments, the polypeptides comprise a serum binding protein moiety. In some embodiments, the serum binding protein moiety is an immunoglobulin single variable domain. In some embodiments, the immunoglobulin single variable domain is a Nanobody®, a $V_{HH}$, a humanized $V_{HH}$ or a camelized $V_H$.

Two or more immunoglobulin single variable domains can be combined in a single polypeptide, resulting in a multivalent and/or multispecific polypeptide, e.g. a bispecific polypeptide. Multivalent and/or multispecific polypeptides allow for improved avidity of the construct (i.e., for a desired antigen) as compared to a single immunoglobulin single variable domains, and/or for constructs that can bind to two or more different antigens. In some embodiments, the multispecific polypeptides include two or more immunoglobulin single variable domains that bind to the same target, thereby increasing the affinity for binding to a single antigen. In some embodiments, the polypeptide is biparatopic. The bispecific or multispecific polypeptides of the present invention comprise or essentially consist of at least two building blocks, e.g. ISVs, of which the first building block, e.g. the first ISV, has an increased affinity for its antigen, i.e. the first target, upon binding by the second building block, e.g. the second ISV, to its antigen, i.e. the second target. Such increased affinity (apparent affinity), due to avidity effects, is also called 'conditional bispecific or multispecific binding'. Such bispecific or multispecific polypeptide is also called 'a conditionally binding bispecific or multispecific polypeptide of the invention'.

It will be appreciated that the order of the first building block and the second building block on the polypeptide (orientation) can be chosen according to the needs of the person skilled in the art, as well as the relative affinities which may depend on the location of these building blocks in the polypeptide. Whether the polypeptide comprises a linker, is a matter of design choice. However, some orientations, with or without linkers, may provide preferred binding characteristics in comparison to other orientations. For instance, the order of the first and the second building block in the polypeptide of the invention can be (from N-terminus to C-terminus): (i) first building block (e.g. a first ISV such as a first Nanobody)-[linker]-second building block (e.g. a second ISV such as a second Nanobody); or (ii) second building block (e.g. a second ISV such as a second Nanobody)-[linker]-first building block (e.g. a first ISV such as a first Nanobody); (wherein the linker is optional). All orientations are encompassed by the invention. Polypeptides that contain an orientation of building blocks that provides desired (binding) characteristics can be easily identified by routine screening, for instance as exemplified in the experimental section.

As noted before, the inventors demonstrated inter alia that accomplishing resistance by HIV against the bispecific polypeptide is extremely difficult, even in a forced laboratory setting (see Example 8). It was surprisingly observed that even in a HIV strain made resistant against one target, e.g. the anti-CD4 moiety, the bispecific polypeptide was still potent in inhibiting HIV infection. Hence, this property expands the use of a bispecific polypeptide to a possible efficacy against heterogeneous strains not inherently resistant to one moiety agent and another HIV strain not inherently resistant against another moiety.

The invention relates to a method of inhibiting HIV infection of a susceptible cell in a subject by an HIV virus that is resistant, or has become resistant, to a CD4 antagonist, which comprises subjecting the susceptible cell to an effective HIV infection inhibiting dose of a polypeptide as described herein (which inhibits HIV fusion with CD4 CXCR4+ cells), preferably wherein the effective HIV infection inhibiting dose comprises from 0.1 mg per kg to 25 mg per kg of the subject's body weight, so as to thereby inhibit the infection of the susceptible cell by HIV1 that is resistant, or has become resistant, to the CD4 antagonist.

As used herein, the term "potency" is a measure of an agent, such as a polypeptide, ISV or Nanobody, its biological activity. Potency of an agent can be determined by any suitable method known in the art, such as for instance as described in the experimental section. Cell culture based potency assays are often the preferred format for determining biological activity since they measure the physiological response elicited by the agent and can generate results within a relatively short period of time. Various types of cell based assays, based on the mechanism of action of the product, can be used, including but not limited to proliferation assays, cytotoxicity assays, reporter gene assays, cell surface receptor binding assays and assays to measure induction/inhibition of functionally essential protein or other signal molecule (such as phosphorylated proteins, enzymes, cytokines, cAMP and the like), all well known in the art. Results from cell based potency assays can be expressed as "relative potency" as determined by comparison of the bispecific polypeptide of the invention to the response obtained for the corresponding reference monovalent ISV, e.g. a polypeptide comprising only one ISV or one Nanobody, optionally further comprising an irrelevant Nanobody (cf. experimental section).

A compound, e.g. the bispecific polypeptide, is said to be more potent than the reference compound, e.g. a compound such as a small molecule or a (conventional) antibody directed at the same target or the corresponding monovalent or monospecific ISV or Nanobody or polypeptide comprising the corresponding monovalent or monospecific ISV or Nanobody, when the response obtained for the compound, e.g. the bispecific polypeptide, is at least 2 times, but preferably at least 3 times, such as at least 4 times, at least 5 times, at least 6 times, at least 7 times, at least 8 times, at least 9 times, at least 10 times, at least 15 times, at least 20 times, at least 25 times, at least 50 times, at least 75 times, at least 100 times, and even more preferably even at least 200 times, or even at least 500 times, or even 1000 times better (e.g. functionally better) than the response by the reference compound, e.g. the corresponding monovalent ISV or Nanobody in a given assay.

The cell of the invention relates in particular to mammalian cells, and preferably to primate cells and even more preferably to human cells.

The cell is preferably an immune cell, such as a T-helper cell, monocyte, macrophage, or dendritic cell, preferably a CD4$^+$ T-helper cell (also known as CD4 cell, CD4$^+$ cell, T-helper cell or T4 cell), preferably a CD4$^+$CXCR4$^+$ cell, even more preferably a human cell. In some embodiments, the cell is in vivo. In some embodiments, the cell is in vitro.

The membrane (also called plasma membrane or phospholipid bilayer) surrounds the cytoplasm of a cell, which is the outer boundary of the cell, i.e. the membrane is the surface of the cell. This membrane serves to separate and protect a cell from its surrounding environment and is made mostly from a double layer of phospholipids. Embedded within this membrane is a variety of protein molecules, such as channels, pumps and cellular receptors. Since the membrane is fluid, the protein molecules can travel within the membrane.

For a general description of immunoglobulin single variable domains, reference is made to the further description below, as well as to the prior art cited herein. In this respect, it should however be noted that this description and the prior art mainly describes immunoglobulin single variable domains of the so-called "V$_H$3 class" (i.e., immunoglobulin single variable domains with a high degree of sequence homology to human germline sequences of the V$_H$3 class such as DP-47, DP-51 or DP-29), which form a preferred aspect of this invention. It should, however, be noted that the invention in its broadest sense generally covers any type of immunoglobulin single variable domains and for example also covers the immunoglobulin single variable domains belonging to the so-called "V$_H$4 class" (i.e., immunoglobulin single variable domains with a high degree of sequence homology to human germline sequences of the V$_H$4 class such as DP-78), as for example described in WO 07/118670.

Generally, immunoglobulin single variable domains (in particular V$_{HH}$ sequences and sequence optimized immunoglobulin single variable domains) can in particular be characterized by the presence of one or more "Hallmark residues" (as described herein) in one or more of the framework sequences (again as further described herein).

Thus, generally, an immunoglobulin single variable domain can be defined as an amino acid sequence with the (general) structure (cf. formula 1 below)

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively.

In a preferred aspect, the invention provides polypeptides comprising at least an immunoglobulin single variable domain that is an amino acid sequence with the (general) structure

FR1-CDR1-FR2-CR2CDR2-FR3-CDR-CDR3-FR4 in which FR1 to FR4 refer to framework regions 1 to 4, respectively, and in which CDR1 to CDR3 refer to the complementarity determining regions 1 to 3, respectively, and in which:

i) at least one of the amino acid residues at positions 11, 37, 44, 45, 47, 83, 84, 103, 104 and 108 according to the Kabat numbering are chosen from the Hallmark residues mentioned in Table A-1 below; and in which:

ii) said amino acid sequence has at least 80%, more preferably 90%, even more preferably 95% amino acid identity with at least one of the immunoglobulin single variable domains as shown in WO 2009/138519 (see SEQ ID NOs: 1 to 125 in WO 2009/138519), in which for the purposes of determining the degree of amino acid identity, the amino acid residues that form the CDR sequences (indicated with X in the sequences) are disregarded; and in which:

iii) the CDR sequences are generally as further defined herein (e.g., the CDR1, CDR2 and CDR3 in a combination as can be determined with the information provided herein, noting that the CDR definitions are calculated according to the Kabat numbering system).

TABLE A-1

Hallmark Residues in VHHs

| Position | Human V$_H$3 | Hallmark Residues |
|---|---|---|
| 11 | L, V; predominantly L | L, S, V, M, W, F, T, Q, E, A, R, G, K, Y, N, P, I; preferably L |
| 37 | V, I, F; usually V | F$^{(1)}$, Y, V, L, A, H, S, I, W, C, N, G, D, T, P, preferably F$^{(1)}$ or Y |
| 44$^{(8)}$ | G | E$^{(3)}$, Q$^{(3)}$, G$^{(2)}$, D, A, K, R, L, P, S, V, H, T, N, W, M, I; preferably G$^{(2)}$, E$^{(3)}$ or Q$^{(3)}$; most preferably G$^{(2)}$ or Q$^{(3)}$. |
| 45$^{(8)}$ | L | L$^{(2)}$, R$^{(3)}$, P, H, F, G, Q, S, E, T, Y, C, I, D, V; preferably L$^{(2)}$ or R$^{(3)}$ |
| 47$^{(8)}$ | W, Y | F$^{(1)}$, L$^{(1)}$ or W$^{(2)}$ G, I, S, A, V, M, R, Y, E, P, T, C, H, K, Q, N, D; preferably W$^{(2)}$, L$^{(1)}$ or F$^{(1)}$ |
| 83 | R or K; usually R | R, K$^{(5)}$, T, E$^{(5)}$, Q, N, S, I, V, G, M, L, A, D, Y, H; preferably K or R; most preferably K |
| 84 | A, T, D; predominantly A | P$^{(5)}$, S, H, L, A, V, I, T, F, D, R, Y, N, Q, G, E; preferably P |
| 103 | W | W$^{(4)}$, R$^{(6)}$, G, S, K, A, M, Y, L, F, T, N, V, Q, P$^{(6)}$, E, C; preferably W |

TABLE A-1-continued

Hallmark Residues in VHHs

| Position | Human $V_H3$ | Hallmark Residues |
|---|---|---|
| 104 | G | G, A, S, T, D, P, N, E, C, L; preferably G |
| 108 | L, M or T; predominantly L | Q, L[7], R, P, E, K, S, T, M, A, H; preferably Q or L[7] |

Notes:
[1]In particular, but not exclusively, in combination with KERE or KQRE at positions 43-46.
[2]Usually as GLEW at positions 44-47.
[3]Usually as KERE or KQRE at positions 43-46, e.g. as KEREL, KEREF, KQREL, KQREF, KEREG, KQREW or KQREG at positions 43-47. Alternatively, also sequences such as TERE (for example TEREL), TQRE (for example TQREL), KECE (for example KECEL or KECER), KQCE (for example KQCEL), RERE (for example REREG), RQRE (for example RQREL, RQREF or RQREW), QERE (for example QEREG), QQRE, (for example QQREW, QQREL or QQREF), KGRE (for example KGREG), KDRE (for example KDREV) are possible. Some other possible, but less preferred sequences include for example DECKL and NVCEL.
[4]With both GLEW at positions 44-47 and KERE or KQRE at positions 43-46.
[5]Often as KP or EP at positions 83-84 of naturally occurring $V_{HH}$ domains.
[6]In particular, but not exclusively, in combination with GLEW at positions 44-47.
[7]With the proviso that when positions 44-47 are GLEW, position 108 is always Q in (non-humanized) $V_{HH}$ sequences that also contain a W at 103.
[8]The GLEW group also contains GLEW-like sequences at positions 44-47, such as for example GVEW, EPEW, GLER, DQEW, DLEW, GIEW, ELEW, GPEW, EWLP, GPER, GLER and ELEW.

The immunoglobulins of the invention may also contain a C-terminal extension (X)n (in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I)), for which reference is made to WO 12/175741 and US provisional applications, all entitled "Improved immunoglobulin variable domains": U.S. 61/994,552 filed May 16, 2014; U.S. 61/014,015 filed Jun. 18, 2014; U.S. 62/040,167 filed Aug. 21, 2014; and U.S. 62/047,560, filed Sep. 8, 2014 (all assigned to Ablynx N.V.).

Again, such immunoglobulin single variable domains may be derived in any suitable manner and from any suitable source, and may for example be naturally occurring $V_{HH}$ sequences (i.e., from a suitable species of Camelid, e.g., llama) or synthetic or semi-synthetic VHs or VLs (e.g., from human). Such immunoglobulin single variable domains may include "humanized" or otherwise "sequence optimized" VHHs, "camelized" immunoglobulin sequences (and in particular camelized heavy chain variable domain sequences, i.e., camelized VHs), as well as human VHs, human VLs, camelid VHHs that have been altered by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing as further described herein. As mentioned herein, a particularly preferred class of immunoglobulin single variable domains of the invention comprises immunoglobulin single variable domains with an amino acid sequence that corresponds to the amino acid sequence of a naturally occurring $V_{HH}$ domain, but that has been "humanized", i.e. by replacing one or more amino acid residues in the amino acid sequence of said naturally occurring $V_{HH}$ sequence (and in particular in the framework sequences) by one or more of the amino acid residues that occur at the corresponding position(s) in a $V_H$ domain from a conventional 4-chain antibody from a human being (e.g. indicated above). This can be performed in a manner known per se, which will be clear to the skilled person, for example on the basis of the further description herein and the prior art on humanization referred to herein. Again, it should be noted that such humanized immunoglobulin single variable domains of the invention can be obtained in any suitable manner known per se and thus are not strictly limited to polypeptides that have been obtained using a polypeptide that comprises a naturally occurring $V_{HH}$ domain as a starting material.

Another particularly preferred class of immunoglobulin single variable domains of the invention comprises immunoglobulin single variable domains with an amino acid sequence that corresponds to the amino acid sequence of a naturally occurring $V_H$ domain, but that has been "camelized", i.e. by replacing one or more amino acid residues in the amino acid sequence of a naturally occurring $V_H$ domain from a conventional 4-chain antibody by one or more of the amino acid residues that occur at the corresponding position(s) in a $V_{HH}$ domain of a heavy chain antibody. This can be performed in a manner known per se, which will be clear to the skilled person, for example on the basis of the description herein. Such "camelizing" substitutions are preferably inserted at amino acid positions that form and/or are present at the $V_H$—$V_L$ interface, and/or at the so-called Camelidae hallmark residues, as defined herein (see also for example WO 94/04678 and Davies and Riechmann (1994 and 1996)). Preferably, the $V_H$ sequence that is used as a starting material or starting point for generating or designing the camelized immunoglobulin single variable domains is preferably a $V_H$ sequence from a mammal, more preferably the $V_H$ sequence of a human being, such as a $V_H3$ sequence. However, it should be noted that such camelized immunoglobulin single variable domains of the invention can be obtained in any suitable manner known per se and thus are not strictly limited to polypeptides that have been obtained using a polypeptide that comprises a naturally occurring $V_H$ domain as a starting material.

For example, again as further described herein, both "humanization" and "camelization" can be performed by providing a nucleotide sequence that encodes a naturally occurring $V_{HH}$ domain or $V_H$ domain, respectively, and then changing, in a manner known per se, one or more codons in said nucleotide sequence in such a way that the new nucleotide sequence encodes a "humanized" or "camelized" immunoglobulin single variable domain of the invention, respectively. This nucleic acid can then be expressed in a manner known per se, so as to provide the desired immunoglobulin single variable domains of the invention. Alternatively, based on the amino acid sequence of a naturally occurring $V_{HH}$ domain or $V_H$ domain, respectively, the amino acid sequence of the desired humanized or camelized immunoglobulin single variable domains of the invention, respectively, can be designed and then synthesized de novo using techniques for peptide synthesis known per se. Also, based on the amino acid sequence or nucleotide sequence of a naturally occurring $V_{HH}$ domain or $V_H$ domain, respectively, a nucleotide sequence encoding the desired humanized or camelized immunoglobulin single variable domains of the invention, respectively, can be designed and then synthesized de novo using techniques for nucleic acid synthesis known per se, after which the nucleic acid thus obtained can be expressed in a manner known per se, so as to provide the desired immunoglobulin single variable domains of the invention.

Generally, proteins or polypeptides that comprise or essentially consist of a single building block, single immunoglobulin single variable domain or single Nanobody will be referred to herein as "monovalent" proteins or polypeptides or as "monovalent constructs", or as monovalent building block, monovalent immunoglobulin single variable domain or monovalent Nanobody, respectively. Proteins and polypeptides that comprise or essentially consist of two or more immunoglobulin single variable domains (such as at least two immunoglobulin single variable domains of the invention) will be referred to herein as "multivalent" proteins or polypeptides or as "multivalent constructs", and these provide certain advantages compared to the corresponding monovalent immunoglobulin single variable domains of the invention. Some non-limiting examples of such multivalent constructs will become clear from the further description herein. The polypeptides of the invention are "multivalent", i.e. comprising two or more building blocks or ISVs of which at least the first building block, ISV or Nanobody and the second building block, ISV or Nanobody are different, and directed against different targets, such as antigens or antigenic determinants. Polypeptides of the invention that contain at least two building blocks, ISVs or Nanobodies, in which at least one building block, ISV or Nanobody is directed against a first antigen (i.e., against the first target, such as e.g. CD4) and at least one building block, ISV or Nanobody is directed against a second antigen (i.e., against the second target which is different from the first target, such as e.g. a CR, e.g. CXCR4), will also be referred to as "multispecific" polypeptides of the invention, and the building blocks, ISVs or Nanobodies present in such polypeptides will also be referred to herein as being in a "multivalent format". Thus, for example, a "bispecific" polypeptide of the invention is a polypeptide that comprises at least one building block, ISV or Nanobody directed against a first target (e.g. CD4) and at least one further building block, ISV or Nanobody directed against a second target (i.e., directed against a second target different from said first target, such as e.g. CR, e.g. CXCR4), whereas a "trispecific" polypeptide of the invention is a polypeptide that comprises at least one building block, ISV or Nanobody directed against a first target (e.g., CD4), a second building block, ISV or Nanobody directed against a second target different from said first target (e.g. CR, such as e.g. CXCR4) and at least one further building block, ISV or Nanobody directed against a third antigen (i.e., different from both the first and the second target), such as, for instance, serum albumin; etc. As will be clear from the description, the invention is not limited to bispecific polypeptides, in the sense that a multispecific polypeptide of the invention may comprise at least a first building block, ISV or Nanobody against a first target, a second building block, ISV or Nanobody against a second target and any number of building blocks, ISVs or Nanobodies directed against one or more targets, which may be the same or different from the first and/or second target, respectively. The building blocks, ISVs or Nanobodies can optionally be linked via linker sequences.

Accordingly, the present invention also relates to a trispecific or multispecific polypeptide, comprising or essentially consisting of at least three binding moieties, such as three ISVs, wherein at least one of said at least three binding moieties is directed against a first target with a low, moderate of high affinity, at least one of said at least three binding moieties is directed against a second target with a high affinity and at least a third binding moiety increasing half-life, such as e.g. an albumin binder.

As will be clear from the further description above and herein, the immunoglobulin single variable domains of the invention can be used as "building blocks" to form polypeptides of the invention, e.g., by suitably combining them with other groups, residues, moieties or binding units, in order to form compounds or constructs as described herein (such as, without limitations, the bi-/tri-/tetra-/multivalent and bi-/tri-/tetra-/multispecific polypeptides of the invention described herein) which combine within one molecule one or more desired properties or biological functions.

The compounds or polypeptides of the invention can generally be prepared by a method which comprises at least one step of suitably linking the one or more immunoglobulin single variable domains of the invention to the one or more further groups, residues, moieties or binding units, optionally via the one or more suitable linkers, so as to provide the compound or polypeptide of the invention. Polypeptides of the invention can also be prepared by a method which generally comprises at least the steps of providing a nucleic acid that encodes a polypeptide of the invention, expressing said nucleic acid in a suitable manner, and recovering the expressed polypeptide of the invention. Such methods can be performed in a manner known per se, which will be clear to the skilled person, for example on the basis of the methods and techniques further described herein.

The process of designing/selecting and/or preparing a compound or polypeptide of the invention, starting from an amino acid sequence of the invention, is also referred to herein as "formatting" said amino acid sequence of the invention; and an amino acid of the invention that is made part of a compound or polypeptide of the invention is said to be "formatted" or to be "in the format of" said compound or polypeptide of the invention. Examples of ways in which an amino acid sequence of the invention can be formatted and examples of such formats will be clear to the skilled person based on the disclosure herein; and such formatted immunoglobulin single variable domains form a further aspect of the invention.

For example, such further groups, residues, moieties or binding units may be one or more additional immunoglobulin single variable domains, such that the compound or construct is a (fusion) protein or (fusion) polypeptide. In a preferred but non-limiting aspect, said one or more other groups, residues, moieties or binding units are immunoglobulin sequences. Even more preferably, said one or more other groups, residues, moieties or binding units are chosen from the group consisting of domain antibodies, immunoglobulin single variable domains that are suitable for use as a domain antibody, single domain antibodies, immunoglobulin single variable domains (ISVs) that are suitable for use as a single domain antibody, "dAb" 's, immunoglobulin single variable domains that are suitable for use as a dAb, or Nanobodies. Alternatively, such groups, residues, moieties or binding units may for example be chemical groups, residues, moieties, which may or may not by themselves be biologically and/or pharmacologically active. For example, and without limitation, such groups may be linked to the one or more immunoglobulin single variable domains of the invention so as to provide a "derivative" of an amino acid sequence or polypeptide of the invention, as further described herein.

Also within the scope of the present invention are compounds or constructs, which comprise or essentially consist of one or more derivatives as described herein, and optionally further comprise one or more other groups, residues, moieties or binding units, optionally linked via one or more linkers. Preferably, said one or more other groups, residues, moieties or binding units are immunoglobulin single variable domains. In the compounds or constructs described above, the one or more immunoglobulin single variable domains of the invention and the one or more groups, residues, moieties or binding units may be linked directly to each other and/or via one or more suitable linkers or spacers. For example, when the one or more groups, residues, moieties or binding units are immunoglobulin single variable domains, the linkers may also be immunoglobulin single variable domains, so that the resulting compound or construct is a fusion protein or fusion polypeptide.

Accordingly, the present invention relates to a polypeptide as described herein, wherein said ISV is a Nanobody®, a $V_{HH}$, a humanized $V_{HH}$, or a camelized $V_H$.

The first building block, ISV, such as e.g. a Nanobody, or VHH of the invention has an affinity for its—the first—target, i.e. CD4 and polymorphic variants. The first building block, ISV or Nanobody of the invention may for example be directed against an antigenic determinant, epitope, part, domain, subunit or confirmation (where applicable) of said first target. The first building block, e.g. the first ISV, such as e.g. a Nanobody, or VHH, is chosen for its affinity for its target per se, disregarding the influence of any avidity effects. Preferred first building blocks are depicted in Table A-2(B).

"CD4" or "T-cell surface glycoprotein CD4" means the mature, native, membrane-bound CD4 protein comprising a cytoplasmic domain, a hydrophobic transmembrane domain, and an extracellular domain which binds to the HIV-1 gp120 envelope glycoprotein. CD4 is also known as T-cell surface antigen T4/Leu-3. Preferably CD4 is human CD4, preferably represented by Uniprot accession number P01730-1 (OMIM: 186940), for instance as represented by the amino acid sequence:

(SEQ ID NO: 1)
MNRGVPFRHLLLVLQLALLPAATQGKKVVLGKKGDTVELTCTASQKKSIQ

FHWKNSNQIKILGNQGSFLTKGPSKLNDRADSRRSLWDQGNFPLIIKNLK

IEDSDTYICEVEDQKEEVQLLVFGLTANSDTHLLQGQSLTLTLESPPGSS

PSVQCRSPRGKNIQGGKTLSVSQLELQDSGTWTCTVLQNQKKVEFKIDIV

VLAFQKASSIVYKKEGEQVEFSFPLAFTVEKLTGSGELWWQAERASSSKS

WITFDLKNKEVSVKRVTQDPKLQMGKKLPLHLTLPQALPQYAGSGNLTLA

LEAKTGKLHQEVNLVVMRATQLQKNLTCEVWGPTSPKLMLSLKLENKEAK

VSKREKAVWVLNPEAGMWQCLLSDSGQVLLESNIKVLPTWSTPVQPMALI

VLGGVAGLLLFIGLGIFFCVRCRHRRRQAERMSQIKRLLSEKKTCQCPHR

FQKTCSPI.

As noted before, HIV infection is characterized by a decline in the number of CD4+ T-cells in the infected person. The CD4 count of a healthy adult/adolescent ranges from 500 cells/ml to 1,200 cells/ml. The CD4 count measures the number of CD4 cells in a sample of blood. HIV infection reduces the number cells comprising CD4. A very low CD4 count (less than 200 cells/mm$^3$) is one of the ways to determine whether a person living with HIV has progressed to stage 3 infection (AIDS).

The present invention relates to a polypeptide as described herein, wherein said polypeptide has an on rate constant (Kon) to said CD4 selected from the group consisting of at least about $10^2$ M$^{-1}$s$^{-1}$, at least about $10^3$ M$^{-1}$s$^{-1}$, at least about $10^4$ M$^{-1}$s$^{-1}$, at least about $10^5$ M$^{-1}$s$^{-1}$, at least about $10^6$ M$^{-1}$s$^{-1}$, $10^7$ M$^{-1}$s$^{-1}$, at least about $10^8$ M$^{-1}$s$^{-1}$, at least about $10^9$ M$^{-1}$s$^{-1}$, and at least about $10^{10}$ M$^{-1}$s$^{-1}$, preferably as measured by surface plasmon resonance The present invention relates to a polypeptide as described herein, wherein said polypeptide has an off rate constant (Koff) to said CD4 selected from the group consisting of at most about $10^{-3}$s$^{-1}$, at most about $10^{-4}$s$^{-1}$, at most about $10^{-5}$s$^{-1}$, at most about $10^{-6}$s$^{-1}$, at most about $10^{-7}$s$^{-1}$, at most about $10^{-8}$s$^{-1}$, at most about $10^{-9}$s$^{-1}$, and at most about $10^{-10}$s$^{-1}$, preferably as measured by surface plasmon resonance.

The present invention relates to a polypeptide as described herein, wherein said polypeptide has a dissociation constant (K$_D$) to said CD4 selected from the group consisting of: at most about $10^{-7}$ M, at most about $10^{-8}$ M, at most about $10^{-9}$ M, at most about $10^{-10}$ M, at most about $10^{-11}$ M, and at most about $10^{-12}$ M, preferably as measured by surface plasmon resonance.

Accordingly, the present invention relates to a polypeptide as described herein, wherein said first ISV binds to CD4 with an average KD value of between 10 nM and 0.1 pM, such as at an average KD value of 10 nM or less, even more preferably at an average KD value of 9 nM or less, such as less than 8, 7, 6, 5, 4, 3, 2, 1, 0.5 nM or even less, such as less than 400, 300, 200, 100, 50, 40, 30, 20, 10, 9, 8, 7, 6, 5, 4, 3, 2, 1, 0.5 pM, or even less such as less than 0.4 pM, preferably measured by SPR, for instance as determined by a KinExA. Kinetic Exclusion Assay (KINEXA®) (Drake et al. 2004, Analytical Biochemistry 328: 35-43) measures binding events in solution without labeling of the binding partners and is based upon kinetically excluding the dissociation of a complex.

Accordingly, the present invention relates to a polypeptide as described herein, wherein said first ISV has a high affinity when measured as a monovalent.

Accordingly, the present invention relates to a polypeptide as described herein, wherein said average KD is measured by surface plasmon resonance (SPR) on recombinant protein.

The present invention also relates to a polypeptide as described herein, wherein said first ISV binds to a first target on the surface of a cell with an EC$_{50}$ value of between 10 nM and 0.1 pM, such as at an average EC$_{50}$ value of 10 nM or less, even more preferably at an average KD value of 9 nM or less, such as less than 8, 7, 6, 5, 4, 3, 2, 1, 0.5 nM or even less, such as less than 400, 300, 200, 100, 50, 40, 30, 20, 10, 9, 8, 7, 6, 5, 4, 3, 2, 1, 0.5 pM, or even less such as less than 0.4 pM.

Accordingly the present invention relates to a polypeptide as described herein, wherein said average EC$_{50}$ is measured on cells comprising said target 1 but substantially lacking said target 2.

Accordingly, the present invention relates to a polypeptide as described herein, wherein said average KD is determined by FACS, BIACORE®, ELISA, on a monovalent first ISV, such as a Nanobody, or a polypeptide comprising a monovalent first ISV, such as a Nanobody.

It has been shown in the examples that the KD correlates well with the $EC_{50}$.

It is also expected that the immunoglobulin single variable domains and polypeptides of the invention will generally bind to all naturally occurring or synthetic analogs, variants, mutants, alleles, parts and fragments of its targets; or at least to those analogs, variants, mutants, alleles, parts and fragments of the CD4, and in particular human CD4 that contain one or more antigenic determinants or epitopes that are essentially the same as the antigenic determinant(s) or epitope(s) to which the immunoglobulin single variable domains and polypeptides of the invention bind to CD4, and in particular to human CD4. Again, in such a case, the immunoglobulin single variable domains and polypeptides of the invention may bind to such analogs, variants, mutants, alleles, parts and fragments with an affinity and/or specificity that are the same as, or that are different from (i.e., higher than or lower than), the affinity and specificity with which the immunoglobulin single variable domains of the invention bind to (wild-type) receptor, e.g. CD4.

The present invention further relates to CD4 binders comprised in the polypeptide of the invention which do not or only minimally impair or inhibit a natural function(s) of CD4, in which CD4 functions as a receptor assisting the T-cell receptor (TCR) in communicating with an antigen-presenting cell. Using its intracellular domain, CD4 amplifies the signal generated by the TCR by recruiting an enzyme, the tyrosine kinase Lck, which is essential for activating many molecular components of the signaling cascade of an activated T-cell. Various types of T helper cells are thereby produced. CD4 also interacts directly with MHC class II molecules on the surface of the antigen-presenting cell using its extracellular domain. The person skilled in the art is fully cknowledgeable of determining and measuring the (natural) function(s) of CD4, for instance by ALPHASCREEN® assay, competition ELISA, or FACS on cells and e.g., described in the experimental part.

Accordingly the present invention relates to a polypeptide as described herein, wherein said first ISV inhibits a pharmacologic effect of said first target by less than about 50%, such as 40%, 30%, or 20% or even less than 10%, e.g. relative to the inhibition in the absence of said first ISV.

The present invention relates to a polypeptide as described herein, wherein said polypeptide inhibits multimerisation by CD4 by less than about 50%, such as 40%, 30%, or 20% or even less than 10%, such as less than 5%.

Accordingly the present invention relates to a polypeptide as described herein, wherein said first ISV inhibits multimerisation of said first target (with T-cell receptor) by less than about 50%, such as 40%, 30%, or 20% or even less than 10%, e.g. relative to the inhibition in the absence of said first ISV.

Accordingly the present invention relates to a polypeptide as described herein, wherein said first ISV binds to an allosteric site regarding the natural function of CD4.

Accordingly the present invention relates to a polypeptide as described herein, wherein said first ISV does not substantially or only marginally inhibit a (natural) function of said first target, e.g. assisting the T-cell receptor (TCR) in communicating with an antigen-presenting cell and/or recruiting tyrosine kinase Lck.

The present invention relates to a polypeptide as described herein, wherein said polypeptide inhibits recruiting Lck by CD4 by less than about 50%, such as 40%, 30%, or 20% or even less than 10%, such as less than 5%.

Accordingly the present invention relates to a polypeptide as described herein, wherein said first ISV inhibits signalling, e.g. recruiting Lck, by said first target by less than about 50%, such as 40%, 30%, or 20% or even less than 10%, e.g. relative to the inhibition in the absence of said first ISV.

Accordingly the present invention relates to a polypeptide as described herein, wherein said first ISV inhibits a (natural) function of said first target by less than about 50%, such as 40%, 30%, or 20% or even less than 10%, e.g. relative to the inhibition in the absence of said first ISV.

Accordingly the present invention relates to a polypeptide as described herein, wherein said first ISV inhibits chemotaxis by less than about 50%, such as 40%, 30%, or 20% or even less than 10% in an chemotaxis assay, e.g. relative to the inhibition in the absence of said first ISV.

In a preferred embodiment, the present invention relates to a polypeptide as described herein, wherein said first ISV essentially consists of 4 framework regions (FR1 to FR4, respectively) and 3 complementarity determining regions (CDR1 to CDR3 respectively), in which (i) CDR1 is chosen from the group consisting of SEQ ID NOs: 82-85; and amino acid sequences that have 1, 2 or 3 amino acid difference(s) with SEQ ID NOs: 82-85;

(ii) CDR2 is chosen from the group consisting of SEQ ID NOs: 88-91; and amino acid sequences that have 1, 2 or 3 amino acid difference(s) with SEQ ID NOs: 88-91; and (iii) CDR3 is chosen from the group consisting of SEQ ID NO: 96-99 and amino acid sequences that have 1, 2, 3 or 4 amino acid difference(s) with SEQ ID NOs: 96-99;

The present invention also relates to a polypeptide as described herein, wherein said first ISV essentially consists of 4 framework regions (FR1 to FR4, respectively) and 3 complementarity determining regions (CDR1 to CDR3 respectively), in which said ISV is chosen from the group consisting of CDR1 is SEQ ID NO: 82, CDR2 is SEQ ID NO: 88, and CDR3 is SEQ ID NO: 96;

CDR1 is SEQ ID NO: 83, CDR2 is SEQ ID NO: 89, and CDR3 is SEQ ID NO: 97;

CDR1 is SEQ ID NO: 84, CDR2 is SEQ ID NO: 90, and CDR3 is SEQ ID NO: 98; and

CDR1 is SEQ ID NO: 85, CDR2 is SEQ ID NO: 91, and CDR3 is SEQ ID NO: 99.

Accordingly, the present invention relates to a polypeptide as described herein, in which said first ISV essentially consists of 4 framework regions (FR1 to FR4, respectively) and 3 complementarity determining regions (CDR1 to CDR3 respectively), in which CDR1 is SEQ ID NO: 85, CDR2 is SEQ ID NO: 91 and CDR3 is SEQ ID NO: 99.

The present invention relates to a polypeptide as described herein, wherein said first ISV is chosen from the group consisting of 01B6 (SEQ ID NO: 17), 01E2 (SEQ ID NO: 18), 01H12 (SEQ ID NO: 19) and 03F11 (SEQ ID NO: 20), preferably said first ISV is 03F11 (SEQ ID NO: 20).

As described herein, a polypeptide of the invention contains at least two building blocks, such as ISVs, e.g. Nanobodies, of the invention of which the second building block, ISV, e.g. Nanobody, is directed against a second target involved in HIV infection, i.e. a co-receptor for HIV infection, including related polymorphic variants. Preferred second building blocks are depicted in Table A-2(A).

It is also expected that the immunoglobulin single variable domains and polypeptides of the invention will generally bind to all naturally occurring or synthetic analogs, variants, mutants, alleles, parts and fragments of its targets; or at least to those analogs, variants, mutants, alleles, parts and fragments of the co-receptor, such as CXCR4, and in particular human CXCR4 that contain one or more antigenic determinants or epitopes that are essentially the same as the antigenic determinant(s) or epitope(s) to which the immunoglobulin single variable domains and polypeptides of the invention bind to the co-receptor, preferably CXCR4 and in particular to human CXCR4. Again, in such a case, the immunoglobulin single variable domains and polypeptides of the invention may bind to such analogs, variants, mutants, alleles, parts and fragments with an affinity and/or specificity that are the same as, or that are different from (i.e., higher than or lower than), the affinity and specificity with which the immunoglobulin single variable domains of the invention bind to (wild-type) co-receptor, e.g. CXCR4.

The present invention relates to a polypeptide as described herein, wherein said polypeptide has an on rate constant (Kon) to said CR selected from the group consisting of at least about $10^2$ $M^{-1}s^{-1}$, at least about $10^3$ $M^{-1}s^{-1}$, at least about $10^4$ $M^{-1}s^{-1}$, at least about $10^5$ $M^{-1}s^{-1}$, at least about $10^6$ $M^{-1}s^{-1}$, $10^7$ $M^{-1}s^{-1}$, at least about $10^8$ $M^{-1}s^{-1}$, at least about $10^9$ $M^{-1}s^{-1}$, and at least about $10^{10}$ $M^{-1}s^{-1}$, preferably as measured by surface plasmon resonance, said CR is preferably CXCR4.

The present invention relates to a polypeptide as described herein, wherein said polypeptide has an off rate constant (Koff) to said CR selected from the group consisting of at most about $10^3 s^{-1}$, at most about $10^4 s^{-1}$, at most about $10^{-5} s^{-1}$, at most about $10^{-6} s^{-1}$, at most about $10^{-7} s^{-1}$, at most about $10^{-8} s^{-1}$, at most about $10^{-9} s^{-1}$, and at most about $10^{-10} s^{-1}$, preferably as measured by surface plasmon resonance, said CR is preferably CXCR4.

The present invention relates to a polypeptide as described herein, wherein said polypeptide has a dissociation constant ($K_D$) to said CR selected from the group consisting of: at most about $10^{-7}$ M, at most about $10^{-8}$ M, at most about $10^{-9}$ M, at most about $10^{-10}$ M, at most about $10^{-11}$ M, and at most about $10^{-12}$ M, preferably as measured by surface plasmon resonance, said CR is preferably CXCR4.

The present invention relates to a polypeptide as described herein, wherein said second ISV binds to said CR with an average KD value of between 10 nM and 0.1 pM, such as at an average KD value of 10 nM or less, even more preferably at an average KD value of 9 nM or less, such as less than 8, 7, 6, 5, 4, 3, 2, 1, 0.5 nM or even less, such as less than 400, 300, 200, 100, 50, 40, 30, 20, 10, 9, 8, 7, 6, 5, 4, 3, 2, 1, 0.5 pM, or even less such as less than 0.4 pM, preferably measured by SPR, for instance as determined by a KinExA, said CR is preferably CXCR4.

When, designing the polypeptides of the invention, the second building block, e.g. the second ISV, can be chosen for its affinity per se, disregarding the influence of any avidity effects.

In a further aspect, the present invention relates to a polypeptide as described herein, wherein said second ISV has a high affinity when measured as a monovalent.

The present invention relates also to a polypeptide as described herein, wherein said average KD is determined (indirectly) by any technique known in the art, such as for instance SPR, FACS, or ELISA on a monovalent second ISV.

The second ISV of the invention may for example be directed against a second antigenic determinant, epitope, part, domain, subunit or confirmation (where applicable) of said co-receptor, and in particular human CXCR4.

The second target of the invention can be any target, such as a cellular receptor, on the surface of a cell which is known to participate as a co-receptor in HIV entry.

Accordingly, the present invention relates to a polypeptide as described herein, wherein said second ISV inhibits binding of HIV to said second target, such as e.g. CR, e.g. CXCR4, by about 10%, 20%, 30%, 40%, 50%, 60%, 80%, 90% and preferably 95% or even 100%, e.g. relative to the inhibition in the absence of said second ISV.

Accordingly, the present invention relates to a polypeptide as described herein, wherein said second ISV inhibits the pharmacologic effect of HIV infection, such as e.g. entry of HIV into a target cell, replication of HIV, HIV reverse transcriptase activity, HIV-induced cell death, and/or HIV-induced cell-cell syncytia formation, in which said second target is involved by about 20%, 30%, 40%, 50%, 60%, 80%, 90% and preferably 95% or even 100%, e.g. relative to the pharmacologic effect in the absence of said second ISV.

Accordingly, the present invention relates to a polypeptide as described herein, wherein said second ISV displaces about 20%, 30%, 40%, 50%, 60%, 80%, 90% and preferably 95% or more of HIV to said co-receptor, e.g. relative to the displacement in the absence of said second ISV.

Preferably, the polypeptide when bound impairs or inhibits HIV infection. In a preferred embodiment the function of said second target and or said second target is not or only minimally impaired upon binding of the bispecific polypeptide. Consequently, binding of the bispecific polypeptide results in limited or negligible side-effects and/or toxicity.

As used herein, the co-receptor includes, without limitation, extracellular portions of the co-receptor capable of binding the HIV envelope protein. The person skilled in the art will appreciate that more information on the sequence, function and ligands of co-receptors for HIV infection, such as, e.g. CXCR4, CCR5, CCR1, CCR2, CCR3, CCR8, CX3CR1, FPRL1, GPR1, GPR15, APJ, STRL33 and D6 can be found via the OMIM and Uniprot websites. The specific OMIM and Uniprot accession numbers are provided in the table below.

| Receptor | OMIM | Uniprot |
| --- | --- | --- |
| CXCR4 | 162643 | P61073 |
| CCR5 | 601373 | P51681 |
| CCR1 | 601159 | P32246 |
| CCR2 | 601267 | P41597 |
| CCR3 | 601268 | P51677 |
| CCR8 | 601834 | P51685 |
| CX3CR1 | 601470 | P49238 |
| CXCR6 | 605163 | O00574 |
| FPRL1 | 136538 | P25090 |
| GPR1 | 600239 | P46091 |
| GPR15 | 601166 | P49685 |
| APJ | 600052 | P35414 |
| D6 | 602648 | O00590 |

The present invention relates to a polypeptide as described herein, wherein said CR is chosen from the group consisting of CXCR4, CCR5, CCR1, CCR2, CCR3, CCR8, CX3CR1, CXCR6, FPRL1, GPR1, GPR15, APJ, STRL33 and D6, as well as polymorphic variants thereof. Preferably said co-receptor is CXC chemokine receptor 4 (CXCR4). The co-receptor is preferably a human co-receptor, preferably human CXCR4.

The C-C chemokine receptor type 5, also known as CCR5 or CD195, is a protein on the surface of white blood cells that is involved in the immune system as it acts as a receptor for chemokines. The natural ligands for this receptor, RANTES, MIP-1β, and MIP-1α. Preferably, the CCR5 amino acid sequence is represented by:

(SEQ ID NO: 3)
MDYQVSSPIYDINYYTSEPCQKINVKQIAARLLPPLYSLVFIFGFVGNML

VILILINCKRLKSMIDIYLLNLAISDLFFLLTVPFWAHYAAAQWDFGNIM

CQLLTGLYFIGFFSGIFFIILLTIDRYLAVVHAVFALKARTVIFGVVISV

ITWVVAVFASLPGIIFIRSQKEGLHYTCSSHFPYSQYQFWKNFQTLKIVI

LGLVLPLLVMVICYSGILKILLRCRNEKKRHRAVRLIFTIMIVYFLFWAP

YNIVLLLNIFQEFFGLNNCSSSNRLDQAMQVIETLGMTHCCINPIIYAFV

GEKFRNYLLVFFQKHIAKRFCKCCSIFQQEAPERASSVYTRSTGEQEISV

GL.

CCR1 has also been designated CD191 (cluster of differentiation 191). The ligands of this receptor include macrophage inflammatory protein 1 alpha (MIP-1 alpha), regulated on activation normal T expressed and secreted protein (RANTES), monocyte chemoattractant protein 3 (MCP-3), and myeloid progenitor inhibitory factor-1 (MPIF-1).

C-C chemokine receptor type 2 (CCR2 or CD192). CCR2 has two predominant forms, CC CKR2A and CC CKR2B. CCR2 is the receptor for CCL2, the predominant agonist for CC CKR2A is MCP1, while both MCP1 and MCP3 are ligands for the CC CKR2B isoform.

C-C chemokine receptor type 3 (CCR3) is a protein that in humans is encoded by the CCR3 gene (also designated as CD193). This receptor binds and responds to a variety of chemokines, including eotaxin (CCL11), eotaxin-3 (CCL26), MCP-3 (CCL7), MCP-4 (CCL13), and RANTES (CCL5).

Chemokine (C-C motif) receptor 8, also known as CCR8, is a protein which in humans is encoded by the CCR8 gene. CCR8 has also been designated CDw198. The ligand of the CCR8 is CCL1. CCL8 also functions as a CCR8 agonist.

CX3C chemokine receptor 1 (CX3CR1) also known as the fractalkine receptor or G-protein coupled receptor 13 (GPR13) is a protein that in humans is encoded by the CX3CR1 gene. This receptor binds the chemokine CX3CL1 (also called neurotactin or fractalkine).

C-X-C chemokine receptor type 6 (CXCR6) is a protein that in humans is encoded by the CXCR6 gene. CXCR6 has also been designated CD186 (cluster of differentiation 186) and STRL33. STRL33 is expressed in lymphoid tissues and activated T-cells, and is induced in activated peripheral blood lymphocytes. STRL33 is a receptor for one of the chemokines. Other names for this receptor are Bonzo and TYMSTR.

FPRL1: N-formyl peptide receptor 2 is a G-protein coupled receptor (GPCR) protein that in humans is encoded by the FPR2 gene.

GPR1 is a member of the G protein-coupled receptor family of transmembrane receptors. It functions as a receptor for chemerin.

G-protein coupled receptor 15 (GPR15) is a protein that in humans is encoded by the GPR15 gene an orphan heterotrimeric guanine nucleotide-binding protein (G protein)-coupled receptor.

The apelin receptor (also known as the APJ receptor) is a G protein-coupled receptor which binds apelin and Apela/ELABELA/Toddler.

D6 or Chemokine-binding protein 2 is a protein that in humans is encoded by the CCBP2 gene.

CXCR4 is also known as fusin or CD184. A summary of CXCR4 function is provided, for instance, in Steen et al. (Targeting CXCR4 in HIV Cell-Entry Inhibition, Mini-Reviews in Medicinal Chemistry, 2009, 9, 1605-1621). The function of CXCR4 is regulated predominantly by the interaction of CXCR4 with its natural ligand Stromal Cell Derived Factor-1 (SDF-1), also called CXCL12 (chemokine C-X-C motif ligand 12. However, MIF can also function as a ligand for CXCR4 (See e.g., Schwartz et al., FEBS Lett 2009, 583: 2749; Bernhagen et al., Nat. Med. 2007, 13: 587). SDF-1 is found in two forms, SDF-1α/CXC12a and SDF-1β/CXC12b, which are produced by alternate splicing of the two genes. CXCR4 is more broadly expressed than most other chemokine receptors and was for a long time thought to be strictly monogamous in its relationship with the natural ligand, SDF-1. However, CXCR7 also uses SDF-1 as a ligand, and recent evidence has emerged that ubiquitin can also function as a ligand of CXCR4 (Saini V et al., (2010). *J. Biol. Chem.* 285 (20): 15566-76). The CXCR4/SDF-1 axis is involved in immune cell trafficking as it regulates chemotaxis of B cells, plasma cells, CD4$^+$ T-cells, and dendritic cells in vivo and activates the tight adhesion of rolling T-cells on activated epithelial cells and their subsequent transendothelial migration. The CXCR4/SDF-1 axis is required for normal myelopoiesis and lymphopoiesis and is in addition critical for proper embryonic development of numerous organ systems. CXCR4 is expressed in numerous tissues, such as peripheral blood leukocytes, spleen, thymus, spinal cord, heart, placenta, lung, liver, skeletal muscle, kidney pancreas, cerebellum, cerebral cortex and medulla, brain microvascular, coronary artery and umbilical cord endothelial cells. Mice lacking CXCR4 or SDF-1 have impaired hematopoiesis, derailed cerebellar neuron migration, defective formation of large vessels and cardiac ventricular septal defects, which can lead to cardiac failure (See e.g., Ma et al., PNAS 1998, 95:9448-9453; Zou et al., Nature 1998, 393:595-599). Preferably, the CXCR4 amino acid sequence is represented by:

(SEQ ID NO: 2)
MEGISSIPLPLLQIYTSDNYTEEMGSGDYDSMKEPCFREENANFNKIFLP

TIYSIIFLTGIVGNGLVILVMGYQKKLRSMTDKYRLHLSVADLLFVITLP

FWAVDAVANWYFGNFLCKAVHVIYTVNLYSSVLILAFISLDRYLAIVHAT

NSQRPRKLLAEKVVYVGVWIPALLLTIPDFIFANVSEADDRYICDRFYPN

DLWVVVFQFQHIMVGLILPGIVILSCYCIIISKLSHSKGHQKRKALKTTV

ILILAFFACWLPYYIGISIDSFILLEIIKQGCEFENTVHKWISITEALAF

FHCCLNPILYAFLGAKFKTSAQHALTSVSRGSSLKILSKGKRGGHSSVST

ESESSSFHSS.

While CXCR4, CCR5, CCR1, CCR2, CCR3, CCR8, CX3CR1, FPRL1, GPR1, GPR15, APJ, STRL33 and D6 can be used by HIV as a co-receptor to enter a cell, the "natural" function of CXCR4, CCR5, CCR1, CCR2, CCR3, CCR8, CX3CR1, FPRL1, GPR1, GPR15, APJ, STRL33 and D6 is in chemokine signaling. A "natural" function of the co-receptor (second target) relates to any change in a measurable biological or biochemical property elicited by said co-receptor (in the absence of HIV binding), including physiological changes of the cell such as changes in proliferation, differentiation, migration, survival, apoptosis, transport processes, metabolism, motility, cytokine release, cytokine composition, second messengers, enzymes, receptors, etc. due to chemokine signalling. Preferably the function of a target is determined by cell culture based potency assays as well known in the art. The "natural" function(s) of the co-receptor can be determined by any suitable assay known by the person skilled in the art, such as ELISA, FACS, Scatchard analysis, ALPHASCREEN®, SPR, functional assays, etc., for instance as discussed herein.

The efficacy or potency of the immunoglobulin single variable domains and polypeptides of the invention, and of compositions comprising the same on the natural function on said CR, can be tested using any suitable in vitro assay, cell-based assay, in vivo assay and/or animal model known per se, or any combination thereof, depending on the specific disease or disorder involved. Suitable assays and animal models will be clear to the skilled person, and for example include ligand displacement assays (Burgess et al., Cancer Res 2006 66:1721-9), dimerization assays (WO2009/007427A2, Goetsch, 2009), signaling assays (Burgess et al., Mol Cancer Ther 9:400-9), proliferation/survival assays (Pacchiana et al., J Biol Chem 2010 September M110.134031), cell adhesion assays (Holt et al., Haematologica 2005 90:479-88) and migration assays (Kong-Beltran et al., Cancer Cell 6:75-84), endothelial cell sprouting assays (Wang et al., J Immunol. 2009; 183:3204-11), and in vivo xenograft models (Jin et al., Cancer Res. 2008 68:4360-8), as well as the assays and animal models used in the experimental part below and in the prior art cited herein. A means to express the inhibition of said second target is by $IC_{50}$.

In one aspect, the disclosure provides an immunoglobulin single variable domain that inhibits binding of HIV to a co-receptor, preferably CXCR4, and does not displace a natural ligand from this co-receptor.

The present invention relates to a polypeptide according to any of the preceding claims, wherein said polypeptide inhibits binding of a natural ligand to said CR by less than about 50%, such as 40%, 30%, or 20% or even less than 10%, such as less than 5%.

In some embodiments, the natural ligand is Stromal Cell-Derived Factor-1 beta (SDF-1β) or Stromal Cell-Derived Factor-1 alpha (SDF-1α). In some embodiments, the $IC_{50}$ of SDF-1α or SDF-113 displacement from CXCR4 in the presence of the polypeptide of the invention is 10 nM or higher. In some embodiments, the $IC_{50}$ of SDF-1α or SDF-1β displacement from CXCR4 in the presence of the immunoglobulin single variable domain is 250 nM or higher. In some embodiments, the $IC_{50}$ of SDF-1α or SDF-1β displacement from CXCR4 in the presence of the polypeptide of the invention is 1 µM or higher. In some embodiments, the $IC_{50}$ of SDF-1α or SDF-1β displacement from CXCR4 in the presence of the immunoglobulin single variable domain is greater than the $IC_{50}$ of HIV inhibition.

In some embodiments, the $IC_{50}$ of HIV inhibition is lower than 50 nM, lower than 10 nM, or lower than 1 nM. In some embodiments the $IC_{50}$ of SDF-1α or SDF-1β displacement from CXCR4 in the presence of the polypeptide is greater than the $IC_{50}$ of HIV inhibition.

In some embodiments, the $IC_{50}$ of displacement of SDF-1α or SDF-1β from CXCR4 in the presence of the immunoglobulin single variable domain or polypeptide construct thereof is greater than the $IC_{50}$ of the inhibition of binding of HIV to the CR, such as CXCR4 by the immunoglobulin single variable domain or polypeptide constructs thereof by 1 pM or more, 10 pM or more, 100 pM or more, 500 pM or more, 1 nM or more, 10 nM or more, 20 nM or more, 30 nM or more, 40 nM or more, 50 nM or more, 60 nM or more, 70 nM or more, 80 nM or more, 100 nM or more, 500 nM or more, 1 µM or more, 10 µM or more, 50 µM or more, 100 µM or more, up to 1 mM.

In some embodiments, the $IC_{50}$ of displacement of SDF-1α or SDF-1β from CXCR4 in the presence of the immunoglobulin single variable domain or polypeptide thereof is greater than the $IC_{50}$ of the inhibition of binding of HIV to CXCR4 by the immunoglobulin single variable domain or polypeptide thereof by 1% or more, 2% or more, 5% or more, 10% or more, 20% or more, 50% or more, 100% or more, 2× higher or more, 5× higher or more, 10× higher or more, 20× higher or more, 50× higher or more, 100× higher or more, 1000× higher or more, up to 10,000× higher or more.

In some embodiments, the inhibition of HIV binding to CD4 and/or a co-receptor such as e.g. CXCR4 by the polypeptide of the invention is stronger (e.g., has a lower $IC_{50}$) than the inhibition of HIV binding to CXCR4 by AMD3100.

In some embodiments, the inhibition of HIV binding to CD4 and/or a co-receptor such as e.g. CXCR4 by the polypeptide of the invention is stronger (e.g., has a lower $IC_{50}$) than the inhibition of HIV binding to CXCR4 by 283D2-20GS-283D4 (see WO2009/138519).

Since various cell surface receptors require dimerization for activation, it is preferred that in such cases the second ISV of the invention does not impair these dimerization sites.

In some embodiments, the immunoglobulin single variable domains and polypeptides thereof do not displace a natural ligand from the co-receptor, e.g. CXCR4. In some embodiments, the natural ligand is Stromal Cell-Derived Factor-113 (SDF-1β) or Stromal Cell-Derived Factor-1 α (SDF-1α).

Displacing, as used herein, includes both complete and partial displacement. Thus, the disclosure embraces immunoglobulin single variable domains and polypeptides comprising one or more immunoglobulin single variable domains that do not displace natural ligand, or that displace less than 1%, less than 2%, less than 5%, less than 10%, less than 20%, less than 30%, less than 40%, less than 50%, less than 60%, less than 70%, less than 80%, less than 90%, up to less than 99% of displacement of a natural ligand from the CR, e.g. CXCR4. In some embodiments, the $IC_{50}$ of displacement of the natural ligand from the CR, such as e.g. SDF-1α or SDF-1β from CXCR4, in the presence of the immunoglobulin single variable domain or polypeptide thereof is 1 pM or higher, 10 pM or higher, 100 pM or higher, 500 pM or higher, 1 nM or higher, 10 nM or higher, 20 nM or higher, 30 nM or higher, 40 nM or higher, 50 nM or higher, 60 nM or higher, 70 nM or higher, 80 nM or higher, 100 nM or higher, 500 nM or higher, 1 µM or higher, 10 µM or higher, 50 µM or higher, 100 µM or higher, up to 1 mM.

The present invention also relates to a polypeptide as described herein, wherein said second ISV essentially consists of 4 framework regions (FR1 to FR4, respectively) and 3 complementarity determining regions (CDR1 to CDR3 respectively), in which
(i) CDR1 is chosen from the group consisting of SEQ ID NOs: 34-40; and amino acid sequences that have 1, 2 or 3 amino acid difference(s) with SEQ ID NOs: 34-408;

(ii) CDR2 is chosen from the group consisting of SEQ ID NOs: 48-56; and amino acid sequences that have 1, 2 or 3 amino acid difference(s) with SEQ ID NOs: 48-56; and (iii) CDR3 is chosen from the group consisting of SEQ ID NO: 67-75 and amino acid sequences that have 1, 2, 3 or 4 amino acid difference(s) with SEQ ID NOs: 67-75.

The present invention also relates to a polypeptide as described herein, wherein said second ISV essentially consists of 4 framework regions (FR1 to FR4, respectively) and 3 complementarity determining regions (CDR1 to CDR3 respectively), in which said ISV is chosen from the group consisting of CDR1 is SEQ ID NO: 34, CDR2 is SEQ ID NO: 48, and CDR3 is SEQ ID NO: 67;
CDR1 is SEQ ID NO: 34, CDR2 is SEQ ID NO: 49, and CDR3 is SEQ ID NO: 68;
CDR1 is SEQ ID NO: 35, CDR2 is SEQ ID NO: 50, and CDR3 is SEQ ID NO: 69;
CDR1 is SEQ ID NO: 36, CDR2 is SEQ ID NO: 51, and CDR3 is SEQ ID NO: 70;
CDR1 is SEQ ID NO: 37, CDR2 is SEQ ID NO: 52, and CDR3 is SEQ ID NO: 71;
CDR1 is SEQ ID NO: 35, CDR2 is SEQ ID NO: 53, and CDR3 is SEQ ID NO: 72;
CDR1 is SEQ ID NO: 38, CDR2 is SEQ ID NO: 54, and CDR3 is SEQ ID NO: 73;
CDR1 is SEQ ID NO: 39, CDR2 is SEQ ID NO: 55, and CDR3 is SEQ ID NO: 74; and
CDR1 is SEQ ID NO: 40, CDR2 is SEQ ID NO: 56, and CDR3 is SEQ ID NO: 75.

Accordingly, the present invention relates to a polypeptide as described herein, in which said second ISV essentially consists of 4 framework regions (FR1 to FR4, respectively) and 3 complementarity determining regions (CDR1 to CDR3 respectively), in which CDR1 is SEQ ID NO: 35, CDR2 is SEQ ID NO: 50 and CDR3 is SEQ ID NO: 69.

Accordingly, the present invention relates to a polypeptide as described herein, wherein said second ISV is chosen from the group consisting of 238D4 (SEQ ID NO: 4), 281A5 (SEQ ID NO: 5), 281E10 (SEQ ID NO: 6), 281D4 (SEQ ID NO: 7), 281A6 (SEQ ID NO: 8), 281F12 (SEQ ID NO: 9), 283B6 (SEQ ID NO: 10), 283E2 (SEQ ID NO: 11), 283F1 (SEQ ID NO: 12), 15F5 (SEQ ID NO: 13), 15G11 (SEQ ID NO: 14), 15A1 (SEQ ID NO: 15) and 10C3 (SEQ ID NO: 16), preferably in which said second ISV is 281F12 (SEQ ID NO: 9).

In an embodiment, the present invention relates to a polypeptide comprising a first and a second immunoglobulin single variable domain (ISV), wherein said first ISV binds to CD4 and/or polymorphic variants present on the surface of a cell; said second ISV binds to a co-receptor (CR) present on the surface of said cell, preferably wherein said CR is chosen from the group consisting of CXCR4, CCR5, CCR1, CCR2, CCR3, CCR8, CX3CR1, CXCR6, FPRL1, GPR1, GPR15, APJ, and D6 and related polymorphic variants. Preferably said CR is CXCR4.

In a preferred embodiment, the present invention relates to a polypeptide as described herein, wherein said first ISV essentially consists of 4 framework regions (FR1 to FR4, respectively) and 3 complementarity determining regions (CDR1 to CDR3 respectively), in which (i) CDR1 is chosen from the group consisting of SEQ ID NOs: 82-85; and amino acid sequences that have 1, 2 or 3 amino acid difference(s) with SEQ ID NOs: 82-85;

(ii) CDR2 is chosen from the group consisting of SEQ ID NOs: 88-91; and amino acid sequences that have 1, 2 or 3 amino acid difference(s) with SEQ ID NOs: 88-91; and (iii) CDR3 is chosen from the group consisting of SEQ ID NO: 96-99 and amino acid sequences that have 1, 2, 3 or 4 amino acid difference(s) with SEQ ID NOs: 96-99;

and, wherein said second ISV essentially consists of 4 framework regions (FR1 to FR4, respectively) and 3 complementarity determining regions (CDR1 to CDR3 respectively), in which (i) CDR1 is chosen from the group consisting of SEQ ID NOs: 34-40; and amino acid sequences that have 1, 2 or 3 amino acid difference(s) with SEQ ID NOs: 34-40;

(ii) CDR2 is chosen from the group consisting of SEQ ID NOs: 48-56; and amino acid sequences that have 1, 2 or 3 amino acid difference(s) with SEQ ID NOs: 48-56; and (iii) CDR3 is chosen from the group consisting of SEQ ID NO: 67-75 and amino acid sequences that have 1, 2, 3 or 4 amino acid difference(s) with SEQ ID NOs: 67-75.

The present invention also relates to a polypeptide as described herein, wherein said first ISV essentially consists of 4 framework regions (FR1 to FR4, respectively) and 3 complementarity determining regions (CDR1 to CDR3 respectively), in which said ISV is chosen from the group consisting of CDR1 is SEQ ID NO: 82, CDR2 is SEQ ID NO: 88, and CDR3 is SEQ ID NO: 96;
CDR1 is SEQ ID NO: 83, CDR2 is SEQ ID NO: 89, and CDR3 is SEQ ID NO: 97;
CDR1 is SEQ ID NO: 84, CDR2 is SEQ ID NO: 90, and CDR3 is SEQ ID NO: 98; and
CDR1 is SEQ ID NO: 85, CDR2 is SEQ ID NO: 91, and CDR3 is SEQ ID NO: 99.

wherein said second ISV essentially consists of 4 framework regions (FR1 to FR4, respectively) and 3 complementarity determining regions (CDR1 to CDR3 respectively), in which said ISV is chosen from the group consisting of CDR1 is SEQ ID NO: 34, CDR2 is SEQ ID NO: 48, and CDR3 is SEQ ID NO: 67;
CDR1 is SEQ ID NO: 34, CDR2 is SEQ ID NO: 49, and CDR3 is SEQ ID NO: 68;
CDR1 is SEQ ID NO: 35, CDR2 is SEQ ID NO: 50, and CDR3 is SEQ ID NO: 69;
CDR1 is SEQ ID NO: 36, CDR2 is SEQ ID NO: 51, and CDR3 is SEQ ID NO: 70;
CDR1 is SEQ ID NO: 37, CDR2 is SEQ ID NO: 52, and CDR3 is SEQ ID NO: 71;
CDR1 is SEQ ID NO: 35, CDR2 is SEQ ID NO: 53, and CDR3 is SEQ ID NO: 72;
CDR1 is SEQ ID NO: 38, CDR2 is SEQ ID NO: 54, and CDR3 is SEQ ID NO: 73;
CDR1 is SEQ ID NO: 39, CDR2 is SEQ ID NO: 55, and CDR3 is SEQ ID NO: 74; and
CDR1 is SEQ ID NO: 40, CDR2 is SEQ ID NO: 56, and CDR3 is SEQ ID NO: 75.

In a preferred embodiment, the present invention relates to a polypeptide as described herein, wherein said first ISV essentially consists of 4 framework regions (FR1 to FR4, respectively) and 3 complementarity determining regions (CDR1 to CDR3 respectively), in which (i) CDR1 is chosen from the group consisting of SEQ ID NO: 85 and amino acid sequences that have 1, 2 or 3 amino acid difference(s) with SEQ ID NO: 85;

(ii) CDR2 is chosen from the group consisting of SEQ ID NO: 91 and amino acid sequences that have 1, 2 or 3 amino acid difference(s) with SEQ ID NO: 91; and (iii) CDR3 is chosen from the group consisting of SEQ ID NO: 99 and amino acid sequences that have 1, 2, 3 or 4 amino acid difference(s) with SEQ ID NO: 99;

and, wherein said second ISV essentially consists of 4 framework regions (FR1 to FR4, respectively) and 3 complementarity determining regions (CDR1 to CDR3 respectively), in which (i) CDR1 is chosen from the group consisting of SEQ ID NO: 35 and amino acid sequences that have 1, 2 or 3 amino acid difference(s) with SEQ ID NO: 35;

(ii) CDR2 is chosen from the group consisting of SEQ ID NO: 50 and amino acid sequences that have 1, 2 or 3 amino acid difference(s) with SEQ ID NO: 50; and (iii) CDR3 is chosen from the group consisting of SEQ ID NO: 69 and amino acid sequences that have 1, 2, 3 or 4 amino acid difference(s) with SEQ ID NO: 69.

In a preferred embodiment, the present invention relates to a polypeptide as described herein, wherein said first ISV essentially consists of 4 framework regions (FR1 to FR4, respectively) and 3 complementarity determining regions (CDR1 to CDR3 respectively), in which (i) CDR1 is represented by SEQ ID NO: 85;
(ii) CDR2 is represented by SEQ ID NO: 91; and
(iii) CDR3 is represented by SEQ ID NO: 99;

and, wherein said second ISV essentially consists of 4 framework regions (FR1 to FR4, respectively) and 3 complementarity determining regions (CDR1 to CDR3 respectively), in which (i) CDR1 is represented by SEQ ID NO: 35;
(ii) CDR2 is represented by SEQ ID NO: 50; and
(iii) CDR3 is represented by SEQ ID NO: 69.

In a preferred embodiment, the present invention relates to a polypeptide as described herein, wherein said first ISV is chosen from the group consisting of 01B6 (SEQ ID NO: 17), 01E2 (SEQ ID NO: 18), 01H12 (SEQ ID NO: 19) and 03F11 (SEQ ID NO: 20), and wherein said second ISV is chosen from the group consisting of 238D4 (SEQ ID NO: 4), 281A5 (SEQ ID NO: 5), 281E10 (SEQ ID NO: 6), 281D4 (SEQ ID NO: 7), 281A6 (SEQ ID NO: 8), 281F12 (SEQ ID NO: 9), 283B6 (SEQ ID NO: 10), 283E2 (SEQ ID NO: 11), 283F1 (SEQ ID NO: 12), 15F5 (SEQ ID NO: 13), 15G11 (SEQ ID NO: 14), 15A1 (SEQ ID NO: 15) and 10C3 (SEQ ID NO: 16).

In a preferred embodiment, the present invention relates to a polypeptide chosen from the group consisting of 03F11-9GS-281F12 (SEQ ID NO: 101), 03F11-25GS-281F12 (SEQ ID NO: 102), 03F11-35GS-281F12 (SEQ ID NO: 103), 281F12-9GS-03F11 (SEQ ID NO: 104), 281F12-25GS-03F11 (SEQ ID NO: 105), 281F12-35GS-03F11 (SEQ ID NO: 106), 15G11(Q108L)-15GS-ALB11-15GS-03F11(Q108L) (SEQ ID NO: 107), 15F05(Q108L)-15GS-ALB11-15GS-03F11(Q108L) (SEQ ID NO: 108), and 281F12(Q108L)-15GS-ALB11-15GS-03F11(Q108L) (SEQ ID NO: 109).

In a specific, but non-limiting aspect of the invention, which will be further described herein, the polypeptides of the invention have an increased half-life in serum (as further described herein) compared to the immunoglobulin single variable domain from which they have been derived. For example, an immunoglobulin single variable domain of the invention may be linked (chemically or otherwise) to one or more groups or moieties that extend the half-life (such as PEG), so as to provide a derivative of an amino acid sequence of the invention with increased half-life.

As demonstrated in the examples, half-life extension did not affect potency substantially. This indicates that half-life extended bispecific constructs are still capable of binding simultaneously to their respective targets.

In a specific aspect of the invention, a compound of the invention or a polypeptide of the invention may have an increased half-life, compared to the corresponding amino acid sequence of the invention. Some preferred, but non-limiting examples of such compounds and polypeptides will become clear to the skilled person based on the further disclosure herein, and for example comprise immunoglobulin single variable domains or polypeptides of the invention that have been chemically modified to increase the half-life thereof (for example, by means of pegylation); immunoglobulin single variable domains of the invention that comprise at least one additional binding site for binding to a serum protein (such as serum albumin); or polypeptides of the invention which comprise at least one amino acid sequence of the invention that is linked to at least one moiety (and in particular at least one amino acid sequence) which increases the half-life of the amino acid sequence of the invention. Examples of polypeptides of the invention which comprise such half-life extending moieties or immunoglobulin single variable domains will become clear to the skilled person based on the further disclosure herein; and for example include, without limitation, polypeptides in which the one or more immunoglobulin single variable domains of the invention are suitably linked to one or more serum proteins or fragments thereof (such as (human) serum albumin or suitable fragments thereof) or to one or more binding units that can bind to serum proteins (such as, for example, domain antibodies, immunoglobulin single variable domains that are suitable for use as a domain antibody, single domain antibodies, immunoglobulin single variable domains that are suitable for use as a single domain antibody, "dAb" 's, immunoglobulin single variable domains that are suitable for use as a dAb, or Nanobodies that can bind to serum proteins such as serum albumin (such as human serum albumin), serum immunoglobulins such as IgG, or transferrin; reference is made to the further description and references mentioned herein); polypeptides in which an amino acid sequence of the invention is linked to an Fc portion (such as a human Fc) or a suitable part or fragment thereof; or polypeptides in which the one or more immunoglobulin single variable domains of the invention are suitable linked to one or more small proteins or peptides that can bind to serum proteins, such as, without limitation, the proteins and peptides described in WO 91/01743, WO 01/45746, WO 02/076489, WO2008/068280, WO2009/127691 and PCT/EP2011/051559.

Generally, the compounds or polypeptides of the invention with increased half-life preferably have a half-life that is at least 1.5 times, preferably at least 2 times, such as at least 5 times, for example at least 10 times or more than 20 times, greater than the half-life of the corresponding amino acid sequence of the invention per se. For example, the compounds or polypeptides of the invention with increased half-life may have a half-life e.g., in humans that is increased with more than 1 hours, preferably more than 2 hours, more preferably more than 6 hours, such as more than 12 hours, or even more than 24, 48 or 72 hours, compared to the corresponding amino acid sequence of the invention per se.

In a preferred, but non-limiting aspect of the invention, such compounds or polypeptides of the invention have a serum half-life e.g. in humans that is increased with more than 1 hours, preferably more than 2 hours, more preferably more than 6 hours, such as more than 12 hours, or even more than 24, 48 or 72 hours, compared to the corresponding amino acid sequence of the invention per se.

In another preferred, but non-limiting aspect of the invention, such compounds or polypeptides of the invention exhibit a serum half-life in human of at least about 12 hours, preferably at least 24 hours, more preferably at least 48 hours, even more preferably at least 72 hours or more. For example, compounds or polypeptides of the invention may have a half-life of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

In a particularly preferred but non-limiting aspect of the invention, the invention provides a polypeptide of the invention comprising a first and a second immunoglobulin single variable domain (ISV); and further comprising one or more (preferably one) serum albumin binding immunoglobulin single variable domain as described herein, e.g. the serum albumin binding immunoglobulin single variable domain of Alb8, Alb23, Alb129, Alb132, Alb11, Alb11 (S112K)-A, Alb82, Alb82-A, Alb82-AA, Alb82-AAA, Alb82-G, Alb82-GG, Alb82-GGG (cf. Table HLE Below).

The present invention relates to a polypeptide as described herein, wherein said serum protein binding moiety binds serum albumin.

The present invention relates to a polypeptide as described herein, wherein said serum protein binding moiety is an immunoglobulin single variable domain binding serum albumin.

The present invention relates to a polypeptide as described herein, wherein said ISV binding serum albumin essentially consists of 4 framework regions (FR1 to FR4, respectively) and 3 complementarity determining regions (CDR1 to CDR3 respectively), in which CDR1 is SFGMS (SEQ ID NO: 124), CDR2 is SISGSGSDTLYADSVKG (SEQ ID NO: 125), and in which CDR3 is GGSLSR (SEQ ID NO: 126).

The present invention relates to a polypeptide as described herein, wherein said ISV binding serum albumin comprises Alb8, Alb23, Alb129, Alb132, Alb11, Alb11 (S112K)-A, Alb82, Alb82-A, Alb82-AA, Alb82-AAA, Alb82-G, Alb82-GG, Alb82-GGG.

In the polypeptides of the invention, the two or more building blocks, ISVs, such as e.g. Nanobodies, and the optionally one or more polypeptides one or more other groups, drugs, agents, residues, moieties or binding units may be directly linked to each other (as for example described in WO 99/23221) and/or may be linked to each other via one or more suitable spacers or linkers, or any

TABLE HLE

| Name | SEQ ID NO | Amino acid sequence |
|---|---|---|
| Alb8 | 111 | EVQLVESGGGLVQPGNSLRLSCAASGFTFSSFGMSWVRQAPGKGLEWVSSISGSGSDTL<br>YADSVKGRFTISRDNAKTTLYLQMNSLRPEDTAVYYCTIGGSLSRSSQGTLVTVSS |
| Alb23 | 112 | EVQLLESGGGLVQPGGSLRLSCAASGFTFRSFGMSWVRQAPGKGPEWVSSISGSGSDTL<br>YADSVKGRFTISRDNSKNTLYLQMNSLRPEDTAVYYCTIGGSLSRSSQGTLVTVSS |
| Alb129 | 113 | EVQLVESGGGVVQPGNSLRLSCAASGFTFSSFGMSWVRQAPGKGLEWVSSISGSGSDTL<br>YADSVKGRFTISRDNAKTTLYLQMNSLRPEDTATYYCTIGGSLSRSSQGTLVTVSSA |
| Alb132 | 114 | EVQLVESGGGVVQPGGSLRLSCAASGFTFRSFGMSWVRQAPGKGPEWVSSISGSGSDT<br>LYADSVKGRFTISRDNSKNTLYLQMNSLRPEDTATYYCTIGGSLSRSSQGTLVTVSSA |
| Alb11 | 115 | EVQLVESGGGLVQPGNSLRLSCAASGFTFSSFGMSWVRQAPGKGLEWVSSISGSGSDTL<br>YADSVKGRFTISRDNAKTTLYLQMNSLRPEDTAVYYCTIGGSLSRSSQGTLVTVSS |
| Alb11 (S112K)-A | 116 | EVQLVESGGGLVQPGNSLRLSCAASGFTFSSFGMSWVRQAPGKGLEWVSSISGSGSDTL<br>YADSVKGRFTISRDNAKTTLYLQMNSLRPEDTAVYYCTIGGSLSRSSQGTLVKVSSA |
| Alb82 | 117 | EVQLVESGGGVVQPGNSLRLSCAASGFTFSSFGMSWVRQAPGKGLEWVSSISGSGSDTL<br>YADSVKGRFTISRDNAKTTLYLQMNSLRPEDTALYYCTIGGSLSRSSQGTLVTVSS |
| Alb82-A | 118 | EVQLVESGGGVVQPGNSLRLSCAASGFTFSSFGMSWVRQAPGKGLEWVSSISGSGSDTL<br>YADSVKGRFTISRDNAKTTLYLQMNSLRPEDTALYYCTIGGSLSRSSQGTLVTVSSA |
| Alb82-AA | 119 | EVQLVESGGGVVQPGNSLRLSCAASGFTFSSFGMSWVRQAPGKGLEWVSSISGSGSDTL<br>YADSVKGRFTISRDNAKTTLYLQMNSLRPEDTALYYCTIGGSLSRSSQGTLVTVSSAA |
| Alb82-AAA | 120 | EVQLVESGGGVVQPGNSLRLSCAASGFTFSSFGMSWVRQAPGKGLEWVSSISGSGSDTL<br>YADSVKGRFTISRDNAKTTLYLQMNSLRPEDTALYYCTIGGSLSRSSQGTLVTVSSAAA |
| Alb82-G | 121 | EVQLVESGGGVVQPGNSLRLSCAASGFTFSSFGMSWVRQAPGKGLEWVSSISGSGSDTL<br>YADSVKGRFTISRDNAKTTLYLQMNSLRPEDTALYYCTIGGSLSRSSQGTLVTVSSG |
| Alb82-GG | 122 | EVQLVESGGGVVQPGNSLRLSCAASGFTFSSFGMSWVRQAPGKGLEWVSSISGSGSDTL<br>YADSVKGRFTISRDNAKTTLYLQMNSLRPEDTALYYCTIGGSLSRSSQGTLVTVSSGG |
| Alb82-GGG | 123 | EVQLVESGGGVVQPGNSLRLSCAASGFTFSSFGMSWVRQAPGKGLEWVSSISGSGSDTL<br>YADSVKGRFTISRDNAKTTLYLQMNSLRPEDTALYYCTIGGSLSRSSQGTLVTVSSGGG |

Accordingly, the present invention relates to a polypeptide as described herein, further comprising a serum protein binding moiety.

combination thereof. Suitable spacers or linkers for use in multivalent and multispecific polypeptides will be clear to the skilled person, and may generally be any linker or spacer used in the art to link amino acid sequences. Preferably, said linker or spacer is suitable for use in constructing proteins or polypeptides that are intended for pharmaceutical use. In contrast to expectations, there was no apparent effect of linker length between the first ISV and second ISV as demonstrated in the examples.

Some particularly preferred spacers include the spacers and linkers that are used in the art to link antibody fragments or antibody domains. These include the linkers mentioned in the general background art cited above, as well as for example linkers that are used in the art to construct diabodies or ScFv fragments (in this respect, however, it should be noted that, whereas in diabodies and in ScFv fragments, the linker sequence used should have a length, a degree of flexibility and other properties that allow the pertinent $V_H$ and $V_L$ domains to come together to form the complete antigen-binding site, there is no particular limitation on the length or the flexibility of the linker used in the polypeptide of the invention, since each Nanobody by itself forms a complete antigen-binding site).

For example, a linker may be a suitable amino acid sequence, and in particular amino acid sequences of between 1 and 50, preferably between 1 and 30, such as between 1 and 10 amino acid residues. Some preferred examples of such amino acid sequences include gly-ser linkers, for example of the type $(gly_x ser_y)_z$, such as (for example $(gly_4 ser)_3$ or $(gly_3 ser_2)_3$, as described in WO 99/42077 and the GS30, GS15, GS9 and GS7 linkers described in the applications by Ablynx mentioned herein (see for example WO 06/040153 and WO 06/122825), as well as hinge-like regions, such as the hinge regions of naturally occurring heavy chain antibodies or similar sequences (such as described in WO 94/04678). Preferred linkers are depicted in Table Linkers below.

TABLE Linkers

| Name | SEQ ID NO | Amino acid sequence |
|---|---|---|
| 5GS | 127 | GGGGS |
| 7GS | 128 | SGGSGGS |
| 9GS | 129 | GGGGSGGGS |
| 10GS | 130 | GGGGSGGGGS |
| 15GS | 131 | GGGGSGGGGSGGGGS |
| 18GS | 132 | GGGGSGGGGSGGGGGGS |
| 20GS | 133 | GGGGSGGGGSGGGGSGGGGS |
| 25GS | 134 | GGGGSGGGGSGGGGSGGGGSGGGGS |
| 30GS | 135 | GGGGSGGGGSGGGGSGGGGSGGGGSGGGGS |
| 35GS | 136 | GGGGSGGGGSGGGGSGGGGSGGGGSGGGGSGGGGS |

Some other particularly preferred linkers are poly-alanine (such as AAA), as well as the linkers GS30 (SEQ ID NO: 85 in WO 06/122825) and GS9 (SEQ ID NO: 84 in WO 06/122825).

Other suitable linkers generally comprise organic compounds or polymers, in particular those suitable for use in proteins for pharmaceutical use. For instance, poly(ethyleneglycol) moieties have been used to link antibody domains, see for example WO 04/081026.

It is encompassed within the scope of the invention that the length, the degree of flexibility and/or other properties of the linker(s) used (although not critical, as it usually is for linkers used in ScFv fragments) may have some influence on the properties of the final polypeptide of the invention, including but not limited to the affinity, specificity or avidity for a chemokine, or for one or more of the other antigens. Based on the disclosure herein, the skilled person will be able to determine the optimal linker(s) for use in a specific polypeptide of the invention, optionally after some limited routine experiments.

For example, in multivalent polypeptides of the invention that comprise building blocks, ISVs or Nanobodies directed against a first and second target, the length and flexibility of the linker are preferably such that it allows each building block, ISV or Nanobody of the invention present in the polypeptide to bind to its cognate target, e.g. the antigenic determinant on each of the targets. Again, based on the disclosure herein, the skilled person will be able to determine the optimal linker(s) for use in a specific polypeptide of the invention, optionally after some limited routine experiments.

It is also within the scope of the invention that the linker(s) used confer one or more other favourable properties or functionality to the polypeptides of the invention, and/or provide one or more sites for the formation of derivatives and/or for the attachment of functional groups (e.g. as described herein for the derivatives of the Nanobodies of the invention). For example, linkers containing one or more charged amino acid residues can provide improved hydrophilic properties, whereas linkers that form or contain small epitopes or tags can be used for the purposes of detection, identification and/or purification. Again, based on the disclosure herein, the skilled person will be able to determine the optimal linkers for use in a specific polypeptide of the invention, optionally after some limited routine experiments.

Finally, when two or more linkers are used in the polypeptides of the invention, these linkers may be the same or different. Again, based on the disclosure herein, the skilled person will be able to determine the optimal linkers for use in a specific polypeptide of the invention, optionally after some limited routine experiments.

Usually, for easy of expression and production, a polypeptide of the invention will be a linear polypeptide. However, the invention in its broadest sense is not limited thereto. For example, when a polypeptide of the invention comprises three of more building blocks, ISV or Nanobodies, it is possible to link them by use of a linker with three or more "arms", which each "arm" being linked to a building block, ISV or Nanobody, so as to provide a "star-shaped" construct. It is also possible, although usually less preferred, to use circular constructs.

Accordingly, the present invention relates to a polypeptide as described herein, wherein said first ISV and said second ISV and possibly said ISV binding serum albumin are directly linked to each other or are linked via a linker.

The present invention relates to a polypeptide as described herein, wherein said linker is chosen from the group consisting of linkers of 5GS, 7GS, 9GS, 10GS, 15GS, 18GS, 20GS, 25GS and 30GS.

The present invention relates to a polypeptide as described herein, wherein said serum protein binding moiety is a non-antibody based polypeptide (e.g. PEG).

In the present, medical context, HIV infection is the tendency of a medical condition to become progressively worse and if not treated results in AIDS and potentially in death. HIV infection results in a decline in the number of CD4+ T-cells in the infected person. Below a critical number of CD4+ T-cells, cell-mediated immunity is effectively lost, and a variety of infections by opportunistic microorganisms appear, resulting in Acquired Immunodeficiency Syndrome (AIDS). These phenomena of (progressing) HIV infection are well known in the art.

The pharmacologic effect of the polypeptides of the invention therefore will reside eventually in inhibiting or impairing at least one, but preferably more than one result of an HIV infection.

In one aspect, the disclosure provides methods for lowering the HIV-titer (e.g. viral load) in a subject, the method comprising administering to the subject a therapeutically effective amount of an immunoglobulin single variable domain or a polypeptide comprising one or more immunoglobulin single variable domains of the invention to lower the HIV-titer in the subject. In some embodiments, the administered immunoglobulin single variable domain or polypeptide thereof inhibits binding of HIV to CD4 and/or a CR, such as e.g. CXCR4 receptor but preferably does not displace a natural ligand from said CR, such as e.g. CXCR4. In some embodiments, the administered immunoglobulin single variable domain or polypeptide thereof have only minimal undesirable side effects.

The immunoglobulin single variable domains and polypeptides thereof inhibit binding of HIV to CD4 and/or a CR, such as e.g. CXCR4. By binding the CD4 and/or a CR, such as e.g. CXCR4 the immunoglobulin single variable domain or polypeptide thereof prevents HIV from entering the cell. HIV cannot survive for prolonged periods of time outside of a cellular environment. Thus, if HIV cannot enter the cell and remains in the extracellular environment, HIV will eventually expire and be disposed of by the body, eventually resulting in the lowering of the HIV-titer in a person.

Methods for determining the amount of HIV in a subject (the HIV-titer) are routine in the art (cf. supra). Generally, a blood sample from a subject is provided and the amount of HIV (e.g., the amount of HIV-particles) is determined either directly (by assaying for the presence of HIV) or indirectly (e.g., by assaying for the presence of antibodies against HIV). Determining the presence of HIV, or antibodies against HIV, is routine in the art and can be performed, for instance, by ELISA. Additional methods of determining the amount of HIV in a subject include the functional inhibition assays discussed above, assays to determine the presence and amount of specific antigens, such as the p24 antigen test (commercially available for instance through PerkinElmer, and Advanced Bioscience Laboratories), and assays to determine the presence and amount of specific nucleic acids encoding the HIV genome, for instance through reverse transcriptase activity (e.g., ExaVir Load; Cavidi Tech-AB, Uppsala, Sweden; See e.g., Sivapalasingam et al., J Clin Microbiol 2005, 43, 3793).

The methods disclosed herein are applicable to any form of HIV including HIV-1 and HIV-2, and all of the subclasses, e.g., HIV-1B, HIV-1D, etc. In some embodiments, the methods disclosed herein are applicable to viruses related to HIV, such as the simian virus SIV.

The present invention relates to a polypeptide as described herein, for use in treating a subject in need thereof (infected with HIV, preferably HIV-1, preferably subtype C).

The present invention relates to a pharmaceutical composition comprising a polypeptide as described herein.

The present invention relates to a method for delivering a prophylactic and/or therapeutic polypeptide to a specific location, tissue or cell type in the body, the method comprising the steps of administering to a subject a polypeptide as described herein.

The present invention relates to a method for treating a subject in need thereof comprising administering a polypeptide as described herein.

Also, the present invention relates to a method for treating a subject as described above, wherein said subject is infected with HIV R5, HIV X4, and/or HIV X4R5.

In one aspect, the disclosure provides a method for treating a subject suffering from infection by HIV, the method comprising administering to the subject an immunoglobulin single variable domain or a polypeptide construct comprising one or more immunoglobulin single variable domains to treat the infection by HIV. In some embodiments, the administered immunoglobulin single variable domain or polypeptide constructs thereof inhibits binding of HIV to CD4 and/or a CR, such as e.g. CXCR4 but preferably does not displace a natural ligand from said CR, such as e.g. CXCR4. In some embodiments, the administered immunoglobulin single variable domain or polypeptides construct thereof have only minimal undesirable side effects.

The term "treating a subject suffering from HIV infection" as used herein refers to any method that results in a reduction in the severity of symptoms (e.g., opportunistic microbial infections) or number of symptoms (e.g., number of opportunistic infections) associated with HIV infection in a subject.

In some embodiments, treating a subject suffering from HIV results in an increase in the white blood cell count in said subject.

In some embodiments, treating a subject suffering from HIV results in an increase in the number of CD4+ T-cells in the subject.

In some embodiments, treating a subject suffering from HIV results in a decrease in the HIV-titer in the subject.

Accordingly, the present invention relates to a method for lowering the HIV-titer in a subject, the method comprising administering to the subject a therapeutically effective amount of a polypeptide as described herein to lower the HIV-titer in the subject.

In some embodiments, treating a subject suffering from HIV results in a decrease in the number of opportunistic microbial infections in the person.

Whether treatment is effective can be assessed, for instance, by determining the change in one or more physiological parameters associated with HIV infection (e.g., lowering of HIV-titer, decrease of the number of infected cells, increase in the amount of CD4+ T-cells), or by assessing the health of a subject at the whole-body level (e.g., decrease in the number of opportunistic infections).

In one aspect, the disclosure provides methods for treating a subject suffering from HIV infection with minimal unwanted side effects. Traditional anti-HIV treatment regimens (e.g., ART), including the administration of HIV-protease inhibitors and HIV-reverse transcriptase inhibitors is associated with a number of unwanted side effects, including liver toxicity, bloating, loss of appetite, etc. A person of ordinary skill in the art can determine if unwanted side effects have decreased, e.g., by assessing the level of liver toxicity, bloating, etc. In some embodiments, the unwanted side effects are side effects associated with stem cell mobilization. Methods of determining the level of stem cell mobilization are known in the art.

A subject, as used herein, includes a mammal that is susceptible to HIV infection (e.g., a human), or infection by a related virus such as SIV (e.g., a monkey). In some embodiments, the subject is a primate. In some embodiment, the subject is human. In some embodiments, the subject is receiving, or has received, one or more anti-HIV treatment regimens (e.g., ART therapy or a component thereof).

As demonstrated in the present invention, it is very difficult for HIV strain to become resistant to the polypeptide of the invention, even when using monovalent Nanobodies for inducing resistance.

Surprisingly, even on viruses that are resistant to one of the receptors, the bispecific polypeptide retains a strong potency in the picoMolar range in inhibition of HIV1 entry, suggesting that functionality of only one of the arms of the bispecific polypeptides is sufficient for the potent inhibition, when the other arm can provide binding avidity.

Accordingly, the invention relates to a method for treating a subject infected with HIV, comprising administering a polypeptide as described herein, wherein said HIV does not develop, e.g. delays, resistance to said polypeptide for at least 3 months, such as at least 6 months, or even longer such as e.g. 9 m, 11 m, 1 y, 1.5 y, 2 y or even longer.

In the above methods, the amino acid sequences, ISV's, such as e.g. Nanobodies, and/or polypeptides of the invention and/or the compositions comprising the same can be administered in any suitable manner, depending on the specific pharmaceutical formulation or composition to be used. Thus, the amino acid sequences, ISV's, such as e.g. Nanobodies, and/or polypeptides of the invention and/or the compositions comprising the same can for example be administered orally, intraperitoneally (e.g. intravenously, subcutaneously, intramuscularly, or via any other route of administration that circumvents the gastrointestinal tract), intranasally, transdermally, topically, by means of a suppository, by inhalation, again depending on the specific pharmaceutical formulation or composition to be used. The clinician will be able to select a suitable route of administration and a suitable pharmaceutical formulation or composition to be used in such administration, depending on the disease or disorder to be prevented or treated and other factors well known to the clinician.

The amino acid sequences, ISV's, such as e.g. Nanobodies, and/or polypeptides of the invention and/or the compositions comprising the same are administered according to a regime of treatment that is suitable for preventing and/or treating the HIV infection to be prevented or treated. The clinician will generally be able to determine a suitable treatment regimen, depending on factors such as the stage of the HIV infection to be treated, the severity of the HIV infection to be treated and/or the severity of the symptoms thereof, the specific amino acid sequence, ISV, such as e.g. a Nanobody, or polypeptide of the invention to be used, the specific route of administration and pharmaceutical formulation or composition to be used, the age, gender, weight, diet, general condition of the patient, and similar factors well known to the clinician.

Generally, the treatment regimen will comprise the administration of one or more amino acid sequences, ISV's, such as e.g. Nanobodies, and/or polypeptides of the invention, or of one or more compositions comprising the same, in one or more pharmaceutically effective amounts or doses. The specific amount(s) or doses to be administered can be determined by the clinician, again based on the factors cited above.

Generally, for the prevention and/or treatment of an HIV infection mentioned herein and depending on the specific strain or type and stage of the disease to be treated, the potency of the specific amino acid sequence, ISV, such as e.g. a Nanobody, and polypeptide of the invention to be used, the specific route of administration and the specific pharmaceutical formulation or composition used, the amino acid sequences, ISV's, such as e.g. Nanobodies, and polypeptides of the invention will generally be administered in an amount between 1 gram and 0.01 milligram per kg body weight per day, preferably between 0.1 gram and 0.01 milligram per kg body weight per day, such as about 0.1, 1, 10, 100 or 1000 milligram per kg body weight per day, e.g. from 0.1 mg per kg to 25 mg per kg of the subject's body weight; either continuously (e.g. by infusion), as a single daily dose or as multiple divided doses during the day. The clinician will generally be able to determine a suitable daily dose, depending on the factors mentioned herein. It will also be clear that in specific cases, the clinician may choose to deviate from these amounts, for example on the basis of the factors cited above and his expert judgment. Generally, some guidance on the amounts to be administered can be obtained from the amounts usually administered for comparable conventional antibodies or antibody fragments against the same target administered via essentially the same route, taking into account however differences in affinity/avidity, efficacy, biodistribution, half-life and similar factors well known to the skilled person.

Usually, in the above method, a single amino acid sequence, ISV, such as e.g. a Nanobody, or polypeptide of the invention will be used. It is however within the scope of the invention to use two or more amino acid sequences, ISV's, such as e.g. Nanobodies, and/or polypeptides of the invention in combination.

The ISV's, such as e.g. Nanobodies, amino acid sequences and polypeptides of the invention may also be used in combination with one or more further pharmaceutically active compounds or principles, i.e. as a combined treatment regimen, which may or may not lead to a synergistic effect. Again, the clinician will be able to select such further compounds or principles, as well as a suitable combined treatment regimen, based on the factors cited above and his expert judgment.

In particular, the amino acid sequences, ISV's, such as e.g. Nanobodies, and polypeptides of the invention may be used in combination with other pharmaceutically active compounds or principles that are or can be used for the prevention and/or treatment of the HIV infection and/or any opportunistic infection, disease and/or disorder cited herein, as a result of which a synergistic effect may or may not be obtained. Examples of such compounds and principles, as well as routes, methods and pharmaceutical formulations or compositions for administering them will be clear to the clinician.

When two or more substances or principles are to be used as part of a combined treatment regimen, they can be administered via the same route of administration or via different routes of administration, at essentially the same time or at different times (e.g. essentially simultaneously, consecutively, or according to an alternating regime). When the substances or principles are to be administered simultaneously via the same route of administration, they may be administered as different pharmaceutical formulations or compositions or part of a combined pharmaceutical formulation or composition, as will be clear to the skilled person.

In order to evade HIV resistance and prolong efficacy, contemporary anti-HIV treatment regimens comprise a cocktail of anti-HIV drugs. Hence, it is advantageous to include the polypeptide of the invention into an anti-HIV treatment regimen, such as e.g. ART therapy or a component thereof. In some embodiments, the subject is treated with a polypeptide of the invention and ART therapy or a component thereof, such as e.g. one or more protease inhibitors (PRs), e.g. amprenavir (AMP), atazanavir (ATV), indinavir (IDV), lopinavir (LPV), nelfinavir (NFV), ritonavir (RTV) or saquinavir (SQV); and/or reverse transcriptase inhibitors (RTIs), e.g. a non-nucleoside reverse transcriptase inhibitor (NNRTI) [abacavir (ABC), delavirdine (DLV), efavirenz (EFV), nevirapine (NVP) and tenofovir (TFV)]; or a nucleoside analogue reverse transcriptase inhibitor (NRTI) [didanosine (ddl), stavudine (d4T), lamivudine (3TC) and zidovudine (ZDV)].

In some embodiments, HIV is, or has become, resistant to one or more anti-HIV treatment regimens (e.g., ART therapy or a component thereof), for instance, wherein HIV is, or has become, resistant to one or more protease inhibitors (PRs), e.g. amprenavir (AMP), atazanavir (ATV), indinavir (IDV), lopinavir (LPV), nelfinavir (NFV), ritonavir (RTV) or saquinavir (SQV); and/or reverse transcriptase inhibitors (RTIs), e.g. a non-nucleoside reverse transcriptase inhibitor (NNRTI) [abacavir (ABC), delavirdine (DLV), efavirenz (EFV), nevirapine (NVP) and tenofovir (TFV)]; or a nucleoside analogue reverse transcriptase inhibitor (NRTI) [didanosine (ddl), stavudine (d4T), lamivudine (3TC) and zidovudine (ZDV)].

The present invention also relates to a method for treating a subject infected with HIV, comprising administering a polypeptide as described herein, wherein said subject is resistant against at least one other anti-HIV agent.

In some embodiments, the subject has unwanted side effects when receiving one or more anti-HIV treatment regimens (e.g., ART therapy or a component thereof).

The present invention relates to a method for treating a subject as described herein in a combination treatment with PR, RTI and/or NRTI.

The present invention also relates to a method of treating a symptom of acquired immune deficiency syndrome in a human subject infected with HIV that is, or has become, resistant to a non-antibody CD4 and/or CR (e.g. CXCR4) antagonist, comprising administering to the human subject a polypeptide of the invention, in an amount effective to treat the symptom of acquired immune deficiency syndrome in the human subject.

In one aspect, the disclosure provides a method for suppressing infection of a cell expressing CD4 and/or a CR, such as e.g. CXCR4, by a virus, the method comprising contacting the cell expressing CD4 and/or a CR, such as e.g. CXCR4 with any of the polypeptide constructs of the invention to suppress infection of the cell by the virus. In some embodiments, the method allows for the suppression of the infection of a cell in vitro, i.e., wherein the cell is not in a subject. In some embodiments, the method allows for the suppression of the infection of a cell in vivo, i.e., wherein the cell is in a subject.

In an embodiment, the present invention provides a method for inhibiting binding of an HIV to CR, the method comprising contacting CR with a polypeptide of the invention to inhibit binding of the virus to CR, wherein contacting CR with the polypeptide inhibits binding of HIV to CR, and wherein contacting CR with the polypeptide does not displace a natural ligand from CR.

In an embodiment, the present invention provides a method for decreasing displacement of a natural ligand bound from CR by an HIV, the method comprising contacting CR with a polypeptide of the invention, wherein the contacting decreases the displacement of the natural ligand from CR by the HIV.

In an embodiment, the present invention provides a method for suppressing infection of a cell expressing CR by a virus, the method comprising contacting the cell expressing CR with a polypeptide of the invention to suppress infection of the cell by the virus, preferably, wherein contacting CR with the polypeptide does not displace a natural ligand from said CR.

In an embodiment, the present invention provides a method of inhibiting in a human subject the onset or progression of an HIV-associated disorder, the inhibition of which is effected by inhibiting fusion of an HIV having resistance to (i) one or more HIV protease inhibitors, (ii) one or more HIV reverse transcriptase inhibitors, (iii) one or more HIV protease inhibitors and one or more HIV reverse transcriptase inhibitors, or (iv) one ISV of a polypeptide of the invention, to $CXCR4^+CD4^+$ target cells in the subject, comprising administering to the subject at a predefined interval effective fusion-inhibitory dose of a polypeptide of the invention, preferably wherein each administration of the polypeptide delivers to the subject from 0.1 mg per kg to 25 mg per kg of the subject's body weight, so as to thereby inhibit the onset or progression of the HIV-associated disorder in the subject.

In one aspect, the disclosure provides a method for preventing HIV infection in a subject, the method comprising administering to the subject an immunoglobulin single variable domain or a polypeptide construct comprising one or more immunoglobulin single variable domains to prevent HIV infection in the subject. In some embodiments, the administered immunoglobulin single variable domain or polypeptide constructs thereof inhibits binding of HIV to CD4 and/or a CR, such as e.g. CXCR4 but does not displace a natural ligand from said CR such as e.g. CXCR4. In some embodiments, the administered immunoglobulin single variable domain or polypeptides construct thereof have only minimal undesirable side effects.

The present invention relates to a method for preventing HIV infection in a subject, the method comprising administering to the subject a therapeutically effective amount of a polypeptide as described herein to prevent infection of the subject by HIV.

In one aspect, the disclosure provides methods of preventing HIV infection in a subject. In some embodiments, preventing HIV infection is achieved by precluding HIV from entering and/or accumulating in $CD4^+$ T-cells in the subject. Thus, in some embodiments, infection by HIV is prevented even after a subject has been exposed to an HIV, and may have one or more signs of having been exposed to HIV, by preventing HIV from entering and/or accumulating in the $CD4^+$ T-cells in the subject.

Preventing HIV infection refers both to complete and partial prevention (e.g., a percentage reduction, for example about 5%, about 10%, about 20%, about 30%, about 40%, about 50%, about 60%, about 70%, about 80%, about 90%, or higher or lower or intermediate percentages of getting infected by HIV). For instance, a subject may have a 50% chance of getting infected by HIV upon exposure to the HIV through a specific route (e.g., intravenous injection), but administration of the immunoglobulin single variable domains disclosed herein or polypeptide constructs thereof results in only a 10% chance of getting infected upon exposure (thus resulting in an 80% reduction in the chance of getting infected).

Prevention of infection can be determined using established simian models of HIV and SIV infection. For instance, a group of animals (e.g., monkeys) can be administered the immunoglobulin single variable domains or polypeptides constructs thereof and subsequently be exposed to HIV/SIV, while a control group, which is was also exposed to HIV/SIV, was not administered the immunoglobulin single variable domains or polypeptides constructs thereof. If the incidence of HIV/SIV infection in the group to which the immunoglobulin single variable domains or polypeptides constructs thereof have been administered is lower than in the control group, then the immunoglobulin single variable domains and constructs thereof are effective in preventing infection by HIV.

In an embodiment, the present invention provides a method of reducing the likelihood of a human subject's contracting infection by an HIV having resistance to (i) one or more HIV protease inhibitors, (ii) one or more HIV reverse transcriptase inhibitors, (iii) one or more HIV protease inhibitors and one or more HIV reverse transcriptase inhibitors, or (iv) one ISV of a polypeptide of the invention, which comprises administering to the subject at a predefined schedule the polypeptide of the invention, preferably wherein each administration of the polypeptide delivers to the subject from 0.1 mg per kg to 25 mg per kg of the subject's body weight, so as to thereby reduce the likelihood of the subject's contracting an infection by a resistant HIV.

In some embodiments, the methods of treatment comprise administering one or more of the immunoglobulin single variable domains and the polypeptide constructs comprising immunoglobulin single variable domains described herein and one or more known or putative anti-viral compounds or compounds displaying anti-viral activity. Known or putative anti-viral compounds are compounds that suppress or inhibit viral infection, viral replication and/or the development of disease associated with viral infection. In some embodiments, the known or putative anti-viral compound is a known or putative anti-HIV compound.

Anti-viral drugs can be classified as targeting one of the life cycle stages of the virus. One category of anti-viral drugs are based on interfering with viral entry. As described herein, a virus binds to a specific receptor to infiltrate a target cell. Viral entry can be suppressed by blocking off the viral entry way. Anti-viral drugs that have this mode of action are anti-receptor antibodies, natural ligands of the receptor and small molecules that can bind to the receptor. A second category of anti-viral drugs are compounds that suppress viral synthesis. Anti-viral drugs that have this mode of action are nucleoside analogues that are similar to the DNA and RNA building blocks but deactivate the protein machinery (e.g., reverse transcriptase or DNA polymerase) used to replicate the virus. Other drugs are targeted at blocking the transcription factors of viral DNA, ribozymes, which can interfere with the production of viral DNA. Other drugs target viral RNA for destruction, including siRNAs and antisense nucleic acids against viral nucleic acid sequences. Yet another class of anti-viral drugs relates to drugs that can interfere with the function of virus specific proteins. This class includes the HIV protease inhibitors. Anti-viral drugs also include drugs directed at the release stage of the virus. This category of drugs includes compounds that interfere with the proteins necessary to build the viral particles. Another class of anti-viral drugs are drugs that stimulate the immune system in targeting viral infection. Drugs that fall in this class are interferons, which inhibit viral synthesis in infected cells and antibodies that can target an infected cell for destruction by the immune system. Other anti-viral agents are described in U.S. Pat. Nos. 6,130,326, and 6,440,985, and published US patent application 2002/0095033. Accordingly, it should be appreciated that compounds identified herein have anti-viral activity and may act through any anti-viral mechanism described above. In some embodiments, compounds identified herein inhibit or suppress viral replication (e.g., viral DNA replication).

In some embodiments, the anti-viral compounds are anti-viral compounds that are anti-HIV compounds. In some embodiments, the anti-viral compounds are used in anti-HIV therapy, such as for instance, the anti-viral compounds described in Tables 1, 4 and 5 of WO2009/014638. In some embodiments, the anti-HIV compound is an HIV protease inhibitor or HIV reverse transcriptase inhibitor.

The anti-viral activity of a compound may be assayed in an in vitro cell based assay. Anti-viral activity may result from i) the interaction of a compound with the virus to prevent infection of a cell or to prevent replication, development, and/or proliferation of the virus after infection, ii) the effect of a compound on a cell to prevent infection by the virus or to prevent replication, development, and/or proliferation of the virus after infection, or iii) any other mechanism, or any combination thereof. Regardless of the mode of action, a composition may have anti-viral activity if it reduces the percentage or number of infected cells in a cell-based assay. In some embodiments, a compound (or a combination of two or more compounds) has anti-viral activity when it reduces the percentage or number of infected cells by at least 20%, at least 30%, at least 40%, at least 50%, or more (e.g., in a cell-based assay). In some embodiments, a compound has anti-viral activity when it reduces the amount of viral nucleic acids within a cell. In certain embodiments, a compound inhibits the replication of viral nucleic acids within a cell (e.g., a compound reduces the amount of viral replication by about 5%, about 10%, about 20%, about 30%, about 40%, about 50%, about 60%, about 70%, about 80%, about 90%, or higher or lower or intermediate percentages of reduction). It should be appreciated that a reduction in viral replication may be measured using a cellular assay and measuring the amount of viral DNA or the rate of viral DNA replication over time (or any other measure of viral replication) in the presence of a compound and comparing it to the viral replication in the absence of the compound or in the presence of a control compound.

In some embodiments, the methods of treatment and/or prevention comprise administering one or more of the immunoglobulin single variable domains and the polypeptide constructs comprising immunoglobulin single variable domains described herein and administering a vaccine against a DNA virus. A vaccine is defined as a pharmaceutical composition that when administered to a subject in an effective amount stimulates the production of protective antibody or protective T-cell response. In some embodiments, the vaccine is protein vaccine comprising one or more polypeptide sequences encoded by a DNA virus sequence. In some embodiments, the vaccine is a nucleic acid vaccine comprising DNA viral nucleic acids. Administration regimes for vaccines are known to a person of ordinary skill in the art. In some embodiments, ranges of amounts of polypeptide vaccines for prophylaxis of DNA viral infection are from 0.01 to 100 microgram/dose, for example 0.1 to 50 microgram/dose. Several doses may be needed per subject in order to achieve a sufficient immune response and subsequent protection against DNA viral infection (e.g., "immunizing" a subject). The term "immunizing" refers to the ability of a substance to cause a humoral and/or cellular response in a subject, whether alone or when linked to a carrier, in the presence or absence of an adjuvant, and also refers to an immune response that blocks the infectivity, either partially or fully, of an infectious agent.

In some embodiments, the methods of treatment or prevention comprise administering one or more of the immunoglobulin single variable domains and the polypeptide constructs comprising immunoglobulin single variable domains described herein and administering a compound or therapy that reduces unwanted side effects of HIV-therapy. Examples of such compounds include anti-nausea, appetite enhancers and anti-depressants.

In one aspect, the disclosure provides methods for the administration of therapeutically effective amounts of immunoglobulin single variable domains and polypeptide constructs comprising one or more immunoglobulin single variable domains. A therapeutically effective amount of an ISV or polypeptide is a dosage of the immunoglobulin single variable domain or polypeptide to provide a medically desirable result (e.g., lowering of the HIV-titer). The effective amount will vary with the particular condition being treated, the age and physical condition of the subject being treated, the severity of the condition, the duration of the treatment, the nature of the concurrent therapy (if any), the specific route of administration and like factors within the knowledge and expertise of the health practitioner. For example, a therapeutically effective amount for treating or preventing a disease or condition (e.g., suffering from infection by HIV) would be an amount sufficient to decrease the progression of, or inhibit the disease or condition, or its symptoms. Similarly, a therapeutically effective amount for lowering the HIV titer in a subject would be an amount sufficient to lower the HIV titer in a subject. It should be appreciated that non-immunoglobulin single variable domains therapies can be administered in therapeutically effective amounts as well.

In one aspect, the disclosure provides methods for the administration of immunoglobulin single variable domain and polypeptide constructs thereof comprising one or more immunoglobulin single variable domains. In some embodiments, the immunoglobulin single variable domain or polypeptide is administered as a pharmaceutical composition. The pharmaceutical composition, in addition to the immunoglobulin single variable domains and polypeptide constructs thereof includes a pharmaceutically-acceptable carrier.

As described in detail, the pharmaceutical compositions of the disclosure may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Formulations of the disclosure include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient (e.g., immunoglobulin single variable domain or polypeptide constructs thereof) which can be combined with a carrier material to produce a single dosage form will vary depending upon the host being treated, and the particular mode of administration. The amount of active ingredient that can be combined with a carrier material to produce a single dosage form will generally be that amount of the compound which produces a therapeutic effect. Generally, this amount will range from about 1% to about 99% of active ingredient, preferably from about 5% to about 70%, most preferably from about 10% to about 30%.

In certain embodiments, a formulation comprises an excipient selected from the group consisting of cyclodextrins, liposomes, micelle forming agents, e.g., bile acids, and polymeric carriers, e.g., polyesters and polyanhydrides. In certain embodiments, an aforementioned formulation renders orally bioavailable an immunoglobulin single variable domain or polypeptide construct.

Methods of preparing these formulations or compositions include the step of bringing into association an immunoglobulin single variable domain or polypeptide construct with the carrier and, optionally, one or more accessory ingredients. In general, the formulations are prepared by uniformly and intimately bringing into association an immunoglobulin single variable domain or polypeptide construct with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an immunoglobulin single variable domain or polypeptide construct as an active ingredient. An immunoglobulin single variable domain or polypeptide construct invention may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and nonionic surfactants; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxy-propylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent.

The tablets, and other solid dosage forms of the pharmaceutical compositions, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal or vaginal administration may be presented as a suppository, which may be prepared by mixing an immunoglobulin single variable domain or polypeptide construct with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations suitable for vaginal administration also include pessaries, tampons, creams, gels, pastes, foams or spray formulations containing such carriers as are known in the art to be appropriate.

Dosage forms for the topical or transdermal administration of an immunoglobulin single variable domain or polypeptide construct include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of an immunoglobulin single variable domain or polypeptide construct to the body. Dissolving or dispersing the compound in the proper medium can make such dosage forms. Absorption enhancers can also be used to increase the flux of the compound across the skin. Either providing a rate controlling membrane or dispersing the compound in a polymer matrix or gel can control the rate of such flux.

Ophthalmic formulations, eye ointments, powders, solutions and the like, are also contemplated as being within the scope of this disclosure.

Pharmaceutical compositions suitable for parenteral administration comprise one or more an immunoglobulin single variable domains or polypeptide constructs in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and non-aqueous carriers, which may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly-(orthoesters) and poly(anhydrides). Depot injectable formulations are also prepared by entrapping the drug in liposomes or microemulsions, which are compatible with body tissue.

The embodiments illustrated and discussed in this specification are intended only to teach those skilled in the art the best way known to the inventors to make and use the invention. Modifications and variation of the above-described embodiments of the invention are possible without departing from the invention, as appreciated by those skilled in the art in light of the above teachings. It is therefore understood that, within the scope of the claims and their equivalents, the invention may be practiced otherwise than as specifically described.

The entire contents of all of the references (including literature references, issued patents, published patent applications, and co pending patent applications) cited throughout this application are hereby expressly incorporated by reference, in particular for the teaching that is referenced hereinabove.

The Figures and the Experimental Part/Examples are only given to further illustrate the invention and should not be interpreted or construed as limiting the scope of the invention and/or of the appended claims in any way, unless explicitly indicated otherwise herein.

TABLE A-2

(A) CDR's and framework sequences of Nanobodies against human CXCR4 ("ID" represents SEQ ID NO:")

| ID | Clone | ID | Framework 1 | ID | CDR 1 | ID | Framework 2 | ID | CDR 2 | ID | Framework 3 | ID | CDR 3 | ID | Framework 4 |
|---|---|---|---|---|---|---|---|---|---|---|---|---|---|---|---|
| 4 | 238 D4 | 21 | EVQLMESGGGLV QAGGSLRLSCAAS GRTFN | 34 | NYAMG | 41 | WFRRAPGKE REFVA | 48 | AITRSGVRSGVS AIYGDSVKD | 57 | RFTISRDNAKNTLYL QMNSLKPEDTAVYT CAA | 67 | SAIGSGALRRF EYDY | 76 | SGQGTQVT VSS |
| 5 | 281A5 | 22 | EVQLVESGGGLV QAGGSLRLSCAAS GRTFN | 34 | NYAMG | 41 | WFRRAPGKE REFVA | 48 | AITRSGVRSGVS AIYGDSVKD | 57 | RFTISRDNAKNTLYL QMNSLKPEDTAVYT CAA | 67 | SAIGSGALRRF EYDY | 76 | SGQGTQVT VSS |
| 6 | 281E10 | 23 | EVQLVESGGGLV QAGGSLRLSCKAS GGTFN | 34 | NYAMG | 41 | WFRRAPGKE REFVA | 48 | AITRSGVRSGVS AIYGDSVKD | 58 | RFTISRDNVKNTLYL QMNTLKPEDTAVYT CAA | 67 | SAIGSGALRRF EYDY | 76 | SGQGTQVT VSS |
| 7 | 281D4 | 24 | EVQLVESGGGLV QAGGSLRLSCAAS GGTFN | 34 | NYAMG | 41 | WFRRAPGKE REFVA | 49 | AISRSGVRTGVS ALYGDSVKD | 59 | RFTISRDNAKNTLYL QMNKMKPEDTAVY TCAA | 68 | SAIGSGALRRF EYDS | 76 | SGQGTQVT VSS |
| 8 | 281A6 | 25 | EVQLVESGGGLV QTGGSLRLSCAAS GGTFN | 34 | NYAMG | 41 | WFRRAPGKE REFVA | 49 | AISRSGVRTGVS ALYGDSVKD | 59 | RFTISRDNAKNTLYL QMNKMKPEDTAVY TCAA | 68 | SAIGSGALRRF EYDS | 76 | SGQGTQVT VSS |
| 9 | 281F12 | 26 | EVQLVESGGGLV QAGDSLRLSCAAS GRAFS | 35 | RYAMG | 42 | WFRQAPGKE REFVA | 50 | AIGWGPSKTNY ADSVKG | 60 | RFTISRDNAKNTYL QMNTLKPEDTAVYS CAA | 69 | KFVNTDSTWS RSEMYTY | 77 | WGQGTQVT VSS |
| 10 | 283B6 | 27 | EVQLVASGGGLV QAGGSLRLSCAVS GTTFS | 36 | VATLG | 43 | WYRQAPGKE RAIVA | 51 | DISSGGSTNYAD SVRG | 61 | RFTISRDNAKNLAYL QMNSLEPEDTAVYY CNA | 70 | RTSGWRTRSN Y | 77 | WGQGTQVT VSS |
| 11 | 283E2 | 28 | EVQLVESGGGLV QAGDSLRLSCAVS GTTFS | 36 | VATLG | 43 | WYRQAPGKE RAIVA | 51 | DISSGGSTNYAD SVRG | 61 | RFTISRDNAKNLAYL QMNSLEPEDTAVYY CNA | 70 | RTSGWRTRSN Y | 77 | WGQGTQVT VSS |
| 12 | 283F1 | 29 | EVQLVESGGGLV QAGGSLRLSCVAS VNIFG | 37 | STAMA | 44 | WFRQAPGKQ RNIVA | 52 | SISSGGRINYAD SRKG | 62 | RFTISRDNTKNTVHL QMNSLEPEDTAVYY CAA | 71 | GRIGQRTLTFT PDY | 77 | WGQGTQVT VSS |
| 13 | 15F5 | 30 | EVQLVESGGGLV RAGDSLRLSCAAS GRAFS | 35 | RYAMG | 45 | WFRQALGKE RELVA | 53 | AIGWSPTHTYY ADSVKG | 63 | RFTMSRDNGKNTVF LQMNSLNPEDTAVY YCAA | 72 | KYSSRDAAYR SDYDYNY | 77 | WGQGTQVT VSS |
| 14 | 15G11 | 31 | EVQLVESGGGLV QAGDSLRVSCAA SGRTS | 38 | SYAMA | 46 | WFRQAPGKE REFVG | 54 | TISRTNSRTKYA DFVEG | 64 | RFTISRDNAKSTLSL QMTSLKPEDTAVYY CAA | 73 | KWTGNSYHDY TWSKVDEYNV | 77 | WGQGTQVT VSS |
| 15 | 15A1 | 32 | EVQLVESGGGLV QAGGSLRLSCAAS GRTF | 39 | SRAAMG | 46 | WFRQAPGKE REFVG | 55 | CALSSAGSALTA DSVKG | 65 | RFTISRDNAKNMVY LQMNNLKPEDTAVY SCVA | 74 | GGYCTRAGVY PY | 77 | WGQGTQVT VSS |

-continued

| ID | Clone | FR1 | ID | CDR1 | ID | FR2 | ID | CDR2 | ID | FR3 | ID | CDR3 | ID | FR4 |
|---|---|---|---|---|---|---|---|---|---|---|---|---|---|---|
| 16 | 10C03 CNA | EVQLVESGGGLV QPGGSLRLSCAAS GTIF | 33 | STSTMG | 40 | WYSQAPGKQ RELVA | 47 | DITFLGSAKYAD SVKG | 56 | RFTISRDKIKNTVYL QMNSLKPEDTAAYY | 66 | RQSTFRGVHY NY | 75 | WGQGTQVT VSS |

Table A-2(B)
CDR's and framework sequences of Nanobodies against human CD4 ("ID" represents SEQ ID NO:")

| ID | Clone | FR1 | ID | CDR1 | ID | FR2 | ID | CDR2 | ID | FR3 | ID | CDR3 | ID | FR4 |
|---|---|---|---|---|---|---|---|---|---|---|---|---|---|---|
| 17 | 01B6 | EVQLVESGGGLVQS GGSLRLSCAASGFT FS | 78 | GYWMY | 82 | WVRQAPGK GLENS | 86 | AISPGGGST YYPDSVKG | 88 | RFTISRDNAKNTL YLQMNSLKPEDTA LYYCAS | 92 | SLTATHTYEYD Y | 96 | WGQGTQV TVSS |
| 18 | 01E2 | EVQLVESGGGLVQA GGSLRLSCAASGRT SA | 79 | SYSMG | 83 | WFRQAPGK EREFVA | 42 | AISWSGDET SYADSVKG | 89 | RFTIARGNAKNTV YLQMNSLKSEDTA IYYCAG | 93 | DRWRPAGLQW DY | 97 | WGQGTQV TVSS |
| 19 | 01H12 | EVQLVESGGGLVQA GGSLKLSCAASRSI LD | 80 | FNAMG | 84 | WVRQAPGK QREWVT | 87 | TIARAGATK YADSVKG | 90 | RFSISRDNAKNTV YLQMSSLKPEDTA TYYCNA | 94 | RVFDLPNDY | 98 | WGQGTQV TVSS |
| 20 | 03F11 | EVQLVESGGGSVQP GGSLTLSCGTSGRT FN | 81 | VMG | 85 | WFRQAPGK EREFVA | 42 | AVRWSTGI YYTQYADSV KS | 91 | RFTISRDNAKNTV YLEMNSLKPEDTA VYYCAA | 95 | DTYNSNPARWD GYDF | 99 | RCQGTQV TVSS |

EXPERIMENTAL SECTION

Example 1: Introduction

HIV diversity is so extensive, especially in the envelope gp120, that designing an HIV vaccine capable of eliciting broadly cross-reactive neutralizing antibodies is an extraordinarily difficult challenge.

The virus replicates rapidly and has a high mutation rate creating highly diverse 'quasi species'. These quasi species are fertile substrates for Darwinian selective pressures favoring the best-adapted, most 'fit' genetic variants. Efforts to develop effective treatments and vaccines must overcome the complex evolutionary dynamics in HIV-infected individuals and within affected populations.

As HIV spreads from individual to individual, genetically diverse viruses confront the most highly polymorphic gene family in humans—that encoding the human leukocyte antigen (HLA) class I and II proteins. These proteins determine which specific peptide sequences (epitopes) are presented to and recognized by host $CD8^+$ and $CD4^+$ T-cells, respectively. In the confrontation between genetically diverse HIV variants and genetically diverse human hosts, viral variants can be selected that harbor mutations in specific viral epitopes that escape recognition by host immune effector cells, resulting in resistant HIV.

Figure 1:
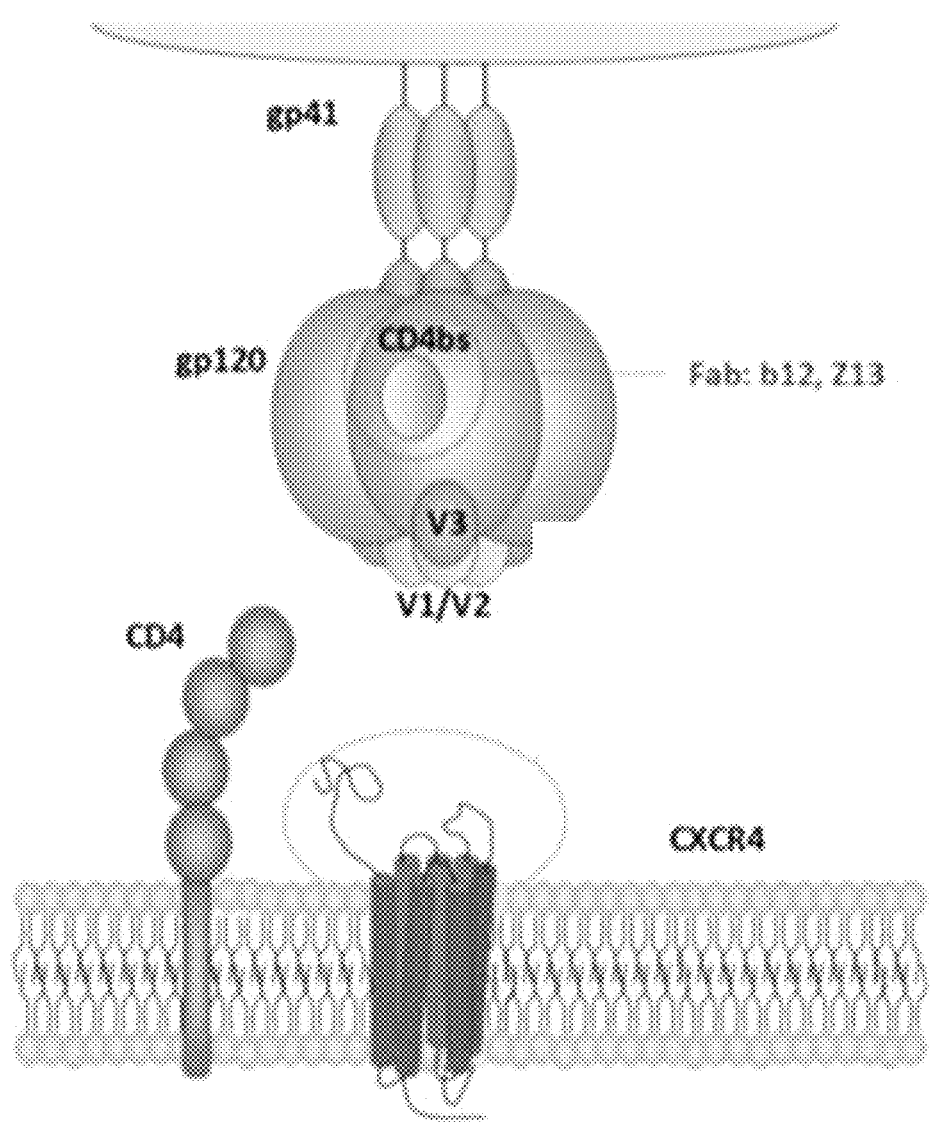
FIG. 1: Schematic representation of the model system.
Figure 2A:
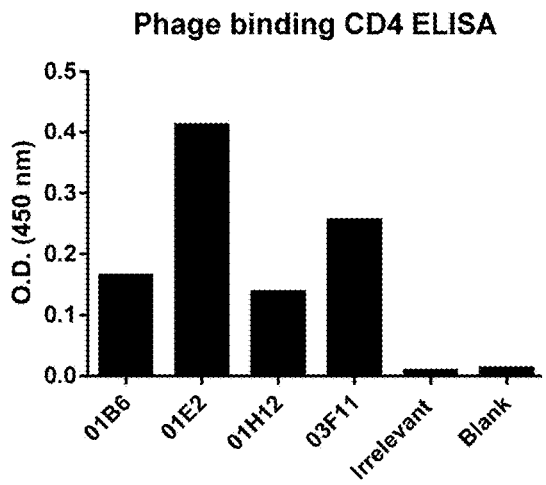
FIGS. 2A-2D: Identification of human CD4-specific Nanobodies directed against the gp120 binding site.
Figure 2B:
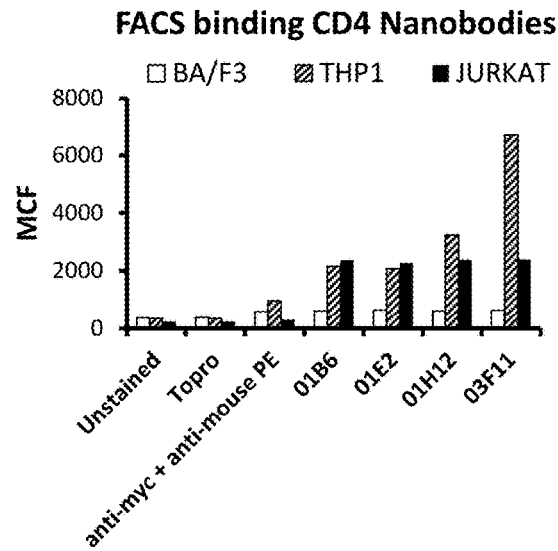
Figure 2C:
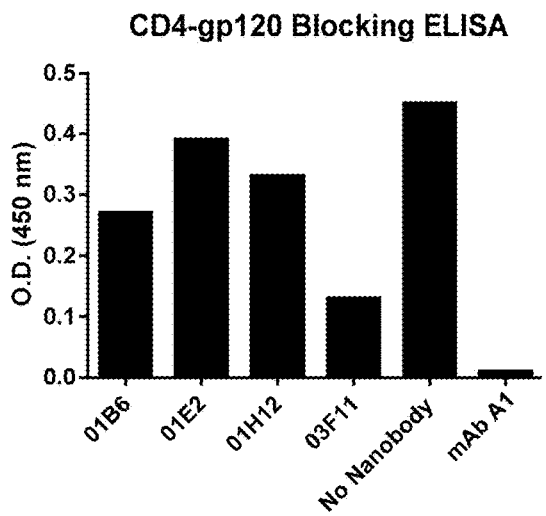
Figure 2D:
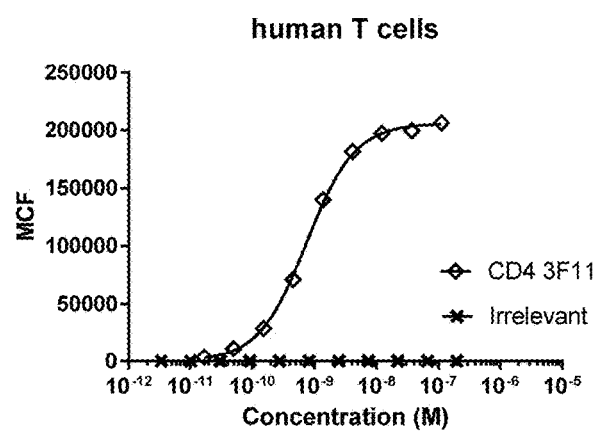

However, although the viral diversity is extremely high, most HIV groups, strains, clades and subtypes are in need of the cellular receptor CD4 as well as the co-receptors CXCR4 (X4), CCR5 (R5) or both CCR5/CXCR4 (dual tropic R5/X4), to enter and infect mainly the $CD4^+$ target immune T-cells (see FIG. 1).

The present inventors hypothesized that the simultaneous blockade of both the receptor and a co-receptor could not only prevent HIV entry, but also defer if not preclude resistance. Surprisingly, the use of bispecific CXCR4-CD4 polypeptides outperformed the combination of the individual blockers and could prevent HIV entry and overcome resistance.

Example 2: Identification and Characteristics of Monovalent CD4 Nanobodies

Example 2.1: Selection of CD4 Nanobody Candidates

A panel of CD4 Nanobodies was previously identified from immune libraries with human peripheral blood lymphocytes. Llama 58, 59 and 60 were immunized according to standard protocols with 6 boosts at two week intervals, each of them with approximately $1 \times 10^8$ human peripheral blood lymphocytes (hPBLs). Blood was collected 4 and 9 days after the final boost. In addition, approximately 1 g of lymph node biopsies were collected from animals 4 days after final boost.

Peripheral blood mononuclear cells were prepared from blood samples using Ficoll-Hypaque according to the manufacturer's instructions. Next, total RNA was extracted from these cells and lymph node tissue, if available, and used as starting material for RT-PCR to amplify Nanobody encoding gene fragments. These fragments were cloned into phagemid vector pAX50. Phage was prepared according to standard methods (see for example the prior art and applications filed by applicant cited herein).

Selections of phage displaying CD4 binding Nanobodies Phage libraries 58, 59 and 60 were used for selections on recombinant human CD4 (ImmunoDiagnostics, Inc., cat #7001, lot #5S30/1.5). Recombinant human CD4 was immobilized directly on Maxisorp 96 well microtiter plates (Nunc) at 10 µg/ml, 0.1 µg/ml and 0 µg/ml (control). Following incubation with the phage libraries and extensive washing, bound phage was eluted with 100 mM triethylamine (TEA). The eluted phage were amplified and applied in a similar second round of selection. After elution with TEA the second round obtained phage were again amplified and applied into a similar third round selection in which following incubation with the phage and extensive washing, bound phage was a-specifically eluted with TEA, or specifically with 250 nM of gp120 HIV-1 IIIB (Immunodiagnostic). Individual colonies obtained from the eluted phage pools were grown and i) induced for new phage production and ii) induced with IPTG for Nanobody expression and extraction (periplasmic extracts) according to standard methods (see for example the prior art and applications filed by applicant cited herein).

2.2 Screening for CD4 Binding Nanobodies

In order to determine binding specificity to CD4, the selected clones were tested in an ELISA binding assay setup, using the monoclonal phage pools. Shortly, 1 µg/ml receptor recombinant human CD4 (ImmunoDiagnostics Inc., cat #7001) was immobilized on Maxisorp ELISA plates (Nunc) and free binding sites were blocked using 4% Marvel skimmed milk in PBS. Next, 15 µl of supernatant from the monoclonal phage inductions of the different clones in 100 µl 1% Marvel PBS were allowed to bind to the immobilized antigen. After incubation and a wash step, phage binding was revealed using a HRP-conjugated monoclonal-anti-M13 antibody (Gentaur Cat #27942101). Binding specificity was determined based on OD values compared to controls having received no phage or an irrelevant phage. FIG. 2 shows binding of 4 clones to recombinant human CD4 in phage ELISA. The sequences are depicted in Table 2.2

TABLE 2.2

| CD4 Nanobodies |
| --- |
| >01B6 (SEQ ID NO: 17)<br>EVQLVESGGGLVQSGGSLRLSCAASGFTFSGYWMYWVRQAPGKGLEWVSA<br>ISPGGGSTYYPDSVKGRFTISRDNAKNTLYLQMNSLKPEDTALYYCASSL<br>TATHTYEYDYWGQGTQVTVSS |
| >01E2 (SEQ ID NO: 18)<br>EVQLVESGGGLVQAGGSLRLSCAASGRTSASYSMGWFRQAPGKEREFVAA<br>ISWSGDETSYADSVKGRFTIARGNAKNTVYLQMNSLKSEDTAIYYCAGDR<br>WWRPAGLQWDYWGQGTQVTVSS |
| >01H12 (SEQ ID NO: 19)<br>EVQLVESGGGLVQAGGSLKLSCAASRSILDFNAMGWYRQAPGKQREWVTT<br>IARAGATKYADSVKGRFSISRDNAKNTVYLQMSSLKPEDTATYYCNARVF<br>DLPNDYWGQGTQVTVSS |
| >03F11 (SEQ ID NO: 20)<br>EVQLVESGGGSVQPGGSLTLSCGTSGRTFNVMGWFRQAPGKEREFVAAVR<br>WSSTGIYYTQYADSVKSRFTISRDNAKNTVYLEMNSLKPEDTAVYYCAAD<br>TYNSNPARWDGYDFRGQGTQVTVSS |

CD4 binding Nanobodies were subjected to sequence analysis, and unique clones were recloned into an *E. coli* expression vector, allowing further characterisation as purified Nanobodies. Monovalent CD4 Nanobodies were produced as C-terminal linked myc, His6-tagged proteins in expression vector pAX50.

To check whether the selected Nanobodies recognize cell-surface expressed CD4, a Flow cytometry experiment was performed where the purified CD4 Nanobodies were tested for specific binding to Jurkat and THP-1 cells expressing human CD4. Murine Ba/F3 myeloid cells were used as negative control cells. Purified Nanobodies (100 nM) were allowed to bind to $10^5$ cells for 30 minutes at 4° C. in a final volume of 100 µl of 10% FBS (Invitrogen, Cat 10270-106) in PBS (Invitrogen #14190). Bound Nanobodies were detected with mouse anti-myc antibody (Serotec, Cat #MCA2200) followed by goat anti-mouse-PE antibody (Jackson #115-115-164). Dead cells percentage population was determined by staining the cells with TOPRO3 (Molecular probes T3605). Using a BD FACS Array Bioanalyzer system, a PE filter 585/42 and a Topro filter 661/16, twenty thousand events were acquired. TOPRO3+ cells were excluded, and the mean channel fluorescence (MCF) was calculated. Expression of CD4 in Jurkat and THP-1 cells was confirmed by using 10 µg/ml of an anti-CD4 monoclonal antibody (Diaclone, clone B-A1 cat #854.030.000). Staining of the cells with anti-myc and/or the goat anti mouse-PE antibodies antibody was performed as negative controls. The results obtained for 4 different Nanobodies and control antibodies are shown in FIG. 2, confirming that all Nanobodies are binding to CD4 expressed on a cell surface, with Nanobody 03F11 showing the highest binding signal on THP-1 cells.

2.3 Screening for Nanobodies Blocking CD4-Gp120 Interaction

Besides its role on T-cells, CD4 also serves as primary receptor for HIV entry. Therefore purified CD4 Nanobodies were analysed for the capacity to block the interaction of CD4 with the viral gp120 protein. Monovalent His-tagged Nanobodies were purified from periplasmic extracts by affinity and desalting chromatography and used in an ELISA-based competition setup. In short, 1 µg/ml of gp120 HIV-1 IIIB (Immunodiagnostic) was captured by 20 µg/ml of sheep anti-gp120 antibody D7324 (Aalto Bio Reagents) previously coated in 96 well Maxisorp microtiter plates (Nunc) and blocked with 1% casein in PBS. In parallel, 0.5 µg/ml of biotinylated CD4 was incubated with 500 nM of the different purified Nanobodies in 100 µl 0.1% Casein/PBS. After 1 hour, the biotinylated CD4-Nanobody pre-mixes were incubated 1 hour with the captured gp120. Bound biotinylated CD4 was detected using HRP-conjugated Extravidin (Sigma E2886). A blocking mouse anti-CD4 IgG2a antibody (Diaclone, clone B-A1 cat #854.030.000) was used as positive control. Blocking activity was determined as loss of O.D. signal, as compared to wells where no Nanobody was added.

FIG. 2 panel C shows results of this blocking assay using a selection of clones binding to human CD4.

The results indicate that Nanobodies 03F11 and 01B6 block the in vitro interaction of CD4 with gp120.

2.4 Characterisation of CD4 Nanobody 3F11

Nanobody 03F11 (also designated as 3F11) was subsequently analysed for dose-dependent binding to primary human T cells, MOLM-13 and THP-1 cells in FACS, using detection of the anti-flag-tag. The $EC_{50}$ values results are depicted in Table 2.4. Also on primary cells, 03F11 showed strong binding, with an $EC_{50}$ value of 0.76 nM (FIG. 2 Panel D). To confirm the specificity of the anti-CD4 Nanobody, binding of 03F11 was also assessed to cytotoxic CD8+ T cells isolated from human PBMCs using the CD8 T Cell Isolation Kit (Miltenyi Biotech, Cat. 130-096-495), resulting in 94% purity of CD8+ cells. No binding was observed to cytotoxic CD8+ T cells with the anti-CD4 03F11 Nanobody (data not shown).

The results indicate that Nanobodies are capable of binding to the receptor CD4 and preventing the interaction with the HIV-1 gp120 binding.

TABLE 2.4

Characteristics of monovalent CD4 Nanobody 3F11.

| Nanobody | ID | FACS binding | | | HIV-1 neutralization |
| | | MOLM-13 $EC_{50}$ (nM) | THP-1 $EC_{50}$ (nM) | T-cells $EC_{50}$ (nM) | MT-4 + NL4.3 $IC_{50}$ (nM) |
|---|---|---|---|---|---|
| CD4 | 3F11 | 0.6 | 1.0 | 0.76 | 34.7 |

Example 3 Identification and Selection of CXCR4 Nanobody Candidates

In the present example, the inventors set out to identify and characterize anti-CXCR4 Nanobodies which were able to act as functional antagonists in HIV1 infectivity assays.

Preferably, these CXCR4 Nanobodies would bind to an epitope(s) that interferes with gp120 interaction but not with binding of the ligand CXCL12, because of which the Nanobodies would not interfere with natural CXCR4 signal transduction.

3.1 Ligand Displacement of CXCR4 Nanobodies

To this end, CXCR4 Nanobodies were analysed for their binding to HEK293T-CXCR4 cells, and their ability to compete with the ligand CXCL12 (or SDF-1a) for receptor binding in a radio-ligand displacement assay. The sequences of the respective CXCR4 Nanobodies are depicted in Table 3.1A.

TABLE 3.1A

CXCR4 Nanobodies

```
>281A5 (SEQ ID NO: 5)
EVQLVESGGGLVQAGGSLRLSCAASGRTFNNYAMGWFRRAPGKEREFVAA
ITRSGVRSGVSAIYGDSVKDRFTISRDNAKNTLYLQMNSLKPEDTAVYTC
AASAIGSGALRRFEYDYSGQGTQVTVSS

>281E10 (SEQ ID NO: 6)
EVQLVESGGGLVQAGGSLRLSCKASGGTFNNYAMGWFRRAPGKEREFVAA
ITRSGVRSGVSAIYGDSVKDRFTISRDNVKNTLYLQMNTLKPEDTAVYTC
AASAIGSGALRRFEYDYSGQGTQVTVSS

>281D4 (SEQ ID NO: 7)
EVQLVESGGGLVQAGGSLRLSCAASGGTFNNYAMGWFRRAPGKEREFVAA
ISRSGVRTGVSALYGDSVKDRFTISRDNAKNTLYLQMNKMKPEDTAVYTC
AASAIGSGALRRFEYDSSGQGTQVTVSS

>281A6 (SEQ ID NO: 8)
EVQLVESGGGLVQTGGSLRLSCAASGGTFNNYAMGWFRRAPGKEREFVAA
ISRSGVRTGVSALYGDSVKDRFTISRDNAKNTLYLQMNKMKPEDTAVYTC
AASAIGSGALRRFEYDSSGQGTQVTVSS

>281F12 (SEQ ID NO: 9)
EVQLVESGGGLVQAGDSLRLSCAASGRAFSRYAMGWFRQAPGKEREFVAA
IGWGPSKTNYADSVKGRFTISRDNAKNTVYLQMNTLKPEDTAVYSCAAKF
VNTDSTWSRSEMYTYWGQGTQVTVSS

>283B6 (SEQ ID NO: 10)
EVQLVASGGGLVQAGGSLRLSCAVSGTTFSVATLGWYRQAPGQQRALVAD
ISSGGSTNYADSVRGRFTISRDNAKNLAYLQMNSLKPEDTAVYYCNARTS
GWRTRSNYWGQGTQVTVSS
```

TABLE 3.1A-continued

CXCR4 Nanobodies

>283E2 (SEQ ID NO: 11)
EVQLVESGGGLVQAGGSLRLSCAVSGTTFSVATLGWYRQAPGQQRALVAD
ISSGGSTNYADSVRGRFTISRDNAKNLAYLQMNSLKPEDTAVYYCNARTS
GWRTRSNYWGQGTQVTVSS

>283F1 (SEQ ID NO: 12)
EVQLVESGGGLVQAGGSLRLSCVASVNIFGSIAMAWYRQAPGKQRNLVAS
ISSGGRINYADSRKGRFTISRDNTKNTVHLQMNSLEPEDTAVYYCAAGRI
GQRTLTFTPDYWGQGTQVTVSS

238D4 (SEQ ID NO: 4)
EVQLMESGGGLVQAGGSLRLSCAASGRTFNNYAMGWFRRAPGKEREFVAA
ITRSGVRSGVSAIYGDSVKDRFTISRDNAKNTLYLQMNSLKPEDTAVYTC
AASAIGSGALRRFEYDYSGQGTQVTVSS

15F5 (SEQ ID NO: 13)
EVQLVESGGGLVRAGDSLRLSCAASGRAFSRYAMGWFRQALGKERELVAA
IGWSPTHTYYADSVKGRFTMSRDNGKNTVFLQMNSLNPEDTAVYYCAAKY
SSRDAAYRSDYDYNYWGQGTQVTVSS

15G11 (SEQ ID NO: 14)
EVQLVESGGGLVQAGDSLRVSCAASGRTSSYAMAWFRQAPGKEREFVGTI
SRTNSRTKYADFVEGRFTISRDNAKSTLSLQMTSLKPEDTAVYYCAAKWT
GNSYHDYTWSKVDEYNVWGQGTQVTVSS

15A1 (SEQ ID NO: 15)
EVQLVESGGGLVQAGGSLRLSCAASGRTFSRAAMGWFRQAPGKEREFVGC
ALSSAGSALTADSVKGRFTISRDNAKNMVYLQMNNLKPEDTAVYSCVAGG
YCTRAGVYPYWGQGTQVTVSS

10C3 (SEQ ID NO: 16)
EVQLVESGGGLVQPGGSLRLSCAASGTIFSTSTMGWYSQAPGKQRELVAD
ITFLGSAKYADSVKGRFTISRDKIKNTVYLQMNSLKPEDTAAYYCNARQS
TFRGVHYNYWGQGTQVTVSS

In short, membrane extracts of HEK293 cells transiently transfected with CXCR4 were incubated with serial dilutions of purified Nanobodies and 75 pM of $[^{125}I]$-CXCL12. Non-specific binding was determined in presence of 100 nM cold SDF-1. The assay was performed three times, and average percentages of SDF-1 inhibition and Ki values were calculated (Table 3.1B).

TABLE 3.1B

Ligand displacement affinity of monovalent CXCR4 Nanobodies.

| ID | $[^{125}I]$ SDF-1 displacement on CXCR4-Hek pKi +/−SEM (n = 3 |
|---|---|
| 281F12 | 7.57 +/− 0.30 |
| 281D4 | 8.27 +/− 0.05 |
| 281A6 | 8.63 +/− 0.02 |
| 281E10 | 9.21 +/− 0.12 |
| 283B6 | 8.78 +/− 0.24 |
| 283E2 | 8.29 +/− 0.11 |
| 281A5 | 8.12 +/− 0.08 |
| 283F1 | 7.93 +/− 0.41 |

In FIG. 2.1, is shown that 281F12 had a moderate potency, with a Ki of 27 nM, and only partial efficacy, while other CXCR4 Nanobodies showed full efficacy in displacing the binding of ligand to the CXCR4 receptor.

This would indicate that Nanobody 281F12 does not or only minimally impairs natural CXCR4 signal transduction.

3.2 Inhibition of HIV-1 Replication by Nanobodies

To determine if monovalent CXCR4 Nanobodies as well as the monovalent CD4 3F11 Nanobody are capable of blocking the replication of the CXCR4-using HIV1 strains, HIV-1 infection assays were performed with both CXCR4 and CCR5 specific HIV clones.

The NL4.3, the CCR5-using (R5) HIV-1 strain BaL, the dual-tropic (R5/X4) HIV-1 strain HE and the dual-tropic (R5/X4) HIV-2 ROD strain were investigated on human MT-4 cells, that endogenously express CD4 and CXCR4, but not CCR5. Activity ($IC_{50}$) and toxicity ($CC_{50}$) were determined using microscopic evaluation and MTS viability staining method. The CXCR4-using (X4) HIV-1 clone NL4.3 was obtained from the National Institutes of Health NIAID AIDS Reagent program (Bethesda, Md.), the CCR5-using (R5) HIV-1 strain BaL was obtained from the Medical Research Council AIDS reagent project (Herts, UK). The dual-tropic (R5/X4) HIV-1 HE strain was initially isolated from a patient at the University Hospital in Leuven. In all experiments AMD3100, a specific CXCR4 antagonist, and maraviroc, a specific CCR5 antagonist, were used as controls. The MT-4 cells were seeded out in 96-well plates. Nanobodies were added at different concentrations together with HIV-1 and the plates were maintained at 37° C. in 10% $CO_2$. Cytopathic effect induced by the virus was monitored by daily microscopic evaluation of the virus-infected cell cultures. At day 4-5 after infection, when strong cytopathic effect was observed in the positive control (i.e., untreated HIV-infected cells), the cell viability was assessed via the in situ reduction of the tetrazolium compound MTS, using the CellTiter 96® AQ$_{ueous}$ One Solution Cell Proliferation Assay (Promega, Madison, Wis.). The absorbance was measured spectrophotometrically at 490 nm with a 96-well plate reader (Molecular Devices, Sunnyvale, Calif.) and compared with four cell control replicates (cells without virus and drugs) and four virus control wells (virus-infected cells without drugs). The $IC_{50}$, i.e., the drug concentration that inhibits HIV-induced cell death by 50%, was calculated for each polypeptide from the dose-response curve. The $CC_{50}$ or 50% cytotoxic concentration of each of the polypeptides was determined from the reduction of viability of uninfected cells exposed to the agents.

The respective $IC_{50}$ values for the CXCR4 Nanobodies on MT-4 cells are depicted in Table 3.2. The $IC_{50}$ values for the CD4 Nanobodies are depicted in Table 2.4. Nanobody 03F11 directed against CD4 inhibits X4 HIV-1 NL4.3 replication with an $IC_{50}$ of 0.52 µg/ml in MT-4 cells, corresponding to 34.7 nM. The anti-CXCR4-directed Nanobody 281F12 had a comparable potency and inhibited HIV-1 NL4.3 replication with an average $IC_{50}$ of 0.34 µg/ml, corresponding to 22.7 nM.

The same set of CXCR4 Nanobodies were also evaluated on human PBMCs (endogenously expressing subpopulations of CD4, CXCR4 and CCR5) against HIV-1 X4 NL4.3 strain, HIV-1 X4 UG270 clinical isolate clade D, X4 HIV-1 CI #17 clinical isolate clade B, X4 HIV-1 CM237 clinical isolate clade B and against HIV-1 R5 BaL strain. Again, AMD3100 and AMD14031 (maraviroc) were used as controls in all experiments. Peripheral blood mononuclear cells (PBMCs) from healthy donors were isolated by density centrifugation (Lymphoprep; Nycomed Pharma, AS Diagnostics, Oslo, Norway) and stimulated with phytohemagglutin for 3 days. The activated cells were washed with PBS and viral infections were performed as described previously (Schols et al. J Exp Med 1997; 186:1383-1388). PHA-stimulated blasts were seeded at 0.5×10$^6$ cells per well into a 48-well plate (Costar; Elscolab, Kruibeke, Belgium) containing varying concentrations of compound in medium containing IL-2. The virus stocks were added at a final dose of 100 TCID50 of HIV-1 or HIV-2. At 8-10 days after the start of the infection, viral p24 Ag was detected in the culture supernatant by an enzyme-linked immunosorbent assay (Perkin Elmer, Brussels, Belgium). For HIV-2 p27 Ag detection, the INNOTEST from Innogenetics (Temse, Belgium) was used.

Table 3.2 summarizes the results of the HIV neutralization on 4 X4 HIV-1 strains by CXCR4 Nanobodies.

The results indicate that CXCR4 Nanobodies showed consistent neutralization capacity on different clinical isolates that are dependent on CXCR4, whereas none of these was able to block infection of the BaL strain ($IC_{50}$>1000 ng/mL, data not shown). Of the tested panel, 281E10 and 283F1 were very potent antagonists on all X4 strains, whereas 281F12 was the least potent Nanobody, with $IC_{50}$ ranging between 9-16 nM. The potency in HIV1 neutralisation is in the same affinity range as the ligand displacement Ki of 26 nM.

The inhibition of HIV-1 replication (combined with its poor ligand displacement capacity) makes CXCR4 Nanobody 281F12 a suitable initial candidate for use in formatting into bispecific constructs with CD4 Nanobody 3F11.

TABLE 3.2

CXCR4 Nanobodies were evaluated for blocking the infectivity of distinct clinical HIV1 isolates in PBMC, i.e. HIV-1 X4 NL4.3 strain, HIV-1 X4 UG270 clinical isolate (clade D), HIV-1 CI#17 clinical isolate (clade B), HIV-1 CM237 clinical isolate (clade B) and against HIV-1 R5 BaL strain. The Nanobodies are ranked according to potency. As control compounds AMD3100 (specific CXCR4 antagonist) and maraviroc (specific CCR5 antagonist) were included.

| HIV1 strain | | | | | |
|---|---|---|---|---|---|
| compound | M, Average 2 donors | NL4.3 X4 | UG270 Clade D | CI#17 Clade B | CM237 Clade B |
| 283F1 | $IC_{50}$ | 7.6E-10 | 1.0E-09 | 2.0E-09 | 1.2E-09 |
|  | $IC_{90}$ | 3.6E-09 | 8.1E-09 | 9.1E-09 | 5.1E-09 |
| 281E10 | $IC_{50}$ | 1.2E-09 | 1.8E-09 | 1.3E-09 | 6.7E-10 |
|  | $IC_{90}$ | 3.5E-09 | 7.7E-09 | 8.1E-09 | 4.0E-09 |
| 283B6 | $IC_{50}$ | 1.6E-09 | 1.9E-09 | 2.8E-09 | 2.0E-09 |
|  | $IC_{90}$ | 7.3E-09 | 6.4E-09 | 9.9E-09 | 7.3E-09 |
| 283E2 | $IC_{50}$ | 4.1E-09 | 1.3E-09 | 3.7E-09 | 3.3E-09 |
|  | $IC_{90}$ | 1.2E-08 | 1.4E-08 | 1.7E-08 | 1.7E-08 |
| 281D4 | $IC_{50}$ | 1.2E-09 | 7.8E-09 | 1.5E-08 | 3.3E-09 |
|  | $IC_{90}$ | 3.8E-09 | 2.7E-08 | 3.3E-08 | 1.0E-08 |
| 281A6 | $IC_{50}$ | 2.5E-09 | 1.1E-08 | 2.0E-08 | 9.9E-09 |
|  | $IC_{90}$ | 9.1E-09 | 2.7E-08 | 6.1E-08 | 2.7E-08 |
| 281A5 | $IC_{50}$ | 2.3E-08 | 4.0E-09 | 1.2E-08 | 1.8E-08 |
|  | $IC_{90}$ | 5.95E-08 | 7.33E-09 | >5.7E-08 | 4.9E-08 |
| 281F12 | $IC_{50}$ | 1.4E-08 | 1.2E-08 | 8.9E-09 | 1.6E-08 |
|  | $IC_{90}$ | 5.7E-08 | 2.4E-09 | 4.0E-08 | 4.9E-08 |
| irrelevant | $IC_{50}$ | >5.7E-08 | >5.7E-08 | >5.7E-08 | >5.7E-08 |
|  | $IC_{90}$ | >5.7E-08 | >5.7E-08 | >5.7E-08 | >5.7E-08 |
| AMD3100 | $IC_{50}$ | 1.3E-08 | 1.6E-08 | 2.2E-08 | 1.0E-08 |
|  | $IC_{90}$ | 4.2E-08 | 4.1E-08 | 4.7E-08 | 2.4E-08 |

Example 4: Combination Studies with Monovalent CXCR4 and CD4 Nanobodies

To test the combinatorial effects of CXCR4 and CD4 Nanobodies on HIV-1 activity, each of the selected Nanobodies was tested alone or in combination with another anti-HIV compound.

The anti-HIV compounds used were (1) AMD3100 (plerixafor, trade name Mozobil, Genzyme), which is a specific CXCR4 antagonist; (2) T-20 (enfuvirtide, trade name FUZEON®, Roche), which is a gp41-mimicking peptide acting as a HIV fusion inhibitor; (3) CADA (cyclotriaza-disulfonamide), which is a CD4 down-modulating compound acting as a specific CD4-targeted HIV entry inhibitor; (4) RPA-T4 (anti-CD4 mouse mAb), which binds to the D1 domain of CD4 and can block HIV gp120 binding and inhibit syncytia formation.

The anti-HIV-1 $EC_{50}$ and $EC_{95}$ before and after combination were determined by measuring the cytopathic effect of NL4.3 in MT-4 cells, using the MTS viability staining method described above. Combination indices (CI) were calculated using CalcuSyn software (Biosoft, Cambridge, UK) based on the median effect principle of Chou and Talalay (Chou and Talalay, 1984). The derived combination index equation for two drugs is:

$$CI = \frac{(D)_1}{(D_x)_1} + \frac{(D)_2}{(D_x)_2} = \frac{(D)_1}{(D_m)_1[f_a/(1-f_a)]^{1/m_1}} + \frac{(D)_2}{(D_m)_2[f_a/(1-f_a)]^{1/m_2}}$$

Where $(Dx)_1$ is for $(D)_1$ "alone" that inhibits a system x %, and $(Dx)_2$ is for $(D)_2$ "alone" that inhibits a system x % whereas in the numerator, $(D)_1+(D)_2$, "in combination" also inhibit x %. Note that the denominators of the last two terms are the expression of MEE. CI-value<0.9 indicates synergism, 0.9<CI<1.1 indicates additive effects and CI>1.1 indicates antagonism.

The respective CI values of the tested combinations are depicted in Table 4. Synergy of the anti-CD4 Nanobody 3F11 was observed in combination with the Nanobody 281F12 (anti-CXCR4), with AMD3100 (anti-CXCR4), with T-20 (FUZEON®) and with CADA (downregulation of CD4). However, antagonism was observed with the anti-CD4 monoclonal antibody RPA-T4, suggesting that these compounds may bind to overlapping epitopes on CD4. Synergy of the anti-CXCR4 Nanobody 281F12 was observed with CADA and T-20, but only additive affects were observed with AMD3100 (Table 4).

Together these results argue for the combined blockade of HIV1 entry by a bispecific polypeptide (e.g. CXCR4 Nanobody 281F12 and CD4 Nanobody 3F11).

TABLE 4

Combination index (CI) determination in MT-4 cells infected with HIV-1 NL4.3

| Agent 1 | Agent 2; | directed against | $CI_{50\%}$ | $CI_{75\%}$ | $CI_{95\%}$ | synergy |
|---|---|---|---|---|---|---|
| 3F11 | 281F12 | CXCR4 | 0.65 ± 0.12 | 0.58 ± 0.12 | 0.51 ± 0.12 | +++ |
|  | AMD3100 | CXCR4 | 0.65 ± 0.09 | 0.60 ± 0.11 | 0.56 ± 0.14 | +++ |
|  | CADA | CD4 | 0.50 ± 0.09 | 0.40 ± 0.06 | 0.28 ± 0.04 | ++++ |
|  | RPA-T4 mAb | CD4 | 1.3 ± 0.2 | 1.6 ± 0.4 | 3.8 ± 1.4 | Antagonism |
|  | T-20 | HIV1 | 0.57 ± 0.16 | 0.50 ± 0.19 | 0.43 ± 0.24 | +++ |

TABLE 4-continued

Combination index (CI) determination in MT-4 cells infected with HIV-1 NL4.3

| Agent 1 | Agent 2 | directed against | $CI_{50\%}$ | $CI_{75\%}$ | $CI_{95\%}$ | synergy |
|---|---|---|---|---|---|---|
| 281F12 | AMD3100 | CXCR4 | 1.15 ± 0.06 | 1.11 ± 0.05 | 1.05 ± 0.05 | Additivity |
| | CADA | CD4 | 0.80 ± 0.10 | 0.73 ± 0.05 | 0.64 ± 0.02 | +++ |
| | T-20 | HIV1 | 0.70 ± 0.20 | 0.66 ± 0.30 | 0.66 ± 0.43 | +++ |

Dose Reduction: reduction in CBA concentration after combination compared to single drug treatment
CI (Combination index): CI represented by the mean ± SEM from 2-5 independent experiments in duplicate. CI <0.9: synergy; 0.9 < CI < 1.1: additive effect and CI >1.1: antagonism
Synergy level: synergy calculated at the $EC_{95}$-level: +, slight synergism (CI: 0.85-0.90); ++, moderate synergism (CI: 0.70-0.85); +++, synergism (CI, 0.30-0.70); ++++, strong synergism (CI, 0.10-0.30)

Example 5. Construction of Bispecific CXCR4-CD4 Polypeptides

Example 4 demonstrated the synergy effects of the combined blockade of HIV1 entry by the individual CXCR4 Nanobody 281F12 (SEQ ID NO: 9) and CD4 Nanobody 3F11 (SEQ ID NO: 20). Next, the inventors set out to assess the effects of dual blockade of both CD4 and CXCR4 receptors in bispecific constructs on HIV infectivity. Bispecific CXCR4-CD4 polypeptides were generated as set out below.

Since CXCR4 and CD4 act as co-receptors for gp120, they are expected to be in close proximity on the cell surface. CCR5, CXCR4, and CD4 are found predominantly on microvilli on the cell surface, forming homogeneous microclusters in all cell types, including macrophages and T-cells. Moreover, gp120 induces CD4-CXCR4 membrane colocalization. However, the optimal distance between the two Nanobody building blocks for simultaneous binding to both receptors and subsequent blockade of HIV1 entry is not known. For this reason bispecific polypeptides were generated with flexible spacers of different lengths for linking the two Nanobody building blocks: $(Gly_4SerGly_4)$ (9GS), $(Gly_4Ser)_5$ (25GS), and $(Gly_4Ser)_7$ (35GS), respectively.

Constructs of the anti-CD4 Nanobody 3F11 and anti-CXCR4 Nanobody 281F12 were introduced in the production vector pAX100. This vector is derived from pUC119 and contains a LacZ promoter, a kanamycin resistance gene, a multiple cloning site, an OmpA leader sequence, a C-terminal c-myc tag and a His6 tag. Bispecific constructs were generated with 281F12 positioned in both N-terminal and C-terminal position of 3F11, genetically fused with the respective linker, yielding 8 different bispecific constructs (Table 5A). The correct nucleotide sequence of all constructs was confirmed by sequence analysis (see Table 5B) for an overview of all sequences). Monovalent and bispecific Nanobody constructs were produced in E. coli and purified as myc-His tagged proteins by immobilized metal affinity chromatography (IMAC) using Nickel SEPHAROSE® 6 FF. Nanobodies were eluted from the column with 250 mM imidazole and subsequently desalted towards dPBS.

TABLE 5A

| Panel of CXCR4-CD4 Nanobodies | |
|---|---|
| CD4-CXCR4 | 03F11-9GS-281F12 |
| | 03F11-25GS-281F12 |
| | 03F11-35GS-281F12 |
| CXCR4-CD4 | 281F12-9GS-03F11 |
| | 281F12-25GS-03F11 |
| | 281F12-35GS-03F11 |

Subsequently, the correct monovalent and bispecific Nanobody constructs were recloned into the pAX205 vector for production in the yeast Pichia pastoris as FLAG3-His6-tagged proteins Plasmids encoding bispecific constructs were linearized by digestion with restriction enzymes prior to the transformation into P. pastoris strain X-33. Small scale test expressions of P. pastoris transformants were done in to select for the clone with good expression levels. Hereto 4 ml scale expressions were performed of 4 clones of each construct in 24-wells deep well plates. Expression of the Nanobody constructs in the medium was evaluated by SDS-PAGE. Medium fractions were collected and used as starting material for immobilized metal affinity chromatography (IMAC) using Nickel SEPHAROSE® 6 FF. Nanobody constructs were eluted from the column with 250 mM imidazole and subsequently desalted on SEPHADEX® G-25 Superfine on the Atoll (ATO002) towards dPBS. The purity and integrity of Nanobody constructs was verified by SDS-PAGE and western blot using anti-VHH and anti-tag detection.

TABLE 5B

| Name | SEQ ID | Amino acid sequence |
|---|---|---|
| 03F11-9GS-281F12 | 101 | EVQLVESGGGSVQPGGSLTLSCGTSGRTFNVMGWFRQAPGKEREFVAAVRWSSTGIYYTQYADSVKSRFTISRDNAKNTVYLEMNSLKPEDTAVYYCAADTYNSNPARWDGYDFRGQGTQVTVSSGGGGSGGGGSEVQLVESGGGLVQAGDSLRLSCAASGRAFSRYAMGWFRQAPGKEREFVAAIGWGPSKTNYADSVKGRFTISRDNAKNTVYLQMNTLKPEDTAVYSCAAKFVNTDSTWSRSEMYTYWGQGTQVTVSS |
| 03F11-25G5-281F12 | 102 | EVQLVESGGGSVQPGGSLTLSCGTSGRTFNVMGWFRQAPGKEREFVAAVRWSSTGIYYTQYADSVKSRFTISRDNAKNTVYLEMNSLKPEDTAVYYCAADTYNSNPARWDGYDFRGQGTQVTVSSGGGGSGGGGSGGGGSGGGGSGGGGSEVQLVESGGGLVQAGDSLRLSCAASGRAFSRYAMGWFRQAPGKEREFVAAIGWGPSKTNYADSVKGRFTISRDNAKNTVYLQMNTLKPEDTAVYSCAAKFVNTDSTWSRSEMYTYWGQGTQVTVSS |

TABLE 5B-continued

| Name | SEQ ID | Amino acid sequence |
|---|---|---|
| 03F11-35G5-281F12 | 103 | EVQLVESGGGSVQPGGSLTLSCGTSGRTFNVMGWFRQAPGKEREFVAAVRWSSTGIYYTQYADSVKSRFTISRDNAKNTVYLEMNSLKPEDTAVYYCAADTYNSNPARWDGYDFRGQGTQVTVSSGGGGSGGGGSGGGGSGGGGSGGGGSGGGGSGGGGSEVQLVESGGGLVQAGDSLRLSCAASGRAFSRYAMGWFRQAPGKEREFVAAIGWGPSKTNYADSVKGRFTISRDNAKNTVYLQMNTLKPEDTAVYSCAAKFVNTDSTWSRSEMYTYWGQGTQVTVSS |
| 281F12-9G5-03F11 | 104 | EVQLVESGGGLVQAGDSLRLSCAASGRAFSRYAMGWFRQAPGKEREFVAAIGWGPSKTNYADSVKGRFTISRDNAKNTVYLQMNTLKPEDTAVYSCAAKFVNTDSTWSRSEMYTYWGQGTQVTVSSGGGGSGGGGSEVQLVESGGGSVQPGGSLTLSCGTSGRTFNVMGWFRQAPGKEREFVAAVRWSSTGIYYTQYADSVKSRFTISRDNAKNTVYLEMNSLKPEDTAVYYCAADTYNSNPARWDGYDFRGQGTQVTVSS |
| 281F12-25G5-03F11 | 105 | EVQLVESGGGLVQAGDSLRLSCAASGRAFSRYAMGWFRQAPGKEREFVAAIGWGPSKTNYADSVKGRFTISRDNAKNTVYLQMNTLKPEDTAVYSCAAKFVNTDSTWSRSEMYTYWGQGTQVTVSSGGGGSGGGGSGGGGSGGGGSGGGGSEVQLVESGGGSVQPGGSLTLSCGTSGRTFNVMGWFRQAPGKEREFVAAVRWSSTGIYYTQYADSVKSRFTISRDNAKNTVYLEMNSLKPEDTAVYYCAADTYNSNPARWDGYDFRGQGTQVTVSS |
| 281F12-35G5-03F11 | 106 | EVQLVESGGGLVQAGDSLRLSCAASGRAFSRYAMGWFRQAPGKEREFVAAIGWGPSKTNYADSVKGRFTISRDNAKNTVYLQMNTLKPEDTAVYSCAAKFVNTDSTWSRSEMYTYWGQGTQVTVSSGGGGSGGGGSGGGGSGGGGSGGGGSGGGGSGSEVQLVESGGGSVQPGGSLTLSCGTSGRTFNVMGWFRQAPGKEREFVAAVRWSSTGIYYTQYADSVKSRFTISRDNAKNTVYLEMNSLKPEDTAVYYCAADTYNSNPARWDGYDFRGQGTQVTVSS |

Example 6. Binding Analysis of Bispecific CXCR4-CD4 Polypeptides

To assess if the formatting into bispecific constructs affected the binding of the CXCR4 Nanobody to CXCR4, the entire set of bispecific polypeptides was analysed for binding to CXCR4 on viral lipoparticles (Integral Molecular). Briefly 2 units of null VLPs and hCXCR4 lipoparticles were coated on 96-wells maxisorp plates overnight at 4° C. In the next day free binding sites were blocked using 4% marvel skimmed milk in PBS for 2 h at room temperature. Then, after washing the plate 3 times with PBS, 100 nM, 10 nM, 1 nM and 0 nM of purified polypeptides were added to the coated wells and incubated for 1 h at room temperature. After washing 3 times with PBS, bound polypeptides were detected with mouse anti-c-myc (Roche, cat #11667149001) and rabbit anti-Mouse-HRP (DAKO, cat #P0260) antibodies both for 1 h at room temperature. Binding was determined based on O.D. values and compared to controls: an irrelevant Nanobody, a non-coated well, both parental monovalent building blocks and a monoclonal anti-CXCR4 antibody 12G5 (R&D Systems, cat #MAB170).

FIG. 2.2 shows the results of the binding ELISA to CXCR4 lipoparticles versus control lipoparticles. An orientation effect for bispecific constructs with the CD4 Nanobody is observed, and CXCR4 binding was only retained with the CXCR4 Nanobody placed at the N-terminal position. A change in linker length could not overcome this loss of target binding of the CXCR4 Nanobody, except perhaps for the CD4-25GS-CXCR4 construct, which seemed to be less impaired than the two other bispecifics with the CXCR4 moiety in the C-terminal position.

The panel of CXCR4-CD4 bispecific polypeptides was analysed for dose-dependent binding to cell lines with different relative expression levels of the two targets CXCR4 and CD4 in flow cytometry. Cells were incubated with Fc-blocking solution (Miltenyi Biotec cat #130-059-901) for 30 minutes before staining with monoclonal anti-CXCR4 antibody 12G5 (R&D #MAB170) and monoclonal anti-CD4 antibody BA1 (Diaclone #854030000). Bound polypeptides were detected with mouse anti-c-myc (AbD Serotec, cat #MCA2200) and Goat anti-Mouse-PE (Jackson ImmunoResearch, cat #115-115-171) antibodies both for 30 min shaking at 4° C. Binding was determined based on MCF values and compared to controls.

Expression levels of CD4 and CXCR4 on Jurkat cells, THP-1 cells and Molm-13 cells are depicted in FIG. 2.3, as well as the binding curves of monovalent and bispecific Nanobody constructs to each of the cell lines.

$EC_{50}$ values of Jurkat cells and Molm-13 cells are listed in Table 6. Jurkat E6.1 cells show a heterogeneous population of cells expressing no or low levels of CD4. Monovalent CD4 3F11 Nanobody showed only a very low MCF level of binding to Jurkat cells, although the $EC_{50}$ value was similar to that on THP-1 and MOLM-13 cells ($EC_{50}$ of 1.1 nM vs 0.5 nM vs 0.7 nM, respectively).

TABLE 6

Binding affinity and potency of bispecific CXCR4-CD4 polypeptides to cells with different expression levels of CXCR4 and CD4. Functional blockade was assessed by measuring the inhibition of SDF-1 mediated chemotaxis via CXCR4. Results are average values of 3 experiments.

| | | CXCR4+/CD4+ MOLM-13 cells | | | CXCR4+/CD4$^{low}$ Jurkat E6-1 cells | | |
| | | Inhibition of SDF-1a-mediated chemotaxis | | | Inhibition of SDF-1a-mediated chemotaxis | | |
| ID | Target | Binding EC$_{50}$ (nM) | IC$_{50}$ (nM) | Ratio to 281F12 # | Binding EC$_{50}$ (nM) | IC$_{50}$ (nM) | Ratio to 281F12 # |
| --- | --- | --- | --- | --- | --- | --- | --- |
| 281F12 | CXCR4 | 5.2 | 86.0 | — | 7.0 | 84.2 | — |
| 281F12-3F11 | CXCR4-CD4 | 1.1 | 0.59 | 146 | 11 | 110 | 0.8 |
| 3F11-281F12 | CD4-CXCR4 | 0.7 | 1.29 | 67 | 1.1 | 460 | 0.2 |
| 3F11 | CD4 | 0.7 | — | — | 1.4 | — | — |

Fold increase in potency of bispecific relative to monovalent CXCR4 Nanobody 281F12.

On Jurkat cells, the bispecific CXCR4-CD4 Nanobody constructs have similar EC$_{50}$ values as the monovalent CXCR4 Nanobody construct, in line with the high CXCR4 expression levels. The bispecific Nanobody constructs have a slightly higher fluorescence level than monovalent CXCR4 Nanobodies. On double-positive THP-1 cells, a clear shift in the curves of the bispecific CXCR4-CD4 Nanobody constructs is observed compared to both monovalent Nanobody constructs. Bispecific Nanobody constructs reach much higher plateau MCF levels. The difference in EC$_{50}$ values between bispecifics and monovalent Nanobody constructs however is only moderate (EC$_{50}$ 0.29 nM (CXCR4-CD4) vs 0.5 nM (CD4) vs 3.1 nM (CXCR4)). On MOLM-13 cells the EC$_{50}$ value of the bispecific polypeptides is similar to that of CD4 Nanobody 3F11. Also here increased plateau levels are observed. The binding curves of the inverse orientation (CD4-CXCR4) bispecific Nanobody constructs overlap with the monovalent CD4 Nanobody 3F11.

This increase in total fluorescence in flow cytometry may represent additive binding (binding to each target alone), as well as simultaneous binding to both targets on the cell surface.

Example 7: Bispecific Constructs Show Increased Affinity and Inhibitory Potency for CXCR4

7.1: Inhibition of CXCR4-Mediated Chemotaxis by CXCR4-CD4 Bispecific Constructs To assess if bispecific CXCR4-CD4 polypeptides show increased affinity and potency on cells expressing both receptors, a CXCR4-dependent functional assay was performed. Dose-dependent inhibition of CXCL12-induced chemotaxis by the panel of bispecific CD4-CXCR4 Nanobodies was determined on Jurkat (CXCR4+/CD4$^{low}$), and Molm-13 cells (CXCR4++/CD4++) for direct comparison of cells expressing both or only one receptor.

Bispecific polypeptides were analyzed for inhibition of CXCL12-induced chemotaxis on cells endogenously expressing CXCR4. As chemoattractant a concentration of 750 pM SDF-1α (R&D Systems) was used on 100,000 cells/well for the Jurkat cell line, and 500,000 cells/well for the MOLM-13 cell line. SDF-1α and serially diluted Nanobody constructs were added to the bottom of a small chemotaxis plate (Neuprobe 106-5) in a total volume of 29 µl. A chemotaxis filter membrane (ChemoTx® Disposibla, pore size 5 µm) was placed on top of the wells, ensuring that the membrane was in contact with the solution in the wells below. A Nanobody dilution (10 µl at 5× the serially diluted final concentration as below the membrane in each well) was added on top of the membrane, followed by 40 µl of cell suspension. The plates were incubated for 3 hours at 37° C. in a humidified incubator (5% CO$_2$). After incubation, the filters were carefully removed and the cells in the well below were resuspended in the existing solution. The complete cell suspension was transferred to the corresponding wells of white polystyrene Costar plates. After this, 30 µl of Cell Titer Glo reagent (Promega G7571) was added to each well, followed by a 10 minute incubation, with shaking in the dark. Luminescence was measured (1 sec/well) using an Envision 2103 Multilabel Reader with emission filter 700 (Perkin Elmer). On each plate the corresponding monovalent CXCR4 Nanobody was included as reference, allowing to calculate the fold increase of the bispecific within each plate. As additional control, 1:1 mixtures of monovalent Nanobodies were included. As reference, anti-CXCR4 antibody 12G5 was included on each plate.

Results of a representative example are shown in FIG. 2.4, and IC$_{50}$ values are presented in Table 6 (average of n=3 experiments).

The bispecific CXCR4-CD4 constructs showed a strong potency enhancement of about 150-fold on double-positive cells compared to the monovalent CXCR4 Nanobody, whereas the CD4 Nanobody by itself did not have any effect on SDF-1 function. Remarkably, bispecific constructs in the inverse orientation were still able to block CXCR4 function, despite their strongly reduced affinity for CXCR4 due to the C-terminal position in the construct, although the blockade was only partial.

Since the functional blockade is mainly mediated via CXCR4, avidity by the simultaneous binding of the anti-CD4 Nanobody is expected to translate into increased potency in inhibition of chemotaxis.

This indicates that each of the Nanobodies in the bispecific construct is capable of binding simultaneously to their respective target, and contributes to avidity on cells that co-express both the receptor and co-receptor.

7.2. Inhibition of CXCL12 to CXCR4 by Bispecific CXCR4-CD4 Nanobody Constructs The capacity of the monovalent and bispecific CXCR4-CD4 Nanobody constructs to displace the natural ligand of CXCR4, SDF-1 or CXCL-12, was assessed in a binding inhibition assay on CD4+ T-cells (SUPT-1 cells) by flow cytometry. Briefly, human T-lymphoid SupT1-CXCR4 cells were washed once with assay buffer (Hanks' balanced salt solution with 20 mM HEPES buffer and 0.2% bovine serum albumin, pH 7.4) and then incubated for 15 min at room temperature with the agents diluted in assay buffer at the indicated concentrations. CXCL12$^{AF647}$ (human CXCL12 carrying an AlexaFluor 647 moiety at its second to last amino acid position) was obtained from Almac Sciences (Craigavon, UK). After the incubation period with the compounds, CXCL12$^{AF647}$ (25 ng/ml) diluted in assay buffer was added to the cell-compound mixtures and incubated at room temperature for 30 min. Thereafter, the cells were washed twice in assay buffer, fixed in 1% paraformaldehyde in phosphate buffered saline (PBS), and analyzed on the FL4 channel of a FACSCalibur flow cytometer equipped with a 635-nm red diode laser (Becton Dickinson). The percentages of inhibition of CXCL12$^{AF647}$ binding were calculated according to the formula $(1-[MFI-MFI_{NC}]/[MFI_{PC}-MFI_{NC}]) \times 100$ where MFI is the mean fluorescence intensity of the cells incubated with CXCL12$^{AF647}$ in the presence of the inhibitor, $MFI_{NC}$ is the mean fluorescence intensity measured in the negative control (i.e., autofluorescence of unlabeled cells), and $MFI_{PC}$ is the mean fluorescence intensity of the positive control (i.e., cells exposed to CXCL12$^{AF647}$ alone).

The respective $IC_{50}$ values are shown in Table 7.2.

The anti-CXCR4 Nanobody 281F12 blocked binding of the specifically labelled CXCL12$^{AF647}$ to CXCR4 expressed with an $IC_{50}$ of 6.3 nM. The bispecific constructs 3F11-281F12 and 281F12-3F11 were very similar with potencies of 1.5 nM and 0.97 nM, respectively, 4 to 6.5-fold better relative to monovalent Nanobody 281F12 on T-cells. The anti-CD4 Nanobody 3F11 did not interfere with CXCL12$^{AF647}$ binding to CXCR4 on T-cells.

vale, Calif., USA), in essence as described by Princen et al. (Princen et al., 2003 Cytometry 51, 35-45).

The $IC_{50}$ values are shown in Table 7.2.

None of the monovalent polypeptides induced by themselves any significant $Ca^{2+}$-signaling. No differences in $IC_{50}$ values were observed between the different orientations of the bispecific polypeptides CXCR4-CD4 and CD4-CXCR4 in inhibiting CXCL-12-induced $Ca^{2+}$-signaling in U87.CD4.CXCR4 cells. Potency enhancements relative to monovalent polypeptide CXCR4 281F12, which had an $IC_{50}$ of 66.7 nM, were 12 to 20-fold. Monovalent Nanobody 3F11 displayed no CXCL-12-induced $Ca^{2+}$-signaling inhibition.

Taken together, these results indicate that the simultaneous binding to both CD4 and CXCR4 by the bispecific CXCR4-CD4 construct on cells that co-express both targets enhances the affinity and potency of the CXCR4 binding moiety, without clear influence on orientation.

7.4 Inhibition of Anti-CXCR4 Antibody Binding by Bispecific CXCR4-CD4 Polypeptide Constructs The capacity of the monovalent and bispecific CXCR4-CD4 Nanobody constructs to displace the binding of anti-CXCR4 mAb 12G5 was assessed on different cell lines, SUPT-1 CD4$^+$ T-cells, THP-1, and Jurkat cells by flow cytometry.

In short, cells were washed once with assay buffer (Hanks' balanced salt solution with 20 mM HEPES buffer and 0.2% bovine serum albumin, pH 7.4) and then incubated for 15 min at room temperature with the Nanobodies diluted in assay buffer at the indicated concentrations. Next, anti-CXCR4 mAb 12G5 (PE-labelled, 10 nM) was added to the

TABLE 7.2

Inhibition of ligand binding and activation of CXCR4 by CXCR4-CD4 polypeptides.

| ID | Target | SDF-1$^{AF647}$-displacement SUPT-1 cells $IC_{50}$ (nM) n = 3 | SDF-1 induced $Ca^{2+}$ signaling U87-CD4-CXCR4 $IC_{50}$ (nM) n = 3 | Anti-CXCR4 mAb 12G5 binding inhibition SUPT-1 cells $IC_{50}$ (nM) | THP-1 cells $IC_{50}$ (nM) | Jurkat cells $IC_{50}$ (nM) |
|---|---|---|---|---|---|---|
| 3F11 | CD4 | — | — | — | — | — |
| 281F12 | CXCR4 | 6.3E−09 | 6.67E−08 | 5.13E−08 | 4.93e−08 | 1.37e−08 |
| 281F12-3F11 | CXCR4-CD4 | 9.6E−10 | 5.31E−09 | 1.50E−09 | 2.48e−09 | 2.93e−08 |
| 3F11-281F12 | CD4-CXCR4 | 1.5E−09 | 3.43E−09 | 5.66E−08 | no fit | 6.31e−07 |
| AMD3100 | CXCR4 | 9.3E−08 | 4.1E−07 | 1.25E−09 | | |

7.3 Inhibition of SDF-1-Induced Calcium Signaling by Bispecific CXCR4-CD4 Polypeptide Constructs The capacity of the monovalent and bispecific CXCR4-CD4 constructs to inhibit down-stream signal transduction of CXCR4 receptor was assessed in inhibiting CXCL-12-induced $Ca^{2+}$-signaling. To this end U87.CD4.CXCR4 glioblastoma cells were loaded with the fluorescent calcium indicator Fluo-3 acetoxymethyl (Molecular Probes) at 4 µM in assay buffer (Hanks' balanced salt solution with 20 mM HEPES buffer and 0.2% bovine serum albumin, pH 7.4) for 45 min at room temperature. After thorough washing with assay buffer, cells were pre-incubated for 10 min at 37° C. in the same buffer with the Nanobody constructs or AMD3100 for 10 min at 37° C. Next the intracellular calcium mobilization in response to CXCL12 was measured at 37° C. by monitoring the fluorescence as a function of time simultaneously in all the wells by using a Fluorometric Imaging Plate Reader (FLIPR; Molecular Devices, Sunnycell-agent mixtures and incubated at room temperature for 30 min. Thereafter, the cells were washed twice in assay buffer. In case of SUPT-1, cells were fixed in 1% paraformaldehyde in phosphate buffered saline (PBS). Subsequently, the cells were analyzed on the FL2 channel of a FACS Calibur flow cytometer (Becton-Dickinson).

Results are depicted in Table 7.2 and FIG. 3.

On Jurkat cells, the bispecific 281F12-3F11 Nanobody construct lost 2-fold potency compared to monovalent CXCR4 Nanobody construct, in the inverse orientation a ~50-fold loss was observed. On SUPT-1 and THP-1 cells, which co-express CXCR4 and CD4, the bispecific 281F12-3F11 Nanobody construct showed enhanced displacement of 12G5 mAb binding compared to monovalent 281F12 Nanobody construct albeit with bi-phasic curves. It was hypothesized that this is due to the avidity provided by the CD4 binding of the 3F11 Nanobody arm.

Example 8: Potent and Broad HIV1 Neutralization by Bispecific CXCR4-CD4 Constructs The specificity of the inhibitory effects of the bispecific CXCR4-CD4 constructs and the corresponding monovalent CXCR4 and CD4 constructs were tested on CXCR4-using (X4) HIV-1 clone NL4.3 infecting MT-4 cells, and in phytohemagglutin (PHA) stimulated PBMCs (expressing CD4$^+$/CXCR4$^+$/CCR5$^+$) from different healthy donors. The CCR5-using (R5) HIV-1 strain BaL was used to infect PBMCs.

8.1. HIV-1 Infection Assays

The anti-HIV-1 potencies of the bispecific CD4-CXCR4 Nanobody constructs and the corresponding monovalent CXCR4 and CD4 Nanobody constructs were determined by measuring the cytopathic effect of distinct HIV-1 strains in MT-4 and U87 cell lines, or by quantification of the viral p24 antigen production in the culture supernatant of PBMCs, as described in Example 3.2.

The HIV1 neutralisation results in MT-4 cells were depicted as $IC_{50}$ values in Table 8.1.1.

In MT-4 cells infected with the NL4.3 strain, the CXCR4 Nanobody specifically inhibited anti-X4 HIV1 entry via CXCR4, but did not inhibit binding to CCR5. The CD4 Nanobody effectively blocked both X4 HIV1 infection, with a similar $IC_{50}$ value as the CXCR4 monovalent in MT-4 cells. Bispecific CXCR4-CD4 constructs were extremely potent in inhibiting HIV-1 X4 virus replication in MT-4 cells in PHA-stimulated PBMCs, with 30-370 pM potencies. For the bispecific CXCR4-CD4 constructs potency increases were between 250-320 fold compared to the monovalent CXCR4 Nanobody, with the shortest linker seeming to be slightly better than the longer linkers. Bispecific polypeptides with Nanobodies in the inverse orientation, i.e. with the reduced affinity towards CXCR4, were less active in this functional assay, but still considerable more potent than the CD4 monovalent.

Next, we assessed if the observed potencies of the bispecific constructs were due to the combined blockade by the CXCR4 and CD4 Nanobodies, or whether linking of the two Nanobodies into the bispecific construct was necessary for the potency enhancement. To this end, the inhibition of NL4.3 infectivity in MT-4 cells was compared for bispecific 281F12-35GS-3F11 Nanobody construct, and monovalent Nanobodies either alone or in a 1:1 molar ratio.

Results are shown in FIG. 4.

While the mixture of monovalent CXCR4 and CD4 Nanobody constructs resulted in an approximately 2-fold improved $IC_{50}$ compared to the best monovalent Nanobody, the bispecific construct gave a 320-fold improvement, with 150 pM potency. Thus, the simultaneous binding to both CXCR4 and CD4 of the bispecific CXCR4-CD4 polypeptides resulted in avidity and strongly enhanced potencies in the neutralization of CXCR4-using HIV-1 compared to the monovalent counterparts alone or the combination of the monovalents. The linking is important, but no clear effect of linker lengths is apparent.

TABLE 8.1.1

Anti-HIV specificity profile of bispecific Nanobodies with different linker lengths for CXCR4-tropic NL4.3 (X4), and CCR5-tropic (R5) BaL viruses.

| | $IC_{50}$ (nM) Cells + HIV strain | | | |
|---|---|---|---|---|
| Nanobody | MT-4 + NL 4.3 (X4) n = 3 | U87 + NL 4.3 (X4) n = 3 | PBMC + NL 4.3 (X4) n = 3 | PBMC + BaL (R5) n = 3 |
| CD4 3F11 | 35.3 | >1333 | 580 # | 610 |
| CXCR4 281F12 | 22.9 | >6666 | 27.7 | >1666 |
| CD4-9GS-CXCR4 | 14.9 | >3333 | 17.0 | >666 |
| CD4-25GS-CXCR4 | 9.2 | >3333 | 8.7 | 383.3 |
| CD4-35GS-CXCR4 | 6.1 | >3333 | 28.9 | 38.4 |
| CXCR4-9GS-CD4 | 0.20 | 0.53 | 0.03 | |
| CXCR4-25GS-CD4 | 0.21 | 2.67 | 0.12 | |
| CXCR4-35GS-CD4 | 0.19 | 2.67 | 0.09 | 2.6 |
| AMD3100 | 4.75 | 10 | 4.5 | — |

High donor variability observed.

The Nanobodies were further evaluated for their anti-HIV activity in PHA-stimulated PBMCs from different donors with additional X4 and dual-tropic X4-R5 specific HIV clones. For these experiments we restricted ourselves to bispecific constructs with the longest linker (35GS; since there was no clear effect of the linker length), along with the corresponding monovalent Nanobodies and AMD3100.

PHA-stimulated blasts were seeded at 0.5×10$^6$ cells per well into a 48-well plate (Costar; Elscolab, Kruibeke, Belgium) containing varying concentrations of compound in medium containing IL-2. The virus stocks were added at a final dose of 100 TCID50 of HIV-1 or HIV-2. At 8-10 days after the start of the infection, viral p24 Ag was detected in the culture supernatant by an enzyme-linked immunosorbent assay (Perkin Elmer, Brussels, Belgium). For HIV-2 p27 Ag detection, the INNOTEST from Innogenetics (Temse, Belgium) was used. In each assay AMD3100 was evaluated as control compound.

Results are shown in Table 8.1.2.

The anti-CXCR4 Nanobody 281F12 inhibited very consistently HIV-1 NL4.3 in every PBMC donor, with an $IC_{50}$ of 46.7 nM. The anti-CD4 monovalent Nanobody 3F11 was weakly active against HIV-1 NL4.3. In 5 different PBMC donors an $IC_{50}$ of about 580 nM was obtained, but not in nine other PBMC donors, where no activity was measured (for reasons that are currently unclear). The bispecific 281F12-35GS-3F11 construct displayed potent anti-HIV-1 activity with an $IC_{50}$ as low as 86.7 pM (2.6 ng/ml), whereas the bispecific 3F11-35GS-281F12 construct consistently inhibited replication with average $IC_{50}$ of 29 nM. AMD3100 had an average $IC_{50}$ of 3.3 nM.

The Nanobodies were further evaluated for their anti-HIV activity to X4-R5 dual-tropic HIV isolates. The dual-tropic (R5/X4) HIV-1 strain HE and the dual-tropic (R5/X4) HIV-2 ROD strain were initially investigated on human MT-4 cells, that endogenously express CD4 and CXCR4, but not CCR5. The (R5/X4) HIV-1 HE strain was initially isolated from a patient at the University Hospital in Leuven. Activity ($IC_{50}$) and toxicity ($CC_{50}$) were determined using microscopic evaluation and MTS viability staining method. Consistent pM potencies were obtained for the most potent bispecific 281F12-3F11 construct on the dual-tropic HIV1 HE and HIV2 ROD strains.

In PBMCs, that express both CCR5 and CXCR4 co-receptors, Nanobody 3F11 was not active against the dual-tropic R5/X4 HIV-1 HE, while Nanobody 281F12 was modestly active with an $IC_{50}$ of 266.7 nM. In contrast, the bispecific 281F12-35GS-3F11 construct displayed potent anti-HIV-1 HE activity with an $IC_{50}$ of 1.5 nM, whereas the bispecific 3F11-35GS-281F12 construct very often its activity. The activity of AMD3100 is also variable and lost in the assays sometimes its activity, very likely due to the level of co-receptor expression of CXCR4 (very high) and CCR5 (very low, but variable 1-20%) on the donor PBMC. Notably, AMD14031/maraviroc never showed any significant anti-HIV-1 HE activity in this cell assay system.

Together these results indicate that bispecific polypeptides have a broad coverage in different X4 and dual-tropic X4-R5 HIV strains, and consistent high potency in the picoMolar-low nanoMolar range in blocking virus infections.

Together these results indicate that the cell binding affinity of the CXCR4 Nanobody, even on R5 HIV1 strains where CXCR4 Nanobody it is not actively contributing to functional entry blockade, the CXCR4 Nanobody contributes to the high potency of the bispecific CXCR4-CD4 polypeptide.

Thus, the bispecific polypeptides of the invention can be effectively used to treat an infection in which HIV is resistant against one moiety or uses another co-receptor (e.g. a CR not targeted by the bispecific polypeptide).

8.3 Neutralization of Entry-Inhibitor Resistant HIV1 Viruses

To substantiate the contribution of an "anchor" in the avidity of the other moiety in the bispecific polypeptide,

TABLE 8.1.2

Anti-HIV activity profile of Nanobodies towards distinct dual tropic isolates on MT-4 cells and on PBMCs, in comparison to the X4 strain NL4.3.

| | Cell | | | | | | | |
|---|---|---|---|---|---|---|---|---|
| | MT-4 | | | PBMC | | | | |
| | | | | HIV strain | | | | |
| | NL4.3 X4 n = 3 | HE R5/X4 n = 3 | HIV-2 ROD R5/X4 n = 3 | NL4.3 X4 n = 10 | HE R5/X4 n = 9 | SM145 R5 n = 2 | DJ259 R5 n = 2 | BaL R5 n = 6 |
| Nanobody | | | | IC50 (M) | | | | |
| 3F11 | 3.47E−08 | 1.00E−08 | 2.27E−08 | 5.0E−07 | >1.7E−06 | 2.7E−08 | 3.1E−08 | 6.1E−07 |
| 281F12 | 2.27E−08 | 1.00E−08 | 8.67E−08 | 4.7E−08 | 3.5E−07 | nd | >1.7E−06 | >1.7E−06 |
| 281F12-35GS-3F11 | 1.87E−10 | 9.06E−11 | 3.00E−10 | 2.9E−10 | 1.5E−09 | 1.6E−09 | 1.5E−09 | 2.6E−09 |
| 3F11-35GS-281F12 | 6.00E−09 | 2.00E−09 | 8.75E−09 | 2.3E−08 | 4.8E−07 | 7.5E−09 | 5.5E−08 | 3.8E−08 |
| AMD3100 | 4.28E−09 | 3.90E−09 | 2.11E−08 | 3.3E−09 | 2.6E−08 | | | — |

8.2 Specificity for CXCR4-Co-Receptor Usage

The potency of the CXCR4 Nanobody is specific for HIV-1 strains that depend on CXCR4 co-receptor usage for entry. One potential disadvantage of blockade of only one of the HIV-1 co-receptors is that it may trigger the re-emergence of the HIV subtype that is not originally targeted.

We tested the HIV activity of bispecific Nanobody constructs on distinct CCR5-dependent HIV-1 strains, (R5) HIV-1 strain BaL (obtained from the Medical Research Council AIDS reagent project (Herts, UK), and the clinical isolates DJ259 (clade C) and SM145 (clade C) on PBMCs of different donors. In R5 viruses only the CD4 Nanobody in the bispecific construct contributes to the virus neutralization. Without being bound to any theory, it was hypothesized that since CXCR4 is expressed on PBMCs, in these cells the CXCR4 Nanobody in the bispecific polypeptide can bind to CXCR4 and contribute to avidity, and in this manner enhance the inhibition potency of the CD4 Nanobody.

Results are shown in Tables 8.1.1 and 8.1.2.

Bispecific CXCR4-CD4 constructs can inhibit infectivity of BaL in MT-4 cells with an $IC_{50}$ value of 2.5 nM, around 200-fold enhanced potency relative to the potency of monovalent CD4 Nanobody (Table 8.1.1). Bispecific CXCR4-CD4 constructs are more potent inhibitors of BaL than constructs in the inverse orientation, probably due to the unfavourable position of 281F12, in which the CXCR4 binding is impaired. The results were confirmed with neutralization of two R5 clinical isolates, SM1145 and DJ259, where the bispecific CXCR4-CD4 construct maintained 1.5 nM potencies, i.e. having 17 and 20 fold better potencies than the monovalent Nanobody 3F11 alone.

blockade of HIV infection was assessed for a panel of HIV-1 mutant viruses that were made resistant for the CXCR4 small molecule inhibitor AMD3100, the CXCR-4 ligand, or the control antibody 12G2 (Polymun Scientific (Vienna, Austria)).

The $IC_{50}$ values of the bispecific CXCR4-CD4 Nanobodies towards AMD3100 resistant virus are depicted in FIG. 5, and in Table 8.3.

Monovalent CXCR4 Nanobodies showed a 100-fold loss in potency, similar as AMD3100, while the CD4 potency was unaffected. Each of the CXCR4-CD4 bispecific polypeptides had retained potencies below 1 nM for blocking infection of AMD3100 resistant virus, 20-fold better than the monovalent CD4 building block. Over the complete panel of resistant viruses, the CXCR4-CD4 bispecific polypeptide retained strong neutralizing potency with $IC_{50}$ values between 0.3-1.1 nM.

Thus, bispecific polypeptides seem relatively insensitive to mutants that no longer bind to one of the targets.

8.4 Generation of 3F11 and 281F12 Resistant HIV-1 NL4.3 Viruses

Viral escape mutants were generated by culturing NL4.3 in the presence of monovalent Nanobodies at $IC_{90}$ concentration over multiple passages. The HIV-1 NL4.3 3F11-resistant virus was obtained after seven months of cell culture, passaging MT-4 cells in increasing concentrations of the monovalent Nanobody (starting from $EC_{50}$ concentrations). The HIV-1 NL4.3 281F12-resistant virus was finally obtained in more than 2 years of dedicated cell culturing passaging HIV-1 NL4.3 in the presence of Nanobody 281F12 directed against CXCR4. For comparison, the generation of resistant AMD3100 strains was obtained after 11 months.

The Env gp120 sequence of the resistant strains were determined, yielding the following mutations: gp120 of 3F11-$^{res}$ strain: V40(A,V), R118(K,R), N158(N,S), S160(N,S), T311(T,I), T378(T,I).

gp120 of 281F12$^{res}$ strain: S169L, V170N, M296I, H300Y (V3 region), S435F, K460N, L464I.

Resistant viral clones thus identified were used for testing the potencies of bispecific polypeptides compared to the monovalent polypeptides.

Respective $IC_{50}$ values are presented in Table 8.3.

Nanobody 3F11 (anti-CD4) lost completely its activity against the HIV-1 NL4.3 3F11$^{res}$ virus but also against the HIV-1 NL4.3 281F12$^{res}$ virus. However, the blocking capacity of 3F11 is maintained on the SDF-1$^{res}$ and AMD3100$^{res}$ viruses, suggesting that the loss is specific to the mutations of the 281F12$^{res}$ strain, and not related to the gp120-CXCR4 interaction per se.

Nanobody 281F12 (anti-CXCR4) completely lost activity against HIV-1 NL4.3 281F12$^{res}$ virus and AMD3100$^{res}$ virus, but was active against the HIV-1 NL4.3 3F11$^{res}$ virus, with an activity comparable to the wild-type virus ($IC_{50}$: 0.3 µg/ml) when the virus stocks were appropriately titrated and re-evaluated in MT-4 cells. AMD3100 almost kept its activity against the HIV-1 NL4.3 3F11$^{res}$ virus ($IC_{50}$ 18 nM, 14 ng/ml), but lost significantly activity against the HIV-1 NL4.3 281F12$^{res}$ virus ($IC_{50}$ 400 nM, 317 ng/ml), suggesting overlapping binding sites on CXCR4.

These data indicate that even on viruses that are resistant to one of the targets, the bispecific CXCR4-CD4 polypeptide retains a strong potency in the picoMolar range in inhibition of HIV1 entry, suggesting that functionality of only one of the arms of the bispecific CXCR4-CD4 polypeptides is sufficient for the potent inhibition, when the other arm can provide binding avidity. Indeed, we have not yet succeeded in generating double resistant HIV.

Together these results indicate that bispecific polypeptides have a broad coverage in different HIV strains (see Table 8.3).

Bispecific polypeptides may thus represent a powerful means to overcome resistance to HIV1 infection.

8.5 Blockade of HIV1 Infectivity in TZM-Bl Cell-Based Assays

The panel of bispecific CXCR4-CD4 polypeptides and the corresponding monospecific Nanobodies were also evaluated for their anti-HIV-1 activity in TZM-bl cells, i.e. HeLa cells that are expressing low levels of CXCR4 transfected with human CD4 and CCR5.

TZM-bl cells were seeded in transparent 96-well plates at $1 \times 10^4$ cells per well in DMEM (Dulbecco's Modified Eagle Medium; Life Technologies, Waltham, Mass., USA) with 10% Fetal Bovine Serum (FBS) and 10 mM HEPES. Subsequently, compounds were added and the cell/compound mixture was incubated at 37° C. After 30 min, HIV was added at 100 pg p-24 HIV-1Ag per well. After 48 h of

TABLE 8.3

Anti-HIV activity profile of bispecific CXCR4-CD4 constructs with entry-inhibitor resistant HIV-1 NL4.3 variants determined in MT-4 cells and PBMCs.

| | $IC_{50}$ (M) Cells MT-4 | | | | | |
|---|---|---|---|---|---|---|
| ID | NL4.3 wt | 3F11 res. | 281F12 res. | AMD-3100 res. | CXCL-12 res. | 2G12 res. |
| 3F11 | 3.47E−08 | >6.7E−06 | >6.7E−06 | 2.27E−08 | 1.53E−07 | 2.33E−08 |
| 281F12 | 2.27E−08 | 8.73E−08 | 2.33E−06 | >1.7E−06 | 2.20E−07 | 1.73E−08 |
| CXCR4-35GS-CD4 | 1.87E−10 | 3.10E−10 | 1.40E−09 | 1.13E−09 | 4.33E−10 | 1.10E−10 |
| CD4-35GS-CXCR4 | 6.00E−09 | 9.57E−08 | >3.1E−07 | 1.40E−08 | 7.00E−08 | 3.00E−09 |
| AMD3100 | 4.28E−09 | 1.85E−08 | 3.99E−07 | 4.04E−07 | 5.03E−08 | |

| | IC50 (M) PBMC | | |
|---|---|---|---|
| ID | NL4.3 WT n = 10 | NL4.3 3F11 res. n = 2 | NL4.3 281F12 res. n = 2 |
| 3F11 | 5.0E−07 | >6.7E−06 | >6.7E−06 |
| 281F12 | 2.8E−08 | 1.2E−07 | 3.1E−07 |
| CXCR4-35GS-CD4 | 8.7E−11 | 1.2E−09 | 1.9E−09 |
| CD4-35GS-CXCR4 | 2.9E−08 | 5.2E−07 | >6.7E−06 |
| AMD3100 | 4.5E−09 | 2.0E−08 | 5.7E−08 |

The bispecific 281F12-35GS-3F11 polypeptide kept full activity against the HIV-1 NL4.3 3F11$^{res}$ virus, and remarkably lost only about 8-fold activity against the HIV-1 NL4.3 281F12$^{res}$ virus (from 187 pM to 1.4 nM comparing wild-type and resistant virus), while the potency towards NL4.3 3F11$^{res}$ virus was almost intact. The bispecific 3F11-35GS-281F12 polypeptide, that is largely dependent on CD4 Nanobody binding for its functionality, lost 16-fold activity against the HIV-1 NL4.3 3F11$^{res}$ virus (from 6 nM to 96 nM comparing wild-type and resistant virus) and completely lost its activity against the HIV-1 NL4.3 281F12$^{res}$ virus.

incubation, the assay plates were analyzed. For the analysis, Steadylite plus substrate solution (PerkinElmer, Waltham, Mass., USA) was added to the assay plates. The luminescent signal of the lysed cell suspension was analyzed in white 96-well plates on a SpectraMax L luminescence microplate reader (Molecular Devices, Sunnyvale, Calif., USA) after a 10 min incubation period in the dark. Luciferase activity induced by HIV-1 Tat protein expression was measured as an assessment of the amount of HIV replication (cf. Measuring HIV neutralization in a luciferase reporter gene assay. Montefiori, Methods Mol Biol. 2009; 485:395-405).

The results are provided in Table 8.5

TABLE 8.5

Anti-HIV activity profile of CXCR4-CD4 polypeptides in TZM-bl cell-based assays.

| | Cells TZM-bl HIV strain | | | | |
|---|---|---|---|---|---|
| | R5 | | X4 | | |
| ID | SM145 $IC_{50}$ (M) n = 2 | DJ259 $IC_{50}$ (M) n = 2 | NL4.3 WT $IC_{50}$ (M) n = 4 | NL4.3 281F12 res $IC_{50}$ (M) n = 3 | NL4.3 3F11 res $IC_{50}$ (M) n = 3 |
| 3F11 | 8.33E−09 | 1.69E−07 | 1.31E−07 | >6.7E−06 | >6.7E−06 |
| 281F12 | >6.7E−06 | >6.7E−06 | 2.35E−08 | 3.66E−07 | 4.56E−08 |
| 281F12-35GS-3F11 | 1.19E−08 | 1.56E−07 | 2.66E−11 | 2.52E−11 | 3.78E−11 |
| 3F11-35GS-281F12 | 1.41E−08 | 1.73E−07 | 1.82E−09 | 6.8E−08 | 4.53E−09 |
| AMD3100 | | | 4.11E−07 | 4.92E−06 | 9.15E−07 |
| AMD14031 | 2.82E−06 | 7.54E−06 | | | |

In these cells, Nanobody 3F11 (anti-CD4) inhibits X4 HIV-1 NL4.3 replication with an $IC_{50}$ of 131 nM, while the anti-CXCR4 Nanobody 281F12 had an $IC_{50}$ of 23.5 nM. The bispecific polypeptide 281F12-35GS-3F11 displayed anti-HIV-1 activity with an $IC_{50}$ as low as 27 pM, while 3F11-35GS-281F12 inhibited X4 HIV-1 NL4.3 in TZM-bl cells with an $IC_{50}$ of 1.8 nM. The potencies were preserved in NL4.3 strains that were resistant to either the CXCR4 281F12 or the CD4 3F11 Nanobodies.

None of the Nanobodies or bispecific polypeptides, nor AMD3100, was active against the dual-tropic R5/X4 HIV-1 HE, the dual-tropic R5/X4 HIV-2 ROD and the R5 HIV-1 BaL virus in TZM-bl cells. Of note, the specific CCR5 inhibitor AMD14031/maraviroc that was used as control in these assays did not block HIV-1 NL4.3, HIV-1 HE nor HIV-2 ROD, but potently blocked R5 HIV-1 BaL virus ($IC_{50}$: 4.2 µM). On two other R5 clinical isolates, the bispecific CXCR4-CD4 Nanobody retained nM potency, with both orientations having similar activities.

Example 9: Inhibition of HIV-Mediated Cell-Cell Fusion

During HIV transmission, CD4$^+$ T-cells can not only become infected by cell-free virions but, importantly, also by close cell-cell contacts with donor HIV-infected T-cells. To mimic these cell-cell interactions we co-cultured persistently HIV-1-infected cells (HUT-78/HIV-1) with non-infected SupT1 CD4$^+$ target T-cells. Many syncytia, or giant cells, are formed between infected and uninfected T-cells in less than 20 hours. Persistently HIV-1 infected HUT-78 cells were generated by infection of HUT-78 cells with NL4.3 or HIV1 IIIb. The cells were subcultured every 3-4 days and persistent virus infection was monitored in the culture supernatants using HIV-1 p24 Ag ELISA. For the co-cultivation assay, different concentrations of the test compounds along with 1×10$^5$ SupT1 cells/0.5 mL were added to 96-well plates. HUT-78/HIV-1 cells were thoroughly washed to remove free virus from the culture medium, and 5×10$^4$ cells (50 µl) were transferred to the 96-well plates. After 2 days, the $EC_{50}$-values were determined microscopically, based on the appearance of giant cells or syncytia in the cell co-cultures. The total number of syncytia was counted.

The respective $IC_{50}$ values for inhibition of syncytia formation are shown in Table 9.

TABLE 9

Inhibition of HIV-1-mediated cell-cell fusion by bispecific polypeptides. Co-culture of HIV-1-infected cells (HUT-78/HIV-1 NL4.3 or HIV1 IIIb cells) with non-infected SupT1 CD4$^+$ target T cells.

| | Target cells | |
|---|---|---|
| | SupT1 | SupT1 |
| | Cells/HIV1 strain | |
| Nanobody | HUT-78/NL4.3 $IC_{50}$ (M) n = 4 | HUT-78/IIIb $IC_{50}$ (M) n = 3 |
| 3F11 | 2.80E−06 | 4.6E−06 |
| 281F12 | 3.60E−06 | 1.8E−06 |
| 281F12-35GS-3F11 | 2.31E−09 | 1.1E−09 |
| 3F11-35GS-281F12 | 2.86E−08 | 2.3E−08 |
| AMD3100 | 1.12E−06 | 2.2E−05 |

For monovalent 3F11, the average $IC_{50}$ value was 2.7 µM and 3.6 µM for 281F12. Bispecific polypeptide 281F12-35GS-3F11 blocked potently with an $IC_{50}$ of 2.3 nM, while the bispecific polypeptide 3F11-35GS-281F12 had an $IC_{50}$ value of 28.7 nM. AMD3100 lost activity in this cell-cell transmission assay, compared to its activity in HIV replication assays, displaying an $IC_{50}$ of 1.1 µM.

Thus, bispecific polypeptides are the most potent compounds in interfering with the HIV cellular (co-) receptor/gp120-mediated fusion processes.

Example 10: CXCR4 Nanobodies Binding to the Gp120 Binding Site

We further pursued CXCR4 Nanobodies which specifically block HIV entry and preferably do not interfere with natural CXCR4 signal transduction.

In order to identify CXCR4 Nanobodies that block specifically the interaction of gp120 on CXCR4, but which do not or minimally interfere with CXCL12 binding, a panel of 70 previously identified CXCR4 Nanobodies was analysed for their ability to neutralize infection of NL4.3 HIV1 in MT-4 cells. CXCR4 specific Nanobodies were also evaluated in PBMC isolated from buffy coats of blood from healthy donors and tested against X4 HIV-1 NL4.3 and R5 HIV-1 BaL replication. $IC_{50}$ values of neutralization of MT-4 cells are depicted in FIG. 6, indicating a range of potencies, with the most potent Nanobody 15A01 in the sub-nanoMolar range. None of the CXCR4 Nanobodies neutralized the infection of BaL R5 in PBMCs, as expected (data not shown).

In addition, CXCR4 Nanobodies were analysed for ligand competition by displacement of biotinylated SDF-1 on transient transfected Caki cells expressing hCXCR4 in flow cytometry. To this end, serial dilutions of Nanobodies were pre-incubated with 30 nM of biotinylated SDF-1 (R&D Systems Fluorikine kit) and incubated to Caki-CXCR4 cells for 1 hour at 4 C, after which ligand binding was visualised using extravidin-PE. The biotin-SDF-1 competitor concentration used in this assay was below the $EC_{50}$ value obtained in dose-titration, where $IC_{50}$ values should reflect the Ki. Ligand displacement $IC_{50}$ values were calculated, and compared to the NL4.3 (X4) neutralization potencies.

Comparing the different potencies, several CXCR4 Nanobodies had a larger than 10-fold difference between $IC_{50}$ value in HIV1 neutralisation compared to ligand displacement, as depicted in FIG. 7. CXCR4 Nanobodies 15F5 and 15G11 were of particular interest, showing hardly any ligand displacement to CXCR4. Both Nanobodies have substantial HIV1 neutralisation capacity, with better potencies than 281F12 Nanobody ($IC_{50}$ values of 4.7 nM and 17.7 nM, respectively).

the same results. Binding of the Nanobodies to HEK293T hCXCR4 cells was used for normalization using the following formulas. The percentages of Nanobody binding to the respective mutant receptors were calculated according to the formula: $(1-[(MFI_{hCXCR4} * ratio_{12G5\ mAb}) - MFI_{mutant}]/[MFI_{hCXCR4} * ratio_{12G5\ mAb}]) \times 100$, where MFI is the mean fluorescence intensity of the anti-myc detection, and ratio 12G5 mAb: $(MFI\ 12G5_{mutant}/MFI\ 12G5_{hCXCR4})$. Percentage of binding to the mutant receptors was calculated for each Nanobody concentration, and a position was considered as critical when less than 25% residual binding was observed.

Results of the CXCR4 binding analysis are depicted in Table 11.

CXCR4 Nanobodies 15F5 and 15A1 bind equally well to cyno CXCR4 as to human CXCR4, and are only sensitive to mutation of residue F189V. Binding of Nanobody 15G11 is impaired by mutations at positions F189V, V196E and D187V in the extracellular loop 2, while it binds well to cyno CXCR4. Binding of Nanobody 10C3 is reduced on all tested CXCR4 mutants as well as on cyno CXCR4.

TABLE 11

Binding analysis of CXCR4 Nanobodies to mutant CXCR4 receptors expressed on Hek293T cells.

| | % binding# | | | | | | | |
|---|---|---|---|---|---|---|---|---|
| | cyno CXCR4 | | hCXCR4-V196E | | hCXCR4 D187V | | hCXCR4 F189V | |
| CXCR4 Nb | 100 nM | 10 nM | 100 nM | 10 nM | 100 nM | 10 nM | 100 nM | 10 nM |
| 10C3 | 51.3 | 57.5 | 0.6 | 0.4 | 24.7 | 12.8 | 0.6 | 0.9 |
| 15F5 | 81.1 | 101.9 | 77.6 | 93.3 | 117.1 | 126.2 | 8.8 | 1.5 |
| 15G11 | 96.1 | 95.1 | 39.3 | 22.1 | 50.3 | 35.4 | 0.1 | 0.1 |
| 15A1 | 78.9 | 107.3 | 77.3 | 71.3 | 107.5 | 115.0 | 1.9 | 0.8 |
| 281D4 | 85.9 | 97.0 | 79.5 | 70.5 | 0.6 | 0.9 | 0.5 | 0.5 |
| 12G5 mAb | 100 | 100 | 100 | 100 | 100 | 100 | 100 | 100 |

% binding to cynomolgus (cyno) or mutant CXCR4 receptors expressed on HEK cells, relative to hCXCR4 binding.
Expression levels were normalised to 12G5 binding.

Hence, a panel of Nanobodies was generated having a range of potencies in HIV blocking as well as in ligand displacement.

Example 11: Characterisation of Gp120-Competing CXCR4 Nanobodies

The monovalent CXCR4 Nanobodies that showed binding to the gp120 binding site (15F5, 15G11, 10C3 and 15A1) were further characterized with respect to binding to human and cynomolgus CXCR4, as well as to human CXCR4 variants with defined point mutations in extracellular loop 2 that were previously described (Jaenchen et al. 2011).

CXCR4 Nanobodies were allowed to bind to HEK cells transfected with human CXCR4, cynomolgus ("cyno") CXCR4, hCXCR4-V196E, hCXCR4 D187V, and hCXCR4 F189V, respectively. The anti-CXCR4 mAb 12G5 was binding to all point-mutants and thus served as a control for membrane expression (Jaenchen et al. 2011). For the epitope mapping, transient transfections of the CXCR4 mutants, cyno CXCR4 and wildtype human CXCR4 in the pCDNA3.1 vector were done in HEK293T cells, after which Nanobody binding was assessed by flow cytometry using detection of the Myc-tag, followed by secondary anti-mouse PE. Two concentrations of Nanobody were tested, 10 nM and 100 nM. The experiment was repeated with essentially CXCR4 Nanobodies were further characterized for inhibition of binding of CXCR4 antagonists to CXCR4. For competition experiments, serial dilutions of CXCR4 Nanobodies were pre-incubated with 1 nM of anti-CXCR4 antibody 12G5, and allowed to bind to Jurkat cells. Briefly serial dilutions the different Nanobodies ranging from 500 nM to 0.05 nM were incubated with 1 nM of 12G5 for 1 h at RT. Then, this mix was added and incubated with the cells for 30 min shaking at 4° C. After washing 3× with PBS 10% FBS, bound antibody (12G5) was detected with Goat anti-Mouse-PE (Jackson Immunoresearch, cat #115-115-164) for 30 min shaking at 4° C. Inhibition potency is determined based on the decrease of signal from 12G5 binding in the absence of Nanobody and the signal when in the presence of different amounts of Nanobody.

These results are shown on FIG. 8.

All Nanobodies are able to fully displace binding of 12G5 from CXCR4, with monovalent anti-CXCR4 Nanobody 15F5 being the best competitor with $IC_{50}$ of 1.25 nM, followed by 15G11 (6.2 nM) and 281F12 (13 nM).

To assess competition with anti-CXCR4 AMD3100, a fixed concentration of CXCR4 Nanobodies at their respective $EC_{30}$ binding concentration was pre-incubated with serial dilutions of AMD-3100 ranging from 10 000 nM to 1 nM, and allowed to bind to Jurkat cells for 1 h at RT. In parallel $1 \times 10^5$ cells were incubated with Fc-blocking solution (Miltenyi Biotec cat #130-059-901) for 30 minutes shaking at 4° C., after which the AMD-3100-Nanobody mix was added and incubated for additional 30 minutes at 4° C. After washing 3 times with PBS 10% FBS, bound Nanobodies were detected with mouse anti-c-myc (AbD Serotec, cat #MCA2200) and Goat anti-Mouse-PE (Jackson Immunoreseach, cat #115-115-164) antibodies. Inhibition potency is determined based on the decrease of signal when no ADM3100 is present and the signal when in the presence of increasing concentration of this molecule.

These results are shown on FIG. 8.

AMD3100 can fully compete with the binding of all tested CXCR4 Nanobodies with a potency of 100 nM.

In conclusion, CXCR4 Nanobodies 15F5 and 15G11 are potent HIV1 antagonists, inhibiting with AMD3100 and mAb 12G5 for binding to cell-expressed CXCR4, but are not competing with the CXCR4 ligand CXCL12, and hence are suitable candidates for formatting into bispecific constructs with anti-CD4 Nanobody 3F11.

Example 12: Generation of Half-Life Extended CXCR4-CD4 Bispecific Polypeptides

Bispecific CXCR4-CD4 constructs were formatted with an anti-Albumin Nanobody, in order to extend its half-life in serum for in vivo experiments. To this end the respective CXCR4 Nanobody was fused to an anti-Albumin Nanobody with a flexible 15GS-linker, followed by the CD4 Nanobody linked with a second 15GS linker. CXCR4 Nanobodies 281F12, 15F05 and 15G11 were formatted to half-life extended bispecific constructs (SEQ ID NO: 107, SEQ ID NO: 108, SEQ ID NO: 109). As reference monovalent CXCR4 281F12 was also fused to the anti-Albumin Nanobody (SEQ ID NO: 110). The multivalent constructs were generated by means of separate PCR reactions (1 for the N-terminal, 1 for the middle and 1 for the C-terminal Nanobody subunit) using different sets of primers encompassing specific restriction sites.

All constructs were cloned into a *Pichia pastoris* expression vector derived from pPICZα (Life Technologies) and contains the AOX1 promoter, a resistance gene for Zeocin, the necessary replication origins for both *E. coli* and *P. pastoris* and a multiple cloning site preceded by the coding information for the *S. cerevisiae* α-MF signal peptide. In frame with the Nanobody coding sequence, the vector codes for a C-terminal (Flag)$_3$ tag and a (His)$_6$ tag. The signal peptide directs the expressed Nanobodies to the extracellular environment via the secretory pathway of the eukaryotic host. After sequence confirmation, the pAX159-derived expression constructs were then transformed into *P. pastoris* X-33 according to standard procedures (EasySelect™ *Pichia* Expression Kit Manual, Life Technologies). The purification of Nanobodies from the culture medium was done using standard affinity chromatography on the His-tag, followed by a gel filtration step. The integrity and the purity of all Nanobodies was confirmed by MS analysis and SDS-PAGE. The amino acid sequences are provided in Table 12.

Example 13: Inhibition of CXCR4-Mediated Chemotaxis by Half-Life Extended CXCR4-CD4 Bispecifics To verify the functionality of the half-life extended bispecific CXCR4-CD4 polypeptides, a CXCR4-dependent functional assay was performed, essentially as described in Example 7.1. Dose-dependent inhibition of CXCL12-induced chemotaxis by the half-life extended monovalent 281F12-ALB and bispecific 281F12-ALB-3F11 was determined in comparison to the same construct without the anti-Albumin building block on Jurkat E6 (CXCR4+/CD4 low), and Molm-13 cells (CXCR4++/CD4++). As chemoattractant a concentration of 750 pM SDF-1α (R&D Systems) was used on 100,000 cells/well for the Jurkat cell line, and 1 nM SDF-1α on 500,000 cells/well for the MOLM-13 cell line.

Results of representative experiments are shown in FIG. 9A+B.

The fusion with an anti-Albumin Nanobody did not substantially affect the affinity and potency of monovalent CXCR4 281F12 or bispecific CXCR4-ALB-CD4 constructs on Jurkat cells, with all Nanobody formats showing similar potencies (IC$_{50}$ values between 16 and 80 nM, depending on the assay; FIG. 9A). On double-positive MOLM-13 cells, the potency of the half-life extended bispecific CXCR4-CD4 constructs was similar to the corresponding non half-life extended bispecific counterparts, indicating that the anti-Albumin Nanobody did not affect the simultaneous binding to each of the targets (FIG. 9B).

These results indicate that also the half-life extended bispecific CXCR4-ALB-CD4 constructs are capable of binding simultaneously to their respective targets, and that the potency enhancement in blocking CXCR4 function relative to the monovalent CXCR4-ALB is maintained.

TABLE 12

| Name | ID* | amino acid sequence |
| --- | --- | --- |
| 15G11 (Q108L)-<br>15GS-ALB11-<br>15GS-<br>03F11 (Q108L) | 107 | EVQLVESGGGLVQAGDSLRVSCAASGRTSSYAMAWFRQAPGKEREFVGTISRT<br>NSRTKYADFVEGRFTISRDNAKSTLSLQMTSLKPEDTAVYYCAAKWTGNSYHD<br>YTWSKVDEYNVWGQGTLVTVSSGGGGSGGGGSGGGGSEVQLVESGGGLVQPGN<br>SLRLSCAASGFTFSSFGMSWVRQAPGKGLEWVSSISGSGSDTLYADSVKGRFT<br>ISRDNAKTTLYLQMNSLRPEDTAVYYCTIGGSLSRSSQGTLVTVSSGGGGSGG<br>GGSGGGGSEVQLVESGGGSVQPGGSLTLSCGTSGRTFNVMGWFRQAPGKEREF<br>VAAVRWSSTGIYYTQYADSVKSRFTISRDNAKNTVYLEMNSLKPEDTAVYYCA<br>ADTYNSNPARWDGYDFRGQGTLVTVSS |
| 15F05 (Q108L)-<br>15GS-ALB11-<br>15GS-<br>03F11 (Q108L) | 108 | EVQLVESGGGLVRAGDSLRLSCAASGRAFSRYAMGWFRQALGKERELVAAIGW<br>SPTHTYYADSVKGRFTMSRDNGKNTVFLQMNSLNPEDTAVYYCAAKYSSRDAA<br>YRSDYDYNYWGQGTLVTVSSGGGGSGGGGSGGGGSEVQLVESGGGLVQPGNSL<br>RLSCAASGFTFSSFGMSWVRQAPGKGLEWVSSISGSGSDTLYADSVKGRFTIS<br>RDNAKTTLYLQMNSLRPEDTAVYYCTIGGSLSRSSQGTLVTVSSGGGGSGGGG<br>SGGGGSEVQLVESGGGSVQPGGSLTLSCGTSGRTFNVMGWFRQAPGKEREFVA<br>AVRWSSTGIYYTQYADSVKSRFTISRDNAKNTVYLEMNSLKPEDTAVYYCAAD<br>TYNSNPARWDGYDFRGQGTLVTVSS |

TABLE 12-continued

| Name | ID* | amino acid sequence |
|---|---|---|
| 281F12 (Q108L)-15G5-ALB11-15G5-03F11 (Q108L) | 109 | EVQLVESGGGLVQAGDSLRLSCAASGRAFSRYAMGWFRQAPGKEREFVAAIGW<br>GPSKTNYADSVKGRFTISRDNAKNTVYLQMNTLKPEDTAVYSCAAKFVNTDST<br>WSRSEMYTYWGQGTLVTVSSGGGGSGGGGSGGGGSEVQLVESGGGLVQPGNSL<br>RLSCAASGFTFSSFGMSWVRQAPGKGLEWVSSISGSGSDTLYADSVKGRFTIS<br>RDNAKTTLYLQMNSLRPEDTAVYYCTIGGSLSRSSQGTLVTVSSGGGGSGGGG<br>SGGGGSEVQLVESGGGSVQPGGSLTLSCGTSGRTFNVMGWFRQAPGKEREFVA<br>AVRWSSTGIYYTQYADSVKSRFTISRDNAKNTVYLEMNSLKPEDTAVYYCAAD<br>TYNSNPARWDGYDFRGQGTLVTVSS |
| 281F12 (Q108L)-15G5-ALB11 | 110 | EVQLVESGGGLVQAGDSLRLSCAASGRAFSRYAMGWFRQAPGKEREFVAAIGW<br>GPSKTNYADSVKGRFTISRDNAKNTVYLQMNTLKPEDTAVYSCAAKFVNTDST<br>WSRSEMYTYWGQGTLVTVSSGGGGSGGGGSGGGGSEVQLVESGGGLVQPGNSL<br>RLSCAASGFTFSSFGMSWVRQAPGKGLEWVSSISGSGSDTLYADSVKGRFTIS<br>RDNAKTTLYLQMNSLRPEDTAVYYCTIGGSLSRSSQGTLVTVSS |

*"ID" denotes SEQ ID NO:

Example 14: Blockade of HIV1 Neutralization by Half-Life Extended CXCR4-CD4 Bispecifics The capacity of the half

```
Ala Leu Leu Pro Ala Ala Thr Gln Gly Lys Lys Val Leu Gly Lys
             20                  25                  30

Lys Gly Asp Thr Val Glu Leu Thr Cys Thr Ala Ser Gln Lys Lys Ser
         35                  40                  45

Ile Gln Phe His Trp Lys Asn Ser Asn Gln Ile Lys Ile Leu Gly Asn
 50                      55                  60

Gln Gly Ser Phe Leu Thr Lys Gly Pro Ser Lys Leu Asn Asp Arg Ala
 65                  70                  75                  80

Asp Ser Arg Arg Ser Leu Trp Asp Gln Gly Asn Phe Pro Leu Ile Ile
                 85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Gln Lys Ala Ser
        195                 200                 205

Ser Ile Val Tyr Lys Lys Glu Gly Glu Gln Val Glu Phe Ser Phe Pro
    210                 215                 220

Leu Ala Phe Thr Val Glu Lys Leu Thr Gly Ser Gly Glu Leu Trp Trp
225                 230                 235                 240

Gln Ala Glu Arg Ala Ser Ser Lys Ser Trp Ile Thr Phe Asp Leu
                245                 250                 255

Lys Asn Lys Glu Val Ser Val Lys Arg Val Thr Gln Asp Pro Lys Leu
            260                 265                 270

Gln Met Gly Lys Lys Leu Pro Leu His Leu Thr Leu Pro Gln Ala Leu
        275                 280                 285

Pro Gln Tyr Ala Gly Ser Gly Asn Leu Thr Leu Ala Leu Glu Ala Lys
    290                 295                 300

Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
                325                 330                 335

Lys Leu Met Leu Ser Leu Lys Leu Glu Asn Lys Glu Ala Lys Val Ser
            340                 345                 350

Lys Arg Glu Lys Ala Val Trp Val Leu Asn Pro Glu Ala Gly Met Trp
        355                 360                 365

Gln Cys Leu Leu Ser Asp Ser Gly Gln Val Leu Leu Glu Ser Asn Ile
    370                 375                 380

Lys Val Leu Pro Thr Trp Ser Thr Pro Val Gln Pro Met Ala Leu Ile
385                 390                 395                 400

Val Leu Gly Gly Val Ala Gly Leu Leu Leu Phe Ile Gly Leu Gly Ile
                405                 410                 415

Phe Phe Cys Val Arg Cys Arg His Arg Arg Arg Gln Ala Glu Arg Met
            420                 425                 430

Ser Gln Ile Lys Arg Leu Leu Ser Glu Lys Lys Thr Cys Gln Cys Pro
```

His Arg Phe Gln Lys Thr Cys Ser Pro Ile
    450                 455

<210> SEQ ID NO 2
<211> LENGTH: 360
<212> TYPE: PRT
<213> ORGANISM: Homo sapiens

<400> SEQUENCE: 2

Met Glu Gly Ile Ser Ser Ile Pro Leu Pro Leu Leu Gln Ile Tyr Thr
1               5                   10                  15

Ser Asp Asn Tyr Thr Glu Glu Met Gly Ser Gly Asp Tyr Asp Ser Met
            20                  25                  30

Lys Glu Pro Cys Phe Arg Glu Glu Asn Ala Asn Phe Asn Lys Ile Phe
        35                  40                  45

Leu Pro Thr Ile Tyr Ser Ile Ile Phe Leu Thr Gly Ile Val Gly Asn
    50                  55                  60

Gly Leu Val Ile Leu Val Met Gly Tyr Gln Lys Lys Leu Arg Ser Met
65                  70                  75                  80

Thr Asp Lys Tyr Arg Leu His Leu Ser Val Ala Asp Leu Leu Phe Val
                85                  90                  95

Ile Thr Leu Pro Phe Trp Ala Val Asp Ala Val Ala Asn Trp Tyr Phe
            100                 105                 110

Gly Asn Phe Leu Cys Lys Ala Val His Val Ile Tyr Thr Val Asn Leu
        115                 120                 125

Tyr Ser Ser Val Leu Ile Leu Ala Phe Ile Ser Leu Asp Arg Tyr Leu
    130                 135                 140

Ala Ile Val His Ala Thr Asn Ser Gln Arg Pro Arg Lys Leu Leu Ala
145                 150                 155                 160

Glu Lys Val Val Tyr Val Gly Val Trp Ile Pro Ala Leu Leu Leu Thr
                165                 170                 175

Ile Pro Asp Phe Ile Phe Ala Asn Val Ser Glu Ala Asp Asp Arg Tyr
            180                 185                 190

Ile Cys Asp Arg Phe Tyr Pro Asn Asp Leu Trp Val Val Phe Gln
        195                 200                 205

Phe Gln His Ile Met Val Gly Leu Ile Leu Pro Gly Ile Val Ile Leu
    210                 215                 220

Ser Cys Tyr Cys Ile Ile Ile Ser Lys Leu Ser His Ser Lys Gly His
225                 230                 235                 240

Gln Lys Arg Lys Ala Leu Lys Thr Thr Val Ile Leu Ile Leu Ala Phe
                245                 250                 255

Phe Ala Cys Trp Leu Pro Tyr Tyr Ile Gly Ile Ser Ile Asp Ser Phe
            260                 265                 270

Ile Leu Leu Glu Ile Ile Lys Gln Gly Cys Glu Phe Glu Asn Thr Val
        275                 280                 285

His Lys Trp Ile Ser Ile Thr Glu Ala Leu Ala Phe Phe His Cys Cys
    290                 295                 300

Leu Asn Pro Ile Leu Tyr Ala Phe Leu Gly Ala Lys Phe Lys Thr Ser
305                 310                 315                 320

Ala Gln His Ala Leu Thr Ser Val Ser Arg Gly Ser Ser Leu Lys Ile
                325                 330                 335

Leu Ser Lys Gly Lys Arg Gly Gly His Ser Ser Val Ser Thr Glu Ser
            340                 345                 350

```
Glu Ser Ser Ser Phe His Ser Ser
        355             360
```

<210> SEQ ID NO 3
<211> LENGTH: 352
<212> TYPE: PRT
<213> ORGANISM: Homo sapiens

<400> SEQUENCE: 3

```
Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys Gln Ile Ala Ala Arg Leu
            20                  25                  30

Leu Pro Pro Leu Tyr Ser Leu Val Phe Ile Phe Gly Phe Val Gly Asn
        35                  40                  45

Met Leu Val Ile Leu Ile Leu Ile Asn Cys Lys Arg Leu Lys Ser Met
    50                  55                  60

Thr Asp Ile Tyr Leu Leu Asn Leu Ala Ile Ser Asp Leu Phe Phe Leu
65                  70                  75                  80

Leu Thr Val Pro Phe Trp Ala His Tyr Ala Ala Ala Gln Trp Asp Phe
                85                  90                  95

Gly Asn Thr Met Cys Gln Leu Leu Thr Gly Leu Tyr Phe Ile Gly Phe
            100                 105                 110

Phe Ser Gly Ile Phe Phe Ile Ile Leu Leu Thr Ile Asp Arg Tyr Leu
        115                 120                 125

Ala Val Val His Ala Val Phe Ala Leu Lys Ala Arg Thr Val Thr Phe
    130                 135                 140

Gly Val Val Thr Ser Val Ile Thr Trp Val Val Ala Val Phe Ala Ser
145                 150                 155                 160

Leu Pro Gly Ile Ile Phe Thr Arg Ser Gln Lys Glu Gly Leu His Tyr
                165                 170                 175

Thr Cys Ser Ser His Phe Pro Tyr Ser Gln Tyr Gln Phe Trp Lys Asn
            180                 185                 190

Phe Gln Thr Leu Lys Ile Val Ile Leu Gly Leu Val Leu Pro Leu Leu
        195                 200                 205

Val Met Val Ile Cys Tyr Ser Gly Ile Leu Lys Thr Leu Leu Arg Cys
    210                 215                 220

Arg Asn Glu Lys Lys Arg His Arg Ala Val Arg Leu Ile Phe Thr Ile
225                 230                 235                 240

Met Ile Val Tyr Phe Leu Phe Trp Ala Pro Tyr Asn Ile Val Leu Leu
                245                 250                 255

Leu Asn Thr Phe Gln Glu Phe Gly Leu Asn Asn Cys Ser Ser Ser
            260                 265                 270

Asn Arg Leu Asp Gln Ala Met Gln Val Thr Glu Thr Leu Gly Met Thr
        275                 280                 285

His Cys Cys Ile Asn Pro Ile Ile Tyr Ala Phe Val Gly Glu Lys Phe
    290                 295                 300

Arg Asn Tyr Leu Leu Val Phe Phe Gln Lys His Ile Ala Lys Arg Phe
305                 310                 315                 320

Cys Lys Cys Cys Ser Ile Phe Gln Gln Glu Ala Pro Glu Arg Ala Ser
                325                 330                 335

Ser Val Tyr Thr Arg Ser Thr Gly Glu Gln Glu Ile Ser Val Gly Leu
            340                 345                 350
```

<210> SEQ ID NO 4

<211> LENGTH: 128
<212> TYPE: PRT
<213> ORGANISM: Artificial Sequence
<220> FEATURE:
<223> OTHER INFORMATION: Nanobody Sequence

<400> SEQUENCE: 4

Glu Val Gln Leu Met Glu Ser Gly Gly Gly Leu Val Gln Ala Gly Gly
1               5                   10                  15

Ser Leu Arg Leu Ser Cys Ala Ala Ser Gly Arg Thr Phe Asn Asn Tyr
            20                  25                  30

Ala Met Gly Trp Phe Arg Arg Ala Pro Gly Lys Glu Arg Glu Phe Val
        35                  40                  45

Ala Ala Ile Thr Arg Ser Gly Val Arg Ser Gly Val Ser Ala Ile Tyr
    50                  55                  60

Gly Asp Ser Val Lys Asp Arg Phe Thr Ile Ser Arg Asp Asn Ala Lys
65                  70                  75                  80

Asn Thr Leu Tyr Leu Gln Met Asn Ser Leu Lys Pro Glu Asp Thr Ala
                85                  90                  95

Val Tyr Thr Cys Ala Ala Ser Ala Ile Gly Ser Gly Ala Leu Arg Arg
            100                 105                 110

Phe Glu Tyr Asp Tyr Ser Gly Gln Gly Thr Gln Val Thr Val Ser Ser
        115                 120                 125

<210> SEQ ID NO 5
<211> LENGTH: 128
<212> TYPE: PRT
<213> ORGANISM: Artificial Sequence
<220> FEATURE:
<223> OTHER INFORMATION: Nanobody Sequence

<400> SEQUENCE: 5

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Asn Asn Tyr
            20                  25                  30

Ala Met Gly Trp Phe Arg Arg Ala Pro Gly Lys Glu Arg Glu Phe Val
        35                  40                  45

Ala Ala Ile Thr Arg Ser Gly Val Arg Ser Gly Val Ser Ala Ile Tyr
    50                  55                  60

Gly Asp Ser Val Lys Asp Arg Phe Thr Ile Ser Arg Asp Asn Ala Lys
65                  70                  75                  80

Asn Thr Leu Tyr Leu Gln Met Asn Ser Leu Lys Pro Glu Asp Thr Ala
                85                  90                  95

Val Tyr Thr Cys Ala Ala Ser Ala Ile Gly Ser Gly Ala Leu Arg Arg
            100                 105                 110

Phe Glu Tyr Asp Tyr Ser Gly Gln Gly Thr Gln Val Thr Val Ser Ser
        115                 120                 125

<210> SEQ ID NO 6
<211> LENGTH: 128
<212> TYPE: PRT
<213> ORGANISM: Artificial Sequence
<220> FEATURE:
<223> OTHER INFORMATION: Nanobody Sequence

<400> SEQUENCE: 6

Glu Val Gln Leu Val Glu Ser Gly Gly Gly Leu Val Gln Ala Gly Gly
1               5                   10                  15

Ser Leu Arg Leu Ser Cys Lys Ala Ser Gly Gly Thr Phe Asn Asn Tyr
            20                  25                  30

Ala Met Gly Trp Phe Arg Arg Ala Pro Gly Lys Glu Arg Glu Phe Val
        35                  40                  45

Ala Ala Ile Thr Arg Ser Gly Val Arg Ser Gly Val Ser Ala Ile Tyr
    50                  55                  60

Gly Asp Ser Val Lys Asp Arg Phe Thr Ile Ser Arg Asp Asn Val Lys
65                  70                  75                  80

Asn Thr Leu Tyr Leu Gln Met Asn Thr Leu Lys Pro Glu Asp Thr Ala
                85                  90                  95

Val Tyr Thr Cys Ala Ala Ser Ala Ile Gly Ser Gly Ala Leu Arg Arg
                100                 105                 110

Phe Glu Tyr Asp Tyr Ser Gly Gln Gly Thr Gln Val Thr Val Ser Ser
            115                 120                 125

<210> SEQ ID NO 7
<211> LENGTH: 128
<212> TYPE: PRT
<213> ORGANISM: Artificial Sequence
<220> FEATURE:
<223> OTHER INFORMATION: Nanobody Sequence

<400> SEQUENCE: 7

Glu Val Gln Leu Val Glu Ser Gly Gly Gly Leu Val Gln Ala Gly Gly
1               5                   10                  15

Ser Leu Arg Leu Ser Cys Ala Ala Ser Gly Gly Thr Phe Asn Asn Tyr
            20                  25                  30

Ala Met Gly Trp Phe Arg Arg Ala Pro Gly Lys Glu Arg Glu Phe Val
        35                  40                  45

Ala Ala Ile Ser Arg Ser Gly Val Arg Thr Gly Val Ser Ala Leu Tyr
    50                  55                  60

Gly Asp Ser Val Lys Asp Arg Phe Thr Ile Ser Arg Asp Asn Ala Lys
65                  70                  75                  80

Asn Thr Leu Tyr Leu Gln Met Asn Lys Met Lys Pro Glu Asp Thr Ala
                85                  90                  95

Val Tyr Thr Cys Ala Ala Ser Ala Ile Gly Ser Gly Ala Leu Arg Arg
                100                 105                 110

Phe Glu Tyr Asp Ser Ser Gly Gln Gly Thr Gln Val Thr Val Ser Ser
            115                 120                 125

<210> SEQ ID NO 8
<211> LENGTH: 128
<212> TYPE: PRT
<213> ORGANISM: Artificial Sequence
<220> FEATURE:
<223> OTHER INFORMATION: Nanobody Sequence

<400> SEQUENCE: 8

Glu Val Gln Leu Val Glu Ser Gly Gly Gly Leu Val Gln Thr Gly Gly
1               5                   10                  15

Ser Leu Arg Leu Ser Cys Ala Ala Ser Gly Gly Thr Phe Asn Asn Tyr
            20                  25                  30

Ala Met Gly Trp Phe Arg Arg Ala Pro Gly Lys Glu Arg Glu Phe Val
        35                  40                  45

Ala Ala Ile Ser Arg Ser Gly Val Arg Thr Gly Val Ser Ala Leu Tyr
    50                  55                  60

Gly Asp Ser Val Lys Asp Arg Phe Thr Ile Ser Arg Asp Asn Ala Lys
65                  70                  75                  80

```
Asn Thr Leu Tyr Leu Gln Met Asn Lys Met Lys Pro Glu Asp Thr Ala
                85                  90                  95

Val Tyr Thr Cys Ala Ala Ser Ala Ile Gly Ser Gly Ala Leu Arg Arg
            100                 105                 110

Phe Glu Tyr Asp Ser Ser Gly Gln Gly Thr Gln Val Thr Val Ser Ser
            115                 120                 125

<210> SEQ ID NO 9
<211> LENGTH: 126
<212> TYPE: PRT
<213> ORGANISM: Artificial Sequence
<220> FEATURE:
<223> OTHER INFORMATION: Nanobody Sequence

<400> SEQUENCE: 9

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Ala Phe Ser Arg Tyr
            20                  25                  30

Ala Met Gly Trp Phe Arg Gln Ala Pro Gly Lys Glu Arg Glu Phe Val
        35                  40                  45

Ala Ala Ile Gly Trp Gly Pro Ser Lys Thr Asn Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Thr Leu Lys Pro Glu Asp Thr Ala Val Tyr Ser Cys
                85                  90                  95

Ala Ala Lys Phe Val Asn Thr Asp Ser Thr Trp Ser Arg Ser Glu Met
            100                 105                 110

Tyr Thr Tyr Trp Gly Gln Gly Thr Gln Val Thr Val Ser Ser
            115                 120                 125

<210> SEQ ID NO 10
<211> LENGTH: 119
<212> TYPE: PRT
<213> ORGANISM: Artificial Sequence
<220> FEATURE:
<223> OTHER INFORMATION: Nanobody Sequence

<400> SEQUENCE: 10

Glu Val Gln Leu Val Ala Ser Gly Gly Gly Leu Val Gln Ala Gly Gly
1               5                   10                  15

Ser Leu Arg Leu Ser Cys Ala Val Ser Gly Thr Thr Phe Ser Val Ala
            20                  25                  30

Thr Leu Gly Trp Tyr Arg Gln Ala Pro Gly Gln Gln Arg Ala Leu Val
            35                  40                  45

Ala Asp Ile Ser Ser Gly Gly Ser Thr Asn Tyr Ala Asp Ser Val Arg
    50                  55                  60

Gly Arg Phe Thr Ile Ser Arg Asp Asn Ala Lys Asn Leu Ala Tyr Leu
65                  70                  75                  80

Gln Met Asn Ser Leu Lys Pro Glu Asp Thr Ala Val Tyr Tyr Cys Asn
                85                  90                  95

Ala Arg Thr Ser Gly Trp Arg Thr Arg Ser Asn Tyr Trp Gly Gln Gly
            100                 105                 110

Thr Gln Val Thr Val Ser Ser
            115
```

```
<210> SEQ ID NO 11
<211> LENGTH: 119
<212> TYPE: PRT
<213> ORGANISM: Artificial Sequence
<220> FEATURE:
<223> OTHER INFORMATION: Nanobody Sequence

<400> SEQUENCE: 11

Glu Val Gln Leu Val Glu Ser Gly Gly Gly Leu Val Gln Ala Gly Gly
1               5                   10                  15

Ser Leu Arg Leu Ser Cys Ala Val Ser Gly Thr Thr Phe Ser Val Ala
            20                  25                  30

Thr Leu Gly Trp Tyr Arg Gln Ala Pro Gly Gln Gln Arg Ala Leu Val
        35                  40                  45

Ala Asp Ile Ser Ser Gly Gly Ser Thr Asn Tyr Ala Asp Ser Val Arg
    50                  55                  60

Gly Arg Phe Thr Ile Ser Arg Asp Asn Ala Lys Asn Leu Ala Tyr Leu
65                  70                  75                  80

Gln Met Asn Ser Leu Lys Pro Glu Asp Thr Ala Val Tyr Tyr Cys Asn
                85                  90                  95

Ala Arg Thr Ser Gly Trp Arg Thr Arg Ser Asn Tyr Trp Gly Gln Gly
            100                 105                 110

Thr Gln Val Thr Val Ser Ser
        115

<210> SEQ ID NO 12
<211> LENGTH: 122
<212> TYPE: PRT
<213> ORGANISM: Artificial Sequence
<220> FEATURE:
<223> OTHER INFORMATION: Nanobody Sequence

<400> SEQUENCE: 12

Glu Val Gln Leu Val Glu Ser Gly Gly Gly Leu Val Gln Ala Gly Gly
1               5                   10                  15

Ser Leu Arg Leu Ser Cys Val Ala Ser Val Asn Ile Phe Gly Ser Ile
            20                  25                  30

Ala Met Ala Trp Tyr Arg Gln Ala Pro Gly Lys Gln Arg Asn Leu Val
        35                  40                  45

Ala Ser Ile Ser Ser Gly Gly Arg Ile Asn Tyr Ala Asp Ser Arg Lys
    50                  55                  60

Gly Arg Phe Thr Ile Ser Arg Asp Asn Thr Lys Asn Thr Val His Leu
65                  70                  75                  80

Gln Met Asn Ser Leu Glu Pro Glu Asp Thr Ala Val Tyr Tyr Cys Ala
                85                  90                  95

Ala Gly Arg Ile Gly Gln Arg Thr Leu Thr Phe Thr Pro Asp Tyr Trp
            100                 105                 110

Gly Gln Gly Thr Gln Val Thr Val Ser Ser
        115                 120

<210> SEQ ID NO 13
<211> LENGTH: 126
<212> TYPE: PRT
<213> ORGANISM: Artificial Sequence
<220> FEATURE:
<223> OTHER INFORMATION: Nanobody Sequence

<400> SEQUENCE: 13

Glu Val Gln Leu Val Glu Ser Gly Gly Gly Leu Val Arg Ala Gly Asp
1               5                   10                  15
```

Ser Leu Arg Leu Ser Cys Ala Ala Ser Gly Arg Ala Phe Ser Arg Tyr
            20                  25                  30

Ala Met Gly Trp Phe Arg Gln Ala Leu Gly Lys Glu Arg Glu Leu Val
            35                  40                  45

Ala Ala Ile Gly Trp Ser Pro Thr His Thr Tyr Ala Asp Ser Val
50                      55                  60

Lys Gly Arg Phe Thr Met Ser Arg Asp Asn Gly Lys Asn Thr Val Phe
65                      70                  75                  80

Leu Gln Met Asn Ser Leu Asn Pro Glu Asp Thr Ala Val Tyr Tyr Cys
                85                  90                  95

Ala Ala Lys Tyr Ser Ser Arg Asp Ala Ala Tyr Arg Ser Asp Tyr Asp
                100                 105                 110

Tyr Asn Tyr Trp Gly Gln Gly Thr Gln Val Thr Val Ser Ser
                115                 120                 125

<210> SEQ ID NO 14
<211> LENGTH: 128
<212> TYPE: PRT
<213> ORGANISM: Artificial Sequence
<220> FEATURE:
<223> OTHER INFORMATION: Nanobody Sequence

<400> SEQUENCE: 14

Glu Val Gln Leu Val Glu Ser Gly Gly Gly Leu Val Gln Ala Gly Asp
1               5                   10                  15

Ser Leu Arg Val Ser Cys Ala Ala Ser Gly Arg Thr Ser Ser Tyr Ala
            20                  25                  30

Met Ala Trp Phe Arg Gln Ala Pro Gly Lys Glu Arg Glu Phe Val Gly
            35                  40                  45

Thr Ile Ser Arg Thr Asn Ser Arg Thr Lys Tyr Ala Asp Phe Val Glu
            50                  55                  60

Gly Arg Phe Thr Ile Ser Arg Asp Asn Ala Lys Ser Thr Leu Ser Leu
65                  70                  75                  80

Gln Met Thr Ser Leu Lys Pro Glu Asp Thr Ala Val Tyr Tyr Cys Ala
                85                  90                  95

Ala Lys Trp Thr Gly Asn Ser Tyr His Asp Tyr Thr Trp Ser Lys Val
                100                 105                 110

Asp Glu Tyr Asn Val Trp Gly Gln Gly Thr Gln Val Thr Val Ser Ser
                115                 120                 125

<210> SEQ ID NO 15
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 15

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Arg Ala
            20                  25                  30

Ala Met Gly Trp Phe Arg Gln Ala Pro Gly Lys Glu Arg Glu Phe Val
            35                  40                  45

Gly Cys Ala Leu Ser Ser Ala Gly Ser Ala Leu Thr Ala Asp Ser Val
            50                  55                  60

Lys Gly Arg Phe Thr Ile Ser Arg Asp Asn Ala Lys Asn Met Val Tyr

```
                65                  70                  75                  80
Leu Gln Met Asn Asn Leu Lys Pro Glu Asp Thr Ala Val Tyr Ser Cys
                    85                  90                  95

Val Ala Gly Gly Tyr Cys Thr Arg Ala Gly Val Tyr Pro Tyr Trp Gly
                100                 105                 110

Gln Gly Thr Gln Val Thr Val Ser Ser
            115                 120

<210> SEQ ID NO 16
<211> LENGTH: 120
<212> TYPE: PRT
<213> ORGANISM: Artificial Sequence
<220> FEATURE:
<223> OTHER INFORMATION: Nanobody Sequence

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Ile Phe Ser Thr Ser
                20                  25                  30

Thr Met Gly Trp Tyr Ser Gln Ala Pro Gly Lys Gln Arg Glu Leu Val
            35                  40                  45

Ala Asp Ile Thr Phe Leu Gly Ser Ala Lys Tyr Ala Asp Ser Val Lys
        50                  55                  60

Gly Arg Phe Thr Ile Ser Arg Asp Lys Ile Lys Asn Thr Val Tyr Leu
65                  70                  75                  80

Gln Met Asn Ser Leu Lys Pro Glu Asp Thr Ala Ala Tyr Tyr Cys Asn
                    85                  90                  95

Ala Arg Gln Ser Thr Phe Arg Gly Val His Tyr Asn Tyr Trp Gly Gln
                100                 105                 110

Gly Thr Gln Val Thr Val Ser Ser
            115                 120

<210> SEQ ID NO 17
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 17

Glu Val Gln Leu Val Glu Ser Gly Gly Gly Leu Val Gln Ser Gly Gly
1               5                   10                  15

Ser Leu Arg Leu Ser Cys Ala Ala Ser Gly Phe Thr Phe Ser Gly Tyr
                20                  25                  30

Trp Met Tyr Trp Val Arg Gln Ala Pro Gly Lys Gly Leu Glu Trp Val
            35                  40                  45

Ser Ala Ile Ser Pro Gly Gly Gly Ser Thr Tyr Tyr Pro Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Leu Tyr Tyr Cys
                    85                  90                  95

Ala Ser Ser Leu Thr Ala Thr His Thr Tyr Glu Tyr Asp Tyr Trp Gly
                100                 105                 110

Gln Gly Thr Gln Val Thr Val Ser Ser
            115                 120
```

```
<210> SEQ ID NO 18
<211> LENGTH: 122
<212> TYPE: PRT
<213> ORGANISM: Artificial Sequence
<220> FEATURE:
<223> OTHER INFORMATION: Nanobody Sequence

<400> SEQUENCE: 18

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Ser Ala Ser Tyr
            20                  25                  30

Ser Met Gly Trp Phe Arg Gln Ala Pro Gly Lys Glu Arg Glu Phe Val
        35                  40                  45

Ala Ala Ile Ser Trp Ser Gly Asp Glu Thr Ser Tyr Ala Asp Ser Val
    50                  55                  60

Lys Gly Arg Phe Thr Ile Ala Arg Gly Asn Ala Lys Asn Thr Val Tyr
65                  70                  75                  80

Leu Gln Met Asn Ser Leu Lys Ser Glu Asp Thr Ala Ile Tyr Tyr Cys
                85                  90                  95

Ala Gly Asp Arg Trp Trp Arg Pro Ala Gly Leu Gln Trp Asp Tyr Trp
            100                 105                 110

Gly Gln Gly Thr Gln Val Thr Val Ser Ser
        115                 120

<210> SEQ ID NO 19
<211> LENGTH: 117
<212> TYPE: PRT
<213> ORGANISM: Artificial Sequence
<220> FEATURE:
<223> OTHER INFORMATION: Nanobody Sequence

<400> SEQUENCE: 19

Glu Val Gln Leu Val Glu Ser Gly Gly Gly Leu Val Gln Ala Gly Gly
1               5                   10                  15

Ser Leu Lys Leu Ser Cys Ala Ala Ser Arg Ser Ile Leu Asp Phe Asn
            20                  25                  30

Ala Met Gly Trp Tyr Arg Gln Ala Pro Gly Lys Gln Arg Glu Trp Val
        35                  40                  45

Thr Thr Ile Ala Arg Ala Gly Ala Thr Lys Tyr Ala Asp Ser Val Lys
    50                  55                  60

Gly Arg Phe Ser Ile Ser Arg Asp Asn Ala Lys Asn Thr Val Tyr Leu
65                  70                  75                  80

Gln Met Ser Ser Leu Lys Pro Glu Asp Thr Ala Thr Tyr Tyr Cys Asn
                85                  90                  95

Ala Arg Val Phe Asp Leu Pro Asn Asp Tyr Trp Gly Gln Gly Thr Gln
            100                 105                 110

Val Thr Val Ser Ser
        115

<210> SEQ ID NO 20
<211> LENGTH: 125
<212> TYPE: PRT
<213> ORGANISM: Artificial Sequence
<220> FEATURE:
<223> OTHER INFORMATION: Nanobody Sequence

<400> SEQUENCE: 20

Glu Val Gln Leu Val Glu Ser Gly Gly Gly Ser Val Gln Pro Gly Gly
```

```
                1               5                  10                 15
            Ser Leu Thr Leu Ser Cys Gly Thr Ser Gly Arg Thr Phe Asn Val Met
                           20                  25                  30

Gly Trp Phe Arg Gln Ala Pro Gly Lys Glu Arg Glu Phe Val Ala Ala
                       35                  40                  45

Val Arg Trp Ser Ser Thr Gly Ile Tyr Tyr Thr Gln Tyr Ala Asp Ser
                50                  55                  60

Val Lys Ser Arg Phe Thr Ile Ser Arg Asp Asn Ala Lys Asn Thr Val
             65                  70                  75                  80

Tyr Leu Glu Met Asn Ser Leu Lys Pro Glu Asp Thr Ala Val Tyr Tyr
                            85                  90                  95

Cys Ala Ala Asp Thr Tyr Asn Ser Asn Pro Ala Arg Trp Asp Gly Tyr
                        100                 105                 110

Asp Phe Arg Gly Gln Gly Thr Gln Val Thr Val Ser Ser
                        115                 120                 125
```

<210> SEQ ID NO 21
<211> LENGTH: 30
<212> TYPE: PRT
<213> ORGANISM: Artificial Sequence
<220> FEATURE:
<223> OTHER INFORMATION: Framework 1

<400> SEQUENCE: 21

```
            Glu Val Gln Leu Met Glu Ser Gly Gly Gly Leu Val Gln Ala Gly Gly
             1               5                  10                  15

Ser Leu Arg Leu Ser Cys Ala Ala Ser Gly Arg Thr Phe Asn
                        20                  25                  30
```

<210> SEQ ID NO 22
<211> LENGTH: 30
<212> TYPE: PRT
<213> ORGANISM: Artificial Sequence
<220> FEATURE:
<223> OTHER INFORMATION: Framework 1

<400> SEQUENCE: 22

```
            Glu Val Gln Leu Val Glu Ser Gly Gly Gly Leu Val Gln Ala Gly Gly
             1               5                  10                  15

Ser Leu Arg Leu Ser Cys Ala Ala Ser Gly Arg Thr Phe Asn
                        20                  25                  30
```

<210> SEQ ID NO 23
<211> LENGTH: 30
<212> TYPE: PRT
<213> ORGANISM: Artificial Sequence
<220> FEATURE:
<223> OTHER INFORMATION: Framework 1

<400> SEQUENCE: 23

```
            Glu Val Gln Leu Val Glu Ser Gly Gly Gly Leu Val Gln Ala Gly Gly
             1               5                  10                  15

Ser Leu Arg Leu Ser Cys Lys Ala Ser Gly Gly Thr Phe Asn
                        20                  25                  30
```

<210> SEQ ID NO 24
<211> LENGTH: 30
<212> TYPE: PRT
<213> ORGANISM: Artificial Sequence
<220> FEATURE:
<223> OTHER INFORMATION: Framework 1

```
<400> SEQUENCE: 24

Glu Val Gln Leu Val Glu Ser Gly Gly Gly Leu Val Gln Ala Gly Gly
1               5                   10                  15

Ser Leu Arg Leu Ser Cys Ala Ala Ser Gly Gly Thr Phe Asn
            20                  25                  30

<210> SEQ ID NO 25
<211> LENGTH: 30
<212> TYPE: PRT
<213> ORGANISM: Artificial Sequence
<220> FEATURE:
<223> OTHER INFORMATION: Framework 1

<400> SEQUENCE: 25

Glu Val Gln Leu Val Glu Ser Gly Gly Gly Leu Val Gln Thr Gly Gly
1               5                   10                  15

Ser Leu Arg Leu Ser Cys Ala Ala Ser Gly Gly Thr Phe Asn
            20                  25                  30

<210> SEQ ID NO 26
<211> LENGTH: 30
<212> TYPE: PRT
<213> ORGANISM: Artificial Sequence
<220> FEATURE:
<223> OTHER INFORMATION: Framework 1

<400> SEQUENCE: 26

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Ala Phe Ser
            20                  25                  30

<210> SEQ ID NO 27
<211> LENGTH: 30
<212> TYPE: PRT
<213> ORGANISM: Artificial Sequence
<220> FEATURE:
<223> OTHER INFORMATION: Framework 1

<400> SEQUENCE: 27

Glu Val Gln Leu Val Ala Ser Gly Gly Gly Leu Val Gln Ala Gly Gly
1               5                   10                  15

Ser Leu Arg Leu Ser Cys Ala Val Ser Gly Thr Thr Phe Ser
            20                  25                  30

<210> SEQ ID NO 28
<211> LENGTH: 30
<212> TYPE: PRT
<213> ORGANISM: Artificial Sequence
<220> FEATURE:
<223> OTHER INFORMATION: Framework 1

<400> SEQUENCE: 28

Glu Val Gln Leu Val Glu Ser Gly Gly Gly Leu Val Gln Ala Gly Gly
1               5                   10                  15

Ser Leu Arg Leu Ser Cys Ala Val Ser Gly Thr Thr Phe Ser
            20                  25                  30

<210> SEQ ID NO 29
<211> LENGTH: 30
<212> TYPE: PRT
<213> ORGANISM: Artificial Sequence
<220> FEATURE:
<223> OTHER INFORMATION: Framework 1
```

```
<400> SEQUENCE: 29

Glu Val Gln Leu Val Glu Ser Gly Gly Gly Leu Val Gln Ala Gly Gly
1               5                   10                  15

Ser Leu Arg Leu Ser Cys Val Ala Ser Val Asn Ile Phe Gly
            20                  25                  30

<210> SEQ ID NO 30
<211> LENGTH: 30
<212> TYPE: PRT
<213> ORGANISM: Artificial Sequence
<220> FEATURE:
<223> OTHER INFORMATION: Framework 1

<400> SEQUENCE: 30

Glu Val Gln Leu Val Glu Ser Gly Gly Gly Leu Val Arg Ala Gly Asp
1               5                   10                  15

Ser Leu Arg Leu Ser Cys Ala Ala Ser Gly Arg Ala Phe Ser
            20                  25                  30

<210> SEQ ID NO 31
<211> LENGTH: 29
<212> TYPE: PRT
<213> ORGANISM: Artificial Sequence
<220> FEATURE:
<223> OTHER INFORMATION: Framework 1

<400> SEQUENCE: 31

Glu Val Gln Leu Val Glu Ser Gly Gly Gly Leu Val Gln Ala Gly Asp
1               5                   10                  15

Ser Leu Arg Val Ser Cys Ala Ala Ser Gly Arg Thr Ser
            20                  25

<210> SEQ ID NO 32
<211> LENGTH: 29
<212> TYPE: PRT
<213> ORGANISM: Artificial Sequence
<220> FEATURE:
<223> OTHER INFORMATION: Framework 1

<400> SEQUENCE: 32

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe
            20                  25

<210> SEQ ID NO 33
<211> LENGTH: 29
<212> TYPE: PRT
<213> ORGANISM: Artificial Sequence
<220> FEATURE:
<223> OTHER INFORMATION: Framework 1

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Ile Phe
            20                  25

<210> SEQ ID NO 34
<211> LENGTH: 5
<212> TYPE: PRT
<213> ORGANISM: Artificial Sequence
<220> FEATURE:
```

<223> OTHER INFORMATION: CDR1

<400> SEQUENCE: 34

Asn Tyr Ala Met Gly
1               5

<210> SEQ ID NO 35
<211> LENGTH: 5
<212> TYPE: PRT
<213> ORGANISM: Artificial Sequence
<220> FEATURE:
<223> OTHER INFORMATION: CDR1

<400> SEQUENCE: 35

Arg Tyr Ala Met Gly
1               5

<210> SEQ ID NO 36
<211> LENGTH: 5
<212> TYPE: PRT
<213> ORGANISM: Artificial Sequence
<220> FEATURE:
<223> OTHER INFORMATION: CDR1

<400> SEQUENCE: 36

Val Ala Thr Leu Gly
1               5

<210> SEQ ID NO 37
<211> LENGTH: 5
<212> TYPE: PRT
<213> ORGANISM: Artificial Sequence
<220> FEATURE:
<223> OTHER INFORMATION: CDR1

<400> SEQUENCE: 37

Ser Ile Ala Met Ala
1               5

<210> SEQ ID NO 38
<211> LENGTH: 5
<212> TYPE: PRT
<213> ORGANISM: Artificial Sequence
<220> FEATURE:
<223> OTHER INFORMATION: CDR1

<400> SEQUENCE: 38

Ser Tyr Ala Met Ala
1               5

<210> SEQ ID NO 39
<211> LENGTH: 6
<212> TYPE: PRT
<213> ORGANISM: Artificial Sequence
<220> FEATURE:
<223> OTHER INFORMATION: CDR1

<400> SEQUENCE: 39

Ser Arg Ala Ala Met Gly
1               5

<210> SEQ ID NO 40
<211> LENGTH: 6
<212> TYPE: PRT
<213> ORGANISM: Artificial Sequence
<220> FEATURE:
<223> OTHER INFORMATION: CDR1

```
<400> SEQUENCE: 40

Ser Thr Ser Thr Met Gly
1               5

<210> SEQ ID NO 41
<211> LENGTH: 14
<212> TYPE: PRT
<213> ORGANISM: Artificial Sequence
<220> FEATURE:
<223> OTHER INFORMATION: Framework 2

<400> SEQUENCE: 41

Trp Phe Arg Arg Ala Pro Gly Lys Glu Arg Glu Phe Val Ala
1               5                   10

<210> SEQ ID NO 42
<211> LENGTH: 14
<212> TYPE: PRT
<213> ORGANISM: Artificial Sequence
<220> FEATURE:
<223> OTHER INFORMATION: Framework 2

<400> SEQUENCE: 42

Trp Phe Arg Gln Ala Pro Gly Lys Glu Arg Glu Phe Val Ala
1               5                   10

<210> SEQ ID NO 43
<211> LENGTH: 14
<212> TYPE: PRT
<213> ORGANISM: Artificial Sequence
<220> FEATURE:
<223> OTHER INFORMATION: Framework 2

<400> SEQUENCE: 43

Trp Tyr Arg Gln Ala Pro Gly Gln Gln Arg Ala Leu Val Ala
1               5                   10

<210> SEQ ID NO 44
<211> LENGTH: 14
<212> TYPE: PRT
<213> ORGANISM: Artificial Sequence
<220> FEATURE:
<223> OTHER INFORMATION: Framework 2

<400> SEQUENCE: 44

Trp Tyr Arg Gln Ala Pro Gly Lys Gln Arg Asn Leu Val Ala
1               5                   10

<210> SEQ ID NO 45
<211> LENGTH: 14
<212> TYPE: PRT
<213> ORGANISM: Artificial Sequence
<220> FEATURE:
<223> OTHER INFORMATION: Framework 2

<400> SEQUENCE: 45

Trp Phe Arg Gln Ala Leu Gly Lys Glu Arg Glu Leu Val Ala
1               5                   10

<210> SEQ ID NO 46
<211> LENGTH: 14
<212> TYPE: PRT
<213> ORGANISM: Artificial Sequence
<220> FEATURE:
<223> OTHER INFORMATION: Framework 2
```

```
<400> SEQUENCE: 46

Trp Phe Arg Gln Ala Pro Gly Lys Glu Arg Glu Phe Val Gly
1               5                   10

<210> SEQ ID NO 47
<211> LENGTH: 14
<212> TYPE: PRT
<213> ORGANISM: Artificial Sequence
<220> FEATURE:
<223> OTHER INFORMATION: Framework 2

<400> SEQUENCE: 47

Trp Tyr Ser Gln Ala Pro Gly Lys Gln Arg Glu Leu Val Ala
1               5                   10

<210> SEQ ID NO 48
<211> LENGTH: 21
<212> TYPE: PRT
<213> ORGANISM: Artificial Sequence
<220> FEATURE:
<223> OTHER INFORMATION: CDR 2

<400> SEQUENCE: 48

Ala Ile Thr Arg Ser Gly Val Arg Ser Gly Val Ser Ala Ile Tyr Gly
1               5                   10                  15

Asp Ser Val Lys Asp
            20

<210> SEQ ID NO 49
<211> LENGTH: 21
<212> TYPE: PRT
<213> ORGANISM: Artificial Sequence
<220> FEATURE:
<223> OTHER INFORMATION: CDR 2

<400> SEQUENCE: 49

Ala Ile Ser Arg Ser Gly Val Arg Thr Gly Val Ser Ala Leu Tyr Gly
1               5                   10                  15

Asp Ser Val Lys Asp
            20

<210> SEQ ID NO 50
<211> LENGTH: 17
<212> TYPE: PRT
<213> ORGANISM: Artificial Sequence
<220> FEATURE:
<223> OTHER INFORMATION: CDR 2

<400> SEQUENCE: 50

Ala Ile Gly Trp Gly Pro Ser Lys Thr Asn Tyr Ala Asp Ser Val Lys
1               5                   10                  15

Gly

<210> SEQ ID NO 51
<211> LENGTH: 16
<212> TYPE: PRT
<213> ORGANISM: Artificial Sequence
<220> FEATURE:
<223> OTHER INFORMATION: CDR 2

<400> SEQUENCE: 51

Asp Ile Ser Ser Gly Gly Ser Thr Asn Tyr Ala Asp Ser Val Arg Gly
1               5                   10                  15
```

```
<210> SEQ ID NO 52
<211> LENGTH: 16
<212> TYPE: PRT
<213> ORGANISM: Artificial Sequence
<220> FEATURE:
<223> OTHER INFORMATION: CDR 2

<400> SEQUENCE: 52

Ser Ile Ser Ser Gly Gly Arg Ile Asn Tyr Ala Asp Ser Arg Lys Gly
1               5                   10                  15

<210> SEQ ID NO 53
<211> LENGTH: 17
<212> TYPE: PRT
<213> ORGANISM: Artificial Sequence
<220> FEATURE:
<223> OTHER INFORMATION: CDR 2

<400> SEQUENCE: 53

Ala Ile Gly Trp Ser Pro Thr His Thr Tyr Tyr Ala Asp Ser Val Lys
1               5                   10                  15

Gly

<210> SEQ ID NO 54
<211> LENGTH: 17
<212> TYPE: PRT
<213> ORGANISM: Artificial Sequence
<220> FEATURE:
<223> OTHER INFORMATION: CDR 2

<400> SEQUENCE: 54

Thr Ile Ser Arg Thr Asn Ser Arg Thr Lys Tyr Ala Asp Phe Val Glu
1               5                   10                  15

Gly

<210> SEQ ID NO 55
<211> LENGTH: 17
<212> TYPE: PRT
<213> ORGANISM: Artificial Sequence
<220> FEATURE:
<223> OTHER INFORMATION: CDR 2

<400> SEQUENCE: 55

Cys Ala Leu Ser Ser Ala Gly Ser Ala Leu Thr Ala Asp Ser Val Lys
1               5                   10                  15

Gly

<210> SEQ ID NO 56
<211> LENGTH: 16
<212> TYPE: PRT
<213> ORGANISM: Artificial Sequence
<220> FEATURE:
<223> OTHER INFORMATION: CDR 2

<400> SEQUENCE: 56

Asp Ile Thr Phe Leu Gly Ser Ala Lys Tyr Ala Asp Ser Val Lys Gly
1               5                   10                  15

<210> SEQ ID NO 57
<211> LENGTH: 32
<212> TYPE: PRT
<213> ORGANISM: Artificial Sequence
<220> FEATURE:
<223> OTHER INFORMATION: Framework 3

<400> SEQUENCE: 57
```

Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Val Tyr Thr Cys Ala Ala
            20                  25                  30

<210> SEQ ID NO 58
<211> LENGTH: 32
<212> TYPE: PRT
<213> ORGANISM: Artificial Sequence
<220> FEATURE:
<223> OTHER INFORMATION: Framework 3

<400> SEQUENCE: 58

Arg Phe Thr Ile Ser Arg Asp Asn Val Lys Asn Thr Leu Tyr Leu Gln
1               5                   10                  15

Met Asn Thr Leu Lys Pro Glu Asp Thr Ala Val Tyr Thr Cys Ala Ala
            20                  25                  30

<210> SEQ ID NO 59
<211> LENGTH: 32
<212> TYPE: PRT
<213> ORGANISM: Artificial Sequence
<220> FEATURE:
<223> OTHER INFORMATION: Framework 3

<400> SEQUENCE: 59

Arg Phe Thr Ile Ser Arg Asp Asn Ala Lys Asn Thr Leu Tyr Leu Gln
1               5                   10                  15

Met Asn Lys Met Lys Pro Glu Asp Thr Ala Val Tyr Thr Cys Ala Ala
            20                  25                  30

<210> SEQ ID NO 60
<211> LENGTH: 32
<212> TYPE: PRT
<213> ORGANISM: Artificial Sequence
<220> FEATURE:
<223> OTHER INFORMATION: Framework 3

<400> SEQUENCE: 60

Arg Phe Thr Ile Ser Arg Asp Asn Ala Lys Asn Thr Val Tyr Leu Gln
1               5                   10                  15

Met Asn Thr Leu Lys Pro Glu Asp Thr Ala Val Tyr Ser Cys Ala Ala
            20                  25                  30

<210> SEQ ID NO 61
<211> LENGTH: 32
<212> TYPE: PRT
<213> ORGANISM: Artificial Sequence
<220> FEATURE:
<223> OTHER INFORMATION: Framework 3

<400> SEQUENCE: 61

Arg Phe Thr Ile Ser Arg Asp Asn Ala Lys Asn Leu Ala Tyr Leu Gln
1               5                   10                  15

Met Asn Ser Leu Lys Pro Glu Asp Thr Ala Val Tyr Tyr Cys Asn Ala
            20                  25                  30

<210> SEQ ID NO 62
<211> LENGTH: 32
<212> TYPE: PRT
<213> ORGANISM: Artificial Sequence
<220> FEATURE:
<223> OTHER INFORMATION: Framework 3

```
<400> SEQUENCE: 62

Arg Phe Thr Ile Ser Arg Asp Asn Thr Lys Asn Thr Val His Leu Gln
1               5                   10                  15

Met Asn Ser Leu Glu Pro Glu Asp Thr Ala Val Tyr Tyr Cys Ala Ala
                20                  25                  30

<210> SEQ ID NO 63
<211> LENGTH: 32
<212> TYPE: PRT
<213> ORGANISM: Artificial Sequence
<220> FEATURE:
<223> OTHER INFORMATION: Framework 3

<400> SEQUENCE: 63

Arg Phe Thr Met Ser Arg Asp Asn Gly Lys Asn Thr Val Phe Leu Gln
1               5                   10                  15

Met Asn Ser Leu Asn Pro Glu Asp Thr Ala Val Tyr Tyr Cys Ala Ala
                20                  25                  30

<210> SEQ ID NO 64
<211> LENGTH: 32
<212> TYPE: PRT
<213> ORGANISM: Artificial Sequence
<220> FEATURE:
<223> OTHER INFORMATION: Framework 3

<400> SEQUENCE: 64

Arg Phe Thr Ile Ser Arg Asp Asn Ala Lys Ser Thr Leu Ser Leu Gln
1               5                   10                  15

Met Thr Ser Leu Lys Pro Glu Asp Thr Ala Val Tyr Tyr Cys Ala Ala
                20                  25                  30

<210> SEQ ID NO 65
<211> LENGTH: 32
<212> TYPE: PRT
<213> ORGANISM: Artificial Sequence
<220> FEATURE:
<223> OTHER INFORMATION: Framework 3

<400> SEQUENCE: 65

Arg Phe Thr Ile Ser Arg Asp Asn Ala Lys Asn Met Val Tyr Leu Gln
1               5                   10                  15

Met Asn Asn Leu Lys Pro Glu Asp Thr Ala Val Tyr Ser Cys Val Ala
                20                  25                  30

<210> SEQ ID NO 66
<211> LENGTH: 32
<212> TYPE: PRT
<213> ORGANISM: Artificial Sequence
<220> FEATURE:
<223> OTHER INFORMATION: Framework 3

<400> SEQUENCE: 66

Arg Phe Thr Ile Ser Arg Asp Lys Ile Lys Asn Thr Val Tyr Leu Gln
1               5                   10                  15

Met Asn Ser Leu Lys Pro Glu Asp Thr Ala Ala Tyr Tyr Cys Asn Ala
                20                  25                  30

<210> SEQ ID NO 67
<211> LENGTH: 15
<212> TYPE: PRT
<213> ORGANISM: Artificial Sequence
<220> FEATURE:
<223> OTHER INFORMATION: CDR 3
```

```
<400> SEQUENCE: 67

Ser Ala Ile Gly Ser Gly Ala Leu Arg Arg Phe Glu Tyr Asp Tyr
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: CDR 3

<400> SEQUENCE: 68

Ser Ala Ile Gly Ser Gly Ala Leu Arg Arg Phe Glu Tyr Asp Ser
1               5                   10                  15

<210> SEQ ID NO 69
<211> LENGTH: 17
<212> TYPE: PRT
<213> ORGANISM: Artificial Sequence
<220> FEATURE:
<223> OTHER INFORMATION: CDR 3

<400> SEQUENCE: 69

Lys Phe Val Asn Thr Asp Ser Thr Trp Ser Arg Ser Glu Met Tyr Thr
1               5                   10                  15

Tyr

<210> SEQ ID NO 70
<211> LENGTH: 11
<212> TYPE: PRT
<213> ORGANISM: Artificial Sequence
<220> FEATURE:
<223> OTHER INFORMATION: CDR 3

<400> SEQUENCE: 70

Arg Thr Ser Gly Trp Arg Thr Arg Ser Asn Tyr
1               5                   10

<210> SEQ ID NO 71
<211> LENGTH: 14
<212> TYPE: PRT
<213> ORGANISM: Artificial Sequence
<220> FEATURE:
<223> OTHER INFORMATION: CDR 3

<400> SEQUENCE: 71

Gly Arg Ile Gly Gln Arg Thr Leu Thr Phe Thr Pro Asp Tyr
1               5                   10

<210> SEQ ID NO 72
<211> LENGTH: 17
<212> TYPE: PRT
<213> ORGANISM: Artificial Sequence
<220> FEATURE:
<223> OTHER INFORMATION: CDR 3

<400> SEQUENCE: 72

Lys Tyr Ser Ser Arg Asp Ala Ala Tyr Arg Ser Asp Tyr Asp Tyr Asn
1               5                   10                  15

Tyr

<210> SEQ ID NO 73
<211> LENGTH: 20
<212> TYPE: PRT
```

```
<213> ORGANISM: Artificial Sequence
<220> FEATURE:
<223> OTHER INFORMATION: CDR 3

<400> SEQUENCE: 73

Lys Trp Thr Gly Asn Ser Tyr His Asp Tyr Thr Trp Ser Lys Val Asp
1               5                   10                  15

Glu Tyr Asn Val
            20

<210> SEQ ID NO 74
<211> LENGTH: 12
<212> TYPE: PRT
<213> ORGANISM: Artificial Sequence
<220> FEATURE:
<223> OTHER INFORMATION: CDR 3

<400> SEQUENCE: 74

Gly Gly Tyr Cys Thr Arg Ala Gly Val Tyr Pro Tyr
1               5                   10

<210> SEQ ID NO 75
<211> LENGTH: 12
<212> TYPE: PRT
<213> ORGANISM: Artificial Sequence
<220> FEATURE:
<223> OTHER INFORMATION: CDR 3

<400> SEQUENCE: 75

Arg Gln Ser Thr Phe Arg Gly Val His Tyr Asn Tyr
1               5                   10

<210> SEQ ID NO 76
<211> LENGTH: 11
<212> TYPE: PRT
<213> ORGANISM: Artificial Sequence
<220> FEATURE:
<223> OTHER INFORMATION: Framework 4

<400> SEQUENCE: 76

Ser Gly Gln Gly Thr Gln Val Thr Val Ser Ser
1               5                   10

<210> SEQ ID NO 77
<211> LENGTH: 11
<212> TYPE: PRT
<213> ORGANISM: Artificial Sequence
<220> FEATURE:
<223> OTHER INFORMATION: Framework 4

<400> SEQUENCE: 77

Trp Gly Gln Gly Thr Gln Val Thr Val Ser Ser
1               5                   10

<210> SEQ ID NO 78
<211> LENGTH: 30
<212> TYPE: PRT
<213> ORGANISM: Artificial Sequence
<220> FEATURE:
<223> OTHER INFORMATION: Framework 1

<400> SEQUENCE: 78

Glu Val Gln Leu Val Glu Ser Gly Gly Gly Leu Val Gln Ser Gly Gly
1               5                   10                  15

Ser Leu Arg Leu Ser Cys Ala Ala Ser Gly Phe Thr Phe Ser
            20                  25                  30
```

<210> SEQ ID NO 79
<211> LENGTH: 30
<212> TYPE: PRT
<213> ORGANISM: Artificial Sequence
<220> FEATURE:
<223> OTHER INFORMATION: Framework 1

<400> SEQUENCE: 79

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Ser Ala
            20                  25                  30

<210> SEQ ID NO 80
<211> LENGTH: 30
<212> TYPE: PRT
<213> ORGANISM: Artificial Sequence
<220> FEATURE:
<223> OTHER INFORMATION: Framework 1

<400> SEQUENCE: 80

Glu Val Gln Leu Val Glu Ser Gly Gly Gly Leu Val Gln Ala Gly Gly
1               5                   10                  15

Ser Leu Lys Leu Ser Cys Ala Ala Ser Arg Ser Ile Leu Asp
            20                  25                  30

<210> SEQ ID NO 81
<211> LENGTH: 30
<212> TYPE: PRT
<213> ORGANISM: Artificial Sequence
<220> FEATURE:
<223> OTHER INFORMATION: Framework 1

<400> SEQUENCE: 81

Glu Val Gln Leu Val Glu Ser Gly Gly Gly Ser Val Gln Pro Gly Gly
1               5                   10                  15

Ser Leu Thr Leu Ser Cys Gly Thr Ser Gly Arg Thr Phe Asn
            20                  25                  30

<210> SEQ ID NO 82
<211> LENGTH: 5
<212> TYPE: PRT
<213> ORGANISM: Artificial Sequence
<220> FEATURE:
<223> OTHER INFORMATION: CDR 1

<400> SEQUENCE: 82

Gly Tyr Trp Met Tyr
1               5

<210> SEQ ID NO 83
<211> LENGTH: 5
<212> TYPE: PRT
<213> ORGANISM: Artificial Sequence
<220> FEATURE:
<223> OTHER INFORMATION: CDR 1

<400> SEQUENCE: 83

Ser Tyr Ser Met Gly
1               5

<210> SEQ ID NO 84
<211> LENGTH: 5
<212> TYPE: PRT

<213> ORGANISM: Artificial Sequence
<220> FEATURE:
<223> OTHER INFORMATION: CDR 1

<400> SEQUENCE: 84

Phe Asn Ala Met Gly
1               5

<210> SEQ ID NO 85
<211> LENGTH: 3
<212> TYPE: PRT
<213> ORGANISM: Artificial Sequence
<220> FEATURE:
<223> OTHER INFORMATION: CDR 1

<400> SEQUENCE: 85

Val Met Gly
1

<210> SEQ ID NO 86
<211> LENGTH: 14
<212> TYPE: PRT
<213> ORGANISM: Artificial Sequence
<220> FEATURE:
<223> OTHER INFORMATION: Framework 2

<400> SEQUENCE: 86

Trp Val Arg Gln Ala Pro Gly Lys Gly Leu Glu Trp Val Ser
1               5                   10

<210> SEQ ID NO 87
<211> LENGTH: 14
<212> TYPE: PRT
<213> ORGANISM: Artificial Sequence
<220> FEATURE:
<223> OTHER INFORMATION: Framework 2

<400> SEQUENCE: 87

Trp Tyr Arg Gln Ala Pro Gly Lys Gln Arg Glu Trp Val Thr
1               5                   10

<210> SEQ ID NO 88
<211> LENGTH: 17
<212> TYPE: PRT
<213> ORGANISM: Artificial Sequence
<220> FEATURE:
<223> OTHER INFORMATION: CDR 2

<400> SEQUENCE: 88

Ala Ile Ser Pro Gly Gly Gly Ser Thr Tyr Tyr Pro Asp Ser Val Lys
1               5                   10                  15
Gly

<210> SEQ ID NO 89
<211> LENGTH: 17
<212> TYPE: PRT
<213> ORGANISM: Artificial Sequence
<220> FEATURE:
<223> OTHER INFORMATION: CDR 2

<400> SEQUENCE: 89

Ala Ile Ser Trp Ser Gly Asp Glu Thr Ser Tyr Ala Asp Ser Val Lys
1               5                   10                  15
Gly

-continued

```
<210> SEQ ID NO 90
<211> LENGTH: 16
<212> TYPE: PRT
<213> ORGANISM: Artificial Sequence
<220> FEATURE:
<223> OTHER INFORMATION: CDR 2

<400> SEQUENCE: 90

Thr Ile Ala Arg Ala Gly Ala Thr Lys Tyr Ala Asp Ser Val Lys Gly
1               5                   10                  15

<210> SEQ ID NO 91
<211> LENGTH: 20
<212> TYPE: PRT
<213> ORGANISM: Artificial Sequence
<220> FEATURE:
<223> OTHER INFORMATION: CDR 2

<400> SEQUENCE: 91

Ala Val Arg Trp Ser Ser Thr Gly Ile Tyr Tyr Thr Gln Tyr Ala Asp
1               5                   10                  15

Ser Val Lys Ser
            20

<210> SEQ ID NO 92
<211> LENGTH: 32
<212> TYPE: PRT
<213> ORGANISM: Artificial Sequence
<220> FEATURE:
<223> OTHER INFORMATION: Framework 3

<400> SEQUENCE: 92

Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Leu Tyr Tyr Cys Ala Ser
            20                  25                  30

<210> SEQ ID NO 93
<211> LENGTH: 32
<212> TYPE: PRT
<213> ORGANISM: Artificial Sequence
<220> FEATURE:
<223> OTHER INFORMATION: Framework 3

<400> SEQUENCE: 93

Arg Phe Thr Ile Ala Arg Gly Asn Ala Lys Asn Thr Val Tyr Leu Gln
1               5                   10                  15

Met Asn Ser Leu Lys Ser Glu Asp Thr Ala Ile Tyr Tyr Cys Ala Gly
            20                  25                  30

<210> SEQ ID NO 94
<211> LENGTH: 32
<212> TYPE: PRT
<213> ORGANISM: Artificial Sequence
<220> FEATURE:
<223> OTHER INFORMATION: Framework 3

<400> SEQUENCE: 94

Arg Phe Ser Ile Ser Arg Asp Asn Ala Lys Asn Thr Val Tyr Leu Gln
1               5                   10                  15

Met Ser Ser Leu Lys Pro Glu Asp Thr Ala Thr Tyr Tyr Cys Asn Ala
            20                  25                  30

<210> SEQ ID NO 95
<211> LENGTH: 32
```

```
<212> TYPE: PRT
<213> ORGANISM: Artificial Sequence
<220> FEATURE:
<223> OTHER INFORMATION: Framework 3

<400> SEQUENCE: 95

Arg Phe Thr Ile Ser Arg Asp Asn Ala Lys Asn Thr Val Tyr Leu Glu
1               5                   10                  15
Met Asn Ser Leu Lys Pro Glu Asp Thr Ala Val Tyr Tyr Cys Ala Ala
            20                  25                  30

<210> SEQ ID NO 96
<211> LENGTH: 12
<212> TYPE: PRT
<213> ORGANISM: Artificial Sequence
<220> FEATURE:
<223> OTHER INFORMATION: CDR 3

<400> SEQUENCE: 96

Ser Leu Thr Ala Thr His Thr Tyr Glu Tyr Asp Tyr
1               5                   10

<210> SEQ ID NO 97
<211> LENGTH: 13
<212> TYPE: PRT
<213> ORGANISM: Artificial Sequence
<220> FEATURE:
<223> OTHER INFORMATION: CDR 3

<400> SEQUENCE: 97

Asp Arg Trp Trp Arg Pro Ala Gly Leu Gln Trp Asp Tyr
1               5                   10

<210> SEQ ID NO 98
<211> LENGTH: 9
<212> TYPE: PRT
<213> ORGANISM: Artificial Sequence
<220> FEATURE:
<223> OTHER INFORMATION: CDR 3

<400> SEQUENCE: 98

Arg Val Phe Asp Leu Pro Asn Asp Tyr
1               5

<210> SEQ ID NO 99
<211> LENGTH: 15
<212> TYPE: PRT
<213> ORGANISM: Artificial Sequence
<220> FEATURE:
<223> OTHER INFORMATION: CDR 3

<400> SEQUENCE: 99

Asp Thr Tyr Asn Ser Asn Pro Ala Arg Trp Asp Gly Tyr Asp Phe
1               5                   10                  15

<210> SEQ ID NO 100
<211> LENGTH: 11
<212> TYPE: PRT
<213> ORGANISM: Artificial Sequence
<220> FEATURE:
<223> OTHER INFORMATION: Framework 4

<400> SEQUENCE: 100

Arg Gly Gln Gly Thr Gln Val Thr Val Ser Ser
1               5                   10
```

```
<210> SEQ ID NO 101
<211> LENGTH: 261
<212> TYPE: PRT
<213> ORGANISM: Artificial Sequence
<220> FEATURE:
<223> OTHER INFORMATION: Nanobody Sequence

<400> SEQUENCE: 101

Glu Val Gln Leu Val Glu Ser Gly Gly Gly Ser Val Gln Pro Gly Gly
1               5                   10                  15

Ser Leu Thr Leu Ser Cys Gly Thr Ser Gly Arg Thr Phe Asn Val Met
            20                  25                  30

Gly Trp Phe Arg Gln Ala Pro Gly Lys Glu Arg Glu Phe Val Ala Ala
        35                  40                  45

Val Arg Trp Ser Ser Thr Gly Ile Tyr Tyr Thr Gln Tyr Ala Asp Ser
50                  55                  60

Val Lys Ser Arg Phe Thr Ile Ser Arg Asp Asn Ala Lys Asn Thr Val
65                  70                  75                  80

Tyr Leu Glu Met Asn Ser Leu Lys Pro Glu Asp Thr Ala Val Tyr Tyr
                85                  90                  95

Cys Ala Ala Asp Thr Tyr Asn Ser Asn Pro Ala Arg Trp Asp Gly Tyr
            100                 105                 110

Asp Phe Arg Gly Gln Gly Thr Gln Val Thr Val Ser Ser Gly Gly Gly
        115                 120                 125

Gly Ser Gly Gly Gly Gly Ser Glu Val Gln Leu Val Glu Ser Gly Gly
130                 135                 140

Gly Leu Val Gln Ala Gly Asp Ser Leu Arg Leu Ser Cys Ala Ala Ser
145                 150                 155                 160

Gly Arg Ala Phe Ser Arg Tyr Ala Met Gly Trp Phe Arg Gln Ala Pro
                165                 170                 175

Gly Lys Glu Arg Glu Phe Val Ala Ala Ile Gly Trp Gly Pro Ser Lys
            180                 185                 190

Thr Asn Tyr Ala Asp Ser Val Lys Gly Arg Phe Thr Ile Ser Arg Asp
        195                 200                 205

Asn Ala Lys Asn Thr Val Tyr Leu Gln Met Asn Thr Leu Lys Pro Glu
    210                 215                 220

Asp Thr Ala Val Tyr Ser Cys Ala Ala Lys Phe Val Asn Thr Asp Ser
225                 230                 235                 240

Thr Trp Ser Arg Ser Glu Met Tyr Thr Tyr Trp Gly Gln Gly Thr Gln
                245                 250                 255

Val Thr Val Ser Ser
            260

<210> SEQ ID NO 102
<211> LENGTH: 276
<212> TYPE: PRT
<213> ORGANISM: Artificial Sequence
<220> FEATURE:
<223> OTHER INFORMATION: Nanobody Sequence

<400> SEQUENCE: 102

Glu Val Gln Leu Val Glu Ser Gly Gly Gly Ser Val Gln Pro Gly Gly
1               5                   10                  15

Ser Leu Thr Leu Ser Cys Gly Thr Ser Gly Arg Thr Phe Asn Val Met
            20                  25                  30

Gly Trp Phe Arg Gln Ala Pro Gly Lys Glu Arg Glu Phe Val Ala Ala
        35                  40                  45
```

Val Arg Trp Ser Ser Thr Gly Ile Tyr Tyr Thr Gln Tyr Ala Asp Ser
 50                  55                  60

Val Lys Ser Arg Phe Thr Ile Ser Arg Asp Asn Ala Lys Asn Thr Val
 65                  70                  75                  80

Tyr Leu Glu Met Asn Ser Leu Lys Pro Glu Asp Thr Ala Val Tyr Tyr
                 85                  90                  95

Cys Ala Ala Asp Thr Tyr Asn Ser Asn Pro Ala Arg Trp Asp Gly Tyr
             100                 105                 110

Asp Phe Arg Gly Gln Gly Thr Gln Val Thr Val Ser Ser Gly Gly Gly
         115                 120                 125

Gly Ser Gly Gly Gly Gly Ser Gly Gly Gly Gly Ser Gly Gly Gly Gly
     130                 135                 140

Ser Gly Gly Gly Ser Glu Val Gln Leu Val Glu Ser Gly Gly Gly
145                 150                 155                 160

Leu Val Gln Ala Gly Asp Ser Leu Arg Leu Ser Cys Ala Ala Ser Gly
                 165                 170                 175

Arg Ala Phe Ser Arg Tyr Ala Met Gly Trp Phe Arg Gln Ala Pro Gly
             180                 185                 190

Lys Glu Arg Glu Phe Val Ala Ala Ile Gly Trp Gly Pro Ser Lys Thr
         195                 200                 205

Asn Tyr Ala Asp Ser Val Lys Gly Arg Phe Thr Ile Ser Arg Asp Asn
     210                 215                 220

Ala Lys Asn Thr Val Tyr Leu Gln Met Asn Thr Leu Lys Pro Glu Asp
225                 230                 235                 240

Thr Ala Val Tyr Ser Cys Ala Ala Lys Phe Val Asn Thr Asp Ser Thr
                 245                 250                 255

Trp Ser Arg Ser Glu Met Tyr Thr Tyr Trp Gly Gln Gly Thr Gln Val
             260                 265                 270

Thr Val Ser Ser
        275

<210> SEQ ID NO 103
<211> LENGTH: 286
<212> TYPE: PRT
<213> ORGANISM: Artificial Sequence
<220> FEATURE:
<223> OTHER INFORMATION: Nanobody Sequence

<400> SEQUENCE: 103

Glu Val Gln Leu Val Glu Ser Gly Gly Gly Ser Val Gln Pro Gly Gly
 1                   5                  10                  15

Ser Leu Thr Leu Ser Cys Gly Thr Ser Gly Arg Thr Phe Asn Val Met
                 20                  25                  30

Gly Trp Phe Arg Gln Ala Pro Gly Lys Glu Arg Glu Phe Val Ala Ala
             35                  40                  45

Val Arg Trp Ser Ser Thr Gly Ile Tyr Tyr Thr Gln Tyr Ala Asp Ser
 50                  55                  60

Val Lys Ser Arg Phe Thr Ile Ser Arg Asp Asn Ala Lys Asn Thr Val
 65                  70                  75                  80

Tyr Leu Glu Met Asn Ser Leu Lys Pro Glu Asp Thr Ala Val Tyr Tyr
                 85                  90                  95

Cys Ala Ala Asp Thr Tyr Asn Ser Asn Pro Ala Arg Trp Asp Gly Tyr
             100                 105                 110

Asp Phe Arg Gly Gln Gly Thr Gln Val Thr Val Ser Ser Gly Gly Gly
         115                 120                 125

-continued

Gly Ser Gly Gly Gly Gly Ser Gly Gly Gly Ser Gly Gly Gly Gly
    130                 135                 140

Ser Gly Gly Gly Ser Gly Gly Gly Ser Gly Gly Gly Ser
145                 150                 155                 160

Glu Val Gln Leu Val Glu Ser Gly Gly Leu Val Gln Ala Gly Asp
                165                 170                 175

Ser Leu Arg Leu Ser Cys Ala Ala Ser Gly Arg Ala Phe Ser Arg Tyr
        180                 185                 190

Ala Met Gly Trp Phe Arg Gln Ala Pro Gly Lys Glu Arg Glu Phe Val
            195                 200                 205

Ala Ala Ile Gly Trp Gly Pro Ser Lys Thr Asn Tyr Ala Asp Ser Val
        210                 215                 220

Lys Gly Arg Phe Thr Ile Ser Arg Asp Asn Ala Lys Asn Thr Val Tyr
225                 230                 235                 240

Leu Gln Met Asn Thr Leu Lys Pro Glu Asp Thr Ala Val Tyr Ser Cys
                245                 250                 255

Ala Ala Lys Phe Val Asn Thr Asp Ser Thr Trp Ser Arg Ser Glu Met
            260                 265                 270

Tyr Thr Tyr Trp Gly Gln Gly Thr Gln Val Thr Val Ser Ser
        275                 280                 285

<210> SEQ ID NO 104
<211> LENGTH: 260
<212> TYPE: PRT
<213> ORGANISM: Artificial Sequence
<220> FEATURE:
<223> OTHER INFORMATION: Nanobody Sequence

<400> SEQUENCE: 104

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Ala Phe Ser Arg Tyr
            20                  25                  30

Ala Met Gly Trp Phe Arg Gln Ala Pro Gly Lys Glu Arg Glu Phe Val
        35                  40                  45

Ala Ala Ile Gly Trp Gly Pro Ser Lys Thr Asn Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Thr Leu Lys Pro Glu Asp Thr Ala Val Tyr Ser Cys
                85                  90                  95

Ala Ala Lys Phe Val Asn Thr Asp Ser Thr Trp Ser Arg Ser Glu Met
            100                 105                 110

Tyr Thr Tyr Trp Gly Gln Gly Thr Gln Val Thr Val Ser Ser Gly Gly
        115                 120                 125

Gly Ser Gly Gly Gly Gly Ser Glu Val Gln Leu Val Glu Ser Gly Gly
    130                 135                 140

Gly Ser Val Gln Pro Gly Gly Ser Leu Thr Leu Ser Cys Gly Thr Ser
145                 150                 155                 160

Gly Arg Thr Phe Asn Val Met Gly Trp Phe Arg Gln Ala Pro Gly Lys
                165                 170                 175

Glu Arg Glu Phe Val Ala Ala Val Arg Trp Ser Ser Thr Gly Ile Tyr
            180                 185                 190

Tyr Thr Gln Tyr Ala Asp Ser Val Lys Ser Arg Phe Thr Ile Ser Arg
        195                 200                 205

Asp Asn Ala Lys Asn Thr Val Tyr Leu Glu Met Asn Ser Leu Lys Pro
    210                 215                 220
Glu Asp Thr Ala Val Tyr Tyr Cys Ala Ala Asp Thr Tyr Asn Ser Asn
225                 230                 235                 240
Pro Ala Arg Trp Asp Gly Tyr Asp Phe Arg Gly Gln Gly Thr Gln Val
            245                 250                 255
Thr Val Ser Ser
        260

<210> SEQ ID NO 105
<211> LENGTH: 276
<212> TYPE: PRT
<213> ORGANISM: Artificial Sequence
<220> FEATURE:
<223> OTHER INFORMATION: Nanobody Sequence

<400> SEQUENCE: 105

Glu Val Gln Leu Val Glu Ser Gly Gly Gly Leu Val Gln Ala Gly Asp
1               5                   10                  15
Ser Leu Arg Leu Ser Cys Ala Ala Ser Gly Arg Ala Phe Ser Arg Tyr
            20                  25                  30
Ala Met Gly Trp Phe Arg Gln Ala Pro Gly Lys Glu Arg Glu Phe Val
        35                  40                  45
Ala Ala Ile Gly Trp Gly Pro Ser Lys Thr Asn Tyr Ala Asp Ser Val
    50                  55                  60
Lys Gly Arg Phe Thr Ile Ser Arg Asp Asn Ala Lys Asn Thr Val Tyr
65                  70                  75                  80
Leu Gln Met Asn Thr Leu Lys Pro Glu Asp Thr Ala Val Tyr Ser Cys
                85                  90                  95
Ala Ala Lys Phe Val Asn Thr Asp Ser Thr Trp Ser Arg Ser Glu Met
            100                 105                 110
Tyr Thr Tyr Trp Gly Gln Gly Thr Gln Val Thr Val Ser Ser Gly Gly
        115                 120                 125
Gly Gly Ser Gly Gly Gly Ser Gly Gly Gly Ser Gly Gly Gly
    130                 135                 140
Gly Ser Gly Gly Gly Ser Glu Val Gln Leu Val Glu Ser Gly Gly
145                 150                 155                 160
Gly Ser Val Gln Pro Gly Gly Ser Leu Thr Leu Ser Cys Gly Thr Ser
                165                 170                 175
Gly Arg Thr Phe Asn Val Met Gly Trp Phe Arg Gln Ala Pro Gly Lys
            180                 185                 190
Glu Arg Glu Phe Val Ala Ala Val Arg Trp Ser Ser Thr Gly Ile Tyr
        195                 200                 205
Tyr Thr Gln Tyr Ala Asp Ser Val Lys Ser Arg Phe Thr Ile Ser Arg
    210                 215                 220
Asp Asn Ala Lys Asn Thr Val Tyr Leu Glu Met Asn Ser Leu Lys Pro
225                 230                 235                 240
Glu Asp Thr Ala Val Tyr Tyr Cys Ala Ala Asp Thr Tyr Asn Ser Asn
                245                 250                 255
Pro Ala Arg Trp Asp Gly Tyr Asp Phe Arg Gly Gln Gly Thr Gln Val
            260                 265                 270
Thr Val Ser Ser
        275

<210> SEQ ID NO 106
<211> LENGTH: 286

```
<212> TYPE: PRT
<213> ORGANISM: Artificial Sequence
<220> FEATURE:
<223> OTHER INFORMATION: Nanobody Sequence

<400> SEQUENCE: 106

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Ala Phe Ser Arg Tyr
            20                  25                  30

Ala Met Gly Trp Phe Arg Gln Ala Pro Gly Lys Glu Arg Glu Phe Val
        35                  40                  45

Ala Ala Ile Gly Trp Gly Pro Ser Lys Thr Asn Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Thr Leu Lys Pro Glu Asp Thr Ala Val Tyr Ser Cys
                85                  90                  95

Ala Ala Lys Phe Val Asn Thr Asp Ser Thr Trp Ser Arg Ser Glu Met
            100                 105                 110

Tyr Thr Tyr Trp Gly Gln Gly Thr Gln Val Thr Val Ser Ser Gly Gly
        115                 120                 125

Gly Gly Ser Gly Gly Gly Gly Ser Gly Gly Gly Gly Ser Gly Gly Gly
    130                 135                 140

Gly Ser Gly Gly Gly Gly Ser Gly Gly Gly Gly Ser Gly Gly Gly Gly
145                 150                 155                 160

Ser Glu Val Gln Leu Val Glu Ser Gly Gly Ser Val Gln Pro Gly
                165                 170                 175

Gly Ser Leu Thr Leu Ser Cys Gly Thr Ser Gly Arg Thr Phe Asn Val
            180                 185                 190

Met Gly Trp Phe Arg Gln Ala Pro Gly Lys Glu Arg Glu Phe Val Ala
        195                 200                 205

Ala Val Arg Trp Ser Ser Thr Gly Ile Tyr Tyr Thr Gln Tyr Ala Asp
    210                 215                 220

Ser Val Lys Ser Arg Phe Thr Ile Ser Arg Asp Asn Ala Lys Asn Thr
225                 230                 235                 240

Val Tyr Leu Glu Met Asn Ser Leu Lys Pro Glu Asp Thr Ala Val Tyr
                245                 250                 255

Tyr Cys Ala Ala Asp Thr Tyr Asn Ser Asn Pro Ala Arg Trp Asp Gly
            260                 265                 270

Tyr Asp Phe Arg Gly Gln Gly Thr Gln Val Thr Val Ser Ser
        275                 280                 285

<210> SEQ ID NO 107
<211> LENGTH: 398
<212> TYPE: PRT
<213> ORGANISM: Artificial Sequence
<220> FEATURE:
<223> OTHER INFORMATION: Nanobody Sequence

<400> SEQUENCE: 107

Glu Val Gln Leu Val Glu Ser Gly Gly Gly Leu Val Gln Ala Gly Asp
1               5                   10                  15

Ser Leu Arg Val Ser Cys Ala Ala Ser Gly Arg Thr Ser Ser Tyr Ala
            20                  25                  30

Met Ala Trp Phe Arg Gln Ala Pro Gly Lys Glu Arg Glu Phe Val Gly
        35                  40                  45
```

```
Thr Ile Ser Arg Thr Asn Ser Arg Thr Lys Tyr Ala Asp Phe Val Glu
             50                  55                  60

Gly Arg Phe Thr Ile Ser Arg Asp Asn Ala Lys Ser Thr Leu Ser Leu
 65                  70                  75                  80

Gln Met Thr Ser Leu Lys Pro Glu Asp Thr Ala Val Tyr Tyr Cys Ala
                 85                  90                  95

Ala Lys Trp Thr Gly Asn Ser Tyr His Asp Tyr Thr Trp Ser Lys Val
                100                 105                 110

Asp Glu Tyr Asn Val Trp Gly Gln Gly Thr Leu Val Thr Val Ser Ser
            115                 120                 125

Gly Gly Gly Gly Ser Gly Gly Gly Ser Gly Gly Gly Ser Glu
            130                 135                 140

Val Gln Leu Val Glu Ser Gly Gly Leu Val Gln Pro Gly Asn Ser
145                 150                 155                 160

Leu Arg Leu Ser Cys Ala Ala Ser Gly Phe Thr Phe Ser Ser Phe Gly
                165                 170                 175

Met Ser Trp Val Arg Gln Ala Pro Gly Lys Gly Leu Glu Trp Val Ser
            180                 185                 190

Ser Ile Ser Gly Ser Gly Ser Asp Thr Leu Tyr Ala Asp Ser Val Lys
            195                 200                 205

Gly Arg Phe Thr Ile Ser Arg Asp Asn Ala Lys Thr Thr Leu Tyr Leu
210                 215                 220

Gln Met Asn Ser Leu Arg Pro Glu Asp Thr Ala Val Tyr Tyr Cys Thr
225                 230                 235                 240

Ile Gly Gly Ser Leu Ser Arg Ser Ser Gln Gly Thr Leu Val Thr Val
                245                 250                 255

Ser Ser Gly Gly Gly Gly Ser Gly Gly Gly Ser Gly Gly Gly Gly
            260                 265                 270

Ser Glu Val Gln Leu Val Glu Ser Gly Gly Ser Val Gln Pro Gly
            275                 280                 285

Gly Ser Leu Thr Leu Ser Cys Gly Thr Ser Gly Arg Thr Phe Asn Val
            290                 295                 300

Met Gly Trp Phe Arg Gln Ala Pro Gly Lys Glu Arg Glu Phe Val Ala
305                 310                 315                 320

Ala Val Arg Trp Ser Ser Thr Gly Ile Tyr Tyr Thr Gln Tyr Ala Asp
                325                 330                 335

Ser Val Lys Ser Arg Phe Thr Ile Ser Arg Asp Asn Ala Lys Asn Thr
                340                 345                 350

Val Tyr Leu Glu Met Asn Ser Leu Lys Pro Glu Asp Thr Ala Val Tyr
            355                 360                 365

Tyr Cys Ala Ala Asp Thr Tyr Asn Ser Asn Pro Ala Arg Trp Asp Gly
        370                 375                 380

Tyr Asp Phe Arg Gly Gln Gly Thr Leu Val Thr Val Ser Ser
385                 390                 395
```

<210> SEQ ID NO 108
<211> LENGTH: 396
<212> TYPE: PRT
<213> ORGANISM: Artificial Sequence
<220> FEATURE:
<223> OTHER INFORMATION: Nanobody Sequence

<400> SEQUENCE: 108

```
Glu Val Gln Leu Val Glu Ser Gly Gly Gly Leu Val Arg Ala Gly Asp
 1               5                  10                  15
```

Ser Leu Arg Leu Ser Cys Ala Ala Ser Gly Arg Ala Phe Ser Arg Tyr
            20                  25                  30

Ala Met Gly Trp Phe Arg Gln Ala Leu Gly Lys Glu Arg Glu Leu Val
        35                  40                  45

Ala Ala Ile Gly Trp Ser Pro Thr His Thr Tyr Ala Asp Ser Val
50                  55                  60

Lys Gly Arg Phe Thr Met Ser Arg Asp Asn Gly Lys Asn Thr Val Phe
65                  70                  75                  80

Leu Gln Met Asn Ser Leu Asn Pro Glu Asp Thr Ala Val Tyr Tyr Cys
                85                  90                  95

Ala Ala Lys Tyr Ser Ser Arg Asp Ala Ala Tyr Arg Ser Asp Tyr Asp
            100                 105                 110

Tyr Asn Tyr Trp Gly Gln Gly Thr Leu Val Thr Val Ser Ser Gly Gly
        115                 120                 125

Gly Gly Ser Gly Gly Gly Ser Gly Gly Gly Ser Glu Val Gln
130                 135                 140

Leu Val Glu Ser Gly Gly Gly Leu Val Gln Pro Gly Asn Ser Leu Arg
145                 150                 155                 160

Leu Ser Cys Ala Ala Ser Gly Phe Thr Phe Ser Ser Phe Gly Met Ser
                165                 170                 175

Trp Val Arg Gln Ala Pro Gly Lys Gly Leu Glu Trp Val Ser Ser Ile
            180                 185                 190

Ser Gly Ser Gly Ser Asp Thr Leu Tyr Ala Asp Ser Val Lys Gly Arg
        195                 200                 205

Phe Thr Ile Ser Arg Asp Asn Ala Lys Thr Thr Leu Tyr Leu Gln Met
210                 215                 220

Asn Ser Leu Arg Pro Glu Asp Thr Ala Val Tyr Tyr Cys Thr Ile Gly
225                 230                 235                 240

Gly Ser Leu Ser Arg Ser Ser Gln Gly Thr Leu Val Thr Val Ser Ser
                245                 250                 255

Gly Gly Gly Gly Ser Gly Gly Gly Ser Gly Gly Gly Ser Glu
            260                 265                 270

Val Gln Leu Val Glu Ser Gly Gly Ser Val Gln Pro Gly Gly Ser
        275                 280                 285

Leu Thr Leu Ser Cys Gly Thr Ser Gly Arg Thr Phe Asn Val Met Gly
290                 295                 300

Trp Phe Arg Gln Ala Pro Gly Lys Glu Arg Glu Phe Val Ala Ala Val
305                 310                 315                 320

Arg Trp Ser Ser Thr Gly Ile Tyr Tyr Thr Gln Tyr Ala Asp Ser Val
            325                 330                 335

Lys Ser Arg Phe Thr Ile Ser Arg Asp Asn Ala Lys Asn Thr Val Tyr
        340                 345                 350

Leu Glu Met Asn Ser Leu Lys Pro Glu Asp Thr Ala Val Tyr Tyr Cys
            355                 360                 365

Ala Ala Asp Thr Tyr Asn Ser Asn Pro Ala Arg Trp Asp Gly Tyr Asp
            370                 375                 380

Phe Arg Gly Gln Gly Thr Leu Val Thr Val Ser Ser
385                 390                 395

<210> SEQ ID NO 109
<211> LENGTH: 396
<212> TYPE: PRT
<213> ORGANISM: Artificial Sequence
<220> FEATURE:

<223> OTHER INFORMATION: Nanobody Sequence

<400> SEQUENCE: 109

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Ala Phe Ser Arg Tyr
            20                  25                  30

Ala Met Gly Trp Phe Arg Gln Ala Pro Gly Lys Glu Arg Glu Phe Val
        35                  40                  45

Ala Ala Ile Gly Trp Gly Pro Ser Lys Thr Asn Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Thr Leu Lys Pro Glu Asp Thr Ala Val Tyr Ser Cys
                85                  90                  95

Ala Ala Lys Phe Val Asn Thr Asp Ser Thr Trp Ser Arg Ser Glu Met
            100                 105                 110

Tyr Thr Tyr Trp Gly Gln Gly Thr Leu Val Thr Val Ser Ser Gly Gly
        115                 120                 125

Gly Gly Ser Gly Gly Gly Ser Gly Gly Gly Ser Glu Val Gln
130                 135                 140

Leu Val Glu Ser Gly Gly Gly Leu Val Gln Pro Gly Asn Ser Leu Arg
145                 150                 155                 160

Leu Ser Cys Ala Ala Ser Gly Phe Thr Phe Ser Ser Phe Gly Met Ser
                165                 170                 175

Trp Val Arg Gln Ala Pro Gly Lys Gly Leu Glu Trp Val Ser Ser Ile
            180                 185                 190

Ser Gly Ser Gly Ser Asp Thr Leu Tyr Ala Asp Ser Val Lys Gly Arg
        195                 200                 205

Phe Thr Ile Ser Arg Asp Asn Ala Lys Thr Thr Leu Tyr Leu Gln Met
    210                 215                 220

Asn Ser Leu Arg Pro Glu Asp Thr Ala Val Tyr Tyr Cys Thr Ile Gly
225                 230                 235                 240

Gly Ser Leu Ser Arg Ser Ser Gln Gly Thr Leu Val Thr Val Ser Ser
                245                 250                 255

Gly Gly Gly Gly Ser Gly Gly Gly Ser Gly Gly Gly Ser Glu
            260                 265                 270

Val Gln Leu Val Glu Ser Gly Gly Ser Val Gln Pro Gly Gly Ser
        275                 280                 285

Leu Thr Leu Ser Cys Gly Thr Ser Gly Arg Thr Phe Asn Val Met Gly
    290                 295                 300

Trp Phe Arg Gln Ala Pro Gly Lys Glu Arg Glu Phe Val Ala Ala Val
305                 310                 315                 320

Arg Trp Ser Ser Thr Gly Ile Tyr Tyr Thr Gln Tyr Ala Asp Ser Val
                325                 330                 335

Lys Ser Arg Phe Thr Ile Ser Arg Asp Asn Ala Lys Asn Thr Val Tyr
            340                 345                 350

Leu Glu Met Asn Ser Leu Lys Pro Glu Asp Thr Ala Val Tyr Tyr Cys
        355                 360                 365

Ala Ala Asp Thr Tyr Asn Ser Asn Pro Ala Arg Trp Asp Gly Tyr Asp
    370                 375                 380

Phe Arg Gly Gln Gly Thr Leu Val Thr Val Ser Ser
385                 390                 395

```
<210> SEQ ID NO 110
<211> LENGTH: 256
<212> TYPE: PRT
<213> ORGANISM: Artificial Sequence
<220> FEATURE:
<223> OTHER INFORMATION: Nanobody Sequence

<400> SEQUENCE: 110

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Ala Phe Ser Arg Tyr
            20                  25                  30

Ala Met Gly Trp Phe Arg Gln Ala Pro Gly Lys Glu Arg Glu Phe Val
        35                  40                  45

Ala Ala Ile Gly Trp Gly Pro Ser Lys Thr Asn Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Thr Leu Lys Pro Glu Asp Thr Ala Val Tyr Ser Cys
                85                  90                  95

Ala Ala Lys Phe Val Asn Thr Asp Ser Thr Trp Ser Arg Ser Glu Met
            100                 105                 110

Tyr Thr Tyr Trp Gly Gln Gly Thr Leu Val Thr Val Ser Ser Gly Gly
        115                 120                 125

Gly Gly Ser Gly Gly Gly Ser Gly Gly Gly Ser Glu Val Gln
    130                 135                 140

Leu Val Glu Ser Gly Gly Gly Leu Val Gln Pro Gly Asn Ser Leu Arg
145                 150                 155                 160

Leu Ser Cys Ala Ala Ser Gly Phe Thr Phe Ser Ser Phe Gly Met Ser
                165                 170                 175

Trp Val Arg Gln Ala Pro Gly Lys Gly Leu Glu Trp Val Ser Ser Ile
            180                 185                 190

Ser Gly Ser Gly Ser Asp Thr Leu Tyr Ala Asp Ser Val Lys Gly Arg
        195                 200                 205

Phe Thr Ile Ser Arg Asp Asn Ala Lys Thr Thr Leu Tyr Leu Gln Met
    210                 215                 220

Asn Ser Leu Arg Pro Glu Asp Thr Ala Val Tyr Tyr Cys Thr Ile Gly
225                 230                 235                 240

Gly Ser Leu Ser Arg Ser Ser Gln Gly Thr Leu Val Thr Val Ser Ser
                245                 250                 255

<210> SEQ ID NO 111
<211> LENGTH: 115
<212> TYPE: PRT
<213> ORGANISM: Artificial Sequence
<220> FEATURE:
<223> OTHER INFORMATION: Nanobody Sequence

<400> SEQUENCE: 111

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60
```

```
Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Val Tyr Tyr Cys
                 85                  90                  95

Thr Ile Gly Gly Ser Leu Ser Arg Ser Ser Gln Gly Thr Leu Val Thr
            100                 105                 110

Val Ser Ser
        115

<210> SEQ ID NO 112
<211> LENGTH: 115
<212> TYPE: PRT
<213> ORGANISM: Artificial Sequence
<220> FEATURE:
<223> OTHER INFORMATION: Nanobody Sequence

<400> SEQUENCE: 112

Glu Val Gln Leu Leu Glu Ser Gly Gly Leu Val Gln Pro Gly Gly
 1               5                  10                  15

Ser Leu Arg Leu Ser Cys Ala Ala Ser Gly Phe Thr Phe Arg Ser Phe
                20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                 85                  90                  95

Thr Ile Gly Gly Ser Leu Ser Arg Ser Ser Gln Gly Thr Leu Val Thr
            100                 105                 110

Val Ser Ser
        115

<210> SEQ ID NO 113
<211> LENGTH: 116
<212> TYPE: PRT
<213> ORGANISM: Artificial Sequence
<220> FEATURE:
<223> OTHER INFORMATION: Nanobody Sequence

<400> SEQUENCE: 113

Glu Val Gln Leu Val Glu Ser Gly Gly Gly Val Val Gln Pro Gly Asn
 1               5                  10                  15

Ser Leu Arg Leu Ser Cys Ala Ala Ser Gly Phe Thr Phe Ser Ser Phe
                20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Thr Tyr Tyr Cys
                 85                  90                  95

Thr Ile Gly Gly Ser Leu Ser Arg Ser Ser Gln Gly Thr Leu Val Thr
            100                 105                 110

Val Ser Ser Ala
```

-continued

115

<210> SEQ ID NO 114
<211> LENGTH: 116
<212> TYPE: PRT
<213> ORGANISM: Artificial Sequence
<220> FEATURE:
<223> OTHER INFORMATION: Nanobody Sequence

<400> SEQUENCE: 114

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
            115

<210> SEQ ID NO 115
<211> LENGTH: 115
<212> TYPE: PRT
<213> ORGANISM: Artificial Sequence
<220> FEATURE:
<223> OTHER INFORMATION: Nanobody Sequence

<400> SEQUENCE: 115

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 116
<211> LENGTH: 116
<212> TYPE: PRT
<213> ORGANISM: Artificial Sequence
<220> FEATURE:
<223> OTHER INFORMATION: Nanobody Sequence

<400> SEQUENCE: 116

```
Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Lys
            100                 105                 110

Val Ser Ser Ala
            115
```

<210> SEQ ID NO 117
<211> LENGTH: 115
<212> TYPE: PRT
<213> ORGANISM: Artificial Sequence
<220> FEATURE:
<223> OTHER INFORMATION: Nanobody Sequence

<400> SEQUENCE: 117

```
Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser
        115
```

<210> SEQ ID NO 118
<211> LENGTH: 116
<212> TYPE: PRT
<213> ORGANISM: Artificial Sequence
<220> FEATURE:
<223> OTHER INFORMATION: Nanobody Sequence

<400> SEQUENCE: 118

```
Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
```

```
            50                  55                  60
Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Leu Tyr Tyr Cys
                     85                  90                  95

Thr Ile Gly Gly Ser Leu Ser Arg Ser Ser Gln Gly Thr Leu Val Thr
                    100                 105                 110

Val Ser Ser Ala
            115

<210> SEQ ID NO 119
<211> LENGTH: 117
<212> TYPE: PRT
<213> ORGANISM: Artificial Sequence
<220> FEATURE:
<223> OTHER INFORMATION: Nanobody Sequence

<400> SEQUENCE: 119

Glu Val Gln Leu Val Glu Ser Gly Gly Val Val Gln Pro Gly Asn
 1               5                  10                  15

Ser Leu Arg Leu Ser Cys Ala Ala Ser Gly Phe Thr Phe Ser Ser Phe
                 20                  25                  30

Gly Met Ser Trp Val Arg Gln Ala Pro Gly Lys Gly Leu Glu Trp Val
             35                  40                  45

Ser Ser Ile Ser Gly Ser Gly Ser Asp Thr Leu Tyr Ala Asp Ser Val
         50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Leu Tyr Tyr Cys
                     85                  90                  95

Thr Ile Gly Gly Ser Leu Ser Arg Ser Ser Gln Gly Thr Leu Val Thr
                    100                 105                 110

Val Ser Ser Ala Ala
            115

<210> SEQ ID NO 120
<211> LENGTH: 118
<212> TYPE: PRT
<213> ORGANISM: Artificial Sequence
<220> FEATURE:
<223> OTHER INFORMATION: Nanobody Sequence

<400> SEQUENCE: 120

Glu Val Gln Leu Val Glu Ser Gly Gly Val Val Gln Pro Gly Asn
 1               5                  10                  15

Ser Leu Arg Leu Ser Cys Ala Ala Ser Gly Phe Thr Phe Ser Ser Phe
                 20                  25                  30

Gly Met Ser Trp Val Arg Gln Ala Pro Gly Lys Gly Leu Glu Trp Val
             35                  40                  45

Ser Ser Ile Ser Gly Ser Gly Ser Asp Thr Leu Tyr Ala Asp Ser Val
         50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Leu Tyr Tyr Cys
                     85                  90                  95

Thr Ile Gly Gly Ser Leu Ser Arg Ser Ser Gln Gly Thr Leu Val Thr
                    100                 105                 110
```

Val Ser Ser Ala Ala Ala
        115

<210> SEQ ID NO 121
<211> LENGTH: 116
<212> TYPE: PRT
<213> ORGANISM: Artificial Sequence
<220> FEATURE:
<223> OTHER INFORMATION: Nanobody Sequence

<400> SEQUENCE: 121

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Gly
        115

<210> SEQ ID NO 122
<211> LENGTH: 117
<212> TYPE: PRT
<213> ORGANISM: Artificial Sequence
<220> FEATURE:
<223> OTHER INFORMATION: Nanobody Sequence

<400> SEQUENCE: 122

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly
        115

<210> SEQ ID NO 123
<211> LENGTH: 118
<212> TYPE: PRT
<213> ORGANISM: Artificial Sequence
<220> FEATURE:
<223> OTHER INFORMATION: Nanobody Sequence

<400> SEQUENCE: 123

Glu Val Gln Leu Val Glu Ser Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly
        115

<210> SEQ ID NO 124
<211> LENGTH: 5
<212> TYPE: PRT
<213> ORGANISM: Artificial Sequence
<220> FEATURE:
<223> OTHER INFORMATION: CDR 1

<400> SEQUENCE: 124

Ser Phe Gly Met Ser
1               5

<210> SEQ ID NO 125
<211> LENGTH: 17
<212> TYPE: PRT
<213> ORGANISM: Artificial Sequence
<220> FEATURE:
<223> OTHER INFORMATION: CDR 2

<400> SEQUENCE: 125

Ser Ile Ser Gly Ser Gly Ser Asp Thr Leu Tyr Ala Asp Ser Val Lys
1               5                   10                  15

Gly

<210> SEQ ID NO 126
<211> LENGTH: 6
<212> TYPE: PRT
<213> ORGANISM: Artificial Sequence
<220> FEATURE:
<223> OTHER INFORMATION: CDR 3

<400> SEQUENCE: 126

Gly Gly Ser Leu Ser Arg
1               5

<210> SEQ ID NO 127
<211> LENGTH: 5
<212> TYPE: PRT
<213> ORGANISM: Artificial Sequence
<220> FEATURE:
<223> OTHER INFORMATION: Linker

<400> SEQUENCE: 127

Gly Gly Gly Gly Ser
1               5

<210> SEQ ID NO 128
<211> LENGTH: 7
<212> TYPE: PRT
<213> ORGANISM: Artificial Sequence
<220> FEATURE:
<223> OTHER INFORMATION: Linker

<400> SEQUENCE: 128

Ser Gly Gly Ser Gly Gly Ser
1               5

<210> SEQ ID NO 129
<211> LENGTH: 9
<212> TYPE: PRT
<213> ORGANISM: Artificial Sequence
<220> FEATURE:
<223> OTHER INFORMATION: Linker

<400> SEQUENCE: 129

Gly Gly Gly Gly Ser Gly Gly Gly Ser
1               5

<210> SEQ ID NO 130
<211> LENGTH: 10
<212> TYPE: PRT
<213> ORGANISM: Artificial Sequence
<220> FEATURE:
<223> OTHER INFORMATION: Linker

<400> SEQUENCE: 130

Gly Gly Gly Gly Ser Gly Gly Gly Gly Ser
1               5                   10

<210> SEQ ID NO 131
<211> LENGTH: 15
<212> TYPE: PRT
<213> ORGANISM: Artificial Sequence
<220> FEATURE:
<223> OTHER INFORMATION: Linker

<400> SEQUENCE: 131

Gly Gly Gly Gly Ser Gly Gly Gly Gly Ser Gly Gly Gly Gly Ser
1               5                   10                  15

<210> SEQ ID NO 132
<211> LENGTH: 18
<212> TYPE: PRT
<213> ORGANISM: Artificial Sequence
<220> FEATURE:
<223> OTHER INFORMATION: Linker

<400> SEQUENCE: 132

Gly Gly Gly Gly Ser Gly Gly Gly Gly Ser Gly Gly Gly Gly Gly
1               5                   10                  15

Gly Ser

<210> SEQ ID NO 133
<211> LENGTH: 20
<212> TYPE: PRT
<213> ORGANISM: Artificial Sequence
<220> FEATURE:
<223> OTHER INFORMATION: Linker

<400> SEQUENCE: 133

Gly Gly Gly Gly Ser Gly Gly Gly Gly Ser Gly Gly Gly Gly Ser Gly

```
1               5                   10                  15
Gly Gly Gly Ser
            20

<210> SEQ ID NO 134
<211> LENGTH: 25
<212> TYPE: PRT
<213> ORGANISM: Artificial Sequence
<220> FEATURE:
<223> OTHER INFORMATION: Linker

<400> SEQUENCE: 134

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 135
<211> LENGTH: 30
<212> TYPE: PRT
<213> ORGANISM: Artificial Sequence
<220> FEATURE:
<223> OTHER INFORMATION: Linker

<400> SEQUENCE: 135

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 136
<211> LENGTH: 35
<212> TYPE: PRT
<213> ORGANISM: Artificial Sequence
<220> FEATURE:
<223> OTHER INFORMATION: Linker

<400> SEQUENCE: 136

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35
```

The invention claimed is:

1. A method for inhibiting and/or preventing HIV infection in a human subject comprising administering to the human subject a polypeptide comprising a first and a second immunoglobulin single variable domain (ISV) in an amount effective to inhibit and/or prevent the HIV infection in the human subject, wherein said first ISV binds to CD4 present on the surface of a cell; and
said second ISV binds to CXCR4 present on the surface of said cell;
wherein said first ISV essentially consists of 4 framework regions (FR1 to FR4, respectively) and 3 complementarity determining regions (CDR1 to CDR3, respectively), in which:
(i) CDR1 is chosen from the group consisting of SEQ ID NOs: 85, 84, 83 and 82; and amino acid sequences that have 1, 2 or 3 amino acid difference(s) with SEQ ID NOs: 85, 84, 83 and 82; CDR2 is chosen from the group consisting of SEQ ID NOs: 91, 90, 89 and 88; and amino acid sequences that have 1, 2 or 3 amino acid difference(s) with SEQ ID NOs: 91, 90, 89 and 88; and CDR3 is chosen from the group consisting of SEQ ID NO: 99, 98, 97 and 96; and amino acid sequences that have 1, 2, 3 or 4 amino acid difference(s) with SEQ ID NOs: 99, 98, 97 and 96;
(ii) CDR1 is chosen from the group consisting of SEQ ID NOs: 35, 34, 36-40; and amino acid sequences that have 1, 2 or 3 amino acid difference(s) with SEQ ID NOs: 35, 34, 36-40; CDR2 is chosen from the group consisting of SEQ ID NOs: 50, 48-49 and 51-56; and amino acid sequences that have 1, 2 or 3 amino acid difference(s) with SEQ ID NOs: 50, 48-49 and 51-56; and CDR3 is chosen from the group consisting of SEQ ID NO: 69, 67-68, 70-75 and amino acid sequences that have 1, 2, 3 or 4 amino acid difference(s) with SEQ ID NOs: 69, 67-68, 70-75; or (iii) both (i) and (ii).

2. The method according to claim 1, wherein said polypeptide prevents HIV infection for at least 3 months, at least 6 months, at least 9 months, at least 11 months, at least 1 year, at least 1.5 years, or at least 2 years.

3. The method according to claim 1, wherein said polypeptide inhibits HIV infection by about 10%, about 20%, about 30%, about 40%, about 50%, about 60%, about 80%, about 90%, about 95%, or about 100% as measured in a HIV infection assay.

4. The method according to claim 1, wherein said polypeptide inhibits HIV fusion with CD4+CXCR4+ cells.

5. The method according to claim 1, wherein said polypeptide inhibits binding of a natural ligand to said CXCR4 by less than about 50%, less than about 40%, less than about 30%, less than about 20%, less than about 10%, or less than about 5%, wherein the natural ligand is Stromal Cell-Derived Factor-1 beta (SDF-1β) or Stromal Cell-Derived Factor-1 alpha (SDF-1α).

6. The method according to claim 1, wherein said first ISV consists essentially of 4 framework regions (FR1 to FR4, respectively) and 3 complementarity determining regions (CDR1 to CDR3, respectively), in which (i) CDR1 consists of the amino acid sequence of SEQ ID NO: 85 or an amino acid sequence having 1, 2 or 3 amino acid difference(s) with the amino acid sequence of SEQ ID NO: 85; CDR2 consists of the amino acid sequence of SEQ ID NO: 91 or an amino acid sequence having 1, 2 or 3 amino acid difference(s) with the amino acid sequence of SEQ ID NO: 91; and CDR3 consists of the amino acid sequence of SEQ ID NO: 99 or an amino acid sequence having 1, 2, 3 or 4 amino acid difference(s) with the amino acid sequence of SEQ ID NO: 99;

(ii) CDR1 consists of the amino acid sequence of SEQ ID NO: 84 or an amino acid sequence having 1, 2 or 3 amino acid difference(s) with the amino acid sequence of SEQ ID NO: 84; CDR2 consists of the amino acid sequence of SEQ ID NO: 90 or an amino acid sequence having 1, 2 or 3 amino acid difference(s) with the amino acid sequence of SEQ ID NO: 90; and CDR3 consists of the amino acid sequence of SEQ ID NO: 98 or an amino acid sequence having 1, 2, 3 or 4 amino acid difference(s) with the amino acid sequence of SEQ ID NO: 98;

(iii) CDR1 consists of the amino acid sequence of SEQ ID NO: 83 or an amino acid sequence having 1, 2 or 3 amino acid difference(s) with the amino acid sequence of SEQ ID NO: 83; CDR2 consists of the amino acid sequence of SEQ ID NO: 89 or an amino acid sequence having 1, 2 or 3 amino acid difference(s) with the amino acid sequence of SEQ ID NO: 89; and CDR3 consists of the amino acid sequence of SEQ ID NO: 98 or an amino acid sequence having 1, 2, 3 or 4 amino acid difference(s) with the amino acid sequence of SEQ ID NO: 98; or (iv) CDR1 consists of the amino acid sequence of SEQ ID NO: 82 or an amino acid sequence having 1, 2 or 3 amino acid difference(s) with the amino acid sequence of SEQ ID NO: 82; CDR2 consists of the amino acid sequence of SEQ ID NO: 88 or an amino acid sequence having 1, 2 or 3 amino acid difference(s) with the amino acid sequence of SEQ ID NO: 88; and CDR3 consists of the amino acid sequence of SEQ ID NO: 98 or an amino acid sequence having 1, 2, 3 or 4 amino acid difference(s) with the amino acid sequence of SEQ ID NO: 98.

7. The method according to claim 1, wherein said second ISV consists essentially of 4 framework regions (FR1 to FR4, respectively) and 3 complementarity determining regions (CDR1 to CDR3, respectively), in which (i) CDR1 consists of the amino acid sequence of SEQ ID NO: 35 or an amino acid sequence having 1, 2 or 3 amino acid difference(s) with the amino acid sequence of SEQ ID NO: 35; CDR2 consists of the amino acid sequence of SEQ ID NO: 50 or an amino acid sequence having 1, 2 or 3 amino acid difference(s) with the amino acid sequence of SEQ ID NO: 50; and CDR3 consists of the amino acid sequence of SEQ ID NO: 69 or an amino acid sequence having 1, 2, 3 or 4 amino acid difference(s) with the amino acid sequence of SEQ ID NO: 69;

(ii) CDR1 consists of the amino acid sequence of SEQ ID NO: 35 or an amino acid sequence having 1, 2 or 3 amino acid difference(s) with the amino acid sequence of SEQ ID NO: 35; CDR2 consists of the amino acid sequence of SEQ ID NO: 53 or an amino acid sequence having 1, 2 or 3 amino acid difference(s) with the amino acid sequence of SEQ ID NO: 53; and CDR3 consists of the amino acid sequence of SEQ ID NO: 72 or an amino acid sequence having 1, 2, 3 or 4 amino acid difference(s) with the amino acid sequence of SEQ ID NO: 72;

(iii) CDR1 consists of the amino acid sequence of SEQ ID NO: 34 or an amino acid sequence having 1, 2 or 3 amino acid difference(s) with the amino acid sequence of SEQ ID NO: 34; CDR2 consists of the amino acid sequence of SEQ ID NO: 48 or an amino acid sequence having 1, 2 or 3 amino acid difference(s) with the amino acid sequence of SEQ ID NO: 48; and CDR3 consists of the amino acid sequence of SEQ ID NO: 67 or an amino acid sequence having 1, 2, 3 or 4 amino acid difference(s) with the amino acid sequence of SEQ ID NO: 67;

(iv) CDR1 consists of the amino acid sequence of SEQ ID NO: 34 or an amino acid sequence having 1, 2 or 3 amino acid difference(s) with the amino acid sequence of SEQ ID NO: 34; CDR2 consists of the amino acid sequence of SEQ ID NO: 49 or an amino acid sequence having 1, 2 or 3 amino acid difference(s) with the amino acid sequence of SEQ ID NO: 49; and CDR3 consists of the amino acid sequence of SEQ ID NO: 68 or an amino acid sequence having 1, 2, 3 or 4 amino acid difference(s) with the amino acid sequence of SEQ ID NO: 68;

(v) CDR1 consists of the amino acid sequence of SEQ ID NO: 36 or an amino acid sequence having 1, 2 or 3 amino acid difference(s) with the amino acid sequence of SEQ ID NO: 36; CDR2 consists of the amino acid sequence of SEQ ID NO: 51 or an amino acid sequence having 1, 2 or 3 amino acid difference(s) with the amino acid sequence of SEQ ID NO: 51; and CDR3 consists of the amino acid sequence of SEQ ID NO: 70 or an amino acid sequence having 1, 2, 3 or 4 amino acid difference(s) with the amino acid sequence of SEQ ID NO: 70;

(vi) CDR1 consists of the amino acid sequence of SEQ ID NO: 37 or an amino acid sequence having 1, 2 or 3 amino acid difference(s) with the amino acid sequence of SEQ ID NO: 37; CDR2 consists of the amino acid sequence of SEQ ID NO: 52 or an amino acid sequence having 1, 2 or 3 amino acid difference(s) with the amino acid sequence of SEQ ID NO: 52; and CDR3 consists of the amino acid sequence of SEQ ID NO: 71 or an amino acid sequence having 1, 2, 3 or 4 amino acid difference(s) with the amino acid sequence of SEQ ID NO: 71;
(vii) CDR1 consists of the amino acid sequence of SEQ ID NO: 38 or an amino acid sequence having 1, 2 or 3 amino acid difference(s) with the amino acid sequence of SEQ ID NO: 38; CDR2 consists of the amino acid sequence of SEQ ID NO: 54 or an amino acid sequence having 1, 2 or 3 amino acid difference(s) with the amino acid sequence of SEQ ID NO: 54; and CDR3 consists of the amino acid sequence of SEQ ID NO: 73 or an amino acid sequence having 1, 2, 3 or 4 amino acid difference(s) with the amino acid sequence of SEQ ID NO: 73;
(viii) CDR1 consists of the amino acid sequence of SEQ ID NO: 39 or an amino acid sequence having 1, 2 or 3 amino acid difference(s) with the amino acid sequence of SEQ ID NO: 39; CDR2 consists of the amino acid sequence of SEQ ID NO: 55 or an amino acid sequence having 1, 2 or 3 amino acid difference(s) with the amino acid sequence of SEQ ID NO: 55; and CDR3 consists of the amino acid sequence of SEQ ID NO: 74 or an amino acid sequence having 1, 2, 3 or 4 amino acid difference(s) with the amino acid sequence of SEQ ID NO: 74; or
(ix) CDR1 consists of the amino acid sequence of SEQ ID NO: 40 or an amino acid sequence having 1, 2 or 3 amino acid difference(s) with the amino acid sequence of SEQ ID NO: 40; CDR2 consists of the amino acid sequence of SEQ ID NO: 56 or an amino acid sequence having 1, 2 or 3 amino acid difference(s) with the amino acid sequence of SEQ ID NO: 56; and CDR3 consists of the amino acid sequence of SEQ ID NO: 75 or an amino acid sequence having 1, 2, 3 or 4 amino acid difference(s) with the amino acid sequence of SEQ ID NO: 75.

8. The method of claim 7, wherein said first ISV consists essentially of 4 framework regions (FR1 to FR4, respectively) and 3 complementarity determining regions (CDR1 to CDR3, respectively), in which
(i) CDR1 consists of the amino acid sequence of SEQ ID NO: 85 or an amino acid sequence having 1, 2 or 3 amino acid difference(s) with the amino acid sequence of SEQ ID NO: 85; CDR2 consists of the amino acid sequence of SEQ ID NO: 91 or an amino acid sequence having 1, 2 or 3 amino acid difference(s) with the amino acid sequence of SEQ ID NO: 91; and CDR3 consists of the amino acid sequence of SEQ ID NO: 99 or an amino acid sequence having 1, 2, 3 or 4 amino acid difference(s) with the amino acid sequence of SEQ ID NO: 99;
(ii) CDR1 consists of the amino acid sequence of SEQ ID NO: 84 or an amino acid sequence having 1, 2 or 3 amino acid difference(s) with the amino acid sequence of SEQ ID NO: 84; CDR2 consists of the amino acid sequence of SEQ ID NO: 90 or an amino acid sequence having 1, 2 or 3 amino acid difference(s) with the amino acid sequence of SEQ ID NO: 90; and CDR3 consists of the amino acid sequence of SEQ ID NO: 98 or an amino acid sequence having 1, 2, 3 or 4 amino acid difference(s) with the amino acid sequence of SEQ ID NO: 98;
(iii) CDR1 consists of the amino acid sequence of SEQ ID NO: 83 or an amino acid sequence having 1, 2 or 3 amino acid difference(s) with the amino acid sequence of SEQ ID NO: 83; CDR2 consists of the amino acid sequence of SEQ ID NO: 89 or an amino acid sequence having 1, 2 or 3 amino acid difference(s) with the amino acid sequence of SEQ ID NO: 89; and CDR3 consists of the amino acid sequence of SEQ ID NO: 98 or an amino acid sequence having 1, 2, 3 or 4 amino acid difference(s) with the amino acid sequence of SEQ ID NO: 98; or
(iv) CDR1 consists of the amino acid sequence of SEQ ID NO: 82 or an amino acid sequence having 1, 2 or 3 amino acid difference(s) with the amino acid sequence of SEQ ID NO: 82; CDR2 consists of the amino acid sequence of SEQ ID NO: 88 or an amino acid sequence having 1, 2 or 3 amino acid difference(s) with the amino acid sequence of SEQ ID NO: 88; and CDR3 consists of the amino acid sequence of SEQ ID NO: 98 or an amino acid sequence having 1, 2, 3 or 4 amino acid difference(s) with the amino acid sequence of SEQ ID NO: 98.

9. The method according to claim 1, wherein said first ISV consists essentially of 4 framework regions (FR1 to FR4, respectively) and 3 complementarity determining regions (CDR1 to CDR3, respectively), in which
(i) CDR1 consists of the amino acid sequence of SEQ ID NO: 85; CDR2 consists of the amino acid sequence of SEQ ID NO: 91; and CDR3 consists of the amino acid sequence of SEQ ID NO: 99;
(ii) CDR1 consists of the amino acid sequence of SEQ ID NO: 84; CDR2 consists of the amino acid sequence of SEQ ID NO: 90; and CDR3 consists of the amino acid sequence of SEQ ID NO: 98;
(iii) CDR1 consists of the amino acid sequence of SEQ ID NO: 83; CDR2 consists of the amino acid sequence of SEQ ID NO: 89; and CDR3 consists of the amino acid sequence of SEQ ID NO: 98; or
(iv) CDR1 consists of the amino acid sequence of SEQ ID NO: 82; CDR2 consists of the amino acid sequence of SEQ ID NO: 88; and CDR3 consists of the amino acid sequence of SEQ ID NO: 98.

10. The method according to claim 1, wherein said second ISV consists essentially of 4 framework regions (FR1 to FR4, respectively) and 3 complementarity determining regions (CDR1 to CDR3, respectively), in which
(i) CDR1 consists of the amino acid sequence of SEQ ID NO: 35; CDR2 consists of the amino acid sequence of SEQ ID NO: 50; and CDR3 consists of the amino acid sequence of SEQ ID NO: 69;
(ii) CDR1 consists of the amino acid sequence of SEQ ID NO: 35; CDR2 consists of the amino acid sequence of SEQ ID NO: 53; and CDR3 consists of the amino acid sequence of SEQ ID NO: 72;
(iii) CDR1 consists of the amino acid sequence of SEQ ID NO: 34; CDR2 consists of the amino acid sequence of SEQ ID NO: 48; and CDR3 consists of the amino acid sequence of SEQ ID NO: 67;
(iv) CDR1 consists of the amino acid sequence of SEQ ID NO: 34; CDR2 consists of the amino acid sequence of SEQ ID NO: 49; and CDR3 consists of the amino acid sequence of SEQ ID NO: 68;
(v) CDR1 consists of the amino acid sequence of SEQ ID NO: 36; CDR2 consists of the amino acid sequence of SEQ ID NO: 51; and CDR3 consists of the amino acid sequence of SEQ ID NO: 70;
(vi) CDR1 consists of the amino acid sequence of SEQ ID NO: 37; CDR2 consists of the amino acid sequence of SEQ ID NO: 52; and CDR3 consists of the amino acid sequence of SEQ ID NO: 71;

(vii) CDR1 consists of the amino acid sequence of SEQ ID NO: 38; CDR2 consists of the amino acid sequence of SEQ ID NO: 54; and CDR3 consists of the amino acid sequence of SEQ ID NO: 73;

(viii) CDR1 consists of the amino acid sequence of SEQ ID NO: 39; CDR2 consists of the amino acid sequence of SEQ ID NO: 55; and CDR3 consists of the amino acid sequence of SEQ ID NO: 74; or (ix) CDR1 consists of the amino acid sequence of SEQ ID NO: 40; CDR2 consists of the amino acid sequence of SEQ ID NO: 56; and CDR3 consists of the amino acid sequence of SEQ ID NO: 75.

11. The method of claim 10, wherein said first ISV consists essentially of 4 framework regions (FR1 to FR4, respectively) and 3 complementarity determining regions (CDR1 to CDR3, respectively), in which (i) CDR1 consists of the amino acid sequence of SEQ ID NO: 85; CDR2 consists of the amino acid sequence of SEQ ID NO: 91; and CDR3 consists of the amino acid sequence of SEQ ID NO: 99;

(ii) CDR1 consists of the amino acid sequence of SEQ ID NO: 84; CDR2 consists of the amino acid sequence of SEQ ID NO: 90; and CDR3 consists of the amino acid sequence of SEQ ID NO: 98;

(iii) CDR1 consists of the amino acid sequence of SEQ ID NO: 83; CDR2 consists of the amino acid sequence of SEQ ID NO: 89; and CDR3 consists of the amino acid sequence of SEQ ID NO: 98; or (iv) CDR1 consists of the amino acid sequence of SEQ ID NO: 82; CDR2 consists of the amino acid sequence of SEQ ID NO: 88; and CDR3 consists of the amino acid sequence of SEQ ID NO: 98.

12. The method according to claim 1, wherein the polypeptide further comprises a serum protein binding moiety or PEG.

13. The method according to claim 12, wherein said serum protein binding moiety is an immunoglobulin single variable domain binding serum albumin.

14. The method according to claim 2, wherein said polypeptide prevents HIV infection for at least 1 year.

15. The method according to claim 3, wherein said polypeptide inhibits HIV infection by more than 95% as measured in a HIV infection assay.

16. The method according to claim 5, wherein said polypeptide inhibits binding of a natural ligand to said CXCR4 by less than about 10%, wherein the natural ligand is Stromal Cell-Derived Factor-1 beta (SDF-1β) or Stromal Cell-Derived Factor-1 alpha (SDF-1α).

* * * * *